(12) United States Patent
Fitzgerald et al.

(10) Patent No.: US 7,875,711 B2
(45) Date of Patent: Jan. 25, 2011

(54) COMPOSITIONS AND METHODS FOR INHIBITING EXPRESSION OF XBP-1 GENE

(75) Inventors: Kevin Fitzgerald, Brookline, MA (US); Gregory Hinkle, Plymouth, MA (US)

(73) Assignee: Alnylam Pharamaceuticals, Inc., Cambridge, MA (US)

(*) Notice: Subject to any disclaimer, the term of this patent is extended or adjusted under 35 U.S.C. 154(b) by 0 days.

(21) Appl. No.: 12/425,811

(22) Filed: Apr. 17, 2009

(65) Prior Publication Data

US 2009/0275638 A1 Nov. 5, 2009

Related U.S. Application Data

(60) Provisional application No. 61/045,947, filed on Apr. 17, 2008, provisional application No. 61/078,302, filed on Jul. 3, 2008, provisional application No. 61/081,861, filed on Jul. 18, 2008.

(51) Int. Cl.
 *C07H 21/04* (2006.01)
(52) U.S. Cl. ............. 536/24.5; 536/24.1; 536/24.31; 514/44
(58) Field of Classification Search .............. None
 See application file for complete search history.

(56) References Cited

U.S. PATENT DOCUMENTS

| | | | |
|---|---|---|---|
| 2003/0143732 | A1 | 7/2003 | Fosnaugh et al. |
| 2004/0259247 | A1 | 12/2004 | Tuschl et al. |
| 2007/0004664 | A1 | 1/2007 | McSwiggen et al. |
| 2007/0031844 | A1 | 2/2007 | Khvorova et al. |

OTHER PUBLICATIONS

Huang Ihi-Ming et al: "Activation of hepatitis B virus S promoter by a cell type-restricted IREI-dependent pathway induced by endoplasmic reticulum stress." Molecular and Cellular Biology Sep. 2005, vol. 25, No. 17, Sep. 2005, pp. 7522-7533.
Lee Ann-Hwee et al: "Proteasome inhibitors disrupt the unfolded protein response in myeloma cells" Proceedings of the National Academy of Sciences of USA, National Academy of Science, Washington, DC, US, vol. 100, No. 17, Aug. 19, 2003, pp. 9946-9951.
Romero-Ramirez Lorenzo et al: "XBPI is essential for survival under hypoxic conditions and is required for tumor growth." Cancer Research Sep. 1, 2004, vol. 64, No. 17, Sep. 1, 2004, pp. 5943-5947.
Yu Chia-Yi et al: "Flavivirus infection activates the XBP1 pathway of the unfolded protein response to cope with endoplasmic reticulum stress." Journal of Virology Dec. 2006, vol. 80, No. 23, Dec. 2006, pp. 11868-11880.
International Search Report and Written Opinion, PCT/US2009/040962, Nov. 24, 2009, 15 Pages.
Invitation of Pay Additional Fees and, Where Applicable, Protest Fee, Communication Relating to the Results of the Partial International Search, PCT/US2009/040962, Oct. 5, 2009, 7 Pages.
Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated By 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation By Double-Stranded RNA in Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Lee, A.-H., et al., "Regulation of Hepatic Lipogenesis by the Transcription Factor XBP1," Science, Jun. 13, 2008, pp. 1492-1496, vol. 320.

*Primary Examiner*—Kimberly Chong
(74) *Attorney, Agent, or Firm*—Fenwick & West LLP

(57) ABSTRACT

The invention relates to a double-stranded ribonucleic acid (dsRNA) targeting X-Box Protein 1 (XBP-1), and methods of using the dsRNA to inhibit expression of XBP-1.

28 Claims, 6 Drawing Sheets

▼ =other cleavage sites found

FIG. 2

```
GGCGCTGGGCGGCTGCGGCGCGCGGTGCGCGGTGCGTAGTCTGGAGCTATGGTGGTGGTGGCAGCCG
CGCCGAACCCGGCCGACGGGACCCCTAAAGTTCTGCTTCTGTCGGGGCAGCCCGCCTCCGCCGCCGG
AGCCCCGGCCGGCCAGGCCCTGCCGCTCATGGTGCCAGCCCAGAGAGGGGCCAGCCCGGAGGCAGCG
AGCGGGGGCTGCCCCAGGCGCGCAAGCGACAGCGCCTCACGCACCTGAGCCCCGAGGAGAAGGCGC
TGAGGAGGAAACTGAAAAACAGAGTAGCAGCTCAGACTGCCAGAGATCGAAAGAAGGCTCGAATGAG
TGAGCTGGAACAGCAAGTGGTAGATTTAGAAGAAGAGAACCAAAAACTTTTGCTAGAAAATCAGCTT
TTACGAGAGAAAACTCATGGCCTTGTAGTTGAGAACCAGGAGTTAAGACAGCGCTTGGGGATGGATG
CCCTGGTTGCTGAAGAGGAGGCGGAAGCCAAGGGGAATGAAGTGAGGCCAGTGGCCGGGTCTGCTGA
GTCCGCAGCACTCAGACTACGTGCACCTCTGCAGCAGGTGCAGGCCCAGTTGTCACCCCTCCAGAAC
ATCTCCCCATGGATTCTGGCGGTATTGACTCTTCAGATTCAGAGTCTGATATCCTGTTGGGCATTCT
GGACAACTTGGACCCAGTCATGTTCTTCAAATGCCCTTCCCCAGAGCCTGCCAGCCTGGAGGAGCTC
CCAGAGGTCTACCCAGAAGGACCCAGTTCCTTACCAGCCTCCCTTTCTCTGTCAGTGGGGACGTCAT
CAGCCAAGCTGGAAGCCATTAATGAACTAATTCGTTTTGACCACATATATACCAAGCCCCTAGTCTT
AGAGATACCCTCTGAGACAGAGAGCCAAGCTAATGTGGTAGTGAAAATCGAGGAAGCACCTCTCAGC
CCCTCAGAGAATGATCACCCTGAATTCATTGTCTCAGTGAAGGAAGAACCTGTAGAAGATGACCTCG
TTCCGGAGCTGGGTATCTCAAATCTGCTTTCATCCAGCCACTGCCCAAAGCCATCTTCCTGCCTACT
GGATGCTTACAGTGACTGTGGATACGGGGGTTCCCTTTCCCCATTCAGTGACATGTCCTCTCTGCTT
GGTGTAAACCATTCTTGGGAGGACACTTTTGCCAATGAACTCTTTCCCCAGCTGATTAGTGTCTAAG
GAATGATCCAATACTGTTGCCCTTTTCCTTGACTATTACACTGCCTGGAGGATAGCAGAGAAGCCTG
TCTGTACTTCATTCAAAAGCCAAAATAGAGAGTATACAGTCCTAGAGAATTCCTCTATTTGTTCAG
ATCTCATAGATGACCCCCAGGTATTGTCTTTTGACATCCAGCAGTCCAAGGTATTGAGACATATTAC
TGGAAGTAAGAAATATTACTATAATTGAGAACTACAGCTTTTAAGATTGTACTTTTATCTTAAAAGG
GTGGTAGTTTTCCCTAAAATACTTATTATGTAAGGGTCATTAGACAAATGTCTTGAAGTAGACATGG
AATTTATGAATGGTTCTTTATCATTTCTCTTCCCCCTTTTTGGCATCCTGGCTTGCCTCCAGTTTTA
GGTCCTTTAGTTTGCTTCTGTAAGCAACGGGAACACCTGCTGAGGGGCTCTTTCCCTCATGTATAC
TTCAAGTAAGATCAAGAATCTTTTGTGAAATTATAGAAATTTACTATGTAAATGCTTGATGGAATTT
TTTCCTGCTAGTGTAGCTTCTGAAAGGTGCTTTCTCCATTTATTTAAAACTACCCATGCAATTAAAA
GGTACAATGCAAAAAAAAAAAAAAAA
```

FIG. 3

```
GCGGCGCTGGCGTAGACGTTTCCTGGCTATGGTGGTGGTGGCAGCGGCGCCGAGCGCGGCCACGGCG
GCCCCCAAAGTGCTACTCTTATCTGGCCAGCCCGCCTCCGGCGGCCGGGCGCTGCCGCTCATGGTAC
CCGGTCCGCGGGCAGCAGGGTCGGAGGCGAGCGGGACACCGCAGGCTCGCAAGCGGCAGCGGCTCAC
GCACCTGAGCCCGGAGGAGAAAGCGCTGCGGAGGAAACTGAAAAACAGAGTAGCAGCGCAGACTGCT
CGAGATAGAAAGAAAGCCCGGATGAGCGAGCTGGAGCAGCAAGTGGTGGATTTGGAAGAAGAGAACC
ACAAACTCCAGCTAGAAAATCAGCTTTTACGGGAGAAAACTCACGGCCTTGTGGTTGAGAACCAGGA
GTTAAGAACACGCTTGGGAATGGACACGCTGGATCCTGACGAGGTTCCAGAGGTGGAGGCCAAGGGG
AGTGGAGTAAGGCTGGTGGCCGGGTCTGCTGAGTCCGCAGCACTCAGACTATGTGCACCTCTGCAGC
AGGTGCAGGCCCAGTTGTCACCTCCCCAGAACATCTTCCCATGGACTCTGACACTGTTGCCTCTTCA
GATTCTGAGTCTGATATCCTTTGGGCATTCTGGACAAGTTGGACCCTGTCATGTTTTTCAAATGTC
CTTCCCCAGAGTCTGCTAGTCTGGAGGAACTCCCAGAGGTCTACCCAGAAGGACCTAGTTCCTTACC
AGCCTCCCTTTCTCTGTCAGTGGGGACCTCATCAGCCAAGCTGGAAGCCATTAATGAACTCATTCGT
TTTGACCATGTATACACCAAGCCTCTAGTTTTAGAGATCCCCTCTGAGACAGAGAGTCAAACTAACG
TGGTAGTGAAAATTGAGGAAGCACCTCTAAGCTCTTCAGAAGAGGATCACCCTGAATTCATTGTCTC
AGTGAAGAAAGAGCCTTTGGAAGATGACTTCATCCCAGAGCTGGGCATCTCAAACCTGCTTTCATCC
AGCCATTGTCTGAGACCACCTTCTTGCCTGCTGGACGCTCACAGTGACTGTGGATATGAGGGCTCCC
CTTCTCCCTTCAGTGACATGTCTTCTCCACTTGGTACAGACCACTCCTGGGAGGATACTTTTGCCAA
TGAACTTTTCCCCCAGCTGATTAGTGTCTAAAGAGCCACATAACACTGGGCCCCTTTCCCTGACCAT
CACATTGCCTAGAGGATAGCATAGGCCTGTCTCTTTCGTTAAAAGCCAAAGTAGAGGCTGTCTGGCC
TTAGAAGAATTCCTCTAAAGTATTTCAAATCTCATAGATGACTTCCAAGTATTGTCGTTTGACACTC
AGCTGTCTAAGGTATTCAAAGGTATTCCAGTACTACAGCTTTTGAGATTCTAGTTTATCTTAAAGGT
GGTAGTATACTCTAAATCGCAGGGAGGGTCATTTGACAGTTTTTTCCCAGCCTGGCTTCAAACTATG
TAGCCGAGGCTAGGCAGAAACTTCTGACCCTCTTGACCCCACCTCCCAAGTGCTGGGCTTCACCAGG
TGTGCACCTCCACACCTGCCCCCCCGACATGTCAGGTGGACATGGGATTCATGAATGGCCCTTAGCA
TTTCTTTCTCCACTCTCTGCTTCCCAGGTTTCGTAACCTGAGGGGGCTTGTTTTCCCTTATGTGCAT
TTTAAATGAAGATCAAGAATCTTTGTAAAATGATGAAAATTTACTATGTAAATGCTTGATGGATCTT
CTTGCTAGTGTAGCTTCTAGAAGGTGCTTTCTCCATTTATTTAAAACTACCCTTGCAAAAAAAAAAA
AAAAAAAA
```

FIG. 4

```
TGGCTATGGTGGTGGTGGCAGCGGCGCCGAGCGCGGCCTCGGCGGCCCCCAAAGTGCTACTCCTAT
CTGGTCAGCCCGCCTCCGGCGGCCGAGCGCTGCCGCTCATGGTTCCGGGCCCGCGAGCCGCAGGGT
CGGAGGCGAGCGGGACACCGCAGGCTCGCAAGCGGCAGCGCCTCACGCACCTGAGCCCGGAGGAGA
AAGCGCTGCGGAGGAAACTGAAAAACAGAGTAGCAGCACAGACTGCGCGAGATAGAAAGAAAGCCC
GGATGAGCGAGCTGGAGCAGCAAGTGGTGGATTTGGAAGAAGAGAACCAGAAACTCCAGCTAGAAA
ATCAGCTTTTACGAGAGAAAACTCATGGGCTTGTGATTGAGAACCAGGAGTTAAGGACACGCTTGG
GGATGAATGCCCTGGTTACTGAAGAGGTCTCAGAGGCAGAGTCCAAGGGGAATGGAGTAAGGCTGG
TGGCCGGGTCTGCTGAGTCCGCAGCACTCAGACTACGTGCGCCTCTGCAGCAGGTGCAGGCCCAGT
TGTCACCTCCCCAGAACATCTTCCCATGGATTCTGACGCTGTTGCCTCTTCAGATTCTGAGTCTGA
TATCCTTTTGGGCATTCTGGACAAGTTGGACCCTGTCATGTTTTTCAAATGTCCTTCCCCAGAGTC
TGCTAATCTGGAGGAACTCCCAGAGGTCTACCCAGAAGGACCTAGTTCCTTACCAGCCTCCCTTTC
TCTGTCAGTGGGGACCTCATCAGCCAAGCTGGAAGCCATTAATGAACTCATTCGTTTTGACCATGT
ATACACCAAGCCTCTAGTCTTAGAGATCCCTCTGAGACAGAGAGCCAAACTAATGTGGTAGTGAA
AATTGAGGAAGCACCTCTAAGCTCTTCAGAAGAGGATCACCCTGAATTCATTGTCTCAGTGAAGAA
AGAACCTTTGGATGATGACTTCATTCCCGAGCTGGGCATCTCAAACCTGCTTTCATCCAGCCATTG
TCTGAGACCACCTTCCTGCCTGCTGGATGCTCACAGTGACTGTGGATATGAGGGCTCCCCTTCTCC
CTTCAGCGACATGTCTTCTCCACTTGGTACAGACCACTCCTGGGAGGACACTTTTGCCAACGAACT
TTTCCCCCAGCTGATTAGTGTCTAAAGCCACCCACCACTGGGCTCCTTCCCTGATCATCACACTGC
CTAGAGGATAGCATAGGCCTGTCTGCTTCACTAAAAGCCAAAGTAGAGGCTATCTGGCCTTATAAG
AATTCCTCTAAAGTATTTCAAACCTCTTAGATGACTTCCAAGTATTGTCTTTTGACACTCAGCTGT
CTGAGGTCTTCAAAGGTATTCCAATACTACAGCTTTTGAGATTCTCATTATCTTAAAGGTGGTAGC
ATGCTCTAAATCATAGGGAAAGTCATCTGACAGTTATCGTTCAGCCTGGCTATGTAGCCGAGGCTA
AGCTGAAACTTGTGACCCTCTTGACCCCACTCCCAAGTGCTGGACTTTACCAGGTGTGCAGCTCCA
CACCGGCCTCTTCACATGTCCTGAAGTAGACATGAGAGTCACCAGTTCTTTCTCCTCCCCGCCC
CACAGGTTTCTTTTGTTTCCTTCTACAAGCAGAGAAACAGCAACCTGAGGGGCCTGTCCTTCCTTA
TGTCCAGTTCAAGTGAAGATCAAGAATCTTTGTAAAATTATTGGAAATTTACTGTGTAAATGCTTG
ATGGAATCTTCTTGCTAGTGTAGCTTCTAGAAGGTGCTTTCTCCATTTATTTAAAACTACCCATGC
AATTAAAAAAGCAACGCAGCATCCCCGTTGAATGATTTTAAAAAAAAAAAAAAAAAAAAAAAAAA
AAA
```

FIG. 5

```
GGCTGGGCGGCGGCGGCGGCGGCGCGCGGTGCGTAGTCTCGAGCTATGGTGGTGGTGGCAGCCGCAC
CGAGTCCGGCCGACGGGGCCCCTAAAGTACTGCTTCTGTCGGGGCAGCCCGCCTCCGCCGCCGGAGC
CCCGGCCGGCCAGGCCCTGCCGCTCATGGTGCCAGCCCAGAGAGGGGCTAGCCCGGAGGCAGCGAGC
GGGGGGCTGCCCCAGGCGCGCAAGCGGCAGCGCCTCACGCATCTGAGCCCCGAGGAGAAGGCGCTGA
GGAGGAAACTGAAAAACAGAGTAGCAGCTCAGACTGCCAGAGATCGAAAGAAAGCTCGAATGAGTGA
GCTGGAACAGCAAGTGGTAGATTTAGAAGAAGAGAACCAAAAACTTTTGCTAGAAAATCAGCTTTTA
CGAGAGAAAACTCACGGCCTTGTAGTTGAGAACCAGGAGTTAAGACAGCGCCTGGGGATGGATGCCC
TGGTTGCTAAAGAGGAGGCGGAAGCCAAGGGGAATGGAGTGAGGCCAGTGGCCGGGTCTGCTGAGTC
CGCAGTGCAGGCCCAGTTGTCACCCCTCCAGAACATCTCCCCATGGATTCTGGCGGTATTGACTCTT
CAGATTCAGAGTCTGATATCCTGTTGGGCATTCTGGACAACTTGGACCCAGTCATGTTCTTCAAATG
CCCTTCCCCAGAGTCTGCCAGCCTGGAGGAGCTCCCAGAGGTCTACCCAGAAGGACCCAGTTCCTTA
CCAGCCTCCCTTTCTCTGTCAGTGGGGACGTCATCAGCCAAGCTGGAAGCCATTAATGAACTAATTC
GTTTTGACCACATATATACCAAGCCCCTGGTCTTAGAGATACCCTCTGAGACAGAGAGCCAAGCTAA
TGTGGTAGTGAAAATCGAGGAAGCACCTCTCAGCCCCTCAGAGAATGATCACCCTGAATTCATTGTC
TCAGTGAAGGAAGAACCTGTAGAAGATGACCTCATTCCAGAGCTGGGTATCTCAAATCTGCTTTCAT
CCAGCCACTGCCCGAAACCATCTTCCTGCCTACTGGATGCTTACAGTGACTGTGGATATGGGGCTC
CCTTTCCCCCTTCAGTGACATGTCCTCTCCGCTTGGTGTAAACCATTCTTGGGAGGACACTTTTGCC
AATGAACTTTTTCCCCAGCTGATTAGTGTCTAAGGAATGATCCAGTACTGTTGCCCTTTTCCTTGAC
TATTACACTGCCTGGAGGATAGCAGGGAAGCCTGCCTGTGCTTCATTCAAAAAGCCAAAATAGAGAG
TACACAGTCCTAGAGAATTCCTTTCAAGTATTTGTTCAGATCTCATAGATGAGCCCCAGGTACTGTC
TTTTGACATCCAGCAGTCCAAAGTATTGAGACATATTACTGTAATTAAGAAATATTACTATAATTGA
GAACTACAGCTTTTAAGATTGTACTTTTATCTTAAAAGGGTGGTAGTTTGCCCTAAAATACTTATTA
TGTAAGGGTCATTAGACAAATGTCTTGAAGTAGAATTTATGAATGGTTCTTTATCATTTCTCTTCCC
CCTTTTTGGCATCCTGGCTTGCCTCCAGTTTTAGGTCCCTTAGTTTGCTTCTGTAAGCAAAGAGAAC
ACCTGCTGAGGGGCTCTTTCCCTCACGTATACTTCAAGTAAGATCAAGAATCTTTTGTGAAACTAT
AGAAATTTACTATGTAAATGCTTGATGGAATTTTTCCTGCTAGTGTAGCTTCTGAAAGGTGCTTTC
CATTTATTTAAAACTACCCATGCAATTAAAAGGTACAATGCAGCATCCTTGTTCTTTGATTTCTTCT
AGGGCCGTAAGTCTTATTTTCTCTCTAGTTGTTTCTGTGTGCTGTGGTAGGACTTTATCCAACTGAA
GTGAGCCTGCCACTTTTAAAAGTGACTGAAGGCTTTTCCACCTTAATTACTGCCTGCTTTAATTCTG
GATTGCCGTAAGTGATATAAGCTATAATTTGAGCAGTTACTATCTTTCTGAGACAGATTCTTGAGCC
TAACTGACCAATATCACAGCCAGTAAGTGGGAGAGCTAGAACCCTAACCACTATTTGCTATACGATC
TTATAAATGTTAAACAAGGACACACCATCACATATCAAGATTCTCTTGCCCTTATCATGGGAATTAA
GAGCATTTTCTAGACTCAAACTCCCTAGTTTCAACTCTGCCACTGGTAAGCTGGGTAACCCAGGGGT
TAT
```

COMPOSITIONS AND METHODS FOR INHIBITING EXPRESSION OF XBP-1 GENE

CROSS-REFERENCE TO RELATED APPLICATIONS

This application claims priority to U.S. application Ser. No. 61/045,947, filed Apr. 17, 2008; to U.S. Ser. No. 61/078,302, filed Jul. 3, 2008; to U.S. Ser. No. 61/081,861, filed Jul. 18, 2008. The entire contents of each of these provisional applications are hereby incorporated by reference in the present application.

FIELD OF THE INVENTION

The invention relates to a double-stranded ribonucleic acid (dsRNA) targeting X-Box Protein 1 (XBP-1), and methods of using the dsRNA to inhibit expression of XBP-1.

BACKGROUND OF THE INVENTION

X-box binding protein 1 (XBP-1) is a basic leucine zipper transcription factor that is involved in the cellular unfolded protein response (UPR). XBP-1 is known to be active in the endoplasmic reticulum (ER). The ER consists of a system of folded membranes and tubules in the cytoplasm of cells. Proteins and lipids are manufactured and processed in the ER. When unusual demands are placed on the ER, "ER stress" occurs. ER stress can be triggered by a viral infection, gene mutations, exposure to toxins, aggregation of improperly folded proteins or a shortage of intracellular nutrients. The result can be Type II diabetes, metabolic syndrome, a neurological disorder or cancer.

Two XBP-1 isoforms are known to exist in cells: spliced XBP-1S and unspliced XBP-1U. Both isoforms of XBP-1 bind to the 21-bp Tax-responsive element of the human T-lymphotropic virus type 1 (HTLV-1) long terminal repeat (LTR) in vitro and transactivate HTLV-1 transcription. HTLV-1 is associated with a rare form of blood dyscrasia known as Adult T-cell Leukemia/lymphoma (ATLL) and a myelopathy, tropical spastic paresis.

Double-stranded RNA molecules (dsRNA) have been shown to block gene expression in a highly conserved regulatory mechanism known as RNA interference (RNAi). WO 99/32619 (Fire et al.) disclosed the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.).

SUMMARY OF THE INVENTION

The invention provides compositions containing double-stranded ribonucleic acid (dsRNA) and methods for inhibiting the expression of an XBP-1 gene in a cell or mammal. The invention also provides compositions and methods for treating pathological conditions and diseases caused by the expression of XBP-1 gene, such as metabolic disorders (e.g., diabetes or metabolic syndrome), cardiovascular disease, protein folding diseases or cancer. The dsRNAs included in the compositions featured herein include a dsRNA having an RNA strand (the antisense strand) having a region which is less than 30 nucleotides in length, generally 19-24 nucleotides in length, and is substantially complementary to at least part of an mRNA transcript of the XBP-1 gene.

In one aspect, a dsRNA for inhibiting expression of an XBP-1 gene includes at least two sequences that are complementary to each other. The dsRNA includes a sense strand having a first sequence and an antisense strand having a second sequence. The antisense strand includes a nucleotide sequence that is substantially complementary to at least part of an mRNA encoding XBP-1, and the region of complementarity is less than 30 nucleotides in length, and at least 15 nucleotides in length. Generally, the dsRNA is 19 to 24, e.g., 19 to 21 nucleotides in length. In some embodiments the dsRNA is from about 10 to about 15 nucleotides in length, and in other embodiments the dsRNA is from about 25 to about 30 nucleotides in length. The dsRNA, upon contacting with a cell expressing XBP-1, inhibits the expression of an XBP-1 gene by at least 20%, at least 25%, at least 30%, at least 35% or at least 40%, such as when assayed by a method as described herein. In one embodiment, the Factor VII dsRNA is formulated in a stable nucleic acid particle (SNALP).

For example, the dsRNA molecules featured herein can include a first sequence of the dsRNA that is selected from the group consisting of the sense sequences of Tables 2, 4, 8, 9, 11 and 12 and a second sequence that is selected from the group consisting of the antisense sequences of Tables 2, 4, 8, 9, 11 and 12. The dsRNA molecules featured herein can include naturally occurring nucleotides or can include at least one modified nucleotide, such as a 2'-O-methyl modified nucleotide, a nucleotide having a 5'-phosphorothioate group, and a terminal nucleotide linked to a conjugate group, such as to a cholesteryl derivative, to vitamin E, or to a dodecanoic acid bisdecylamide group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such modified sequence will be based on a first sequence of said dsRNA selected from the group consisting of the sense sequences of Tables 2, 4, 8, 9, 11 and 12 and a second sequence selected from the group consisting of the antisense sequences of Tables 2, 4, 8, 9, 11 and 12.

In one aspect, the invention provides a cell containing at least one of the dsRNAs featured in the invention. The cell is generally a mammalian cell, such as a human cell.

In another aspect, the invention provides a pharmaceutical composition for inhibiting the expression of an XBP-1 gene in an organism, generally a human subject. The composition typically includes one or more of the dsRNAs described herein and a pharmaceutically acceptable carrier or delivery vehicle. In one embodiment, the composition is used for treating cancer, e.g., a cancer of the liver.

In another aspect, the invention provides a method for inhibiting the expression of an XBP-1 gene in a cell by performing the following steps:

(a) introducing into the cell a double-stranded ribonucleic acid (dsRNA), wherein the dsRNA includes at least two sequences that are complementary to each other. The dsRNA has a sense strand comprising a first sequence and an antisense strand having a second sequence; the antisense strand has a region of complementarity that is substantially complementary to at least a part of a mRNA encoding XBP-1, and where the region of complementarity is less than 30 nucleotides in length, generally 19-24 nucleotides in length, and where the dsRNA, upon contact with a cell expressing the XBP-1, inhibits expression of the XBP-1 gene by at least 20%, at least 30%, or at least 40%; and (b) maintaining the cell produced in step (a) for a time sufficient to obtain degradation of the mRNA transcript of XBP-1 gene, thereby inhibiting expression of the XBP-1 gene in the cell.

In one embodiment, the method is for inhibiting gene expression in a cell infected with HTLV-1, such as a tumor cell.

In another aspect, the invention provides methods for treating, preventing or managing pathological processes mediated by XBP-1 expression, e.g., a metabolic disease such as diabetes (e.g., Type II diabetes or metabolic syndrome), or cardiovascular disease. The method can include administering to a patient in need of such treatment, prevention or management a therapeutically or prophylactically effective amount of one or more of the dsRNAs featured in the invention. In one embodiment the patient has metabolic syndrome. For example, a patient with metabolic syndrome can have one of more of high cholesterol, obesity, and/or insulin insensitivity. In some embodiments, a patient with metabolic syndrome will also have heart disease. In another embodiment, the patient has a dyslipidemia or a disorder associated with a dyslipidemia. For example, in one embodiment the patient has atherosclerosis, which is often associated with hypercholesterolemia. In another embodiment, the patient has cancer or a neurological disorder. In yet another embodiment, the patient (e.g., a human patient) is infected with a retrovirus, such as HTLV-1. In another embodiment, the patient has a disorder or condition caused by the HTVL-1, such as a myelopathy, e.g., tropical spastic paresis. In one embodiment, administration of the dsRNA targeting XBP-1 alleviates or relieves the severity of at least one symptom of the XBP-1 mediated disorder in the patient.

In another embodiment, the invention provides a vector for inhibiting the expression of an XBP-1 gene in a cell. In one embodiment, the vector includes at least one regulatory sequence operably linked to a nucleotide sequence that encodes at least one strand of one of a dsRNA featured in the invention.

In another embodiment, the invention provides a cell containing a vector for inhibiting the expression of an XBP-1 gene in a cell. The vector includes a regulatory sequence operably linked to a nucleotide sequence that encodes at least one strand of one of the dsRNA featured in the invention.

In a further embodiment, the invention provides a composition containing an XBP-1 dsRNA, in combination with a second dsRNA targeting a second gene involved in a pathological disease, and useful for treating the disease, e.g., diabetes or cardiovascular disease.

BRIEF DESCRIPTION OF THE DRAWINGS

FIG. 2 is the sequence of human XBP-1 mRNA as recorded at RefSeq No. NM_005080.2 (GI Ref. No. 14110394) (SEQ ID NO:4331).

FIG. 3 is the sequence of mouse XBP-1 mRNA as recorded at RefSeq No. NM_013842.2 (GI Ref. No. 13775155) (SEQ ID NO:4332). The underlined sequence is the target of siRNA AD18038.

FIG. 4 is the sequence of rat XBP-1 mRNA as recorded at RefSeq No. NM_001004210.1 (GI Ref. No. 51948391) (SEQ ID NO:4333).

FIG. 5 is the sequence of rhesus XBP-1 as recorded at RefSeq No. XM_001103095.1 (GI Ref. No. 109093732) (SEQ ID NO:4334).

DETAILED DESCRIPTION OF THE INVENTION

Figure 1A:
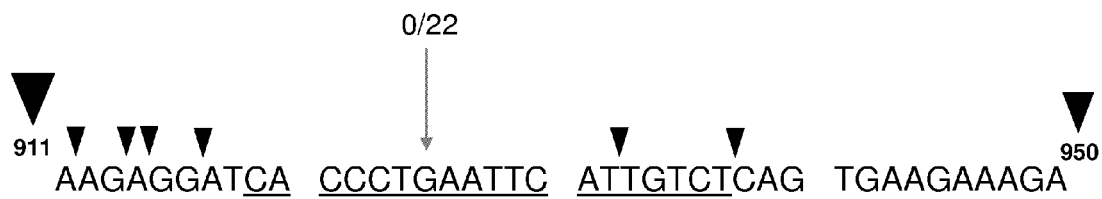
FIGS. 1A and 1B represent the sequence of the XBP-1 5' RACE product around the target sequence of the siRNA AD18038. The intended cleavage site of the siRNA is indicated by a vertical arrow above the sequence. The cleavage sites due to degradation of the 5' RACE product in mice are indicated by arrowheads above the sequence. "0/22" is the number of cleavage events what were observed at the expected XBP-1 siRNA cleavage site in the sample group of negative control mice, which were treated with siRNA LNP01-1955 or PBS (FIG. 1A; SEQ ID NO:4329). "26/34" is the number of cleavage events that were observed at the expected siRNA cleavage site in the sample group of mice treated with the XBP-1 siRNA AD18038 (FIG. 1B; SEQ ID NO:4330). The underlined sequence is the target of the XBP-1 siRNA AD18038.

The invention provides dsRNAs and methods of using the dsRNAs for inhibiting the expression of an XBP-1 gene in a cell or a mammal where the dsRNA targets the XBP-1 gene. The invention also provides compositions and methods for treating pathological conditions and diseases, such as a metabolic disease or a cardiovascular disease, in a mammal caused by the expression of the XBP-1 gene. dsRNA directs the sequence-specific degradation of mRNA through a process known as RNA interference (RNAi).

The dsRNAs of the compositions featured herein include an RNA strand (the antisense strand) having a region which is less than 30 nucleotides in length, generally 19-24 nucleotides in length, and is substantially complementary to at least part of an mRNA transcript of the XBP-1 gene. The use of these dsRNAs enables the targeted degradation of mRNAs of genes that are implicated in replication and or maintenance of cancer cells in mammals. Very low dosages of XBP-1 dsRNAs in particular can specifically and efficiently mediate RNAi, resulting in significant inhibition of expression of the XBP-1 gene. The methods and compositions containing the XBP-1 dsRNA are useful for treating pathological processes mediated by XBP-1 expression, e.g., a metabolic disease or cardiovascular disease.

The following detailed description discloses how to make and use the compositions containing dsRNAs to inhibit the expression of the XBP-1 gene, as well as compositions and methods for treating diseases and disorders caused by the expression of these genes, such as leukemia. The pharmaceutical compositions featured in the invention include a dsRNA having an antisense strand comprising a region of complementarity which is less than 30 nucleotides in length, generally 19-24 nucleotides in length, and is substantially complementary to at least part of an RNA transcript of the XBP-1 gene, together with a pharmaceutically acceptable carrier. The compositions featured in the invention also include a dsRNA having an antisense strand having a region of complementarity which is less than 30 nucleotides in length, generally 19-24 nucleotides in length, and is substantially complementary to at least part of an RNA transcript of the XBP-1 gene.

Accordingly, in some aspects, pharmaceutical compositions containing the XBP-1 dsRNA and a pharmaceutically acceptable carrier, methods of using the compositions to inhibit expression of the XBP-1 gene, and methods of using the pharmaceutical compositions to treat diseases caused by expression of the XBP-1 gene are featured in the invention.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, thymidine and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the invention by a nucleotide containing, for example, inosine. In another example, adenine and cytosine anywhere in the oligonucleotide can be replaced with guanine and uracil, respectively to form G:U Wobble base pairing with the target mRNA. Sequences containing such replacement moieties are suitable for the compositions and methods featured the invention.

As used herein, "XBP-1" refers to X-Box Protein 1, which is also known as Tax-responsive element-binding protein 5, TREB5, and XBP2. XBP-1 sequence can be found as NCBI GeneID:7494 and RefSeq ID number:NM_005080 (human) (FIG. 1) and NM_013842 (mouse, FIG. 2). A dsRNA featured in the invention can target a specific XBP-1 isoform, e.g., the spliced form (XBP-1S) or the unspliced form (XBP-1U), or a dsRNA featured in the invention can target both isoforms by binding to a common region of the mRNA transcript.

As used herein, "target sequence" refers to a contiguous portion of the nucleotide sequence of an mRNA molecule formed during the transcription of the XBP-1 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding XBP-1). For example, a polynucleotide is complementary to at least a part of an XBP-1 mRNA if the sequence is substantially complementary to a non-interrupted portion of an mRNA encoding XBP-1.

The term "double-stranded RNA" or "dsRNA," as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop." Where the two strands are connected covalently by means other than an uninterrupted chain of nucleotides between the 3'-end of one strand and the 5' end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. For example, a dsRNA can have a dinucleotide overhang at the 3' end at one or both of the sense or antisense strands, such as a dTdT (deoxythymidine-deoxythymidine) or a dTsdT (deoxythymidine-(thiophosphate linker)-deoxythymidine) dinucleotide overhang at one or both of the 3' ends of the sense or antisense strands.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). "Substantially identical," as used herein, means there is a very high degree of homology (e.g., 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. The dsRNA is typically 100% complementary to the target RNA, but in some embodiments, the dsRNA may contain single or multiple base-pair random mismatches between the RNA and the target gene.

As used herein, the term "SNALP" refers to a stable nucleic acid-lipid particle. A SNALP represents a vesicle of lipids coating a reduced aqueous interior comprising a nucleic acid such as an iRNA agent or a plasmid from which an iRNA agent is transcribed. SNALPs are described, e.g., in U.S. Patent Application Publication Nos. 20060240093, 20070135372, and U.S. Ser. No. 61/045,228 filed Apr. 15, 2008. These applications are hereby incorporated by reference.

"Introducing into a cell," when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. U.S. Pat. Nos. 5,032,401 and 5,607,677, and U.S. Publication No. 2005/0281781 are hereby incorporated by reference in their entirety. In vitro introduction into a cell includes methods known in the art such as electroporation and lipofection.

The terms "silence," "inhibit the expression of," "down-regulate the expression of," "suppress the expression of," and the like, in as far as they refer to the XBP-1 gene, herein refer to the at least partial suppression of the expression of the XBP-1 gene, as manifested by a reduction of the amount of XBP-1 mRNA which may be isolated from a first cell or group of cells in which the XBP-1 gene is transcribed and which has or have been treated such that the expression of the XBP-1 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to XBP-1 gene expression, e.g., the amount of protein encoded by the XBP-1 gene which is secreted by a cell, or the number of cells displaying a certain phenotype, e.g., apoptosis. In principle, XBP-1 gene silencing may be determined in any cell expressing XBP-1, either constitutively or by genomic engineering, and by any appropriate assay. However, when a reference is needed in order to determine whether a given dsRNA inhibits the expression of the XBP-1 gene by a certain degree and therefore is encompassed by the instant invention, the assay provided in the Examples below shall serve as such reference.

For example, in certain instances, expression of the XBP-1 gene is suppressed by at least about 20%, 25%, 30%, 35%, 40%, 45%, or 50% by administration of the double-stranded oligonucleotide featured in the invention. In some embodiments, the XBP-1 gene is suppressed by at least about 60%, 70%, or 80% by administration of the double-stranded oligonucleotide featured in the invention. In some embodiments, the XBP-1 gene is suppressed by at least about 85%, 90%, or 95% by administration of the double-stranded oligonucleotide featured in the invention.

As used herein in the context of XBP-1 expression, the terms "treat," "treatment," and the like, refer to relief from or alleviation of pathological processes mediated by XBP-1 expression. In the context of the present invention insofar as it relates to any of the other conditions recited herein below (other than pathological processes mediated by XBP-1 expression), the terms "treat," "treatment," and the like mean to relieve or alleviate at least one symptom associated with such condition, or to slow or reverse the progression of such condition, such as the slowing and progression of hepatic carcinoma.

As used herein, the phrases "therapeutically effective amount" and "prophylactically effective amount" refer to an amount that provides a therapeutic benefit in the treatment, prevention, or management of pathological processes mediated by XBP-1 expression or an overt symptom of pathological processes mediated by XBP-1 expression. The specific amount that is therapeutically effective can be readily determined by an ordinary medical practitioner, and may vary depending on factors known in the art, such as, e.g., the type of pathological processes mediated by XBP-1 expression, the patient's history and age, the stage of pathological processes mediated by XBP-1 expression, and the administration of other anti-pathological processes mediated by XBP-1 expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-Stranded Ribonucleic Acid (dsRNA)

In one embodiment, the invention provides double-stranded ribonucleic acid (dsRNA) molecules for inhibiting the expression of an XBP-1 gene in a cell or mammal, e.g., in a human having a metabolic disease, such as diabetes, or cardiovascular disease, where the dsRNA includes an antisense strand having a region of complementarity which is complementary to at least a part of an mRNA formed in the expression of the XBP-1 gene, and where the region of complementarity is less than 30 nucleotides in length, generally 19-24 nucleotides in length, and where said dsRNA, upon contact with a cell expressing said XBP-1 gene, inhibits the expression of said XBP-1 gene by at least 30% as assayed by, for example, a PCR or branched DNA (bDNA) based method. The dsRNA includes two RNA strands that are sufficiently complementary to hybridize to form a duplex structure. One strand of the dsRNA (the antisense strand) includes a region of complementarity that is substantially complementary, and generally fully complementary, to a target sequence, derived from the sequence of an mRNA formed during the expression of the XBP-1 gene, the other strand (the sense strand) includes a region that is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. In some embodiments, the dsRNA is between 10 and 15 nucleotides in length, and in other embodiments, the dsRNA is between 25 and 30 nucleotides in length. The dsRNA featured in the invention may further include one or more single-stranded nucleotide overhangs.

The dsRNA can be synthesized by standard methods known in the art as further discussed below, e.g., by use of an automated DNA synthesizer, such as are commercially available from, for example, Biosearch, Applied Biosystems, Inc. In one embodiment, the XBP-1 gene is the human XBP-1 gene. In specific embodiments, the first sequence is selected from the group consisting of the sense sequences of Tables 2, 4, 8, 9, 11 and 12, and the second sequence is selected from the group consisting of the antisense sequences of Tables 2, 4, 8, 9, 11 and 12. Alternative antisense agents that target elsewhere in the target sequence provided in Tables 2, 4, 8, 9, 11 and 12 can readily be determined using the target sequence and the flanking XBP-1 sequence.

The dsRNA will include at least two nucleotide sequence selected from the groups of sequences provided in Tables 2, 4, 8, 9, 11 and 12. One of the two sequences is complementary to the other of the two sequences, with one of the sequences being substantially complementary to a sequence of an mRNA generated in the expression of the XBP-1 gene. As such, the dsRNA will include two oligonucleotides, where one oligonucleotide is described as the sense strand in Tables 2, 4, 8, 9, 11 and 12 and the second oligonucleotide is described as the antisense strand in Tables 2, 4, 8, 9, 11 and 12.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 2, 4, 8, 9, 11 and 12, the dsRNAs featured in the invention can include at least one strand of a length of minimally 21 nt. It can be reasonably expected that shorter dsRNAs having one of the sequences of Tables 2, 4, 8, 9, 11 and 12 minus only a few nucleotides on one or both ends may be similarly effective as compared to the dsRNAs described above. Hence, dsRNAs having a partial sequence of at least 15, 16, 17, 18, 19, 20, or more contiguous nucleotides from one of the sequences of Tables 2, 4, 8, 9, 11 and 12, and differing in their ability to inhibit the expression of the XBP-1 gene in a FACS assay as described herein below by not more than 5, 10, 15, 20, 25, or 30% inhibition from a dsRNA comprising the full sequence, are contemplated by the invention. Further, dsRNAs that cleave within a desired XBP-1 target sequence can readily be made using the corresponding XBP-1 antisense sequence and a complementary sense sequence.

In addition, the dsRNAs provided in 2, 4, 8, 9, 11 and 12 identify a site in the XBP-1 mRNA that is susceptible to RNAi based cleavage. As such the present invention further features dsRNAs that target within the sequence targeted by one of the agents of the present invention. As used herein a second dsRNA is said to target within the sequence of a first dsRNA if the second dsRNA cleaves the message anywhere within the mRNA that is complementary to the antisense strand of the first dsRNA. Such a second dsRNA will generally consist of at least 15 contiguous nucleotides from one of the sequences provided in Tables 2, 4, 8, 9, 11 and 12 coupled to additional nucleotide sequences taken from the region contiguous to the selected sequence in the XBP-1 gene. For example, the last 15 nucleotides of SEQ ID NO:1 combined with the next six nucleotides from the target XBP-1 gene produces a single strand agent of 21 nucleotides that is based on one of the sequences provided in Tables 2, 4, 8, 9, 11 and 12.

The dsRNA featured in the invention can contain one or more mismatches to the target sequence. In one embodiment, the dsRNA featured the invention contains no more than 3 mismatches. If the antisense strand of the dsRNA contains mismatches to a target sequence, it the area of mismatch is typically not located in the center of the region of complementarity. If the antisense strand of the dsRNA contains mismatches to the target sequence, the mismatch is typically restricted to 5 nucleotides from either end, for example 5, 4, 3, 2, or 1 nucleotide from either the 5' or 3' end of the region of complementarity. For example, for a 23 nucleotide dsRNA strand which is complementary to a region of the XBP-1 gene, the dsRNA generally does not contain any mismatch within the central 13 nucleotides. The methods described within the invention can be used to determine whether a dsRNA containing a mismatch to a target sequence is effective in inhibiting the expression of the XBP-1 gene. Consideration of the efficacy of dsRNAs with mismatches in inhibiting expression of the XBP-1 gene is important, especially if the particular region of complementarity in the XBP-1 gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has a 1-10 nucleotide overhang at the 3' end and/or the 5' end. In one embodiment, the sense strand of the dsRNA has a 1-10 nucleotide overhang at the 3' end and/or the 5' end. In another embodiment, one or more of the nucleotides in the overhang is replaced with a nucleoside thiophosphate.

In yet another embodiment, the dsRNA is chemically modified to enhance stability. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other suitable dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most embodiments featured in the invention include dsRNAs with phosphorothioate backbones and oligonucleosides with heteroatom backbones, and in particular —CH$_2$—NH—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —N(CH$_3$)—CH$_2$—CH$_2$— [wherein the native phosphodiester backbone is represented as —O—P—O—CH$_2$—] of the above-referenced U.S. Pat. No. 5,489,677, and the amide backbones of the above-referenced U.S. Pat. No. 5,602,240. In some embodiments, the dsRNAs featured herein have morpholino backbone structures of the above-referenced U.S. Pat. No. 5,034,506.

Modified dsRNAs may also contain one or more substituted sugar moieties. The dsRNAs featured herein can one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Typical modifications are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. In other embodiments, dsRNAs include one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Other typical modification include 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

Other modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are typical base substitutions, particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs featured in the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584;

5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded dsRNAs

In another aspect, XBP-1 specific dsRNA molecules are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In one embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., Curr. Topics Micro. Immunol. (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., Science (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the dsRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. In one embodiment, the dsRNA featured in the invention is expressed as two separate, complementary single-stranded RNA molecules from a recombinant AAV vector having, for example, either the U6 or H1 RNA promoters, or the cytomegalovirus (CMV) promoter.

A suitable AV vector for expressing the dsRNA featured in the invention, a method for constructing the recombinant AV vector, and a method for delivering the vector into target cells, are described in Xia H et al. (2002), *Nat. Biotech.* 20: 1006-1010.

Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The promoter driving dsRNA expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single XBP-1 gene or multiple XBP-1 genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The XBP-1 specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of the XBP-1 gene, such as pathological processes mediated by XBP-1 expression. Such pharmaceutical compositions are formulated based on the mode of delivery. One example is compositions that are formulated for systemic administration via parenteral delivery.

The pharmaceutical compositions featured herein are administered in dosages sufficient to inhibit expression of the XBP-1 genes. In general, a suitable dose of total dsRNA will be in the range of 0.01 to 200.0 milligrams per kilogram body weight of the recipient per day, generally in the range of 0.02 to 50 mg per kilogram body weight per day. For example, the dsRNA can be administered at 0.01 mg/kg, 0.1 mg/kg, 0.05 mg/kg, 0.5 mg/kg, 1 mg/kg, 2 mg/kg, 3 mg/kg, 5 mg/kg, 10 mg/kg, 20 mg/kg, 30 mg/kg, 40 mg/kg, or 50 mg/kg per single dose. The pharmaceutical composition may be administered once daily or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by XBP-1 expression. Such models are used for in vivo testing of dsRNA, as well as for determining a therapeutically effective dose.

The present invention also includes pharmaceutical compositions and formulations which include the dsRNA compounds featured in the invention. The pharmaceutical compositions of the present invention may be administered in a number of ways depending upon whether local or systemic treatment is desired and upon the area to be treated. Administration may be topical (e.g., by a transdermal patch), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; subdermal, e.g., via an implanted device; or intracranial, e.g., by intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). DsRNAs featured in the invention may be encapsulated within liposomes or may form complexes thereto, in particular to cationic liposomes. Alternatively, dsRNAs may be complexed to lipids, in particular to cationic lipids. Suitable fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. patent application Ser. No. 09/315, 298 filed on May 20, 1999 which is incorporated herein by reference in its entirety.

In one embodiment, a dsRNA featured in the invention is fully encapsulated in the lipid formulation (e.g., to form a SPLP, pSPLP, SNALP, or other nucleic acid-lipid particle). As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-

Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA), or a mixture thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{i2}$), a PEG-dimyristyloxypropyl ($C_{i4}$), a PEG-dipalmityloxypropyl ($C_{i6}$), or a PEG-distearyloxypropyl ($C_{i8}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (Formula 1), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/mL; Cholesterol, 25 mg/mL, PEG-Ceramide C16, 100 mg/mL. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

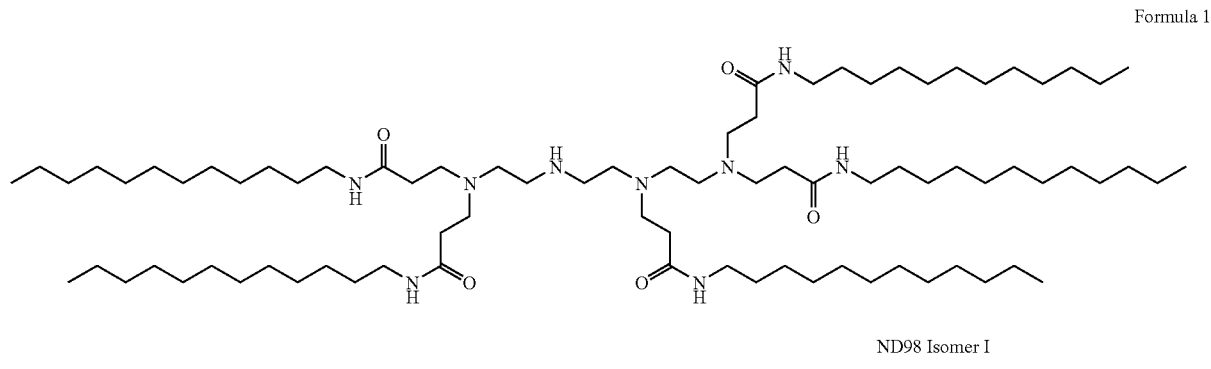

Formula 1

ND98 Isomer I

LNP01 formulations are described, e.g., in International Application Publication No. WO 2008/042973, which is hereby incorporated by reference.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm.

The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application. Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

The compositions of the present invention may be prepared and formulated as emulsions. Emulsions are typically heterogenous systems of one liquid dispersed in another in the form of droplets usually exceeding 0.1.mu·m in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome.™. I (glyceryl dilaurate/cholesterol/po-lyoxyethylene-10-stearyl ether) and Novasome.™. II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $GM_1$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $GM_1$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $GM_1$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an dsRNA RNA. U.S. Pat. No. 5,665,710 to Rahman et al. describes certain methods of encapsulating oligodeoxynucleotides in liposomes. WO 97/04787 to Love et al. discloses liposomes comprising dsRNA dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly dsRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclicureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In some embodiments, pharmaceutical compositions featured in the invention include (a) one or more dsRNA compounds and (b) one or more other chemotherapeutic agents which function by a non-RNAi mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed.

1987, pp. 1206-1228, Berkow et al., eds., Rahway, N.J. When used with the dsRNAs featured in the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions featured in the invention. See, generally, The Merck Manual of Diagnosis and Therapy, 15th Ed., Berkow et al., eds., 1987, Rahway, N.J., pages 2499-2506 and 46-49, respectively). Other non-RNAi chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are typical.

The data obtained from cell culture assays and animal studies can be used in formulation a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the dsRNAs featured in the invention can be administered in combination with other known agents effective in treatment of pathological processes mediated by XBP-1 expression. In any event, the administering physician can adjust the amount and timing of dsRNA administration on the basis of results observed using standard measures of efficacy known in the art or described herein.

Methods for Treating Diseases Caused by Expression of the XBP-1 Gene

The invention relates in particular to the use of a dsRNA targeting XBP-1 and compositions containing at least one such dsRNA, for the treatment of an XBP-1-mediated disorder or disease. For example, a dsRNA targeting an XBP-1 gene can be useful for the treatment of a metabolic disease, such as Type II diabetes and metabolic syndrome, or a cardiovascular disease. "Metabolic syndrome" (also called metabolic syndrome X, X syndrome, insulin resistance syndrome, Reaven's syndrome, and CHAOS) is characterized by a group of metabolic risk factors including: abdominal obesity (excessive fat tissue in and around the abdomen), atherogenic dyslipidemia (blood fat disorders (including high triglycerides, low HDL cholesterol and high LDL cholesterol) that foster plaque build-up in artery walls), elevated blood pressure, insulin resistance or glucose intolerance (due to the body's inability to properly use insulin or blood sugar), a prothrombotic state (e.g., high fibrinogen or plasminogen activator inhibitor-1 in the blood), and a proinflammatory state (e.g., elevated C-reactive protein in the blood). People with metabolic syndrome are at increased risk of coronary heart disease and other diseases related to plaque buildups in artery walls (e.g., stroke and peripheral vascular disease), and Type II diabetes. A "cardiovascular disease," as used herein is a disorder that affects the heart or blood vessels, such as atherosclerosis, coronary artery disease, high blood pressure, congenital heart disease, aneurysm, a heart valve disease, a heart infection, or cardiomyopathy. Other metabolic diseases suitable for treatment with a dsRNA targeting XBP-1 include obesity and insulin resistance.

A dsRNA targeting XBP-1 is also useful for the treatment of a dyslipidemia, such as a hyperlidipemia (e.g., hypercholesterolemia), or a disorder associated with a dyslipidemia, such as atherosclerosis. A "hyperlipidemia" refers to elevated lipid levels in the blood (e.g., in plasma), such as elevated levels of one or more of cholesterol, LDL (low density lipoprotein), VLDL (very low density lipoprotein), triglycerides, or chylomicrons.

A dsRNA targeting XBP-1 is also useful for the treatment of liver disorders, such as a nonalcoholic fatty liver disease (NAFLD), which is a fatty inflammation of the liver not due to excessive use of alcohol, or cirrhosis. For example, a dsRNA targeting XBP-1 can be used to treat non-alcoholic steatohepatitis (NASH), which is one of the most extreme forms of NAFLD, and which is regarded as a major cause of cirrhosis of the liver of unknown cause.

A dsRNA targeting XBP-1 can also be useful for the treatment of cancer, such as a leukemia, e.g., ATLL. A dsRNA targeting XBP-1 can also be used to treat a myelopathy, e.g., tropical spastic paresis (TSP). TSP is a chronic and progressive disease of the nervous system that typically affects adults living in equatorial areas of the world and can cause progressive weakness, stiff muscles, muscle spasms, sensory disturbance, and sphincter dysfunction. A "myelopathy," as used herein, is a neurological deficit related to the spinal cord.

A composition containing a dsRNA targeting XBP-1 may also be used to treat other tumors and cancers, such as breast cancer, lung cancer, head and neck cancer, brain cancer, abdominal cancer, colon cancer, colorectal cancer, esophagus cancer, gastrointestinal cancer, glioma, tongue cancer, neuroblastoma, osteosarcoma, ovarian cancer, pancreatic cancer, prostate cancer, retinoblastoma, Wilm's tumor, multiple myeloma and for the treatment of skin cancer, like melanoma, for the treatment of lymphomas and blood cancer.

Owing to the inhibitory effects on XBP-1 expression, a composition according to the invention or a pharmaceutical composition prepared therefrom can enhance the quality of life.

The invention further relates to the use of a dsRNA or a pharmaceutical composition thereof, e.g., for treating a metabolic disorder, cardiovascular disease, or an HTLV-1 mediated disorder, in combination with other pharmaceuticals and/or other therapeutic methods, e.g., with known pharmaceuticals and/or known therapeutic methods, such as, for example, those which are currently employed for treating these disorder. In one example, administration of a dsRNA targeting XBP-1 can be accompanied by a exercise regimen or by dietary restrictions. A dsRNA featured in the invention can also be administered with a drug or combination of drugs for managing Type II diabetes, e.g., a sulfonylurea, a biguanide, an alpha-glucosidase inhibitor, a thiazolidinedione (e.g., rosiglitazone or pioglitazone), a meglitinide, a D-phenylalanine derivative, an amylin synthetic derivatives, an incretin mimetic, metformin, or an insulin. Exemplary insulins include regular insulins (Humulin®, Novolin®), insulin lispro (Humalog®), insulin aspart (Novolog®), insulin glulisine (Apidra®), prompt insulin zinc (Semilente®, slightly slower acting), inhaled insulin (Exubera®), intermediate-acting insulins, isophane insulin, neutral protamine Hagedorn (NPH), insulin zinc (Lente®), extended insulin zinc insulin (Ultralente®), insulin glargine (Lantus®), and insulin detemir (Levemir®).

In another example, a composition containing a dsRNA targeting XBP-1 is administered in combination with a lipid-lowering drug, such as a statin, e.g., atorvastatin (Lipitor®) or simvastatin (Mevacor®); ezetimibe (Zetia®); a bile-acid sequestrant, such as Questran®; a fibrate, such as gemfibrozil (Lopid®) or fenofibrate (Tricor); or a compound that raises HDL levels, such as nicotinic acid (Niacin).

A dsRNA targeting XBP-1 can also be provided in combination with a vitamin, such as vitamin E or vitamin C, e.g., for treatment of a liver disorder, such as NAFLD or NASH.

In another example, a composition containing a dsRNA targeting XBP-1 is administered in combination with an anti-viral drug, such as zidovudine, ribivirin, vidarabine, acyclovir and ganciclovir, or an anti-inflammatory drug, such as a non-steroidal anti-inflammatory drugs or corticosteroid. See, generally, The Merck Manual of Diagnosis and Therapy, 15th Ed., Berkow et al., eds., 1987, Rahway, N.J., pages 2499-2506 and 46-49, respectively). Administration can also be in combination with an interferon, such as interferon alpha or interferon beta; lioresal, tizanidine, or oxybutynin.

In certain embodiments, administration is with a chemotherapy agent, such as deoxycoformycin, cisplatin, cyclophosphamide, 5-fluorouracil, adriamycin, daunorubicin, tamoxifen aunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the dsRNAs featured in the invention, such chemotherapeutic agents may be used individually (e.g., deoxycoformycin and dsRNA), sequentially (e.g., antiviral and dsRNA for a period of time, followed by deoxycoformycin and dsRNA), or in combination with one or more other such agents (e.g., deoxycoformycin, antiviral and dsRNA, or deoxycoformycin, radiotherapy and dsRNA). Two or more combined compounds may be used together or sequentially.

Patients can be administered a therapeutic amount of dsRNA, such as 0.02, 0.1, 0.5 mg/kg, 1.0 mg/kg, 1.5 mg/kg, 2.0 mg/kg, or 2.5 mg/kg dsRNA. The dsRNA can be administered by intravenous infusion over a period of time, such as over a 5 minute, 10 minute, 15 minute, 20 minute, or 25 minute period. In some embodiments, the administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the dsRNA can reduce LDL levels in the blood of the patient by at least 20%, 25%, 30%, 40%, 50%, 60%, 70%, 80% or 90% or more.

Before administration of a full dose of a dsRNA targeting XBP-1, a patient can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Many XBP-1-associated diseases and disorders are hereditary. Therefore, a patient in need of a dsRNA targeting XBP-1 can be identified by taking a family history. A healthcare provider, such as a doctor, nurse, or family member, can take a family history before prescribing or administering a dsRNA. A DNA test may also be performed on the patient to identify a mutation in the target gene, before a dsRNA is administered to the patient.

Methods for Inhibiting Expression of the XBP-1 Gene

In yet another aspect, the invention provides a method for inhibiting the expression of an XBP-1 gene in a mammal. The method includes administering a composition featured in the invention to the mammal such that expression of the target XBP-1 gene is silenced.

When the organism to be treated is a mammal such as a human, the composition may be administered by any means known in the art including, but not limited to oral or parenteral routes, including intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the dsRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support is used for RNA synthesis. The modified solid support is prepared as follows:

Diethyl-2-azabutane-1,4-dicarboxylate AA

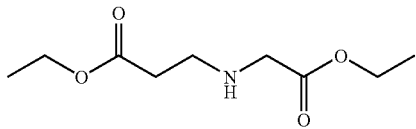

A 4.7 M aqueous solution of sodium hydroxide (50 mL) is added into a stirred, ice-cooled solution of ethyl glycinate hydrochloride (32.19 g, 0.23 mole) in water (50 mL). Then, ethyl acrylate (23.1 g, 0.23 mole) is added and the mixture stirred at room temperature until completion of the reaction is ascertained by TLC. After 19 h the solution is partitioned with dichloromethane (3×100 mL). The organic layer is dried with anhydrous sodium sulfate, filtered and evaporated. The residue is distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

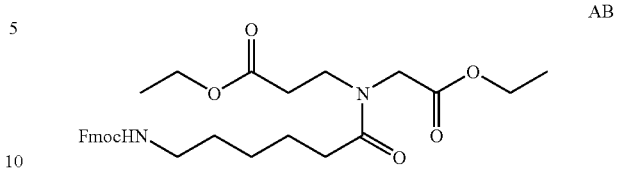

Fmoc-6-amino-hexanoic acid (9.12 g, 25.83 mmol) is dissolved in dichloromethane (50 mL) and cooled with ice. Diisopropylcarbodiimde (3.25 g, 3.99 mL, 25.83 mmol) is added to the solution at 0° C. This is followed by the addition of Diethyl-azabutane-1,4-dicarboxylate (5 g, 24.6 mmol) and dimethylamino pyridine (0.305 g, 2.5 mmol). The solution is brought to room temperature and stirred further for 6 h. Completion of the reaction is ascertained by TLC. The reaction mixture is concentrated under vacuum and ethyl acetate is added to precipitate diisopropyl urea. The suspension is filtered. The filtrate is washed with 5% aqueous hydrochloric acid, 5% sodium bicarbonate and water. The combined organic layer is dried over sodium sulfate and concentrated to give the crude product which is purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

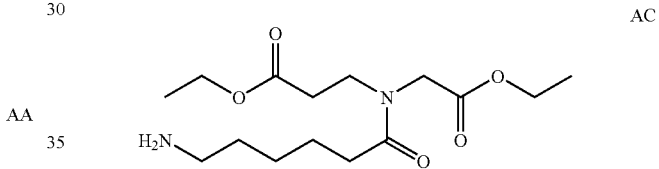

3-{Ethoxycarbonylmethyl-[6-(9H-fluoren-9-ylmethoxycarbonylamino)-hexanoyl]-amino}-propionic acid ethyl ester AB (11.5 g, 21.3 mmol) is dissolved in 20% piperidine in dimethylformamide at 0° C. The solution is continued stirring for 1 h. The reaction mixture is concentrated under vacuum, water is added to the residue, and the product is extracted with ethyl acetate. The crude product is purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

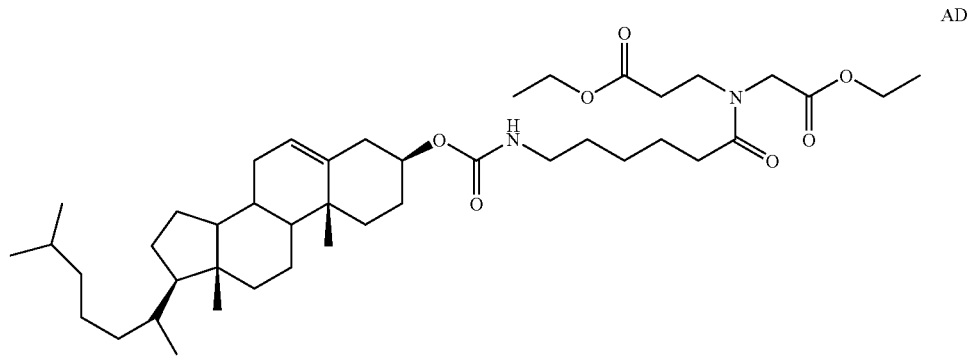

The hydrochloride salt of 3-[(6-Amino-hexanoyl)-ethoxy-carbonylmethyl-amino]-propionic acid ethyl ester AC (4.7 g, 14.8 mmol) is taken up in dichloromethane. The suspension is cooled to 0° C. on ice. Diisopropylethylamine (3.87 g, 5.2 mL, 30 mmol) is added to the suspension. To the resulting solution, cholesteryl chloroformate (6.675 g, 14.8 mmol) is added. The reaction mixture is stirred overnight. The reaction mixture is diluted with dichloromethane and washed with 10% hydrochloric acid. The product is purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a] phenanthren-3-yloxycarbonylamino]-hexanoyl}-4-oxo-pyrrolidine-3-carboxylic acid ethyl ester AE

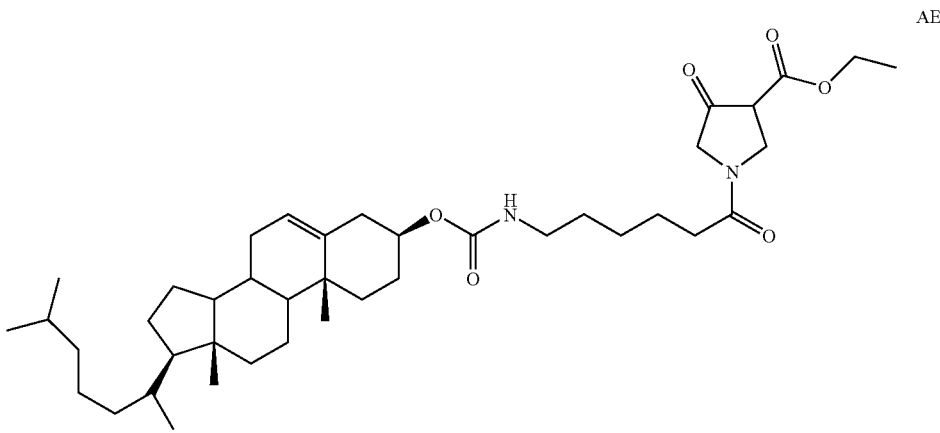

Potassium t-butoxide (1.1 g, 9.8 mmol) is slurried in 30 mL of dry toluene. The mixture is cooled to 0° C. on ice, and 5 g (6.6 mmol) of diester AD is added slowly with stirring within 20 mins. The temperature is kept below 5° C. during the addition. The stirring is continued for 30 mins at 0° C., and 1 mL of glacial acetic acid is added, immediately followed by 4 g of NaH$_2$PO$_4$.H$_2$O in 40 mL of water. The resultant mixture is extracted twice with 100 mL of dichloromethane each, and the combined organic extracts are washed twice with 10 mL of phosphate buffer each, dried, and evaporated to dryness. The residue is dissolved in 60 mL of toluene, cooled to 0° C. and extracted with three 50 mL portions of cold pH 9.5 carbonate buffer. The aqueous extracts are adjusted to pH 3 with phosphoric acid, and extracted with five 40 mL portions of chloroform which are combined, dried and evaporated to dryness. The residue is purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

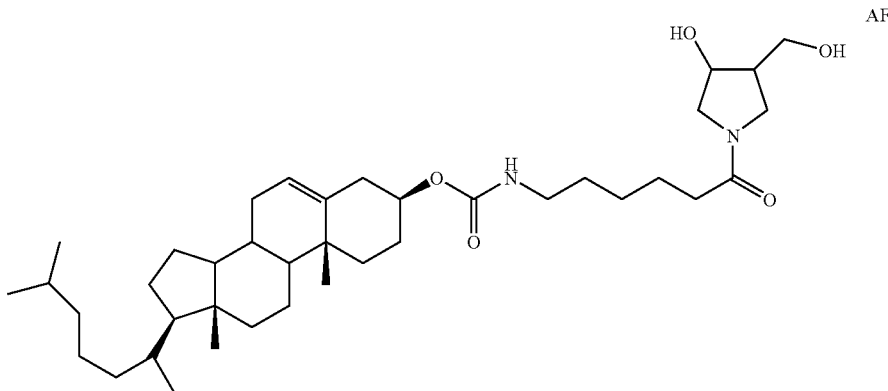

Methanol (2 mL) is added dropwise over a period of 1 h to a refluxing mixture of b-ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) is added, the mixture is extracted with ethylacetate (3×40 mL). The combined ethylacetate layer is dried over anhydrous sodium sulfate and concentrated under vacuum to yield the product which is purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

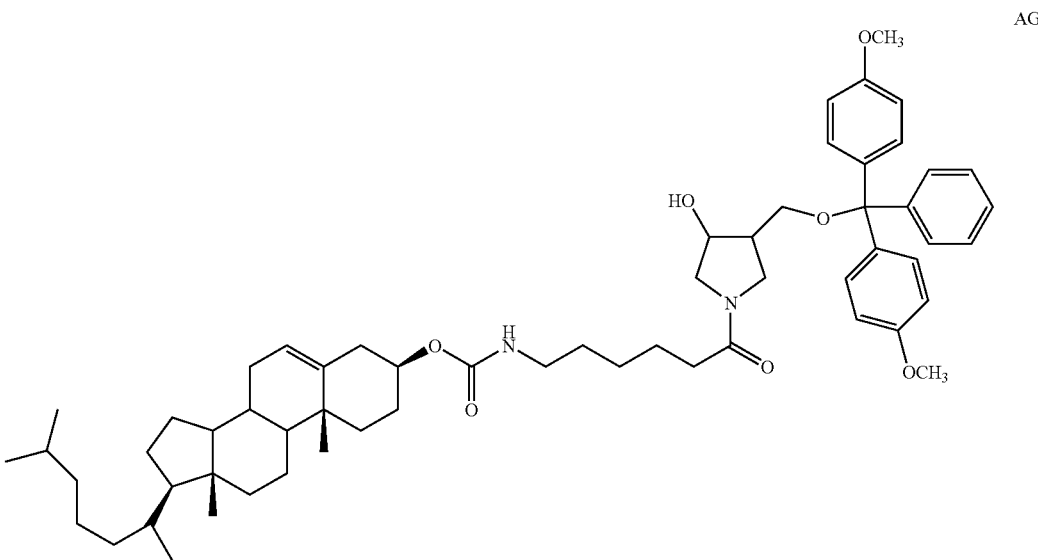

Diol AF (1.25 gm 1.994 mmol) is dried by evaporating with pyridine (2×5 mL) in vacuo. Anhydrous pyridine (10 mL) and 4,4'-dimethoxytritylchloride (0.724 g, 2.13 mmol) are added with stirring. The reaction is carried out at room temperature overnight. The reaction is quenched by the addition of methanol. The reaction mixture is concentrated under vacuum and dichloromethane (50 mL) is added to the residue. The organic layer is washed with 1M aqueous sodium bicarbonate. The organic layer is dried over anhydrous sodium sulfate, filtered and concentrated. The residual pyridine is removed by evaporating with toluene. The crude product is purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15, 16,17-tetradecahydro-1H cyclopenta[a]phenanthren-3-yloxycarbonylamino]-hexanoyl}-pyrrolidin-3-yl) ester AH

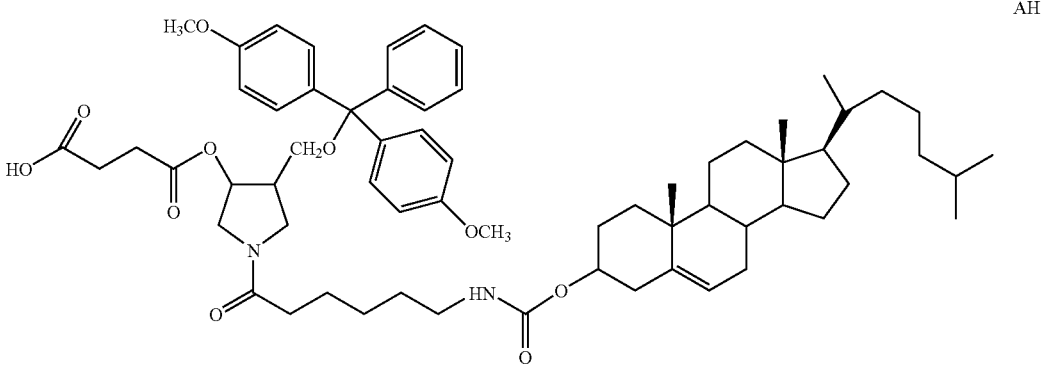

Compound AG (1.0 g, 1.05 mmol) is mixed with succinic anhydride (0.150 g, 1.5 mmol) and DMAP (0.073 g, 0.6 mmol) and dried in a vacuum at 40° C. overnight. The mixture is dissolved in anhydrous dichloroethane (3 mL), triethylamine (0.318 g, 0.440 mL, 3.15 mmol) is added and the solution is stirred at room temperature under argon atmosphere for 16 h. It is then diluted with dichloromethane (40 mL) and washed with ice cold aqueous citric acid (5 wt %, 30 mL) and water (2×20 mL). The organic phase is dried over anhydrous sodium sulfate and concentrated to dryness. The residue is used as such for the next step.

Cholesterol derivatised CPG AI

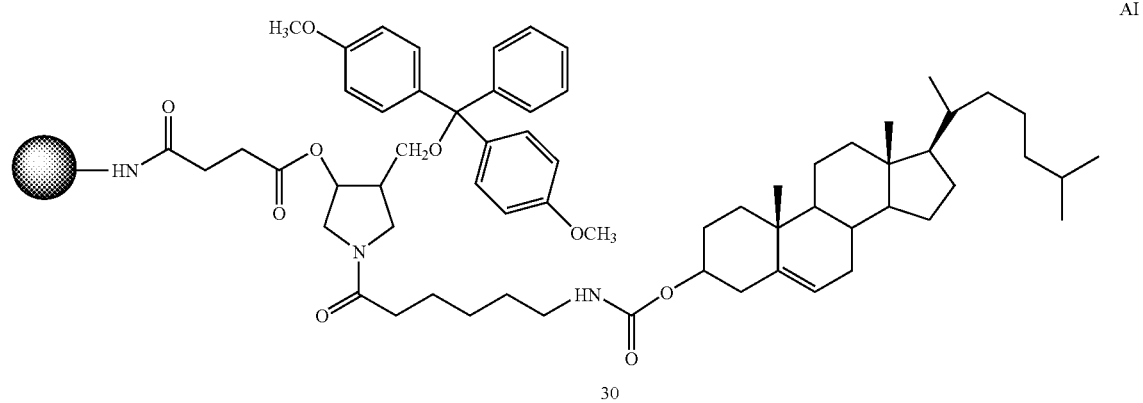

Succinate AH (0.254 g, 0.242 mmol) is dissolved in a mixture of dichloromethane/acetonitrile (3:2, 3 mL). To that solution, DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) are added successively. To the resulting solution triphenylphosphine (0.064 g, 0.242 mmol) in acetonitrile (0.6 ml) is added. The reaction mixture turns bright orange in color. The solution is agitated briefly using a wrist-action shaker (5 mins). Long chain alkyl amine-CPG (LCAA-CPG) (1.5 g, 61 mM) is added. The suspension is agitated for 2 h. The CPG is filtered through a sintered funnel and washed with acetonitrile, dichloromethane and ether successively. Unreacted amino groups are masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") is performed as described in WO 2004/065601, except that, for the cholesteryl derivative, the oxidation step is performed using the Beaucage reagent in order to introduce a phosphorothioate linkage at the 5'-end of the nucleic acid oligomer.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A | Adenosine |
| C | Cytidine |
| G | Guanosine |
| T | thymidine |
| U | uridine |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| N | any nucleotide (G, A, C, U, or T) |
| a | 2'-O-methyladenosine |
| c | 2'-O-methylcytidine |
| g | 2'-O-methylguanosine |
| u | 2'-O-methyluridine |
| sT | phosphorothioate linkage |

Example 2

Synthesis of XBP-1 dsRNAs

XBP-1 sequences were synthesized on MerMade 192 synthesizer at 1 µmol scale.

For all the sequences in Table 2, 'endolight' chemistry was applied as shown below and in Table 4.

All pyrimidines (cytosine and uridine) in the sense strand were replaced with corresponding 2'-O-Methyl bases (2' O-Methyl C and 2'-O-Methyl U)

In the antisense strand, pyrimidines adjacent to (towards 5' position) ribo A nucleoside were replaced with their corresponding 2-O-Methyl nucleosides A two base dTsdT extension at 3' end of both sense and anti sense sequences was introduced The sequence file was converted to a text file to make it compatible for loading in the MerMade 192 synthesis software Solid supported oligonucleotide synthesis using phosphoramidite chemistry was performed to synthesize the XBP-1 sequences.

TABLE 2

Exemplary XBP-1 dsRNAs

| Oligo Name | SEQ ID NO: | sense (5'-3') | SEQ ID NO: | antisense (5'-3') |
|---|---|---|---|---|
| NM_001004210_1128-1146 | 2127 | CCCAGCUGAUUAGUGUCUA | 2128 | UAGACACUAAUCAGCUGGG |
| NM_001004210_1129-1147 | 2129 | CCAGCUGAUUAGUGUCUAA | 2130 | UUAGACACUAAUCAGCUGG |
| NM_001004210_677-695 | 2131 | CUCCCAGAGGUCUACCCAG | 2132 | CUGGGUAGACCUCUGGGAG |
| NM_001004210_893-911 | 2133 | GAUCACCCUGAAUUCAUUG | 2134 | CAAUGAAUUCAGGGUGAUC |
| NM_001004210_895-913 | 2135 | UCACCCUGAAUUCAUUGUC | 2136 | GACAAUGAAUUCAGGGUGA |
| NM_001004210_1127-1145 | 2137 | CCCCAGCUGAUUAGUGUCU | 2138 | AGACACUAAUCAGCUGGGG |
| NM_001004210_894-912 | 2139 | AUCACCCUGAAUUCAUUGU | 2140 | ACAAUGAAUUCAGGGUGAU |
| NM_001004210_1760-1778 | 2141 | CAUUUAUUUAAAACUACCC | 2142 | GGGUAGUUUUAAAUAAAUG |
| NM_001004210_215-233 | 2143 | ACUGAAAAACAGAGUAGCA | 2144 | UGCUACUCUGUUUUUCAGU |
| NM_001004210_1759-1777 | 2145 | CCAUUUAUUUAAAACUACC | 2146 | GGUAGUUUUAAAUAAAUGG |
| NM_001004210_367-385 | 2147 | UUGAGAACCAGGAGUUAAG | 2148 | CUUAACUCCUGGUUCUCAA |
| NM_001004210_896-914 | 2149 | CACCCUGAAUUCAUUGUCU | 2150 | AGACAAUGAAUUCAGGGUG |
| NM_001004210_214-232 | 2151 | AACUGAAAAACAGAGUAGC | 2152 | GCUACUCUGUUUUUCAGUU |
| NM_001004210_216-234 | 2153 | CUGAAAAACAGAGUAGCAG | 2154 | CUGCUACUCUGUUUUUCAG |
| XM_001103095_387-405 | 1 | AGAAAAUCAGCUUUUACGA | 2 | UCGUAAAAGCUGAUUUUCU |
| XM_001103095_1151-1169 | 3 | UCCCCAGCUGAUUAGUGUC | 4 | GACACUAAUCAGCUGGGGA |
| XM_001103095_1466-1484 | 5 | UACUUAUUAUGUAAGGGUC | 6 | GACCCUUACAUAAUAAGUA |
| XM_001103095_1435-1453 | 7 | UAUCUUAAAAGGGUGGUAG | 8 | CUACCACCCUUUUAAGAUA |
| XM_001103095_577-595 | 9 | CCAUGGAUUCUGGCGGUAU | 10 | AUACCGCCAGAAUCCAUGG |
| XM_001103095_790-808 | 11 | UUAAUGAACUAAUUCGUUU | 12 | AAACGAAUUAGUUCAUUAA |
| XM_001103095_1479-1497 | 13 | AGGGUCAUUAGACAAAUGU | 14 | ACAUUUGUCUAAUGACCCU |
| XM_001103095_794-812 | 15 | UGAACUAAUUCGUUUUGAC | 16 | GUCAAAACGAAUUAGUUCA |
| XM_001103095_1150-1168 | 23 | UUCCCCAGCUGAUUAGUGU | 24 | ACACUAAUCAGCUGGGGAA |
| XM_001103095_1473-1491 | 25 | UAUGUAAGGGUCAUUAGAC | 26 | GUCUAAUGACCCUUACAUA |

The synthesis of the sequences in Tables 2 and 4 was performed at 1 μm scale in 96-well plates. The amidite solutions were prepared at 0.1M concentration and ethyl thio tetrazole (0.6M in acetonitrile) was used as an activator.

The synthesized sequences were cleaved and deprotected in 96-well plates, using methylamine in the first step and pyradine.3HF in the second step. The crude sequences thus obtained were precipitated using an acetone:ethanol mix, and the pellets were resuspended in 0.5M sodium acetate buffer. Samples from each sequence were analyzed by LC-MS and the resulting mass data confirmed the identity of the sequences. A selected set of samples was also analyzed by IEX chromatography.

The sequences were purified on an AKTA explorer purification system using a Source Q column. A single peak corresponding to the full length sequence was collected in the eluent and was subsequently analyzed for purity by ion exchange chromatography.

The purified sequences were desalted on a Sephadex G25 column using an AKTA purifier. The desalted XBP-1 sequences were analyzed for concentration and purity. The single strands were then submitted for annealing.

TABLE 3

XBP-1 oligos with Endolight Chemistry Modifications

| Duplex Name | Species specificity and target sequence from 5' to 3' on mRNA transcript | Oligo name Sense | Oligo name Antisense |
|---|---|---|---|
| AD18027 | NM_001004210_1128-1146 | A-31668 | A-31669 |
| AD18028 | NM_001004210_1129-1147 | A-31670 | A-31671 |
| AD18029 | NM_001004210_677-695 | A-31672 | A-31673 |
| AD18030 | NM_001004210_893-911 | A-31674 | A-31675 |
| AD18031 | NM_001004210_895-913 | A-31676 | A-31677 |
| AD18032 | NM_001004210_1127-1145 | A-31678 | A-31679 |
| AD18033 | NM_001004210_894-912 | A-31680 | A-31681 |

TABLE 3-continued

XBP-1 oligos with Endolight Chemistry Modifications

| Duplex Name | Species specificity and target sequence from 5' to 3' on mRNA transcript | Oligo name Sense | Oligo name Antisense |
|---|---|---|---|
| AD18034 | NM_001004210_1760-1778 | A-31682 | A-31683 |
| AD18035 | NM_001004210_215-233 | A-31684 | A-31685 |
| AD18036 | NM_001004210_1759-1777 | A-31686 | A-31687 |
| AD18037 | NM_001004210_367-385 | A-31688 | A-31689 |
| AD18038 | NM_001004210_896-914 | A-31690 | A-31691 |
| AD18039 | NM_001004210_214-232 | A-31692 | A-31693 |
| AD18040 | NM_001004210_216-234 | A-31694 | A-31695 |
| AD18041 | XM_001103095_387-405 | A-31696 | A-31697 |
| AD18042 | XM_001103095_1151-1169 | A-31698 | A-31699 |
| AD18043 | XM_001103095_1466-1484 | A-31700 | A-31701 |
| AD18044 | XM_001103095_1435-1453 | A-31702 | A-31703 |
| AD18045 | XM_001103095_577-595 | A-31704 | A-31705 |
| AD18046 | XM_001103095_790-808 | A-31706 | A-31707 |
| AD18047 | XM_001103095_1479-1497 | A-31708 | A-31709 |
| AD18048 | XM_001103095_794-812 | A-31710 | A-31711 |
| AD18049 | XM_001103095_1150-1168 | A-31712 | A-31713 |
| AD18050 | XM_001103095_1473-1491 | A-31714 | A-31715 |

TABLE 4

XBP-1 sequences with Endolight chemistry modifications

| Oligo name Sense | SEQ ID NO: | Sense (5'-3') | Oligo name Antisense | SEQ ID NO: | Antisense (5'-3') |
|---|---|---|---|---|---|
| A-31668 | 2155 | cccAGcuGAuuAGuGucuAdTsdT | A-31669 | 2156 | uAGAcACuAAUcAGCUGGGdTsdT |
| A-31670 | 2157 | ccAGcuGAuuAGuGucuAAdTsdT | A-31671 | 2158 | UuAGAcACuAAUcAGCUGGGdTsdT |
| A-31672 | 2159 | cucccAGAGGucuAcccAGdTsdT | A-31673 | 2160 | CUGGGuAGACCUCUGGGAGdTsdT |
| A-31674 | 2161 | GAucAcccuGAAuucAuuGdTsdT | A-31675 | 2162 | cAAUGAAUUcAGGGUGAUCdTsdT |
| A-31676 | 2163 | ucAcccuGAAuucAuuGucdTsdT | A-31677 | 2164 | GAcAAUGAAUUcAGGGUGAdTsdT |
| A-31678 | 2165 | ccccAGcuGAuuAGuGucudTsdT | A-31679 | 2166 | AGAcAcuAAUcAGCUGGGGdTsdT |
| A-31680 | 2167 | AucAcccuGAAuucAuuGudTsdT | A-31681 | 2168 | ACAAUGAAUUcAGGGUGAUdTsdT |
| A-31682 | 2169 | cAuuuAuuuAAAAcuAcccdTsdT | A-31683 | 2170 | GGGuAGUUUuAAAuAAAUGdTsdT |
| A-31684 | 2171 | AcuGAAAAAcAGAGuAGcAdTsdT | A-31685 | 2172 | UGCuACUCUGUUUUUcAGUdTsdT |
| A-31686 | 2173 | ccAuuuAuuuAAAAcuAccdTsdT | A-31687 | 2174 | GGuAGUUUuAAAuAAAUGGdTsdT |
| A-31688 | 2175 | uuGAGAAccAGGAGuuAAGdTsdT | A-31689 | 2176 | CUuAACUCCUGGUUCUcAAdTsdT |
| A-31690 | 2177 | cAcccuGAAuucAuuGucudTsdT | A-31691 | 2178 | AGAcAAUGAAUUcAGGGUGAdTsdT |
| A-31692 | 2179 | AAcuGAAAAAcAGAGuAGcAdTsdT | A-31693 | 2180 | GCuACUCUGUUUUUcAGUUdTsdT |
| A-31694 | 2181 | cuGAAAAAcAGAGuAGcAGdTsdT | A-31695 | 2182 | CUGCuACUCUGUUUUUcAGUdTsdT |
| A-31696 | 2183 | AGAAAAucAGcuuuuAcGAdTsdT | A-31697 | 2184 | UCGuAAAAGCUGAUUUUCUdTsdT |
| A-31698 | 2185 | uccccAGcuGAuuAGuGucdTsdT | A-31699 | 2186 | GACACuAAUcAGCUGGGGAdTsdT |
| A-31700 | 2187 | uAcuuAuuAuGuAAGGGucdTsdT | A-31701 | 2188 | GACCCUuAcAuAAuAAGuAdTsdT |
| A-31702 | 2189 | uAucuuAAAAGGGuGGuAGdTsdT | A-31703 | 2190 | CuACcACCCUUUuAAGAuAdTsdT |
| A-31704 | 2191 | ccAuGGAuucuGGcGGuAudTsdT | A-31705 | 2192 | AuACCGCcAGAAUCcAUGGdTsdT |
| A-31706 | 2193 | uuAAuGAcuAAuucGuuudTsdT | A-31707 | 2194 | AAACGAAUuAGUUcAUuAAdTsdT |
| A-31708 | 2195 | AGGGucAuuAGAcAAAuGudTsdT | A-31709 | 2196 | AcAUUUGUCuAAUGACCCUdTsdT |
| A-31710 | 2197 | uGAAcuAAuucGuuuuGAcdTsdT | A-31711 | 2198 | GUcAAAACGAAUuAGUUcAdTsdT |
| A-31712 | 2199 | uuccccAGcuGAuuAGuGudTsdT | A-31713 | 2200 | AcACuAAUcAGCUGGGGAAdTsdT |
| A-31714 | 2201 | uAuGuAAGGGucAuuAGAcdTsdT | A-31715 | 2202 | GUCuAAUGACCCUuAcAuAdTsdT |

Example 3

Single Concentration Silencing Experiment (% Knockdown Relative to Control 12 nM)

Transfection of PC-3 cells was performed in 6-well plates: 31.25 μl (for 12.5 nM) of 200 nM duplex was added to 500 μl Opti-MEM (Invitrogen, Carlsbad, Calif.) in a well of a 6-well plate. 5 μl Lipofectamine™ RNAiMAX (Invitrogen, Carlsbad, Calif.) was added to the wells, mixed and incubated for 15 minutes. 2.0 ml complete growth media without Antibiotics containing $0.6\times10^5$ cells was added, and the mixture was mixed by rocking back and forth for 36 hours. Total RNA was isolated using Qiagen RNeasy kit (Qiagen, Valencia, Calif.) according to the manufacturer's instructions. RNA concentration was measured using a nanodrop and was diluted to 2 μg per 10 μl.

cDNA was synthesized using an ABI High-capacity cDNA reverse transcription kit (Applied Biosystems, Foster City, Calif.) and 2 μg total RNA. Quantitative PCR (qPCR) was performed using probes to amplify XBP-1 and 18S in the same reaction. All reactions were performed in triplicate.

qPCR data were analyzed using the ΔΔCt method using BlockiT™ fluorescent Oligo (Invitrogen, Carlsbad, Calif.), which does not target any human gene, as a negative control.

Generation of IC50s (for AD18028, AD18029, AD18037, AD18038, AD18040)

IC50s were generated for the 5 duplexes that showed the best silencing in the single concentration experiment.

Three sets of transfections were performed in two independent experiments using the dsRNAs shown in Table 4. In the first experiment, qPCR experiment 1 (qPCR1) and branched DNA (bDNA) results were obtained from different transfections that were done in parallel using the same cells and reagents. In the second experiment, qPCR2 results were generated from transfections that were done under the same conditions as the first experiment.

Transfection of PC-3 cells was performed in 96-well plates. The duplex concentrations tested were 50 nM, 10 nM, 5 nM, 1 nM, 0.5 nM, 0.1 nM, 0.05 nM, 0.01 nM, 0.005 nM, 0.001 nM, 0.0005 nM, and 0.0001 nM. Each dsRNA was diluted so that 5 μl would be added to 100 μl for each transfection to give the desired concentration. Transfections were performed using Opti-MEM and lipofectamine, and then cultured in EMEM.

RNA was extracted using an RNAqueous 96 kit (Applied Biosystems/Ambion, Austin, Tex.) according to manufactures instructions.

cDNA synthesis and qPCR were done as described above, and qPCR data were analyzed using the ΔΔCt method using AD-3966 as a control, which targets the Sid1 gene but has been shown to have no activity in cell based assays.

Branched DNA assays were performed using QuantiGene® 2.0 (Panomics, Fremont, Calif.). The bDNA data were analyzed by subtracting the average background from each triplicate sample, averaging the triplicate GAPDH (control probe) and TTR (experimental probe) then taking the ratio:

(experimental probe-background)/(control probe-background).

The results are shown in Tables 5 and 6.

TABLE 5

IC50 results for XBP-1 dsRNA

| oligoName | Human antisScore | Mouse antisScore | Rat antisScore | Rhesus antisScore | IC50 (nM) qPCR 1 | IC50 (nM) qPCR 2 | IC50 (nM) bDNA |
|---|---|---|---|---|---|---|---|
| AD18027 | 3 | 2 | 3 | 3 | | | |
| AD18028 | 3 | 2 | 3.2 | 3 | 0.019 | 0.011 | 0.034 |
| AD18029 | 3 | 1.2 | 2.8 | 3 | 0.03 | 0.020 | 0.026 |
| AD18030 | 3 | 2 | 1 | 2 | | | |
| AD18031 | 3 | 2 | 3 | 2.2 | | | |
| AD18032 | 3 | 2.2 | 3 | 2.8 | | | |
| AD18033 | 3 | 3 | 2.8 | 2 | | | |
| AD18034 | 2.2 | 2 | 2.8 | 2 | | | |
| AD18035 | 2.2 | 2 | 2 | 2.4 | | | |
| AD18036 | 2.2 | 2 | 2 | 2 | | | |
| AD18037 | 2.2 | 2 | 2 | 2.2 | 0.016 | 0.019 | 0.016 |
| AD18038 | 2.2 | 2 | 3 | 2.2 | 0.004 | 0.003 | 0.006 |
| AD18039 | 2.2 | 3 | 2 | 2.2 | | | |
| AD18040 | 2.2 | 2 | 2 | 2 | 0.057 | 0.052 | 0.065 |
| AD18041 | 4 | NH | NH | 3.4 | | | |
| AD18042 | 4 | NH | NH | 3.2 | | | |
| AD18043 | 4 | NH | NH | 3 | | | |
| AD18044 | 3.2 | NH | NH | 3.2 | | | |
| AD18045 | 3.2 | NH | NH | 3.2 | | | |
| AD18046 | 3.2 | NH | NH | 3.2 | | | |
| AD18047 | 3.2 | NH | NH | 3 | | | |
| AD18048 | 3.2 | NH | NH | 3 | | | |
| AD18049 | 3 | NH | NH | 3.2 | | | |
| AD18050 | 3 | NH | NH | 3.2 | | | |

NH = No homology;
bold = perfect match with hamster

TABLE 6

XBP-1 Silencing Data

| oligo Name | % knockdown relative to control (12 nM) (36 hours) | IC50 (nM) qPCR 1 | IC50 (nM) qPCR 2 | IC50 (nM) bDNA |
|---|---|---|---|---|
| AD18027 | 81.993 | | | |
| AD18028 | 90.581 | 0.019 | 0.011 | 0.034 |
| AD18029 | 97.749 | 0.03 | 0.02 | 0.026 |
| AD18030 | 82.845 | | | |
| AD18031 | 34.782 | | | |
| AD18032 | 84.893 | | | |
| AD18033 | 68.971 | | | |
| AD18034 | 42.962 | | | |
| AD18035 | 82.076 | | | |
| AD18036 | 77.26 | | | |
| AD18037 | 94.209 | 0.016 | 0.019 | 0.016 |
| AD18038 | 93.239 | 0.004 | 0.003 | 0.006 |
| AD18039 | 56.873 | | | |
| AD18040 | 93.75 | 0.057 | 0.052 | 0.065 |
| AD18041 | 84.396 | | | |
| AD18042 | ND | | | |
| AD18043 | 27.804 | | | |
| AD18044 | 64.316 | | | |
| AD18045 | 14.933 | | | |
| AD18046 | −2.101 | | | |
| AD18047 | 62.456 | | | |
| AD18048 | 74.534 | | | |
| AD18049 | 2.284 | | | |
| AD18050 | 59.621 | | | |

Example 4

Screening siRNA Sequences for Immunostimulatory Ability

Human PBMC were isolated from freshly collected buffy coats obtained from healthy donors (Research Blood Components, Inc., Boston, Mass.) by a standard Ficoll-Hypaque density centrifugation. Freshly isolated cells ($1 \times 10^5$/well) were seeded in 96-well plates and cultured in RPMI 1640 GlutaMax medium (Invitrogen) supplemented with 10% heat-inactivated fetal bovine serum and 1% antibiotic/antimycotic (Invitrogen).

siRNAs were transfected into PBMC using two separate transfection reagents: GenePorter 2 (GP2; Genlantis) and DOTAP (Roche Applied Science). The transfection reagent was first diluted in Opti-MEM (Invitrogen) for 5 minutes before mixing with an equal volume of Opti-MEM containing the siRNA. siRNA/transfection reagent complexes were incubated as specified by the reagent manufacturers' instructions and subsequently added to PBMC. siRNAs were used at a final concentration of 133 nM. The ratio of RNA to transfection reagent was 33 pmoles and 16.5 pmoles, respectively, per ul of GP2 and DOTAP.

Cytokines were detected and quantified in culture supernatants with a commercially available ELISA kit for IFN-α (BMS216INST) and TNF-α (BMS223INST); both from Bender MedSystems (Vienna, Austria).

The results are shown in Table 7.

TABLE 7

XBP-1 targeted siRNAs are not immunostimulatory for human PBMC

| | Donor A | | Donor B | |
|---|---|---|---|---|
| | pg/ml | | | |
| Transfection | IFN-α | TNF-α | IFN-α | TNF-α |
| Medium only | −36 ± 5 | −20 ± 13 | −35 ± 7 | 125 ± 48 |
| DOTAP only | −49 ± 5 | −39 ± 4 | −36 ± 11 | 110 ± 81 |
| AD-1730 | −6 ± 11 | 1859 ± 276 | 141 ± 42 | 1082 ± 181 |
| AD-1955 | −35 ± 8 | 32 ± 7 | −40 ± 10 | 59 ± 27 |
| AD-2153 | 302 ± 32 | 62 ± 46 | 531 ± 44 | 158 ± 26 |
| AD-5048 | 473 ± 63 | 1244 ± 217 | 592 ± 41 | 785 ± 121 |
| AD-18028 | −39 ± 9 | −39 ± 7 | −23 ± 16 | 162 ± 49 |
| AD-18029 | −35 ± 11 | −31 ± 8 | −26 ± 16 | 24 ± 40 |
| AD-18037 | −28 ± 20 | −24 ± 14 | 30 ± 6 | −44 ± 27 |
| AD-18038 | −24 ± 18 | −5 ± 17 | −37 ± 11 | 32 ± 56 |
| AD-18040 | −31 ± 17 | −12 ± 17 | −37 ± 8 | −43 ± 14 |

Cytokine Responses of Whole PBMC to Duplex siRNAs Targeting XBP-1

Freshly isolated PBMC from two normal donors (A and B) were transfected with test siRNAs using DOTAP and cultured for 24 hours. Subsequently, culture supernatants were collected and IFN-α and TNF-α levels measured by ELISA. AD-1730, AD-1955, and AD-2153 are sequences that bear no known homology to any human genes. AD-1730 and AD-2153 preferentially stimulate TNF-α and IFN-α, respectively. AD-5048 corresponds to a sequence that targets human Apolipoprotein B (Soutschek et al., 2004) and elicits both and IFN-α and TNF-α AD-1995 is a non-stimulatory sequence used as a negative control. The data shown are derived from a single experiment in which four replicate wells were transfected with each siRNA or were treated with either DOTAP or medium alone. Values represent the mean±standard deviation for four biological replicates.

Example 5

The Effect of XBP-1 siRNA on Hepatic Lipogenesis in Mice

Dietary carbohydrates regulate hepatic lipogenesis by controlling the expression of critical enzymes in glycolysis and lipogenic pathways. XBP-1, a regulator of the Unfolded Protein Response (UPR), is important for de novo fatty acid synthesis in the liver, a function unrelated to its role in the UPR. (Lee et al., Science (2009) 320:1492-1496) XBP-1 protein expression is induced in the liver by a high carbohydrate diet and controls the induction of genes involved in fatty acid synthesis. Selective deletion of XBP-1 in liver resulted in marked hypocholesterolemia and hypotriglyceridemia secondary to a decreased production of lipids from the liver. (Lee et al. (2009)) Notably, this phenotype was not accompanied by hepatic steatosis or significantly compromised protein secretory function.

XBP-1 accelerates de novo fatty acid synthesis in the liver while preserving normal hepatic lipid composition, a profile that is highly relevant to the treatment of diseases, such as atherosclerosis, that are associated with dyspipidemia. Inhibition of XBP-1 may also be useful therapeutics for the treatment of Nonalcoholic Fatty Liver Disease (NAFLD) and steatohepatitis (NASH), which lead to accelerated morbidity and mortality.

In order to determine whether XBP-1 downregulation by siRNAs would be an effective strategy to reduce lipid levels and treat dyslipidemias and metabolic syndromes, siRNAs were designed to target XBP-1.

Knock-Down of XBP-1 mRNA in the Liver and Decrease of Plasma Cholesterol Levels by Lipidoid Formulated siRNA Animal dosing: Bolus dosing of LNP01 formulated siRNAs in C57/BL6 mice (5/group, 18-20 g body weight, Charles River Laboratories, MA) was performed by low volume tail vein injection using a 27 G needle. Mice were dosed with two siRNAs targeting XBP-1 (LNP01-18037 and LNP01-18038) and a control luciferase targeting siRNA (LNP01-1955) at 5 and 7.5 mg/kg. Animals were kept under an infrared lamp for approximately 3 min prior to dosing to ease injection. 48 hour post dose animals were sacrificed by $CO_2$-asphyxiation. 0.2 ml blood was collected by retro-orbital bleeding. Liver was harvested and frozen in liquid nitrogen. Serum and livers were stored at −80° C. Total serum cholesterol in mouse serum was measured using the Wako Cholesterol E enzymatic colorimetric method (Wako Chemicals USA, Inc., Richmond, Va., USA) according to manufacturer's instructions. Measurements were taken on a VersaMax™ Tunable microplate reader (Molecular Devices, Sunnyvale, Calif.) using SoftMax® Pro software. Message levels of the target gene XBP-1 were measured via bDNA analysis as below.

bDNA analysis: Frozen livers were grinded using 6850 Freezer/Mill Cryogenic Grinder (SPEX CentriPrep, Inc.) and powders stored at −80° C. until analysis.

Figure 6:
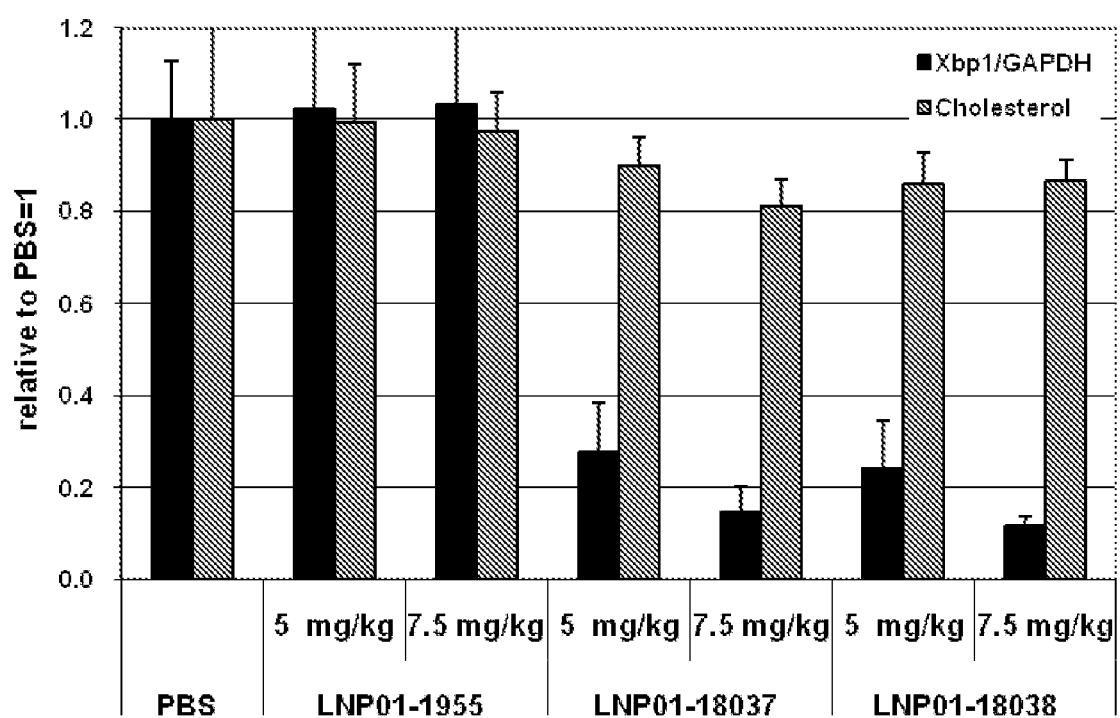
FIG. 6 illustrates mXBP-1 and cholesterol levels after XBP-1 siRNA injection in C57BL/6 mice.

XBP-1 mRNA levels were detected using the branched-DNA technology based QuantiGene® Reagent System (Panomics, Fremont, Calif., U.S.A.) according to the protocol. 10-20 mg of frozen liver powders was lysed in 600 ul of 0.3 ug/ml Proteinase K (Epicentre®, #MPRK092) in Tissue and Cell Lysis Solution (Epicentre®, #MTC096H) at 65° C. for 1 hour. Then 10 ul of the lysates were added to 90 μl of Lysis Working Reagent (1 volume of stock Lysis Mixture in two volumes of water) and incubated at 55° C. overnight on Panomics capture plates with probe sets specific to mouse XBP-1 and mouse GAPDH (Panomics, U.S.A.). Capture plates then were processed for signal amplification and detection according to the protocol and chemiluminescence was read as relative light units (RLUs) on a microplate luminometer Victor2-Light (Perkin Elmer). The ratio of XBP-1 mRNA to GAPDH mRNA in liver lysates was averaged over each treatment group and compared to a control group treated with PBS As shown in FIG. 6, as compared to the PBS control, treatment of mice with compounds LNP01-18037, and LNP01-18038, but not with unrelated siRNA control LNP01-1955 resulted in significant and dose dependent (72-88%) lowering of XBP-1 transcript levels in mouse liver (as indicated by a smaller XBP-1 to GAPDH transcript ratio when normalized to a PBS control group), indicating that siRNA molecules were active in vivo. As shown in FIG. 6, the silencing activity translated in lowering of total cholesterol in those animals.

Example 6

Cleavage of XBP-1 siRNAs

5'RACE was used to examine the cleavage products of XBP-1 siRNAs isolated from livers of mice injected with the oligonucleotides.

Mice were injected with 5 mg/kg or 7.5 mg/kg lipid-formulated XBP-1 siRNAs (LNP01-18038, negative control siRNAs targeting luciferase (LNP01-1955), or PBS. Total RNA was isolated from powdered liver samples using Trizol (Invitrogen) and RNAeasy mini columns (Qiagen). Two micrograms of RNA were used for 5'RACE similar to the Generacer kit (Invitrogen) protocol. The oligonucleotide adaptor was ligated directly to total RNA using T4 RNA ligase (2U) for 1 hour at 37° C. The ligation mixture was reverse transcribed using the XBP-1-specific oligo 5'-GGAAGCAGAGAGTGGAGAAAGAAATGCTAAGG-3' (SEQ ID NO:4335) using Superscript™ III (Invitrogen) for 1 hour at 50° C., then 15 min. at 70° C. cDNA was amplified using 3 ul of cDNA amplified with Platinum Taq (Invitrogen) for 35 cycles where Tm=62° C. with oligos 5'-CGACTGGAGCACGAGGACACTGACATGG-3' (SEQ ID NO:4336) and 5'-CCAGTGTTATGTGGCTCTTTAGACAC-TAATCAG-3' (SEQ ID NO:4337). PCR products were examined by gel electrophoresis, purified, and cloned into pCR4-TOPO vector for sequencing (Invitrogen).

PCR experiments on the 5' RACE product were performed in a blind fashion. One round of PCR was performed using Tm=62° C., for 35 cycles. The expected XBP-1 product size was 320 bp. The PCR products were roughly the correct size in all experimental samples, but products appeared to exhibit a high level of degradation the same location as the siRNA-intended cleavage site. Three bands from each of the experimental groups were cut from agarose gels for cloning and sequencing.

The control groups yielded clones with several degradation products resulting from cleavage around but not located at the expected cleavage site. The expected and observed cleavage products in the negative control samples are shown in FIG. 1A. The AD18038 siRNA was expected to cleave after nucleotide 925 in the XBP-1 transcript (see FIGS. 1A, 1B, and 3). Thus, no cleavage products at nucleotide position 925 were expected, and in fact, none were observed, in the negative control products (FIG. 1A). Degradation products in the negative control samples were found at positions −49, −35, −32(2), −31, −30(2), −28, −24, −22, −16(2), −17, −15, −14, −12, −11, −9, +8, +13, +65, and +68, relative to the intended cleavage site of the XBP-1 siRNA AD18038.

Figure 1B:

The expected siRNA-mediated cleavage product was found in 76.5% of the clones derived from the AD18038-treated groups (FIG. 1B). Degradation products were found from cleavage at positions −30, −10, −8, −5, −3, +1, +3, and +14, relative to the intended cleavage site of the XBP-1 siRNA AD18038.

TABLE 8

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_390-408 | AGAAAAUCAGCUUUUACGA | 1 | UCGUAAAAGCUGAUUUUCU | 2 |
| NM_005080_1184-1202 | UCCCCAGCUGAUUAGUGUC | 3 | GACACUAAUCAGCUGGGGA | 4 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_1494-1512 | UACUUAUUAUGUAAGGGUC | 5 | GACCCUUACAUAAUAAGUA | 6 |
| NM_005080_1463-1481 | UAUCUUAAAAGGGUGGUAG | 7 | CUACCACCCUUUUAAGAUA | 8 |
| NM_005080_610-628 | CCAUGGAUUCUGGCGGUAU | 9 | AUACCGCCAGAAUCCAUGG | 10 |
| NM_005080_823-841 | UUAAUGAACUAAUUCGUUU | 11 | AAACGAAUUAGUUCAUUAA | 12 |
| NM_005080_1507-1525 | AGGGUCAUUAGACAAAUGU | 13 | ACAUUUGUCUAAUGACCCU | 14 |
| NM_005080_827-845 | UGAACUAAUUCGUUUUGAC | 15 | GUCAAAACGAAUUAGUUCA | 16 |
| NM_005080_1503-1521 | UGUAAGGGUCAUUAGACAA | 17 | UUGUCUAAUGACCCUUACA | 18 |
| NM_005080_829-847 | AACUAAUUCGUUUUGACCA | 19 | UGGUCAAAACGAAUUAGUU | 20 |
| NM_005080_1783-1801 | UAUUUAAAACUACCCAUGC | 21 | GCAUGGGUAGUUUUAAAUA | 22 |
| NM_005080_1183-1201 | UUCCCCAGCUGAUUAGUGU | 23 | ACACUAAUCAGCUGGGGAA | 24 |
| NM_005080_1501-1519 | UAUGUAAGGGUCAUUAGAC | 25 | GUCUAAUGACCCUUACAUA | 26 |
| NM_005080_1504-1522 | GUAAGGGUCAUUAGACAAA | 27 | UUUGUCUAAUGACCCUUAC | 28 |
| NM_005080_734-752 | GCUCCCAGAGGUCUACCCA | 29 | UGGGUAGACCUCUGGGAGC | 30 |
| NM_005080_893-911 | GAGCCAAGCUAAUGUGGUA | 31 | UACCACAUUAGCUUGGCUC | 32 |
| NM_005080_1064-1082 | CUGCCUACUGGAUGCUUAC | 33 | GUAAGCAUCCAGUAGGCAG | 34 |
| NM_005080_1066-1084 | GCCUACUGGAUGCUUACAG | 35 | CUGUAAGCAUCCAGUAGGC | 36 |
| NM_005080_1136-1154 | GCUUGGUGUAAACCAUUCU | 37 | AGAAUGGUUUACACCAAGC | 38 |
| NM_005080_1137-1155 | CUUGGUGUAAACCAUUCUU | 39 | AAGAAUGGUUUACACCAAG | 40 |
| NM_005080_1182-1200 | UUUCCCCAGCUGAUUAGUG | 41 | CACUAAUCAGCUGGGGAAA | 42 |
| NM_005080_1186-1204 | CCCAGCUGAUUAGUGUCUA | 43 | UAGACACUAAUCAGCUGGG | 44 |
| NM_005080_1189-1207 | AGCUGAUUAGUGUCUAAGG | 45 | CCUUAGACACUAAUCAGCU | 46 |
| NM_005080_1224-1242 | UGCCCUUUUCCUUGACUAU | 47 | AUAGUCAAGGAAAAGGGCA | 48 |
| NM_005080_1229-1247 | UUUUCCUUGACUAUUACAC | 49 | GUGUAAUAGUCAAGGAAAA | 50 |
| NM_005080_1235-1253 | UUGACUAUUACACUGCCUG | 51 | CAGGCAGUGUAAUAGUCAA | 52 |
| NM_005080_1236-1254 | UGACUAUUACACUGCCUGG | 53 | CCAGGCAGUGUAAUAGUCA | 54 |
| NM_005080_1438-1456 | ACUACAGCUUUUAAGAUUG | 55 | CAAUCUUAAAAGCUGUAGU | 56 |
| NM_005080_1441-1459 | ACAGCUUUUAAGAUUGUAC | 57 | GUACAAUCUUAAAAGCUGU | 58 |
| NM_005080_1442-1460 | CAGCUUUUAAGAUUGUACU | 59 | AGUACAAUCUUAAAAGCUG | 60 |
| NM_005080_1493-1511 | AUACUUAUUAUGUAAGGGU | 61 | ACCCUUACAUAAUAAGUAU | 62 |
| NM_005080_1502-1520 | AUGUAAGGGUCAUUAGACA | 63 | UGUCUAAUGACCCUUACAU | 64 |
| NM_005080_1506-1524 | AAGGGUCAUUAGACAAAUG | 65 | CAUUUGUCUAAUGACCCUU | 66 |
| NM_005080_1594-1612 | UUGCCUCCAGUUUUAGGUC | 67 | GACCUAAAACUGGAGGCAA | 68 |
| NM_005080_1790-1808 | AACUACCCAUGCAAUUAAA | 69 | UUUAAUUGCAUGGGUAGUU | 70 |
| NM_005080_304-322 | ACUGCCAGAGAUCGAAAGA | 71 | UCUUUCGAUCUCUGGCAGU | 72 |
| NM_005080_305-323 | CUGCCAGAGAUCGAAAGAA | 73 | UUCUUUCGAUCUCUGGCAG | 74 |
| NM_005080_395-413 | AUCAGCUUUUACGAGAGAA | 75 | UUCUCUCGUAAAAGCUGAU | 76 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_609-627 | CCCAUGGAUUCUGGCGGUA | 77 | UACCGCCAGAAUCCAUGGG | 78 |
| NM_005080_611-629 | CAUGGAUUCUGGCGGUAUU | 79 | AAUACCGCCAGAAUCCAUG | 80 |
| NM_005080_617-635 | UUCUGGCGGUAUUGACUCU | 81 | AGAGUCAAUACCGCCAGAA | 82 |
| NM_005080_621-639 | GGCGGUAUUGACUCUUCAG | 83 | CUGAAGAGUCAAUACCGCC | 84 |
| NM_005080_641-659 | UUCAGAGUCUGAUAUCCUG | 85 | CAGGAUAUCAGACUCUGAA | 86 |
| NM_005080_648-666 | UCUGAUAUCCUGUUGGGCA | 87 | UGCCCAACAGGAUAUCAGA | 88 |
| NM_005080_651-669 | GAUAUCCUGUUGGGCAUUC | 89 | GAAUGCCCAACAGGAUAUC | 90 |
| NM_005080_735-753 | CUCCCAGAGGUCUACCCAG | 91 | CUGGGUAGACCUCUGGGAG | 92 |
| NM_005080_753-771 | GAAGGACCCAGUUCCUUAC | 93 | GUAAGGAACUGGGUCCUUC | 94 |
| NM_005080_794-812 | GGGGACGUCAUCAGCCAAG | 95 | CUUGGCUGAUGACGUCCCC | 96 |
| NM_005080_826-844 | AUGAACUAAUUCGUUUUGA | 97 | UCAAAACGAAUUAGUUCAU | 98 |
| NM_005080_836-854 | UCGUUUUGACCACAUAUAU | 99 | AUAUAUGUGGUCAAAACGA | 100 |
| NM_005080_840-858 | UUUGACCACAUAUAUACCA | 101 | UGGUAUAUAUGUGGUCAAA | 102 |
| NM_005080_841-859 | UUGACCACAUAUAUACCAA | 103 | UUGGUAUAUAUGUGGUCAA | 104 |
| NM_005080_847-865 | ACAUAUAUACCAAGCCCCU | 105 | AGGGGCUUGGUAUAUAUGU | 106 |
| NM_005080_894-912 | AGCCAAGCUAAUGUGGUAG | 107 | CUACCACAUUAGCUUGGCU | 108 |
| NM_005080_895-913 | GCCAAGCUAAUGUGGUAGU | 109 | ACUACCACAUUAGCUUGGC | 110 |
| NM_005080_896-914 | CCAAGCUAAUGUGGUAGUG | 111 | CACUACCACAUUAGCUUGG | 112 |
| NM_005080_899-917 | AGCUAAUGUGGUAGUGAAA | 113 | UUUCACUACCACAUUAGCU | 114 |
| NM_005080_908-926 | GGUAGUGAAAAUCGAGGAA | 115 | UUCCUCGAUUUUCACUACC | 116 |
| NM_005080_917-935 | AAUCGAGGAAGCACCUCUC | 117 | GAGAGGUGCUUCCUCGAUU | 118 |
| NM_005080_937-955 | GCCCCUCAGAGAAUGAUCA | 119 | UGAUCAUUCUCUGAGGGGC | 120 |
| NM_005080_950-968 | UGAUCACCCUGAAUUCAUU | 121 | AAUGAAUUCAGGGUGAUCA | 122 |
| NM_005080_1185-1203 | CCCCAGCUGAUUAGUGUCU | 123 | AGACACUAAUCAGCUGGGG | 124 |
| NM_005080_1187-1205 | CCAGCUGAUUAGUGUCUAA | 125 | UUAGACACUAAUCAGCUGG | 126 |
| NM_005080_1153-1171 | CUUGGGAGGACACUUUUGC | 127 | GCAAAAGUGUCCUCCCAAG | 128 |
| NM_005080_1787-1805 | UAAAACUACCCAUGCAAUU | 129 | AAUUGCAUGGGUAGUUUUA | 130 |
| NM_005080_606-624 | CUCCCCAUGGAUUCUGGCG | 131 | CGCCAGAAUCCAUGGGGAG | 132 |
| NM_005080_1019-1037 | UAUCUCAAAUCUGCUUUCA | 133 | UGAAAGCAGAUUUGAGAUA | 134 |
| NM_005080_1072-1090 | UGGAUGCUUACAGUGACUG | 135 | CAGUCACUGUAAGCAUCCA | 136 |
| NM_005080_1228-1246 | CUUUUCCUUGACUAUUACA | 137 | UGUAAUAGUCAAGGAAAAG | 138 |
| NM_005080_1461-1479 | UUUAUCUUAAAAGGGUGGU | 139 | ACCACCCUUUUAAGAUAAA | 140 |
| NM_005080_1495-1513 | ACUUAUUAUGUAAGGGUCA | 141 | UGACCCUUACAUAAUAAGU | 142 |
| NM_005080_1496-1514 | CUUAUUAUGUAAGGGUCAU | 143 | AUGACCCUUACAUAAUAAG | 144 |
| NM_005080_1500-1518 | UUAUGUAAGGGUCAUUAGA | 145 | UCUAAUGACCCUUACAUAA | 146 |
| NM_005080_1644-1662 | CCUGCUGAGGGGGCUCUUU | 147 | AAAGAGCCCCCUCAGCAGG | 148 |
| NM_005080_1708-1726 | AUAGAAAUUUACUAUGUAA | 149 | UUACAUAGUAAAUUUCUAU | 150 |

TABLE 8-continued

XBP-1 human/Rhesus siRNAs

| Oligo Name/<br>Positions on target<br>sequence (5'to 3') | sense (5'-3') | SEQ<br>ID<br>NO: | antisense (5'-3') | SEQ<br>ID<br>NO: |
|---|---|---|---|---|
| NM_005080_302-320 | AGACUGCCAGAGAUCGAAA | 151 | UUUCGAUCUCUGGCAGUCU | 152 |
| NM_005080_607-625 | UCCCCAUGGAUUCUGGCGG | 153 | CCGCCAGAAUCCAUGGGGA | 154 |
| NM_005080_824-842 | UAAUGAACUAAUUCGUUUU | 155 | AAAACGAAUUAGUUCAUUA | 156 |
| NM_005080_953-971 | UCACCCUGAAUUCAUUGUC | 157 | GACAAUGAAUUCAGGGUGA | 158 |
| NM_005080_1011-1029 | GAGCUGGGUAUCUCAAAUC | 159 | GAUUUGAGAUACCCAGCUC | 160 |
| NM_005080_1230-1248 | UUUCCUUGACUAUUACACU | 161 | AGUGUAAUAGUCAAGGAAA | 162 |
| NM_005080_1231-1249 | UUCCUUGACUAUUACACUG | 163 | CAGUGUAAUAGUCAAGGAA | 164 |
| NM_005080_1290-1308 | AAAGCCAAAAUAGAGAGUA | 165 | UACUCUCUAUUUUGGCUUU | 166 |
| NM_005080_1331-1349 | AUUUGUUCAGAUCUCAUAG | 167 | CUAUGAGAUCUGAACAAAU | 168 |
| NM_005080_1460-1478 | UUUUAUCUUAAAAGGGUGG | 169 | CCACCCUUUUAAGAUAAAA | 170 |
| NM_005080_1670-1688 | GUAUACUUCAAGUAAGAUC | 171 | GAUCUUACUUGAAGUAUAC | 172 |
| NM_005080_1671-1689 | UAUACUUCAAGUAAGAUCA | 173 | UGAUCUUACUUGAAGUAUA | 174 |
| NM_005080_1735-1753 | UGGAAUUUUUUCCUGCUAG | 175 | CUAGCAGGAAAAAAUUCCA | 176 |
| NM_005080_1744-1762 | UUCCUGCUAGUGUAGCUUC | 177 | GAAGCUACACUAGCAGGAA | 178 |
| NM_005080_1796-1814 | CCAUGCAAUUAAAAGGUAC | 179 | GUACCUUUUAAUUGCAUGG | 180 |
| NM_005080_343-361 | GAACAGCAAGUGGUAGAUU | 181 | AAUCUACCACUUGCUGUUC | 182 |
| NM_005080_374-392 | ACCAAAAACUUUUGCUAGA | 183 | UCUAGCAAAAGUUUUUGGU | 184 |
| NM_005080_375-393 | CCAAAAACUUUUGCUAGAA | 185 | UUCUAGCAAAAGUUUUUGG | 186 |
| NM_005080_608-626 | CCCCAUGGAUUCUGGCGGU | 187 | ACCGCCAGAAUCCAUGGGG | 188 |
| NM_005080_652-670 | AUAUCCUGUUGGGCAUUCU | 189 | AGAAUGCCCAACAGGAUAU | 190 |
| NM_005080_686-704 | AGUCAUGUUCUUCAAAUGC | 191 | GCAUUUGAAGAACAUGACU | 192 |
| NM_005080_909-927 | GUAGUGAAAAUCGAGGAAG | 193 | CUUCCUCGAUUUUCACUAC | 194 |
| NM_005080_951-969 | GAUCACCCUGAAUUCAUUG | 195 | CAAUGAAUUCAGGGUGAUC | 196 |
| NM_005080_952-970 | AUCACCCUGAAUUCAUUGU | 197 | ACAAUGAAUUCAGGGUGAU | 198 |
| NM_005080_825-843 | AAUGAACUAAUUCGUUUUG | 199 | CAAAACGAAUUAGUUCAUU | 200 |
| NM_005080_1194-1212 | AUUAGUGUCUAAGGAAUGA | 201 | UCAUUCCUUAGACACUAAU | 202 |
| NM_005080_831-849 | CUAAUUCGUUUUGACCACA | 203 | UGUGGUCAAAACGAAUUAG | 204 |
| NM_005080_835-853 | UUCGUUUUGACCACAUAUA | 205 | UAUAUGUGGUCAAAACGAA | 206 |
| NM_005080_869-887 | CUUAGAGAUACCCUCUGAG | 207 | CUCAGAGGGUAUCUCUAAG | 208 |
| NM_005080_1246-1264 | ACUGCCUGGAGGAUAGCAG | 209 | CUGCUAUCCUCCAGGCAGU | 210 |
| NM_005080_1453-1471 | AUUGUACUUUUAUCUUAAA | 211 | UUUAAGAUAAAAGUACAAU | 212 |
| NM_005080_1512-1530 | CAUUAGACAAAUGUCUUGA | 213 | UCAAGACAUUUGUCUAAUG | 214 |
| NM_005080_1546-1564 | UAUGAAUGGUUCUUUAUCA | 215 | UGAUAAAGAACCAUUCAUA | 216 |
| NM_005080_1789-1807 | AAACUACCCAUGCAAUUAA | 217 | UUAAUUGCAUGGGUAGUUU | 218 |
| NM_005080_325-343 | GCUCGAAUGAGUGAGCUGG | 219 | CCAGCUCACUCAUUCGAGC | 220 |
| NM_005080_393-411 | AAAUCAGCUUUUACGAGAG | 221 | CUCUCGUAAAAGCUGAUUU | 222 |

TABLE 8-continued

XBP-1 human/Rhesus siRNAs

| Oligo Name/<br>Positions on target<br>sequence (5' to 3') | sense (5'-3') | SEQ ID NO: | antisense (5'-3') | SEQ ID NO: |
|---|---|---|---|---|
| NM_005080_788-806 | GUCAGUGGGGACGUCAUCA | 223 | UGAUGACGUCCCCACUGAC | 224 |
| NM_005080_821-839 | CAUUAAUGAACUAAUUCGU | 225 | ACGAAUUAGUUCAUUAAUG | 226 |
| NM_005080_1514-1532 | UUAGACAAAUGUCUUGAAG | 227 | CUUCAAGACAUUUGUCUAA | 228 |
| NM_005080_1797-1815 | CAUGCAAUUAAAAGGUACA | 229 | UGUACCUUUUAAUUGCAUG | 230 |
| NM_005080_833-851 | AAUUCGUUUUGACCACAUA | 231 | UAUGUGGUCAAAACGAAUU | 232 |
| NM_005080_1509-1527 | GGUCAUUAGACAAAUGUCU | 233 | AGACAUUUGUCUAAUGACC | 234 |
| NM_005080_1802-1820 | AAUUAAAAGGUACAAUGCA | 235 | UGCAUUGUACCUUUUAAUU | 236 |
| NM_005080_391-409 | GAAAAUCAGCUUUUACGAG | 237 | CUCGUAAAAGCUGAUUUUC | 238 |
| NM_005080_843-861 | GACCACAUAUAUACCAAGC | 239 | GCUUGGUAUAUAUGUGGUC | 240 |
| NM_005080_1508-1526 | GGGUCAUUAGACAAAUGUC | 241 | GACAUUUGUCUAAUGACCC | 242 |
| NM_005080_1754-1772 | UGUAGCUUCUGAAAGGUGC | 243 | GCACCUUUCAGAAGCUACA | 244 |
| NM_005080_430-448 | GUUGAGAACCAGGAGUUAA | 245 | UUAACUCCUGGUUCUCAAC | 246 |
| NM_005080_437-455 | ACCAGGAGUUAAGACAGCG | 247 | CGCUGUCUUAACUCCUGGU | 248 |
| NM_005080_1465-1483 | UCUUAAAAGGGUGGUAGUU | 249 | AACUACCACCCUUUUAAGA | 250 |
| NM_005080_1742-1760 | UUUUCCUGCUAGUGUAGCU | 251 | AGCUACACUAGCAGGAAAA | 252 |
| NM_005080_438-456 | CCAGGAGUUAAGACAGCGC | 253 | GCGCUGUCUUAACUCCUGG | 254 |
| NM_005080_1060-1078 | CUUCCUGCCUACUGGAUGC | 255 | GCAUCCAGUAGGCAGGAAG | 256 |
| NM_005080_1067-1085 | CCUACUGGAUGCUUACAGU | 257 | ACUGUAAGCAUCCAGUAGG | 258 |
| NM_005080_1197-1215 | AGUGUCUAAGGAAUGAUCC | 259 | GGAUCAUUCCUUAGACACU | 260 |
| NM_005080_1198-1216 | GUGUCUAAGGAAUGAUCCA | 261 | UGGAUCAUUCCUUAGACAC | 262 |
| NM_005080_1424-1442 | UACUAUAAUUGAGAACUAC | 263 | GUAGUUCUCAAUUAUAGUA | 264 |
| NM_005080_1464-1482 | AUCUUAAAAGGGUGGUAGU | 265 | ACUACCACCCUUUUAAGAU | 266 |
| NM_005080_616-634 | AUUCUGGCGGUAUUGACUC | 267 | GAGUCAAUACCGCCAGAAU | 268 |
| NM_005080_757-775 | GACCCAGUUCCUUACCAGC | 269 | GCUGGUAAGGAACUGGGUC | 270 |
| NM_005080_785-803 | UCUGUCAGUGGGGACGUCA | 271 | UGACGUCCCCACUGACAGA | 272 |
| NM_005080_819-837 | GCCAUUAAUGAACUAAUUC | 273 | GAAUUAGUUCAUUAAUGGC | 274 |
| NM_005080_842-860 | UGACCACAUAUAUACCAAG | 275 | CUUGGUAUAUAUGUGGUCA | 276 |
| NM_005080_845-863 | CCACAUAUAUACCAAGCCC | 277 | GGGCUUGGUAUAUAUGUGG | 278 |
| NM_005080_1013-1031 | GCUGGGUAUCUCAAAUCUG | 279 | CAGAUUUGAGAUACCCAGC | 280 |
| NM_005080_1431-1449 | AUUGAGAACUACAGCUUUU | 281 | AAAAGCUGUAGUUCUCAAU | 282 |
| NM_005080_1673-1691 | UACUUCAAGUAAGAUCAAG | 283 | CUUGAUCUUACUUGAAGUA | 284 |
| NM_005080_283-301 | AAAAACAGAGUAGCAGCUC | 285 | GAGCUGCUACUCUGUUUUU | 286 |
| NM_005080_838-856 | GUUUUGACCACAUAUAUAC | 287 | GUAUAUAUGUGGUCAAAAC | 288 |
| NM_005080_279-297 | ACUGAAAACAGAGUAGCA | 289 | UGCUACUCUGUUUUCAGU | 290 |
| NM_005080_633-651 | UCUUCAGAUUCAGAGUCUG | 291 | CAGACUCUGAAUCUGAAGA | 292 |
| NM_005080_1024-1042 | CAAAUCUGCUUUCAUCCAG | 293 | CUGGAUGAAAGCAGAUUUG | 294 |
| NM_005080_1147-1165 | ACCAUUCUUGGGAGGACAC | 295 | GUGUCCUCCCAAGAAUGGU | 296 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_1154-1172 | UUGGGAGGACACUUUUGCC | 297 | GGCAAAAGUGUCCUCCCAA | 298 |
| NM_005080_1188-1206 | CAGCUGAUUAGUGUCUAAG | 299 | CUUAGACACUAAUCAGCUG | 300 |
| NM_005080_1192-1210 | UGAUUAGUGUCUAAGGAAU | 301 | AUUCCUUAGACACUAAUCA | 302 |
| NM_005080_1195-1213 | UUAGUGUCUAAGGAAUGAU | 303 | AUCAUUCCUUAGACACUAA | 304 |
| NM_005080_1238-1256 | ACUAUUACACUGCCUGGAG | 305 | CUCCAGGCAGUGUAAUAGU | 306 |
| NM_005080_1548-1566 | UGAAUGGUUCUUUAUCAUU | 307 | AAUGAUAAAGAACCAUUCA | 308 |
| NM_005080_1549-1567 | GAAUGGUUCUUUAUCAUUU | 309 | AAAUGAUAAAGAACCAUUC | 310 |
| NM_005080_1677-1695 | UCAAGUAAGAUCAAGAAUC | 311 | GAUUCUUGAUCUUACUUGA | 312 |
| NM_005080_1707-1725 | UAUAGAAAUUUACUAUGUA | 313 | UACAUAGUAAAUUUCUAUA | 314 |
| NM_005080_1713-1731 | AAUUUACUAUGUAAAUGCU | 315 | AGCAUUUACAUAGUAAAUU | 316 |
| NM_005080_1786-1804 | UUAAAACUACCCAUGCAAU | 317 | AUUGCAUGGGUAGUUUUAA | 318 |
| NM_005080_210-228 | GCUGCCCCAGGCGCGCAAG | 319 | CUUGCGCGCCUGGGGCAGC | 320 |
| NM_005080_278-296 | AACUGAAAACAGAGUAGC | 321 | GCUACUCUGUUUUCAGUU | 322 |
| NM_005080_284-302 | AAAACAGAGUAGCAGCUCA | 323 | UGAGCUGCUACUCUGUUUU | 324 |
| NM_005080_290-308 | GAGUAGCAGCUCAGACUGC | 325 | GCAGUCUGAGCUGCUACUC | 326 |
| NM_005080_342-360 | GGAACAGCAAGUGGUAGAU | 327 | AUCUACCACUUGCUGUUCC | 328 |
| NM_005080_431-449 | UUGAGAACCAGGAGUUAAG | 329 | CUUAACUCCUGGUUCUCAA | 330 |
| NM_005080_576-594 | GCAGGCCCAGUUGUCACCC | 331 | GGGUGACAACUGGGCCUGC | 332 |
| NM_005080_602-620 | ACAUCUCCCAUGGAUUCU | 333 | AGAAUCCAUGGGGAGAUGU | 334 |
| NM_005080_618-636 | UCUGGCGGUAUUGACUCUU | 335 | AAGAGUCAAUACCGCCAGA | 336 |
| NM_005080_678-696 | UUGGACCCAGUCAUGUUCU | 337 | AGAACAUGACUGGGUCCAA | 338 |
| NM_005080_796-814 | GGACGUCAUCAGCCAAGCU | 339 | AGCUUGGCUGAUGACGUCC | 340 |
| NM_005080_940-958 | CCUCAGAGAAUGAUCACCC | 341 | GGGUGAUCAUUCUCUGAGG | 342 |
| NM_005080_954-972 | CACCCUGAAUUCAUUGUCU | 343 | AGACAAUGAAUUCAGGGUG | 344 |
| NM_005080_977-995 | GAAGGAAGAACCUGUAGAA | 345 | UUCUACAGGUUCUUCCUUC | 346 |
| NM_005080_1018-1036 | GUAUCUCAAAUCUGCUUUC | 347 | GAAAGCAGAUUUGAGAUAC | 348 |
| NM_005080_1026-1044 | AAUCUGCUUUCAUCCAGCC | 349 | GGCUGGAUGAAAGCAGAUU | 350 |
| NM_005080_1138-1156 | UUGGUGUAAACCAUUCUUG | 351 | CAAGAAUGGUUUACACCAA | 352 |
| NM_005080_1141-1159 | GUGUAAACCAUUCUUGGGA | 353 | UCCCAAGAAUGGUUUACAC | 354 |
| NM_005080_1142-1160 | UGUAAACCAUUCUUGGGAG | 355 | CUCCCAAGAAUGGUUUACA | 356 |
| NM_005080_1155-1173 | UGGGAGGACACUUUUGCCA | 357 | UGGCAAAAGUGUCCUCCCA | 358 |
| NM_005080_1158-1176 | GAGGACACUUUUGCCAAUG | 359 | CAUUGGCAAAAGUGUCCUC | 360 |
| NM_005080_1193-1211 | GAUUAGUGUCUAAGGAAUG | 361 | CAUUCCUUAGACACUAAUC | 362 |
| NM_005080_1196-1214 | UAGUGUCUAAGGAAUGAUC | 363 | GAUCAUUCCUUAGACACUA | 364 |
| NM_005080_1219-1237 | ACUGUUGCCCUUUUCCUUG | 365 | CAAGGAAAAGGGCAACAGU | 366 |
| NM_005080_107-125 | UGUCGGGGCAGCCCGCCUC | 367 | GAGGCGGGCUGCCCCGACA | 368 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_108-126 | GUCGGGCAGCCCGCCUCC | 369 | GGAGGCGGGCUGCCCCGAC | 370 |
| NM_005080_1505-1523 | UAAGGGUCAUUAGACAAAU | 371 | AUUUGUCUAAUGACCCUUA | 372 |
| NM_005080_1567-1585 | UCUCUUCCCCUUUUUGGC | 373 | GCCAAAAAGGGGAAGAGA | 374 |
| NM_005080_1672-1690 | AUACUUCAAGUAAGAUCAA | 375 | UUGAUCUUACUUGAAGUAU | 376 |
| NM_005080_1678-1696 | CAAGUAAGAUCAAGAAUCU | 377 | AGAUUCUUGAUCUUACUUG | 378 |
| NM_005080_1778-1796 | CCAUUUAUUUAAAACUACC | 379 | GGUAGUUUUAAAUAAAUGG | 380 |
| NM_005080_1779-1797 | CAUUUAUUUAAAACUACCC | 381 | GGGUAGUUUUAAAUAAAUG | 382 |
| NM_005080_280-298 | CUGAAAAACAGAGUAGCAG | 383 | CUGCUACUCUGUUUUUCAG | 384 |
| NM_005080_282-300 | GAAAAACAGAGUAGCAGCU | 385 | AGCUGCUACUCUGUUUUUC | 386 |
| NM_005080_288-306 | CAGAGUAGCAGCUCAGACU | 387 | AGUCUGAGCUGCUACUCUG | 388 |
| NM_005080_291-309 | AGUAGCAGCUCAGACUGCC | 389 | GGCAGUCUGAGCUGCUACU | 390 |
| NM_005080_347-365 | AGCAAGUGGUAGAUUUAGA | 391 | UCUAAAUCUACCACUUGCU | 392 |
| NM_005080_397-415 | CAGCUUUUACGAGAGAAAA | 393 | UUUUCUCUCGUAAAAGCUG | 394 |
| NM_005080_398-416 | AGCUUUUACGAGAGAAAAC | 395 | GUUUUCUCUCGUAAAAGCU | 396 |
| NM_005080_399-417 | GCUUUUACGAGAGAAAACU | 397 | AGUUUUCUCUCGUAAAAGC | 398 |
| NM_005080_512-530 | UGAGGCCAGUGGCCGGGUC | 399 | GACCCGGCCACUGGCCUCA | 400 |
| NM_005080_517-535 | CCAGUGGCCGGGUCUGCUG | 401 | CAGCAGACCCGGCCACUGG | 402 |
| NM_005080_596-614 | UCCAGAACAUCUCCCCAUG | 403 | CAUGGGGAGAUGUUCUGGA | 404 |
| NM_005080_598-616 | CAGAACAUCUCCCCAUGGA | 405 | UCCAUGGGGAGAUGUUCUG | 406 |
| NM_005080_601-619 | AACAUCUCCCCAUGGAUUC | 407 | GAAUCCAUGGGGAGAUGUU | 408 |
| NM_005080_605-623 | UCUCCCCAUGGAUUCUGGC | 409 | GCCAGAAUCCAUGGGGAGA | 410 |
| NM_005080_661-679 | UGGGCAUUCUGGACAACUU | 411 | AAGUUGUCCAGAAUGCCCA | 412 |
| NM_005080_688-706 | UCAUGUUCUUCAAAUGCCC | 413 | GGGCAUUUGAAGAACAUGA | 414 |
| NM_005080_691-709 | UGUUCUUCAAAUGCCCUUC | 415 | GAAGGGCAUUUGAAGAACA | 416 |
| NM_005080_828-846 | GAACUAAUUCGUUUUGACC | 417 | GGUCAAAACGAAUUAGUUC | 418 |
| NM_005080_830-848 | ACUAAUUCGUUUUGACCAC | 419 | GUGGUCAAAACGAAUUAGU | 420 |
| NM_005080_834-852 | AUUCGUUUUGACCACAUAU | 421 | AUAUGUGGUCAAAACGAAU | 422 |
| NM_005080_846-864 | CACAUAUAUACCAAGCCCC | 423 | GGGGCUUGGUAUAUAUGUG | 424 |
| NM_005080_870-888 | UUAGAGAUACCCUCUGAGA | 425 | UCUCAGAGGGUAUCUCUAA | 426 |
| NM_005080_891-909 | GAGAGCCAAGCUAAUGUGG | 427 | CCACAUUAGCUUGGCUCUC | 428 |
| NM_005080_900-918 | GCUAAUGUGGUAGUGAAAA | 429 | UUUUCACUACCACAUUAGC | 430 |
| NM_005080_911-929 | AGUGAAAAUCGAGGAAGCA | 431 | UGCUUCCUCGAUUUUCACU | 432 |
| NM_005080_912-930 | GUGAAAAUCGAGGAAGCAC | 433 | GUGCUUCCUCGAUUUUCAC | 434 |
| NM_005080_979-997 | AGGAAGAACCUGUAGAAGA | 435 | UCUUCUACAGGUUCUUCCU | 436 |
| NM_005080_1366-1384 | GUCUUUUGACAUCCAGCAG | 437 | CUGCUGGAUGUCAAAAGAC | 438 |
| NM_005080_150-168 | GGCCCUGCCGCUCAUGGUG | 439 | CACCAUGAGCGGCAGGGCC | 440 |
| NM_005080_1437-1455 | AACUACAGCUUUUAAGAUU | 441 | AAUCUUAAAAGCUGUAGUU | 442 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_482-500 | AAGAGGAGGCGGAAGCCAA | 443 | TTGGCTTCCGCCTCCTCTT | 444 |
| NM_005080_580-598 | GCCCAGUUGUCACCCCUCC | 445 | GGAGGGGUGACAACUGGGC | 446 |
| NM_005080_613-631 | UGGAUUCUGGCGGUAUUGA | 447 | UCAAUACCGCCAGAAUCCA | 448 |
| NM_005080_1065-1083 | UGCCUACUGGAUGCUUACA | 449 | UGUAAGCAUCCAGUAGGCA | 450 |
| NM_005080_614-632 | GGAUUCUGGCGGUAUUGAC | 451 | GUCAAUACCGCCAGAAUCC | 452 |
| NM_005080_640-658 | AUUCAGAGUCUGAUAUCCU | 453 | AGGAUAUCAGACUCUGAAU | 454 |
| NM_005080_1014-1032 | CUGGGUAUCUCAAAUCUGC | 455 | GCAGAUUUGAGAUACCCAG | 456 |
| NM_005080_1015-1033 | UGGGUAUCUCAAAUCUGCU | 457 | AGCAGAUUUGAGAUACCCA | 458 |
| NM_005080_1146-1164 | AACCAUUCUUGGGAGGACA | 459 | UGUCCUCCCAAGAAUGGUU | 460 |
| NM_005080_1232-1250 | UCCUUGACUAUUACACUGC | 461 | GCAGUGUAAUAGUCAAGGA | 462 |
| NM_005080_1234-1252 | CUUGACUAUUACACUGCCU | 463 | AGGCAGUGUAAUAGUCAAG | 464 |
| NM_005080_1237-1255 | GACUAUUACACUGCCUGGA | 465 | UCCAGGCAGUGUAAUAGUC | 466 |
| NM_005080_1443-1461 | AGCUUUUAAGAUUGUACUU | 467 | AAGUACAAUCUUAAAAGCU | 468 |
| NM_005080_1462-1480 | UUAUCUUAAAAGGGUGGUA | 469 | UACCACCCUUUUAAGAUAA | 470 |
| NM_005080_1510-1528 | GUCAUUAGACAAAUGUCUU | 471 | AAGACAUUUGUCUAAUGAC | 472 |
| NM_005080_1591-1609 | GGCUUGCCUCCAGUUUUAG | 473 | CUAAAACUGGAGGCAAGCC | 474 |
| NM_005080_1615-1633 | UUAGUUUGCUUCUGUAAGC | 475 | GCUUACAGAAGCAAACUAA | 476 |
| NM_005080_1716-1734 | UUACUAUGUAAAUGCUUGA | 477 | UCAAGCAUUUACAUAGUAA | 478 |
| NM_005080_1718-1736 | ACUAUGUAAAUGCUUGAUG | 479 | CAUCAAGCAUUUACAUAGU | 480 |
| NM_005080_1725-1743 | AAAUGCUUGAUGGAAUUUU | 481 | AAAAUUCCAUCAAGCAUUU | 482 |
| NM_005080_1748-1766 | UGCUAGUGUAGCUUCUGAA | 483 | UUCAGAAGCUACACUAGCA | 484 |
| NM_005080_1780-1798 | AUUUAUUUAAAACUACCCA | 485 | UGGGUAGUUUUAAAUAAAU | 486 |
| NM_005080_1794-1812 | ACCCAUGCAAUUAAAAGGU | 487 | ACCUUUUAAUUGCAUGGGU | 488 |
| NM_005080_156-174 | GCCGCUCAUGGUGCCAGCC | 489 | GGCUGGCACCAUGAGCGGC | 490 |
| NM_005080_299-317 | CUCAGACUGCCAGAGAUCG | 491 | CGAUCUCUGGCAGUCUGAG | 492 |
| NM_005080_344-362 | AACAGCAAGUGGUAGAUUU | 493 | AAAUCUACCACUUGCUGUU | 494 |
| NM_005080_371-389 | AGAACCAAAAACUUUUGCU | 495 | AGCAAAAGUUUUUGGUUCU | 496 |
| NM_005080_373-391 | AACCAAAAACUUUUGCUAG | 497 | CUAGCAAAAGUUUUUGGUU | 498 |
| NM_005080_524-542 | CCGGGUCUGCUGAGUCCGC | 499 | GCGGACUCAGCAGACCCGG | 500 |
| NM_005080_525-543 | CGGGUCUGCUGAGUCCGCA | 501 | UGCGGACUCAGCAGACCCG | 502 |
| NM_005080_612-630 | AUGGAUUCUGGCGGUAUUG | 503 | CAAUACCGCCAGAAUCCAU | 504 |
| NM_005080_615-633 | GAUUCUGGCGGUAUUGACU | 505 | AGUCAAUACCGCCAGAAUC | 506 |
| NM_005080_645-663 | GAGUCUGAUAUCCUGUUGG | 507 | CCAACAGGAUAUCAGACUC | 508 |
| NM_005080_792-810 | GUGGGGACGUCAUCAGCCA | 509 | UGGCUGAUGACGUCCCCAC | 510 |
| NM_005080_905-923 | UGUGGUAGUGAAAUCGAG | 511 | CUCGAUUUCACUACCACA | 512 |
| NM_005080_976-994 | UGAAGGAAGAACCUGUAGA | 513 | UCUACAGGUUCUUCCUUCA | 514 |

TABLE 8-continued

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_1244-1262 | ACACUGCCUGGAGGAUAGC | 515 | GCUAUCCUCCAGGCAGUGU | 516 |
| NM_005080_1791-1809 | ACUACCCAUGCAAUUAAAA | 517 | UUUUAAUUGCAUGGGUAGU | 518 |
| NM_005080_755-773 | AGGACCCAGUUCCUUACCA | 519 | UGGUAAGGAACUGGGUCCU | 520 |
| NM_005080_799-817 | CGUCAUCAGCCAAGCUGGA | 521 | UCCAGCUUGGCUGAUGACG | 522 |
| NM_005080_832-850 | UAAUUCGUUUUGACCACAU | 523 | AUGUGGUCAAAACGAAUUA | 524 |
| NM_005080_839-857 | UUUUGACCACAUAUAUACC | 525 | GGUAUAUAUGUGGUCAAAA | 526 |
| NM_005080_100-118 | CUGCUUCUGUCGGGCAGC | 527 | GCUGCCCCGACAGAAGCAG | 528 |
| NM_005080_281-299 | UGAAAACAGAGUAGCAGC | 529 | GCUGCUACUCUGUUUUUCA | 530 |
| NM_005080_822-840 | AUUAAUGAACUAAUUCGUU | 531 | AACGAAUUAGUUCAUUAAU | 532 |
| NM_005080_1152-1170 | UCUUGGGAGGACACUUUUG | 533 | CAAAAGUGUCCUCCCAAGA | 534 |
| NM_005080_1191-1209 | CUGAUUAGUGUCUAAGGAA | 535 | UUCCUUAGACACUAAUCAG | 536 |
| NM_005080_1225-1243 | GCCCUUUUCCUUGACUAUU | 537 | AAUAGUCAAGGAAAAGGGC | 538 |
| NM_005080_1227-1245 | CCUUUUCCUUGACUAUUAC | 539 | GUAAUAGUCAAGGAAAAGG | 540 |
| NM_005080_1239-1257 | CUAUUACACUGCCUGGAGG | 541 | CCUCCAGGCAGUGUAAUAG | 542 |
| NM_005080_1430-1448 | AAUUGAGAACUACAGCUUU | 543 | AAAGCUGUAGUUCUCAAUU | 544 |
| NM_005080_1499-1517 | AUUAUGUAAGGGUCAUUAG | 545 | CUAAUGACCCUUACAUAAU | 546 |
| NM_005080_1553-1571 | GGUUCUUUAUCAUUUCUCU | 547 | AGAGAAAUGAUAAAGAACC | 548 |
| NM_005080_1585-1603 | CAUCCUGGCUUGCCUCCAG | 549 | CUGGAGGCAAGCCAGGAUG | 550 |
| NM_005080_1592-1610 | GCUUGCCUCCAGUUUUAGG | 551 | CCUAAAACUGGAGGCAAGC | 552 |
| NM_005080_1743-1761 | UUUCCUGCUAGUGUAGCUU | 553 | AAGCUACACUAGCAGGAAA | 554 |
| NM_005080_154-172 | CUGCCGCUCAUGGUGCCAG | 555 | CUGGCACCAUGAGCGGCAG | 556 |
| NM_005080_193-211 | GAGGCAGCGAGCGGGGGC | 557 | GCCCCCGCUCGCUGCCUC | 558 |
| NM_005080_199-217 | GCGAGCGGGGGCUGCCCC | 559 | GGGGCAGCCCCCGCUCGC | 560 |
| NM_005080_292-310 | GUAGCAGCUCAGACUGCCA | 561 | UGGCAGUCUGAGCUGCUAC | 562 |
| NM_005080_341-359 | UGGAACAGCAAGUGGUAGA | 563 | UCUACCACUUGCUGUUCCA | 564 |
| NM_005080_377-395 | AAAAACUUUUGCUAGAAAA | 565 | UUUUCUAGCAAAAGUUUUU | 566 |
| NM_005080_519-537 | AGUGGCCGGGUCUGCUGAG | 567 | CUCAGCAGACCCGGCCACU | 568 |
| NM_005080_522-540 | GGCCGGGUCUGCUGAGUCC | 569 | GGACUCAGCAGACCCGGCC | 570 |
| NM_005080_577-595 | CAGGCCCAGUUGUCACCCC | 571 | GGGGUGACAACUGGGCCUG | 572 |
| NM_005080_599-617 | AGAACAUCUCCCCAUGGAU | 573 | AUCCAUGGGGAGAUGUUCU | 574 |
| NM_005080_754-772 | AAGGACCCAGUUCCUUACC | 575 | GGUAAGGAACUGGGUCCUU | 576 |
| NM_005080_888-906 | ACAGAGAGCCAAGCUAAUG | 577 | CAUUAGCUUGGCUCUCUGU | 578 |
| NM_005080_939-957 | CCCUCAGAGAAUGAUCACC | 579 | GGUGAUCAUUCUCUGAGGG | 580 |
| NM_005080_964-982 | UCAUUGUCUCAGUGAAGGA | 581 | UCCUUCACUGAGACAAUGA | 582 |
| NM_005080_1012-1030 | AGCUGGGUAUCUCAAAUCU | 583 | AGAUUUGAGAUACCCAGCU | 584 |
| NM_005080_1016-1034 | GGGUAUCUCAAAUCUGCUU | 585 | AAGCAGAUUUGAGAUACCC | 586 |
| NM_005080_1020-1038 | AUCUCAAAUCUGCUUUCAU | 587 | AUGAAAGCAGAUUUGAGAU | 588 |

TABLE 8-continued

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_1025-1043 | AAAUCUGCUUUCAUCCAGC | 589 | GCUGGAUGAAAGCAGAUUU | 590 |
| NM_005080_1027-1045 | AUCUGCUUUCAUCCAGCCA | 591 | UGGCUGGAUGAAAGCAGAU | 592 |
| NM_005080_1028-1046 | UCUGCUUUCAUCCAGCCAC | 593 | GUGGCUGGAUGAAAGCAGA | 594 |
| NM_005080_1030-1048 | UGCUUUCAUCCAGCCACUG | 595 | CAGUGGCUGGAUGAAAGCA | 596 |
| NM_005080_1031-1049 | GCUUUCAUCCAGCCACUGC | 597 | GCAGUGGCUGGAUGAAAGC | 598 |
| NM_005080_1032-1050 | CUUUCAUCCAGCCACUGCC | 599 | GGCAGUGGCUGGAUGAAAG | 600 |
| NM_005080_1033-1051 | UUUCAUCCAGCCACUGCCC | 601 | GGGCAGUGGCUGGAUGAAA | 602 |
| NM_005080_1056-1074 | CCAUCUUCCUGCCUACUGG | 603 | CCAGUAGGCAGGAAGAUGG | 604 |
| NM_005080_1057-1075 | CAUCUUCCUGCCUACUGGA | 605 | UCCAGUAGGCAGGAAGAUG | 606 |
| NM_005080_1058-1076 | AUCUUCCUGCCUACUGGAU | 607 | AUCCAGUAGGCAGGAAGAU | 608 |
| NM_005080_1059-1077 | UCUUCCUGCCUACUGGAUG | 609 | CAUCCAGUAGGCAGGAAGA | 610 |
| NM_005080_1061-1079 | UUCCUGCCUACUGGAUGCU | 611 | AGCAUCCAGUAGGCAGGAA | 612 |
| NM_005080_1063-1081 | CCUGCCUACUGGAUGCUUA | 613 | UAAGCAUCCAGUAGGCAGG | 614 |
| NM_005080_1069-1087 | UACUGGAUGCUUACAGUGA | 615 | UCACUGUAAGCAUCCAGUA | 616 |
| NM_005080_1071-1089 | CUGGAUGCUUACAGUGACU | 617 | AGUCACUGUAAGCAUCCAG | 618 |
| NM_005080_1073-1091 | GGAUGCUUACAGUGACUGU | 619 | ACAGUCACUGUAAGCAUCC | 620 |
| NM_005080_1075-1093 | AUGCUUACAGUGACUGUGG | 621 | CCACAGUCACUGUAAGCAU | 622 |
| NM_005080_1076-1094 | UGCUUACAGUGACUGUGGA | 623 | UCCACAGUCACUGUAAGCA | 624 |
| NM_005080_1078-1096 | CUUACAGUGACUGUGGAUA | 625 | UAUCCACAGUCACUGUAAG | 626 |
| NM_005080_1139-1157 | UGGUGUAAACCAUUCUUGG | 627 | CCAAGAAUGGUUUACACCA | 628 |
| NM_005080_1140-1158 | GGUGUAAACCAUUCUUGGG | 629 | CCCAAGAAUGGUUUACACC | 630 |
| NM_005080_1143-1161 | GUAAACCAUUCUUGGGAGG | 631 | CCUCCCAAGAAUGGUUUAC | 632 |
| NM_005080_1144-1162 | UAAACCAUUCUUGGGAGGA | 633 | UCCUCCCAAGAAUGGUUUA | 634 |
| NM_005080_1145-1163 | AAACCAUUCUUGGGAGGAC | 635 | GUCCUCCCAAGAAUGGUUU | 636 |
| NM_005080_1148-1166 | CCAUUCUUGGGAGGACACU | 637 | AGUGUCCUCCCAAGAAUGG | 638 |
| NM_005080_1156-1174 | GGGAGGACACUUUUGCCAA | 639 | UUGGCAAAAGUGUCCUCCC | 640 |
| NM_005080_1157-1175 | GGAGGACACUUUUGCCAAU | 641 | AUUGGCAAAAGUGUCCUCC | 642 |
| NM_005080_1159-1177 | AGGACACUUUUGCCAAUGA | 643 | UCAUUGGCAAAAGUGUCCU | 644 |
| NM_005080_1160-1178 | GGACACUUUUGCCAAUGAA | 645 | UUCAUUGGCAAAAGUGUCC | 646 |
| NM_005080_1190-1208 | GCUGAUUAGUGUCUAAGGA | 647 | UCCUUAGACACUAAUCAGC | 648 |
| NM_005080_1218-1236 | UACUGUUGCCCUUUUCCUU | 649 | AAGGAAAAGGGCAACAGUA | 650 |
| NM_005080_1220-1238 | CUGUUGCCCUUUUCCUUGA | 651 | UCAAGGAAAAGGGCAACAG | 652 |
| NM_005080_1221-1239 | UGUUGCCCUUUUCCUUGAC | 653 | GUCAAGGAAAAGGGCAACA | 654 |
| NM_005080_1233-1251 | CCUUGACUAUUACACUGCC | 655 | GGCAGUGUAAUAGUCAAGG | 656 |
| NM_005080_1240-1258 | UAUUACACUGCCUGGAGGA | 657 | UCCUCCAGGCAGUGUAAUA | 658 |
| NM_005080_1241-1259 | AUUACACUGCCUGGAGGAU | 659 | AUCCUCCAGGCAGUGUAAU | 660 |

TABLE 8-continued

XBP-1 human/Rhesus siRNAs

| Oligo Name/<br>Positions on target<br>sequence (5'to 3') | sense (5'-3') | SEQ<br>ID<br>NO: | antisense (5'-3') | SEQ<br>ID<br>NO: |
|---|---|---|---|---|
| NM_005080_1242-1260 | UUACACUGCCUGGAGGAUA | 661 | UAUCCUCCAGGCAGUGUAA | 662 |
| NM_005080_1243-1261 | UACACUGCCUGGAGGAUAG | 663 | CUAUCCUCCAGGCAGUGUA | 664 |
| NM_005080_1282-1300 | UCAUUCAAAAAGCCAAAAU | 665 | AUUUUGGCUUUUUGAAUGA | 666 |
| NM_005080_1287-1305 | CAAAAGCCAAAAUAGAGA | 667 | UCUCUAUUUUGGCUUUUG | 668 |
| NM_005080_1289-1307 | AAAAGCCAAAAUAGAGAGU | 669 | ACUCUCUAUUUUGGCUUUU | 670 |
| NM_005080_1310-1328 | ACAGUCCUAGAGAAUUCCU | 671 | AGGAAUUCUCUAGGACUGU | 672 |
| NM_005080_1330-1348 | UAUUUGUUCAGAUCUCAUA | 673 | UAUGAGAUCUGAACAAAUA | 674 |
| NM_005080_1332-1350 | UUUGUUCAGAUCUCAUAGA | 675 | UCUAUGAGAUCUGAACAAA | 676 |
| NM_005080_1333-1351 | UUGUUCAGAUCUCAUAGAU | 677 | AUCUAUGAGAUCUGAACAA | 678 |
| NM_005080_1369-1387 | UUUUGACAUCCAGCAGUCC | 679 | GGACUGCUGGAUGUCAAAA | 680 |
| NM_005080_1370-1388 | UUUGACAUCCAGCAGUCCA | 681 | UGGACUGCUGGAUGUCAAA | 682 |
| NM_005080_1371-1389 | UUGACAUCCAGCAGUCCAA | 683 | UUGGACUGCUGGAUGUCAA | 684 |
| NM_005080_101-119 | UGCUUCUGUCGGGCAGCC | 685 | GGCUGCCCCGACAGAAGCA | 686 |
| NM_005080_1418-1436 | AAAUAUUACUAUAAUUGAG | 687 | CUCAAUUAUAGUAAUAUUU | 688 |
| NM_005080_1419-1437 | AAUAUUACUAUAAUUGAGA | 689 | UCUCAAUUAUAGUAAUAUU | 690 |
| NM_005080_1422-1440 | AUUACUAUAAUUGAGAACU | 691 | AGUUCUCAAUUAUAGUAAU | 692 |
| NM_005080_102-120 | GCUUCUGUCGGGCAGCCC | 693 | GGGCUGCCCCGACAGAAGC | 694 |
| NM_005080_1423-1441 | UUACUAUAAUUGAGAACUA | 695 | UAGUUCUCAAUUAUAGUAA | 696 |
| NM_005080_1425-1443 | ACUAUAAUUGAGAACUACA | 697 | UGUAGUUCUCAAUUAUAGU | 698 |
| NM_005080_1427-1445 | UAUAAUUGAGAACUACAGC | 699 | GCUGUAGUUCUCAAUUAUA | 700 |
| NM_005080_1428-1446 | AUAAUUGAGAACUACAGCU | 701 | AGCUGUAGUUCUCAAUUAU | 702 |
| NM_005080_1429-1447 | UAAUUGAGAACUACAGCUU | 703 | AAGCUGUAGUUCUCAAUUA | 704 |
| NM_005080_1432-1450 | UUGAGAACUACAGCUUUUA | 705 | UAAAAGCUGUAGUUCUCAA | 706 |
| NM_005080_1433-1451 | UGAGAACUACAGCUUUUAA | 707 | UUAAAAGCUGUAGUUCUCA | 708 |
| NM_005080_1435-1453 | AGAACUACAGCUUUUAAGA | 709 | UCUUAAAAGCUGUAGUUCU | 710 |
| NM_005080_1439-1457 | CUACAGCUUUUAAGAUUGU | 711 | ACAAUCUUAAAAGCUGUAG | 712 |
| NM_005080_104-122 | UUCUGUCGGGCAGCCCGC | 713 | GCGGGCUGCCCCGACAGAA | 714 |
| NM_005080_1444-1462 | GCUUUUAAGAUUGUACUUU | 715 | AAAGUACAAUCUUAAAAGC | 716 |
| NM_005080_1445-1463 | CUUUUAAGAUUGUACUUUU | 717 | AAAAGUACAAUCUUAAAAG | 718 |
| NM_005080_1446-1464 | UUUUAAGAUUGUACUUUUA | 719 | UAAAAGUACAAUCUUAAAA | 720 |
| NM_005080_1447-1465 | UUUAAGAUUGUACUUUUAU | 721 | AUAAAAGUACAAUCUUAAA | 722 |
| NM_005080_1448-1466 | UUAAGAUUGUACUUUUAUC | 723 | GAUAAAAGUACAAUCUUAA | 724 |
| NM_005080_1451-1469 | AGAUUGUACUUUUAUCUUA | 725 | UAAGAUAAAAGUACAAUCU | 726 |
| NM_005080_1454-1472 | UUGUACUUUUAUCUUAAAA | 727 | UUUUAAGAUAAAAGUACAA | 728 |
| NM_005080_1458-1476 | ACUUUUAUCUUAAAAGGGU | 729 | ACCCUUUUAAGAUAAAAGU | 730 |
| NM_005080_1459-1477 | CUUUUAUCUUAAAAGGGUG | 731 | CACCCUUUUAAGAUAAAAG | 732 |
| NM_005080_106-124 | CUGUCGGGCAGCCCGCCU | 733 | AGGCGGGCUGCCCCGACAG | 734 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_1466-1484 | CUUAAAAGGGUGGUAGUUU | 735 | AAACUACCACCCUUUUAAG | 736 |
| NM_005080_1486-1504 | CCCUAAAAUACUUAUUAUG | 737 | CAUAAUAAGUAUUUUAGGG | 738 |
| NM_005080_1487-1505 | CCUAAAAUACUUAUUAUGU | 739 | ACAUAAUAAGUAUUUUAGG | 740 |
| NM_005080_1489-1507 | UAAAAUACUUAUUAUGUAA | 741 | UUACAUAAUAAGUAUUUUA | 742 |
| NM_005080_1490-1508 | AAAAUACUUAUUAUGUAAG | 743 | CUUACAUAAUAAGUAUUUU | 744 |
| NM_005080_1491-1509 | AAAUACUUAUUAUGUAAGG | 745 | CCUUACAUAAUAAGUAUUU | 746 |
| NM_005080_109-127 | UCGGGGCAGCCCGCCUCCG | 747 | CGGAGGCGGGCUGCCCCGA | 748 |
| NM_005080_1497-1515 | UUAUUAUGUAAGGGUCAUU | 749 | AAUGACCCUUACAUAAUAA | 750 |
| NM_005080_1498-1516 | UAUUAUGUAAGGGUCAUUA | 751 | UAAUGACCCUUACAUAAUA | 752 |
| NM_005080_110-128 | CGGGGCAGCCCGCCUCCGC | 753 | GCGGAGGCGGGCUGCCCCG | 754 |
| NM_005080_1511-1529 | UCAUUAGACAAAUGUCUUG | 755 | CAAGACAUUUGUCUAAUGA | 756 |
| NM_005080_1513-1531 | AUUAGACAAAUGUCUUGAA | 757 | UUCAAGACAUUUGUCUAAU | 758 |
| NM_005080_1516-1534 | AGACAAAUGUCUUGAAGUA | 759 | UACUUCAAGACAUUUGUCU | 760 |
| NM_005080_1517-1535 | GACAAAUGUCUUGAAGUAG | 761 | CUACUUCAAGACAUUUGUC | 762 |
| NM_005080_1518-1536 | ACAAAUGUCUUGAAGUAGA | 763 | UCUACUUCAAGACAUUUGU | 764 |
| NM_005080_1547-1565 | AUGAAUGGUUCUUUAUCAU | 765 | AUGAUAAAGAACCAUUCAU | 766 |
| NM_005080_1550-1568 | AAUGGUUCUUUAUCAUUUC | 767 | GAAAUGAUAAAGAACCAUU | 768 |
| NM_005080_1551-1569 | AUGGUUCUUUAUCAUUUCU | 769 | AGAAAUGAUAAAGAACCAU | 770 |
| NM_005080_1552-1570 | UGGUUCUUUAUCAUUUCUC | 771 | GAGAAAUGAUAAAGAACCA | 772 |
| NM_005080_1554-1572 | GUUCUUUAUCAUUUCUCUU | 773 | AAGAGAAAUGAUAAAGAAC | 774 |
| NM_005080_1559-1577 | UUAUCAUUUCUCUUCCCCC | 775 | GGGGGAAGAGAAAUGAUAA | 776 |
| NM_005080_1560-1578 | UAUCAUUUCUCUUCCCCCU | 777 | AGGGGGAAGAGAAAUGAUA | 778 |
| NM_005080_1563-1581 | CAUUUCUCUUCCCCCUUUU | 779 | AAAAGGGGGAAGAGAAAUG | 780 |
| NM_005080_1565-1583 | UUUCUCUUCCCCCUUUUUG | 781 | CAAAAAGGGGGAAGAGAAA | 782 |
| NM_005080_1566-1584 | UUCUCUUCCCCCUUUUUGG | 783 | CCAAAAAGGGGGAAGAGAA | 784 |
| NM_005080_1570-1588 | CUUCCCCCUUUUUGGCAUC | 785 | GAUGCCAAAAAGGGGGAAG | 786 |
| NM_005080_1573-1591 | CCCCCUUUUUGGCAUCCUG | 787 | CAGGAUGCCAAAAAGGGGG | 788 |
| NM_005080_1578-1596 | UUUUUGGCAUCCUGGCUUG | 789 | CAAGCCAGGAUGCCAAAAA | 790 |
| NM_005080_1579-1597 | UUUUGGCAUCCUGGCUUGC | 791 | GCAAGCCAGGAUGCCAAAA | 792 |
| NM_005080_1580-1598 | UUUGGCAUCCUGGCUUGCC | 793 | GGCAAGCCAGGAUGCCAAA | 794 |
| NM_005080_1581-1599 | UUGGCAUCCUGGCUUGCCU | 795 | AGGCAAGCCAGGAUGCCAA | 796 |
| NM_005080_1583-1601 | GGCAUCCUGGCUUGCCUCC | 797 | GGAGGCAAGCCAGGAUGCC | 798 |
| NM_005080_1584-1602 | GCAUCCUGGCUUGCCUCCA | 799 | UGGAGGCAAGCCAGGAUGC | 800 |
| NM_005080_1586-1604 | AUCCUGGCUUGCCUCCAGU | 801 | ACUGGAGGCAAGCCAGGAU | 802 |
| NM_005080_1589-1607 | CUGGCUUGCCUCCAGUUUU | 803 | AAAACUGGAGGCAAGCCAG | 804 |
| NM_005080_1590-1608 | UGGCUUGCCUCCAGUUUUA | 805 | UAAAACUGGAGGCAAGCCA | 806 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_1595-1613 | UGCCUCCAGUUUUAGGUCC | 807 | GGACCUAAAACUGGAGGCA | 808 |
| NM_005080_1616-1634 | UAGUUUGCUUCUGUAAGCA | 809 | UGCUUACAGAAGCAAACUA | 810 |
| NM_005080_1617-1635 | AGUUUGCUUCUGUAAGCAA | 811 | UUGCUUACAGAAGCAAACU | 812 |
| NM_005080_1643-1661 | ACCUGCUGAGGGGGCUCUU | 813 | AAGAGCCCCCUCAGCAGGU | 814 |
| NM_005080_1645-1663 | CUGCUGAGGGGGCUCUUUC | 815 | GAAAGAGCCCCCUCAGCAG | 816 |
| NM_005080_1646-1664 | UGCUGAGGGGGCUCUUUCC | 817 | GGAAAGAGCCCCCUCAGCA | 818 |
| NM_005080_1647-1665 | GCUGAGGGGGCUCUUUCCC | 819 | GGGAAAGAGCCCCCUCAGC | 820 |
| NM_005080_1648-1666 | CUGAGGGGGCUCUUUCCCU | 821 | AGGGAAAGAGCCCCCUCAG | 822 |
| NM_005080_1649-1667 | UGAGGGGGCUCUUUCCCUC | 823 | GAGGGAAAGAGCCCCCUCA | 824 |
| NM_005080_1679-1697 | AAGUAAGAUCAAGAAUCUU | 825 | AAGAUUCUUGAUCUUACUU | 826 |
| NM_005080_1680-1698 | AGUAAGAUCAAGAAUCUUU | 827 | AAAGAUUCUUGAUCUUACU | 828 |
| NM_005080_1681-1699 | GUAAGAUCAAGAAUCUUUU | 829 | AAAAGAUUCUUGAUCUUAC | 830 |
| NM_005080_1682-1700 | UAAGAUCAAGAAUCUUUUG | 831 | CAAAAGAUUCUUGAUCUUA | 832 |
| NM_005080_1683-1701 | AAGAUCAAGAAUCUUUUGU | 833 | ACAAAAGAUUCUUGAUCUU | 834 |
| NM_005080_1684-1702 | AGAUCAAGAAUCUUUUGUG | 835 | CACAAAAGAUUCUUGAUCU | 836 |
| NM_005080_1687-1705 | UCAAGAAUCUUUUGUGAAA | 837 | UUUCACAAAAGAUUCUUGA | 838 |
| NM_005080_1709-1727 | UAGAAAUUUACUAUGUAAA | 839 | UUUACAUAGUAAAUUUCUA | 840 |
| NM_005080_1710-1728 | AGAAAUUUACUAUGUAAAU | 841 | AUUUACAUAGUAAAUUUCU | 842 |
| NM_005080_1711-1729 | GAAAUUUACUAUGUAAAUG | 843 | CAUUUACAUAGUAAAUUUC | 844 |
| NM_005080_1712-1730 | AAAUUUACUAUGUAAAUGC | 845 | GCAUUUACAUAGUAAAUUU | 846 |
| NM_005080_1714-1732 | AUUUACUAUGUAAAUGCUU | 847 | AAGCAUUUACUAGUAAAU | 848 |
| NM_005080_1715-1733 | UUUACUAUGUAAAUGCUUG | 849 | CAAGCAUUUACAUAGUAAA | 850 |
| NM_005080_1717-1735 | UACUAUGUAAAUGCUUGAU | 851 | AUCAAGCAUUUACAUAGUA | 852 |
| NM_005080_1719-1737 | CUAUGUAAAUGCUUGAUGG | 853 | CCAUCAAGCAUUUACAUAG | 854 |
| NM_005080_1721-1739 | AUGUAAAUGCUUGAUGGAA | 855 | UUCCAUCAAGCAUUUACAU | 856 |
| NM_005080_1722-1740 | UGUAAAUGCUUGAUGGAAU | 857 | AUUCCAUCAAGCAUUUACA | 858 |
| NM_005080_1723-1741 | GUAAAUGCUUGAUGGAAUU | 859 | AAUUCCAUCAAGCAUUUAC | 860 |
| NM_005080_1726-1744 | AAUGCUUGAUGGAAUUUUU | 861 | AAAAAUUCCAUCAAGCAUU | 862 |
| NM_005080_1727-1745 | AUGCUUGAUGGAAUUUUUU | 863 | AAAAAAUUCCAUCAAGCAU | 864 |
| NM_005080_1728-1746 | UGCUUGAUGGAAUUUUUUC | 865 | GAAAAAAUUCCAUCAAGCA | 866 |
| NM_005080_1729-1747 | GCUUGAUGGAAUUUUUUCC | 867 | GGAAAAAAUUCCAUCAAGC | 868 |
| NM_005080_1736-1754 | GGAAUUUUUUCCUGCUAGU | 869 | ACUAGCAGGAAAAAAUUCC | 870 |
| NM_005080_1739-1757 | AUUUUUUCCUGCUAGUGUA | 871 | UACACUAGCAGGAAAAAAU | 872 |
| NM_005080_1746-1764 | CCUGCUAGUGUAGCUUCUG | 873 | CAGAAGCUACACUAGCAGG | 874 |
| NM_005080_1747-1765 | CUGCUAGUGUAGCUUCUGA | 875 | UCAGAAGCUACACUAGCAG | 876 |
| NM_005080_1749-1767 | GCUAGUGUAGCUUCUGAAA | 877 | UUUCAGAAGCUACACUAGC | 878 |
| NM_005080_1750-1768 | CUAGUGUAGCUUCUGAAAG | 879 | CUUUCAGAAGCUACACUAG | 880 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_1751-1769 | UAGUGUAGCUUCUGAAAGG | 881 | CCUUUCAGAAGCUACACUA | 882 |
| NM_005080_1752-1770 | AGUGUAGCUUCUGAAAGGU | 883 | ACCUUUCAGAAGCUACACU | 884 |
| NM_005080_1753-1771 | GUGUAGCUUCUGAAAGGUG | 885 | CACCUUUCAGAAGCUACAC | 886 |
| NM_005080_1755-1773 | GUAGCUUCUGAAAGGUGCU | 887 | AGCACCUUUCAGAAGCUAC | 888 |
| NM_005080_1758-1776 | GCUUCUGAAAGGUGCUUUC | 889 | GAAAGCACCUUUCAGAAGC | 890 |
| NM_005080_1781-1799 | UUUAUUUAAAACUACCCAU | 891 | AUGGGUAGUUUUAAAUAAA | 892 |
| NM_005080_1782-1800 | UUAUUUAAAACUACCCAUG | 893 | CAUGGGUAGUUUUAAAUAA | 894 |
| NM_005080_1784-1802 | AUUUAAAACUACCCAUGCA | 895 | UGCAUGGGUAGUUUUAAAU | 896 |
| NM_005080_1785-1803 | UUUAAAACUACCCAUGCAA | 897 | UUGCAUGGGUAGUUUUAAA | 898 |
| NM_005080_1788-1806 | AAAACUACCCAUGCAAUUA | 899 | UAAUUGCAUGGGUAGUUUU | 900 |
| NM_005080_1792-1810 | CUACCCAUGCAAUUAAAAG | 901 | CUUUUAAUUGCAUGGGUAG | 902 |
| NM_005080_1793-1811 | UACCCAUGCAAUUAAAAGG | 903 | CCUUUUAAUUGCAUGGGUA | 904 |
| NM_005080_1795-1813 | CCCAUGCAAUUAAAAGGUA | 905 | UACCUUUUAAUUGCAUGGG | 906 |
| NM_005080_1798-1816 | AUGCAAUUAAAAGGUACAA | 907 | UUGUACCUUUUAAUUGCAU | 908 |
| NM_005080_1799-1817 | UGCAAUUAAAAGGUACAAU | 909 | AUUGUACCUUUUAAUUGCA | 910 |
| NM_005080_1800-1818 | GCAAUUAAAAGGUACAAUG | 911 | CAUUGUACCUUUUAAUUGC | 912 |
| NM_005080_1801-1819 | CAAUUAAAAGGUACAAUGC | 913 | GCAUUGUACCUUUUAAUUG | 914 |
| NM_005080_146-164 | GCCAGGCCCUGCCGCUCAU | 915 | AUGAGCGGCAGGGCCUGGC | 916 |
| NM_005080_147-165 | CCAGGCCCUGCCGCUCAUG | 917 | CAUGAGCGGCAGGGCCUGG | 918 |
| NM_005080_148-166 | CAGGCCCUGCCGCUCAUGG | 919 | CCAUGAGCGGCAGGGCCUG | 920 |
| NM_005080_149-167 | AGGCCCUGCCGCUCAUGGU | 921 | ACCAUGAGCGGCAGGGCCU | 922 |
| NM_005080_155-173 | UGCCGCUCAUGGUGCCAGC | 923 | GCUGGCACCAUGAGCGGCA | 924 |
| NM_005080_157-175 | CCGCUCAUGGUGCCAGCCC | 925 | GGGCUGGCACCAUGAGCGG | 926 |
| NM_005080_158-176 | CGCUCAUGGUGCCAGCCCA | 927 | UGGGCUGGCACCAUGAGCG | 928 |
| NM_005080_159-177 | GCUCAUGGUGCCAGCCCAG | 929 | CUGGGCUGGCACCAUGAGC | 930 |
| NM_005080_188-206 | GCCCGGAGGCAGCGAGCGG | 931 | CCGCUCGCUGCCUCCGGGC | 932 |
| NM_005080_189-207 | CCCGGAGGCAGCGAGCGGG | 933 | CCCGCUCGCUGCCUCCGGG | 934 |
| NM_005080_195-213 | GGCAGCGAGCGGGGGCUG | 935 | CAGCCCCCGCUCGCUGCC | 936 |
| NM_005080_196-214 | GCAGCGAGCGGGGGCUGC | 937 | GCAGCCCCCGCUCGCUGC | 938 |
| NM_005080_197-215 | CAGCGAGCGGGGGCUGCC | 939 | GGCAGCCCCCGCUCGCUG | 940 |
| NM_005080_198-216 | AGCGAGCGGGGGCUGCCC | 941 | GGGCAGCCCCCGCUCGCU | 942 |
| NM_005080_205-223 | GGGGGCUGCCCCAGGCGC | 943 | GCGCCUGGGGCAGCCCCC | 944 |
| NM_005080_206-224 | GGGGCUGCCCCAGGCGCG | 945 | CGCGCCUGGGGCAGCCCCC | 946 |
| NM_005080_207-225 | GGGGCUGCCCCAGGCGCGC | 947 | GCGCGCCUGGGGCAGCCCC | 948 |
| NM_005080_211-229 | CUGCCCCAGGCGCGCAAGC | 949 | GCUUGCGCGCCUGGGGCAG | 950 |
| NM_005080_250-268 | AGCCCCGAGGAGAAGGCGC | 951 | GCGCCUUCUCCUCGGGGCU | 952 |

TABLE 8-continued

XBP-1 human/Rhesus siRNAs

| Oligo Name/<br>Positions on target<br>sequence (5' to 3') | sense (5'-3') | SEQ<br>ID<br>NO: | antisense (5'-3') | SEQ<br>ID<br>NO: |
|---|---|---|---|---|
| NM_005080_256-274 | GAGGAGAAGGCGCUGAGGA | 953 | UCCUCAGCGCCUUCUCCUC | 954 |
| NM_005080_263-281 | AGGCGCUGAGGAGGAAACU | 955 | AGUUUCCUCCUCAGCGCCU | 956 |
| NM_005080_264-282 | GGCGCUGAGGAGGAAACUG | 957 | CAGUUUCCUCCUCAGCGCC | 958 |
| NM_005080_285-303 | AAACAGAGUAGCAGCUCAG | 959 | CUGAGCUGCUACUCUGUUU | 960 |
| NM_005080_286-304 | AACAGAGUAGCAGCUCAGA | 961 | UCUGAGCUGCUACUCUGUU | 962 |
| NM_005080_287-305 | ACAGAGUAGCAGCUCAGAC | 963 | GUCUGAGCUGCUACUCUGU | 964 |
| NM_005080_294-312 | AGCAGCUCAGACUGCCAGA | 965 | UCUGGCAGUCUGAGCUGCU | 966 |
| NM_005080_295-313 | GCAGCUCAGACUGCCAGAG | 967 | CUCUGGCAGUCUGAGCUGC | 968 |
| NM_005080_296-314 | CAGCUCAGACUGCCAGAGA | 969 | UCUCUGGCAGUCUGAGCUG | 970 |
| NM_005080_298-316 | GCUCAGACUGCCAGAGAUC | 971 | GAUCUCUGGCAGUCUGAGC | 972 |
| NM_005080_303-321 | GACUGCCAGAGAUCGAAAG | 973 | CUUUCGAUCUCUGGCAGUC | 974 |
| NM_005080_332-350 | UGAGUGAGCUGGAACAGCA | 975 | UGCUGUUCCAGCUCACUCA | 976 |
| NM_005080_339-357 | GCUGGAACAGCAAGUGGUA | 977 | UACCACUUGCUGUUCCAGC | 978 |
| NM_005080_340-358 | CUGGAACAGCAAGUGGUAG | 979 | CUACCACUUGCUGUUCCAG | 980 |
| NM_005080_345-363 | ACAGCAAGUGGUAGAUUUA | 981 | UAAAUCUACCACUUGCUGU | 982 |
| NM_005080_346-364 | CAGCAAGUGGUAGAUUUAG | 983 | CUAAAUCUACCACUUGCUG | 984 |
| NM_005080_348-366 | GCAAGUGGUAGAUUUAGAA | 985 | UUCUAAAUCUACCACUUGC | 986 |
| NM_005080_349-367 | CAAGUGGUAGAUUUAGAAG | 987 | CUUCUAAAUCUACCACUUG | 988 |
| NM_005080_352-370 | GUGGUAGAUUUAGAAGAAG | 989 | CUUCUUCUAAAUCUACCAC | 990 |
| NM_005080_353-371 | UGGUAGAUUUAGAAGAAGA | 991 | UCUUCUUCUAAAUCUACCA | 992 |
| NM_005080_354-372 | GGUAGAUUUAGAAGAAGAG | 993 | CUCUUCUUCUAAAUCUACC | 994 |
| NM_005080_355-373 | GUAGAUUUAGAAGAAGAGA | 995 | UCUCUUCUUCUAAAUCUAC | 996 |
| NM_005080_361-379 | UUAGAAGAAGAGAACCAAA | 997 | UUUGGUUCUCUUCUUCUAA | 998 |
| NM_005080_366-384 | AGAAGAGAACCAAAAACUU | 999 | AAGUUUUUGGUUCUCUUCU | 1000 |
| NM_005080_369-387 | AGAGAACCAAAAACUUUUG | 1001 | CAAAAGUUUUUGGUUCUCU | 1002 |
| NM_005080_370-388 | GAGAACCAAAAACUUUUGC | 1003 | GCAAAAGUUUUUGGUUCUC | 1004 |
| NM_005080_372-390 | GAACCAAAAACUUUUGCUA | 1005 | UAGCAAAAGUUUUUGGUUC | 1006 |
| NM_005080_376-394 | CAAAAACUUUUGCUAGAAA | 1007 | UUUCUAGCAAAAGUUUUUG | 1008 |
| NM_005080_381-399 | ACUUUUGCUAGAAAAUCAG | 1009 | CUGAUUUUCUAGCAAAAGU | 1010 |
| NM_005080_384-402 | UUUGCUAGAAAAUCAGCUU | 1011 | AAGCUGAUUUUCUAGCAAA | 1012 |
| NM_005080_388-406 | CUAGAAAAUCAGCUUUUAC | 1013 | GUAAAAGCUGAUUUUCUAG | 1014 |
| NM_005080_392-410 | AAAAUCAGCUUUUACGAGA | 1015 | UCUCGUAAAAGCUGAUUUU | 1016 |
| NM_005080_394-412 | AAUCAGCUUUUACGAGAGA | 1017 | UCUCUCGUAAAAGCUGAUU | 1018 |
| NM_005080_396-414 | UCAGCUUUUACGAGAGAAA | 1019 | UUUCUCUCGUAAAAGCUGA | 1020 |
| NM_005080_400-418 | CUUUUACGAGAGAAAACUC | 1021 | GAGUUUUCUCUCGUAAAAG | 1022 |
| NM_005080_421-439 | GGCCUUGUAGUUGAGAACC | 1023 | GGUUCUCAACUACAAGGCC | 1024 |
| NM_005080_422-440 | GCCUUGUAGUUGAGAACCA | 1025 | UGGUUCUCAACUACAAGGC | 1026 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_423-441 | CCUUGUAGUUGAGAACCAG | 1027 | CUGGUUCUCAACUACAAGG | 1028 |
| NM_005080_425-443 | UUGUAGUUGAGAACCAGGA | 1029 | UCCUGGUUCUCAACUACAA | 1030 |
| NM_005080_428-446 | UAGUUGAGAACCAGGAGUU | 1031 | AACUCCUGGUUCUCAACUA | 1032 |
| NM_005080_429-447 | AGUUGAGAACCAGGAGUUA | 1033 | UAACUCCUGGUUCUCAACU | 1034 |
| NM_005080_432-450 | UGAGAACCAGGAGUUAAGA | 1035 | UCUUAACUCCUGGUUCUCA | 1036 |
| NM_005080_433-451 | GAGAACCAGGAGUUAAGAC | 1037 | GUCUUAACUCCUGGUUCUC | 1038 |
| NM_005080_434-452 | AGAACCAGGAGUUAAGACA | 1039 | UGUCUUAACUCCUGGUUCU | 1040 |
| NM_005080_435-453 | GAACCAGGAGUUAAGACAG | 1041 | CUGUCUUAACUCCUGGUUC | 1042 |
| NM_005080_436-454 | AACCAGGAGUUAAGACAGC | 1043 | GCUGUCUUAACUCCUGGUU | 1044 |
| NM_005080_459-477 | GGGGAUGGAUGCCCUGGUU | 1045 | AACCAGGGCAUCCAUCCCC | 1046 |
| NM_005080_460-478 | GGGAUGGAUGCCCUGGUUG | 1047 | CAACCAGGGCAUCCAUCCC | 1048 |
| NM_005080_462-480 | GAUGGAUGCCCUGGUUGCU | 1049 | AGCAACCAGGGCAUCCAUC | 1050 |
| NM_005080_486-504 | GGAGGCGGAAGCCAAGGGG | 1051 | CCCCTTGGCTTCCGCCTCC | 1052 |
| NM_005080_510-528 | AGUGAGGCCAGUGGCCGGG | 1053 | CCCGGCCACUGGCCUCACU | 1054 |
| NM_005080_513-531 | GAGGCCAGUGGCCGGGUCU | 1055 | AGACCCGGCCACUGGCCUC | 1056 |
| NM_005080_514-532 | AGGCCAGUGGCCGGGUCUG | 1057 | CAGACCCGGCCACUGGCCU | 1058 |
| NM_005080_515-533 | GGCCAGUGGCCGGGUCUGC | 1059 | GCAGACCCGGCCACUGGCC | 1060 |
| NM_005080_516-534 | GCCAGUGGCCGGGUCUGCU | 1061 | AGCAGACCCGGCCACUGGC | 1062 |
| NM_005080_520-538 | GUGGCCGGGUCUGCUGAGU | 1063 | ACUCAGCAGACCCGGCCAC | 1064 |
| NM_005080_521-539 | UGGCCGGGUCUGCUGAGUC | 1065 | GACUCAGCAGACCCGGCCA | 1066 |
| NM_005080_523-541 | GCCGGGUCUGCUGAGUCCG | 1067 | CGGACUCAGCAGACCCGGC | 1068 |
| NM_005080_578-596 | AGGCCCAGUUGUCACCCCU | 1069 | AGGGGUGACAACUGGGCCU | 1070 |
| NM_005080_581-599 | CCCAGUUGUCACCCCUCCA | 1071 | UGGAGGGGUGACAACUGGG | 1072 |
| NM_005080_582-600 | CCAGUUGUCACCCCUCCAG | 1073 | CUGGAGGGGUGACAACUGG | 1074 |
| NM_005080_583-601 | CAGUUGUCACCCCUCCAGA | 1075 | UCUGGAGGGGUGACAACUG | 1076 |
| NM_005080_584-602 | AGUUGUCACCCCUCCAGAA | 1077 | UUCUGGAGGGGUGACAACU | 1078 |
| NM_005080_585-603 | GUUGUCACCCCUCCAGAAC | 1079 | GUUCUGGAGGGGUGACAAC | 1080 |
| NM_005080_586-604 | UUGUCACCCCUCCAGAACA | 1081 | UGUUCUGGAGGGGUGACAA | 1082 |
| NM_005080_587-605 | UGUCACCCCUCCAGAACAU | 1083 | AUGUUCUGGAGGGGUGACA | 1084 |
| NM_005080_588-606 | GUCACCCCUCCAGAACAUC | 1085 | GAUGUUCUGGAGGGGUGAC | 1086 |
| NM_005080_589-607 | UCACCCCUCCAGAACAUCU | 1087 | AGAUGUUCUGGAGGGGUGA | 1088 |
| NM_005080_590-608 | CACCCCUCCAGAACAUCUC | 1089 | GAGAUGUUCUGGAGGGGUG | 1090 |
| NM_005080_591-609 | ACCCCUCCAGAACAUCUCC | 1091 | GGAGAUGUUCUGGAGGGGU | 1092 |
| NM_005080_597-615 | CCAGAACAUCUCCCCAUGG | 1093 | CCAUGGGGAGAUGUUCUGG | 1094 |
| NM_005080_600-618 | GAACAUCUCCCCAUGGAUU | 1095 | AAUCCAUGGGGAGAUGUUC | 1096 |
| NM_005080_603-621 | CAUCUCCCCAUGGAUUCUG | 1097 | CAGAAUCCAUGGGGAGAUG | 1098 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_619-637 | CUGGCGGUAUUGACUCUUC | 1099 | GAAGAGUCAAUACCGCCAG | 1100 |
| NM_005080_620-638 | UGGCGGUAUUGACUCUUCA | 1101 | UGAAGAGUCAAUACCGCCA | 1102 |
| NM_005080_622-640 | GCGGUAUUGACUCUUCAGA | 1103 | UCUGAAGAGUCAAUACCGC | 1104 |
| NM_005080_623-641 | CGGUAUUGACUCUUCAGAU | 1105 | AUCUGAAGAGUCAAUACCG | 1106 |
| NM_005080_624-642 | GGUAUUGACUCUUCAGAUU | 1107 | AAUCUGAAGAGUCAAUACC | 1108 |
| NM_005080_625-643 | GUAUUGACUCUUCAGAUUC | 1109 | GAAUCUGAAGAGUCAAUAC | 1110 |
| NM_005080_626-644 | UAUUGACUCUUCAGAUUCA | 1111 | UGAAUCUGAAGAGUCAAUA | 1112 |
| NM_005080_629-647 | UGACUCUUCAGAUUCAGAG | 1113 | CUCUGAAUCUGAAGAGUCA | 1114 |
| NM_005080_632-650 | CUCUUCAGAUUCAGAGUCU | 1115 | AGACUCUGAAUCUGAAGAG | 1116 |
| NM_005080_634-652 | CUUCAGAUUCAGAGUCUGA | 1117 | UCAGACUCUGAAUCUGAAG | 1118 |
| NM_005080_637-655 | CAGAUUCAGAGUCUGAUAU | 1119 | AUAUCAGACUCUGAAUCUG | 1120 |
| NM_005080_638-656 | AGAUUCAGAGUCUGAUAUC | 1121 | GAUAUCAGACUCUGAAUCU | 1122 |
| NM_005080_639-657 | GAUUCAGAGUCUGAUAUCC | 1123 | GGAUAUCAGACUCUGAAUC | 1124 |
| NM_005080_642-660 | UCAGAGUCUGAUAUCCUGU | 1125 | ACAGGAUAUCAGACUCUGA | 1126 |
| NM_005080_643-661 | CAGAGUCUGAUAUCCUGUU | 1127 | AACAGGAUAUCAGACUCUG | 1128 |
| NM_005080_644-662 | AGAGUCUGAUAUCCUGUUG | 1129 | CAACAGGAUAUCAGACUCU | 1130 |
| NM_005080_646-664 | AGUCUGAUAUCCUGUUGGG | 1131 | CCCAACAGGAUAUCAGACU | 1132 |
| NM_005080_649-667 | CUGAUAUCCUGUUGGGCAU | 1133 | AUGCCCAACAGGAUAUCAG | 1134 |
| NM_005080_650-668 | UGAUAUCCUGUUGGGCAUU | 1135 | AAUGCCCAACAGGAUAUCA | 1136 |
| NM_005080_653-671 | UAUCCUGUUGGGCAUUCUG | 1137 | CAGAAUGCCCAACAGGAUA | 1138 |
| NM_005080_658-676 | UGUUGGGCAUUCUGGACAA | 1139 | UUGUCCAGAAUGCCCAACA | 1140 |
| NM_005080_659-677 | GUUGGGCAUUCUGGACAAC | 1141 | GUUGUCCAGAAUGCCCAAC | 1142 |
| NM_005080_660-678 | UUGGGCAUUCUGGACAACU | 1143 | AGUUGUCCAGAAUGCCCAA | 1144 |
| NM_005080_663-681 | GGCAUUCUGGACAACUUGG | 1145 | CCAAGUUGUCCAGAAUGCC | 1146 |
| NM_005080_664-682 | GCAUUCUGGACAACUUGGA | 1147 | UCCAAGUUGUCCAGAAUGC | 1148 |
| NM_005080_668-686 | UCUGGACAACUUGGACCCA | 1149 | UGGGUCCAAGUUGUCCAGA | 1150 |
| NM_005080_671-689 | GGACAACUUGGACCCAGUC | 1151 | GACUGGGUCCAAGUUGUCC | 1152 |
| NM_005080_676-694 | ACUUGGACCCAGUCAUGUU | 1153 | AACAUGACUGGGUCCAAGU | 1154 |
| NM_005080_677-695 | CUUGGACCCAGUCAUGUUC | 1155 | GAACAUGACUGGGUCCAAG | 1156 |
| NM_005080_679-697 | UGGACCCAGUCAUGUUCUU | 1157 | AAGAACAUGACUGGGUCCA | 1158 |
| NM_005080_680-698 | GGACCCAGUCAUGUUCUUC | 1159 | GAAGAACAUGACUGGGUCC | 1160 |
| NM_005080_682-700 | ACCCAGUCAUGUUCUUCAA | 1161 | UUGAAGAACAUGACUGGGU | 1162 |
| NM_005080_687-705 | GUCAUGUUCUUCAAAUGCC | 1163 | GGCAUUUGAAGAACAUGAC | 1164 |
| NM_005080_689-707 | CAUGUUCUUCAAAUGCCCU | 1165 | AGGGCAUUUGAAGAACAUG | 1166 |
| NM_005080_695-713 | CUUCAAAUGCCCUUCCCCA | 1167 | UGGGGAAGGGCAUUUGAAG | 1168 |
| NM_005080_696-714 | UUCAAAUGCCCUUCCCCAG | 1169 | CUGGGGAAGGGCAUUUGAA | 1170 |
| NM_005080_698-716 | CAAAUGCCCUUCCCCAGAG | 1171 | CUCUGGGGAAGGGCAUUUG | 1172 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_731-749 | GGAGCUCCCAGAGGUCUAC | 1173 | GUAGACCUCUGGGAGCUCC | 1174 |
| NM_005080_732-750 | GAGCUCCCAGAGGUCUACC | 1175 | GGUAGACCUCUGGGAGCUC | 1176 |
| NM_005080_733-751 | AGCUCCCAGAGGUCUACCC | 1177 | GGGUAGACCUCUGGGAGCU | 1178 |
| NM_005080_736-754 | UCCCAGAGGUCUACCCAGA | 1179 | UCUGGGUAGACCUCUGGGA | 1180 |
| NM_005080_737-755 | CCCAGAGGUCUACCCAGAA | 1181 | UUCUGGGUAGACCUCUGGG | 1182 |
| NM_005080_738-756 | CCAGAGGUCUACCCAGAAG | 1183 | CUUCUGGGUAGACCUCUGG | 1184 |
| NM_005080_740-758 | AGAGGUCUACCCAGAAGGA | 1185 | UCCUUCUGGGUAGACCUCU | 1186 |
| NM_005080_741-759 | GAGGUCUACCCAGAAGGAC | 1187 | GUCCUUCUGGGUAGACCUC | 1188 |
| NM_005080_742-760 | AGGUCUACCCAGAAGGACC | 1189 | GGUCCUUCUGGGUAGACCU | 1190 |
| NM_005080_743-761 | GGUCUACCCAGAAGGACCC | 1191 | GGGUCCUUCUGGGUAGACC | 1192 |
| NM_005080_748-766 | ACCCAGAAGGACCCAGUUC | 1193 | GAACUGGGUCCUUCUGGGU | 1194 |
| NM_005080_749-767 | CCCAGAAGGACCCAGUUCC | 1195 | GGAACUGGGUCCUUCUGGG | 1196 |
| NM_005080_750-768 | CCAGAAGGACCCAGUUCCU | 1197 | AGGAACUGGGUCCUUCUGG | 1198 |
| NM_005080_751-769 | CAGAAGGACCCAGUUCCUU | 1199 | AAGGAACUGGGUCCUUCUG | 1200 |
| NM_005080_752-770 | AGAAGGACCCAGUUCCUUA | 1201 | UAAGGAACUGGGUCCUUCU | 1202 |
| NM_005080_756-774 | GGACCCAGUUCCUUACCAG | 1203 | CUGGUAAGGAACUGGGUCC | 1204 |
| NM_005080_758-776 | ACCCAGUUCCUUACCAGCC | 1205 | GGCUGGUAAGGAACUGGGU | 1206 |
| NM_005080_759-777 | CCCAGUUCCUUACCAGCCU | 1207 | AGGCUGGUAAGGAACUGGG | 1208 |
| NM_005080_760-778 | CCAGUUCCUUACCAGCCUC | 1209 | GAGGCUGGUAAGGAACUGG | 1210 |
| NM_005080_761-779 | CAGUUCCUUACCAGCCUCC | 1211 | GGAGGCUGGUAAGGAACUG | 1212 |
| NM_005080_762-780 | AGUUCCUUACCAGCCUCCC | 1213 | GGGAGGCUGGUAAGGAACU | 1214 |
| NM_005080_767-785 | CUUACCAGCCUCCCUUUCU | 1215 | AGAAAGGGAGGCUGGUAAG | 1216 |
| NM_005080_769-787 | UACCAGCCUCCCUUUCUCU | 1217 | AGAGAAAGGGAGGCUGGUA | 1218 |
| NM_005080_773-791 | AGCCUCCCUUUCUCUGUCA | 1219 | UGACAGAGAAAGGGAGGCU | 1220 |
| NM_005080_779-797 | CCUUUCUCUGUCAGUGGGG | 1221 | CCCCACUGACAGAGAAAGG | 1222 |
| NM_005080_786-804 | CUGUCAGUGGGGACGUCAU | 1223 | AUGACGUCCCCACUGACAG | 1224 |
| NM_005080_787-805 | UGUCAGUGGGGACGUCAUC | 1225 | GAUGACGUCCCCACUGACA | 1226 |
| NM_005080_789-807 | UCAGUGGGGACGUCAUCAG | 1227 | CUGAUGACGUCCCCACUGA | 1228 |
| NM_005080_793-811 | UGGGGACGUCAUCAGCCAA | 1229 | UUGGCUGAUGACGUCCCCA | 1230 |
| NM_005080_795-813 | GGGACGUCAUCAGCCAAGC | 1231 | GCUUGGCUGAUGACGUCCC | 1232 |
| NM_005080_797-815 | GACGUCAUCAGCCAAGCUG | 1233 | CAGCUUGGCUGAUGACGUC | 1234 |
| NM_005080_798-816 | ACGUCAUCAGCCAAGCUGG | 1235 | CCAGCUUGGCUGAUGACGU | 1236 |
| NM_005080_800-818 | GUCAUCAGCCAAGCUGGAA | 1237 | UUCCAGCUUGGCUGAUGAC | 1238 |
| NM_005080_804-822 | UCAGCCAAGCUGGAAGCCA | 1239 | UGGCUUCCAGCUUGGCUGA | 1240 |
| NM_005080_806-824 | AGCCAAGCUGGAAGCCAUU | 1241 | AAUGGCUUCCAGCUUGGCU | 1242 |
| NM_005080_807-825 | GCCAAGCUGGAAGCCAUUA | 1243 | UAAUGGCUUCCAGCUUGGC | 1244 |

TABLE 8-continued

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_808-826 | CCAAGCUGGAAGCCAUUAA | 1245 | UUAAUGGCUUCCAGCUUGG | 1246 |
| NM_005080_809-827 | CAAGCUGGAAGCCAUUAAU | 1247 | AUUAAUGGCUUCCAGCUUG | 1248 |
| NM_005080_810-828 | AAGCUGGAAGCCAUUAAUG | 1249 | CAUUAAUGGCUUCCAGCUU | 1250 |
| NM_005080_811-829 | AGCUGGAAGCCAUUAAUGA | 1251 | UCAUUAAUGGCUUCCAGCU | 1252 |
| NM_005080_813-831 | CUGGAAGCCAUUAAUGAAC | 1253 | GUUCAUUAAUGGCUUCCAG | 1254 |
| NM_005080_814-832 | UGGAAGCCAUUAAUGAACU | 1255 | AGUUCAUUAAUGGCUUCCA | 1256 |
| NM_005080_818-836 | AGCCAUUAAUGAACUAAUU | 1257 | AAUUAGUUCAUUAAUGGCU | 1258 |
| NM_005080_820-838 | CCAUUAAUGAACUAAUUCG | 1259 | CGAAUUAGUUCAUUAAUGG | 1260 |
| NM_005080_837-855 | CGUUUUGACCACAUAUAUA | 1261 | UAUAUAUGUGGUCAAAACG | 1262 |
| NM_005080_844-862 | ACCACAUAUAUACCAAGCC | 1263 | GGCUUGGUAUAUAUGUGGU | 1264 |
| NM_005080_872-890 | AGAGAUACCCUCUGAGACA | 1265 | UGUCUCAGAGGGUAUCUCU | 1266 |
| NM_005080_873-891 | GAGAUACCCUCUGAGACAG | 1267 | CUGUCUCAGAGGGUAUCUC | 1268 |
| NM_005080_874-892 | AGAUACCCUCUGAGACAGA | 1269 | UCUGUCUCAGAGGGUAUCU | 1270 |
| NM_005080_876-894 | AUACCCUCUGAGACAGAGA | 1271 | UCUCUGUCUCAGAGGGUAU | 1272 |
| NM_005080_889-907 | CAGAGAGCCAAGCUAAUGU | 1273 | ACAUUAGCUUGGCUCUCUG | 1274 |
| NM_005080_890-908 | AGAGAGCCAAGCUAAUGUG | 1275 | CACAUUAGCUUGGCUCUCU | 1276 |
| NM_005080_897-915 | CAAGCUAAUGUGGUAGUGA | 1277 | UCACUACCACAUUAGCUUG | 1278 |
| NM_005080_898-916 | AAGCUAAUGUGGUAGUGAA | 1279 | UUCACUACCACAUUAGCUU | 1280 |
| NM_005080_901-919 | CUAAUGUGGUAGUGAAAAU | 1281 | AUUUUCACUACCACAUUAG | 1282 |
| NM_005080_903-921 | AAUGUGGUAGUGAAAAUCG | 1283 | CGAUUUUCACUACCACAUU | 1284 |
| NM_005080_904-922 | AUGUGGUAGUGAAAAUCGA | 1285 | UCGAUUUUCACUACCACAU | 1286 |
| NM_005080_906-924 | GUGGUAGUGAAAAUCGAGG | 1287 | CCUCGAUUUUCACUACCAC | 1288 |
| NM_005080_907-925 | UGGUAGUGAAAAUCGAGGA | 1289 | UCCUCGAUUUUCACUACCA | 1290 |
| NM_005080_910-928 | UAGUGAAAAUCGAGGAAGC | 1291 | GCUUCCUCGAUUUUCACUA | 1292 |
| NM_005080_913-931 | UGAAAAUCGAGGAAGCACC | 1293 | GGUGCUUCCUCGAUUUUCA | 1294 |
| NM_005080_916-934 | AAAUCGAGGAAGCACCUCU | 1295 | AGAGGUGCUUCCUCGAUUU | 1296 |
| NM_005080_918-936 | AUCGAGGAAGCACCUCUCA | 1297 | UGAGAGGUGCUUCCUCGAU | 1298 |
| NM_005080_919-937 | UCGAGGAAGCACCUCUCAG | 1299 | CUGAGAGGUGCUUCCUCGA | 1300 |
| NM_005080_920-938 | CGAGGAAGCACCUCUCAGC | 1301 | GCUGAGAGGUGCUUCCUCG | 1302 |
| NM_005080_922-940 | AGGAAGCACCUCUCAGCCC | 1303 | GGGCUGAGAGGUGCUUCCU | 1304 |
| NM_005080_923-941 | GGAAGCACCUCUCAGCCCC | 1305 | GGGGCUGAGAGGUGCUUCC | 1306 |
| NM_005080_929-947 | ACCUCUCAGCCCCUCAGAG | 1307 | CUCUGAGGGGCUGAGAGGU | 1308 |
| NM_005080_930-948 | CCUCUCAGCCCCUCAGAGA | 1309 | UCUCUGAGGGGCUGAGAGG | 1310 |
| NM_005080_931-949 | CUCUCAGCCCCUCAGAGAA | 1311 | UUCUCUGAGGGGCUGAGAG | 1312 |
| NM_005080_932-950 | UCUCAGCCCCUCAGAGAAU | 1313 | AUUCUCUGAGGGGCUGAGA | 1314 |
| NM_005080_933-951 | CUCAGCCCCUCAGAGAAUG | 1315 | CAUUCUCUGAGGGGCUGAG | 1316 |
| NM_005080_934-952 | UCAGCCCCUCAGAGAAUGA | 1317 | UCAUUCUCUGAGGGGCUGA | 1318 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_935-953 | CAGCCCCUCAGAGAAUGAU | 1319 | AUCAUUCUCUGAGGGGCUG | 1320 |
| NM_005080_936-954 | AGCCCCUCAGAGAAUGAUC | 1321 | GAUCAUUCUCUGAGGGGCU | 1322 |
| NM_005080_938-956 | CCCCUCAGAGAAUGAUCAC | 1323 | GUGAUCAUUCUCUGAGGGG | 1324 |
| NM_005080_941-959 | CUCAGAGAAUGAUCACCCU | 1325 | AGGGUGAUCAUUCUCUGAG | 1326 |
| NM_005080_942-960 | UCAGAGAAUGAUCACCCUG | 1327 | CAGGGUGAUCAUUCUCUGA | 1328 |
| NM_005080_943-961 | CAGAGAAUGAUCACCCUGA | 1329 | UCAGGGUGAUCAUUCUCUG | 1330 |
| NM_005080_944-962 | AGAGAAUGAUCACCCUGAA | 1331 | UUCAGGGUGAUCAUUCUCU | 1332 |
| NM_005080_946-964 | AGAAUGAUCACCCUGAAUU | 1333 | AAUUCAGGGUGAUCAUUCU | 1334 |
| NM_005080_947-965 | GAAUGAUCACCCUGAAUUC | 1335 | GAAUUCAGGGUGAUCAUUC | 1336 |
| NM_005080_948-966 | AAUGAUCACCCUGAAUUCA | 1337 | UGAAUUCAGGGUGAUCAUU | 1338 |
| NM_005080_949-967 | AUGAUCACCCUGAAUUCAU | 1339 | AUGAAUUCAGGGUGAUCAU | 1340 |
| NM_005080_955-973 | ACCCUGAAUUCAUUGUCUC | 1341 | GAGACAAUGAAUUCAGGGU | 1342 |
| NM_005080_956-974 | CCCUGAAUUCAUUGUCUCA | 1343 | UGAGACAAUGAAUUCAGGG | 1344 |
| NM_005080_957-975 | CCUGAAUUCAUUGUCUCAG | 1345 | CUGAGACAAUGAAUUCAGG | 1346 |
| NM_005080_960-978 | GAAUUCAUUGUCUCAGUGA | 1347 | UCACUGAGACAAUGAAUUC | 1348 |
| NM_005080_961-979 | AAUUCAUUGUCUCAGUGAA | 1349 | UUCACUGAGACAAUGAAUU | 1350 |
| NM_005080_965-983 | CAUUGUCUCAGUGAAGGAA | 1351 | UUCCUUCACUGAGACAAUG | 1352 |
| NM_005080_967-985 | UUGUCUCAGUGAAGGAAGA | 1353 | UCUUCCUUCACUGAGACAA | 1354 |
| NM_005080_968-986 | UGUCUCAGUGAAGGAAGAA | 1355 | UUCUUCCUUCACUGAGACA | 1356 |
| NM_005080_971-989 | CUCAGUGAAGGAAGAACCU | 1357 | AGGUUCUUCCUUCACUGAG | 1358 |
| NM_005080_972-990 | UCAGUGAAGGAAGAACCUG | 1359 | CAGGUUCUUCCUUCACUGA | 1360 |
| NM_005080_973-991 | CAGUGAAGGAAGAACCUGU | 1361 | ACAGGUUCUUCCUUCACUG | 1362 |
| NM_005080_980-998 | GGAAGAACCUGUAGAAGAU | 1363 | AUCUUCUACAGGUUCUUCC | 1364 |
| NM_005080_984-1002 | GAACCUGUAGAAGAUGACC | 1365 | GGUCAUCUUCUACAGGUUC | 1366 |
| NM_005080_986-1004 | ACCUGUAGAAGAUGACCUC | 1367 | GAGGUCAUCUUCUACAGGU | 1368 |
| NM_005080_1023-1041 | UCAAAUCUGCUUUCAUCCA | 1369 | UGGAUGAAAGCAGAUUUGA | 1370 |
| NM_005080_1151-1169 | UUCUUGGGAGGACACUUUU | 1371 | AAAAGUGUCCUCCCAAGAA | 1372 |
| NM_005080_1367-1385 | UCUUUUGACAUCCAGCAGU | 1373 | ACUGCUGGAUGUCAAAAGA | 1374 |
| NM_005080_1414-1432 | UAAGAAAUAUUACUAUAAU | 1375 | AUUAUAGUAAUAUUUCUUA | 1376 |
| NM_005080_1415-1433 | AAGAAAUAUUACUAUAAUU | 1377 | AAUUAUAGUAAUAUUUCUU | 1378 |
| NM_005080_1674-1692 | ACUUCAAGUAAGAUCAAGA | 1379 | UCUUGAUCUUACUUGAAGU | 1380 |
| NM_005080_1675-1693 | CUUCAAGUAAGAUCAAGAA | 1381 | UUCUUGAUCUUACUUGAAG | 1382 |
| NM_005080_330-348 | AAUGAGUGAGCUGGAACAG | 1383 | CUGUUCCAGCUCACUCAUU | 1384 |
| NM_005080_333-351 | GAGUGAGCUGGAACAGCAA | 1385 | UUGCUGUUCCAGCUCACUC | 1386 |
| NM_005080_592-610 | CCCCUCCAGAACAUCUCCC | 1387 | GGGAGAUGUUCUGGAGGGG | 1388 |
| NM_005080_665-683 | CAUUCUGGACAACUUGGAC | 1389 | GUCCAAGUUGUCCAGAAUG | 1390 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_815-833 | GGAAGCCAUUAAUGAACUA | 1391 | UAGUUCAUUAAUGGCUUCC | 1392 |
| NM_005080_1029-1047 | CUGCUUUCAUCCAGCCACU | 1393 | AGUGGCUGGAUGAAAGCAG | 1394 |
| NM_005080_1077-1095 | GCUUACAGUGACUGUGGAU | 1395 | AUCCACAGUCACUGUAAGC | 1396 |
| NM_005080_1222-1240 | GUUGCCCUUUUCCUUGACU | 1397 | AGUCAAGGAAAAGGGCAAC | 1398 |
| NM_005080_1285-1303 | UUCAAAAAGCCAAAAUAGA | 1399 | UCUAUUUUGGCUUUUUGAA | 1400 |
| NM_005080_1334-1352 | UGUUCAGAUCUCAUAGAUG | 1401 | CAUCUAUGAGAUCUGAACA | 1402 |
| NM_005080_1335-1353 | GUUCAGAUCUCAUAGAUGA | 1403 | UCAUCUAUGAGAUCUGAAC | 1404 |
| NM_005080_1436-1454 | GAACUACAGCUUUUAAGAU | 1405 | AUCUUAAAAGCUGUAGUUC | 1406 |
| NM_005080_1449-1467 | UAAGAUUGUACUUUUAUCU | 1407 | AGAUAAAAGUACAAUCUUA | 1408 |
| NM_005080_1450-1468 | AAGAUUGUACUUUUAUCUU | 1409 | AAGAUAAAAGUACAAUCUU | 1410 |
| NM_005080_114-132 | GCAGCCCGCCUCCGCCGCC | 1411 | GGCGGCGGAGGCGGGCUGC | 1412 |
| NM_005080_1555-1573 | UUCUUUAUCAUUUCUCUUC | 1413 | GAAGAGAAAUGAUAAAGAA | 1414 |
| NM_005080_1556-1574 | UCUUUAUCAUUUCUCUCC | 1415 | GGAAGAGAAAUGAUAAAGA | 1416 |
| NM_005080_1561-1579 | AUCAUUUCUCUUCCCCCUU | 1417 | AAGGGGGAAGAGAAAUGAU | 1418 |
| NM_005080_1562-1580 | UCAUUUCUCUUCCCCCUUU | 1419 | AAAGGGGAAGAGAAAUGA | 1420 |
| NM_005080_1569-1587 | UCUUCCCCCUUUUUGGCAU | 1421 | AUGCCAAAAGGGGGAAGA | 1422 |
| NM_005080_1588-1606 | CCUGGCUUGCCUCCAGUUU | 1423 | AAACUGGAGGCAAGCCAGG | 1424 |
| NM_005080_1640-1658 | AACACCUGCUGAGGGGCU | 1425 | AGCCCCCUCAGCAGGUGUU | 1426 |
| NM_005080_1641-1659 | ACACCUGCUGAGGGGCUC | 1427 | GAGCCCCUCAGCAGGUGU | 1428 |
| NM_005080_1642-1660 | CACCUGCUGAGGGGCUCU | 1429 | AGAGCCCCUCAGCAGGUG | 1430 |
| NM_005080_1650-1668 | GAGGGGGCUCUUUCCCUCA | 1431 | UGAGGGAAAGAGCCCCCUC | 1432 |
| NM_005080_1686-1704 | AUCAAGAAUCUUUUGUGAA | 1433 | UUCACAAAAGAUUCUUGAU | 1434 |
| NM_005080_1745-1763 | UCCUGCUAGUGUAGCUUCU | 1435 | AGAAGCUACACUAGCAGGA | 1436 |
| NM_005080_138-156 | CCCGGCCGGCCAGGCCCUG | 1437 | CAGGGCCUGGCCGGCCGGG | 1438 |
| NM_005080_145-163 | GGCCAGGCCCUGCCGCUCA | 1439 | UGAGCGGCAGGGCCUGGCC | 1440 |
| NM_005080_190-208 | CCGGAGGCAGCGAGCGGGG | 1441 | CCCCGCUCGCUGCCUCCGG | 1442 |
| NM_005080_191-209 | CGGAGGCAGCGAGCGGGGG | 1443 | CCCCCGCUCGCUGCCUCCG | 1444 |
| NM_005080_192-210 | GGAGGCAGCGAGCGGGGGG | 1445 | CCCCCCGCUCGCUGCCUCC | 1446 |
| NM_005080_259-277 | GAGAAGGCGCUGAGGAGGA | 1447 | UCCUCCUCAGCGCCUUCUC | 1448 |
| NM_005080_261-279 | GAAGGCGCUGAGGAGGAAA | 1449 | UUUCCUCCUCAGCGCCUUC | 1450 |
| NM_005080_289-307 | AGAGUAGCAGCUCAGACUG | 1451 | CAGUCUGAGCUGCUACUCU | 1452 |
| NM_005080_363-381 | AGAAGAAGAACCAAAAA | 1453 | TTTTTGGTTCTCTTCTTCT | 1454 |
| NM_005080_365-383 | AAGAAGAGAACCAAAAACU | 1455 | AGUUUUUGGUUCUCUUCUU | 1456 |
| NM_005080_385-403 | UUGCUAGAAAAUCAGCUUU | 1457 | AAAGCUGAUUUUCUAGCAA | 1458 |
| NM_005080_461-479 | GGAUGGAUGCCCUGGUUGC | 1459 | GCAACCAGGGCAUCCAUCC | 1460 |
| NM_005080_490-508 | GCGGAAGCCAAGGGGAAUG | 1461 | CAUUCCCCUUGGCUUCCGC | 1462 |
| NM_005080_518-536 | CAGUGGCCGGGUCUGCUGA | 1463 | UCAGCAGACCCGGCCACUG | 1464 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_673-691 | ACAACUUGGACCCAGUCAU | 1465 | AUGACUGGGUCCAAGUUGU | 1466 |
| NM_005080_685-703 | CAGUCAUGUUCUUCAAAUG | 1467 | CAUUUGAAGAACAUGACUG | 1468 |
| NM_005080_730-748 | AGGAGCUCCCAGAGGUCUA | 1469 | UAGACCUCUGGGAGCUCCU | 1470 |
| NM_005080_772-790 | CAGCCUCCCUUUCUCUGUC | 1471 | GACAGAGAAAGGGAGGCUG | 1472 |
| NM_005080_801-819 | UCAUCAGCCAAGCUGGAAG | 1473 | CUUCCAGCUUGGCUGAUGA | 1474 |
| NM_005080_817-835 | AAGCCAUUAAUGAACUAAU | 1475 | AUUAGUUCAUUAAUGGCUU | 1476 |
| NM_005080_887-905 | GACAGAGAGCCAAGCUAAU | 1477 | AUUAGCUUGGCUCUCUGUC | 1478 |
| NM_005080_924-942 | GAAGCACCUCUCAGCCCCU | 1479 | AGGGGCUGAGAGGUGCUUC | 1480 |
| NM_005080_927-945 | GCACCUCUCAGCCCCUCAG | 1481 | CUGAGGGGCUGAGAGGUGC | 1482 |
| NM_005080_928-946 | CACCUCUCAGCCCCUCAGA | 1483 | UCUGAGGGGCUGAGAGGUG | 1484 |
| NM_005080_974-992 | AGUGAAGGAAGAACCUGUA | 1485 | UACAGGUUCUUCCUUCACU | 1486 |
| NM_005080_985-1003 | AACCUGUAGAAGAUGACCU | 1487 | AGGUCAUCUUCUACAGGUU | 1488 |
| NM_005080_187-205 | AGCCGGAGGCAGCGAGCG | 1489 | CGCTCGCTGCCTCCGGGCT | 1490 |
| NM_005080_672-690 | GACAACUUGGACCCAGUCA | 1491 | UGACUGGGUCCAAGUUGUC | 1492 |
| NM_005080_771-789 | CCAGCCUCCCUUUCUCUGU | 1493 | ACAGAGAAAGGGAGGCUGG | 1494 |
| NM_005080_1740-1758 | UUUUUUCCUGCUAGUGUAG | 1495 | CUACACUAGCAGGAAAAAA | 1496 |
| NM_005080_1741-1759 | UUUUUCCUGCUAGUGUAGC | 1497 | GCUACACUAGCAGGAAAAA | 1498 |
| NM_005080_662-680 | GGGCAUUCUGGACAACUUG | 1499 | CAAGUUGUCCAGAAUGCCC | 1500 |
| NM_005080_1070-1088 | ACUGGAUGCUUACAGUGAC | 1501 | GUCACUGUAAGCAUCCAGU | 1502 |
| NM_005080_631-649 | ACUCUUCAGAUUCAGAGUC | 1503 | GACUCUGAAUCUGAAGAGU | 1504 |
| NM_005080_647-665 | GUCUGAUAUCCUGUUGGGC | 1505 | GCCCAACAGGAUAUCAGAC | 1506 |
| NM_005080_791-809 | AGUGGGGACGUCAUCAGCC | 1507 | GGCUGAUGACGUCCCCACU | 1508 |
| NM_005080_981-999 | GAAGAACCUGUAGAAGAUG | 1509 | CAUCUUCUACAGGUUCUUC | 1510 |
| NM_005080_1068-1086 | CUACUGGAUGCUUACAGUG | 1511 | CACUGUAAGCAUCCAGUAG | 1512 |
| NM_005080_1391-1409 | GUAUUGAGACAUAUUACUG | 1513 | CAGUAAUAUGUCUCAAUAC | 1514 |
| NM_005080_1426-1444 | CUAUAAUUGAGAACUACAG | 1515 | CUGUAGUUCUCAAUUAUAG | 1516 |
| NM_005080_103-121 | CUUCUGUCGGGGCAGCCCG | 1517 | CGGGCUGCCCCGACAGAAG | 1518 |
| NM_005080_1457-1475 | UACUUUUAUCUUAAAAGGG | 1519 | CCCUUUUAAGAUAAAAGUA | 1520 |
| NM_005080_1568-1586 | CUCUUCCCCCUUUUUGGCA | 1521 | UGCCAAAAAGGGGGAAGAG | 1522 |
| NM_005080_1574-1592 | CCCCUUUUUGGCAUCCUGG | 1523 | CCAGGAUGCCAAAAAGGGG | 1524 |
| NM_005080_1577-1595 | CUUUUUGGCAUCCUGGCUU | 1525 | AAGCCAGGAUGCCAAAAAG | 1526 |
| NM_005080_1730-1748 | CUUGAUGGAAUUUUUUCCU | 1527 | AGGAAAAAAUUCCAUCAAG | 1528 |
| NM_005080_1731-1749 | UUGAUGGAAUUUUUUCCUG | 1529 | CAGGAAAAAAUUCCAUCAA | 1530 |
| NM_005080_1732-1750 | UGAUGGAAUUUUUUCCUGC | 1531 | GCAGGAAAAAAUUCCAUCA | 1532 |
| NM_005080_293-311 | UAGCAGCUCAGACUGCCAG | 1533 | CUGGCAGUCUGAGCUGCUA | 1534 |
| NM_005080_350-368 | AAGUGGUAGAUUUAGAAGA | 1535 | UCUUCUAAAUCUACCACUU | 1536 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_351-369 | AGUGGUAGAUUUAGAAGAA | 1537 | UUCUUCUAAAUCUACCACU | 1538 |
| NM_005080_630-648 | GACUCUUCAGAUUCAGAGU | 1539 | ACUCUGAAUCUGAAGAGUC | 1540 |
| NM_005080_657-675 | CUGUUGGGCAUUCUGGACA | 1541 | UGUCCAGAAUGCCCAACAG | 1542 |
| NM_005080_670-688 | UGGACAACUUGGACCCAGU | 1543 | ACUGGGUCCAAGUUGUCCA | 1544 |
| NM_005080_692-710 | GUUCUUCAAAUGCCCUUCC | 1545 | GGAAGGGCAUUUGAAGAAC | 1546 |
| NM_005080_778-796 | CCCUUUCUCUGUCAGUGGG | 1547 | CCCACUGACAGAGAAAGGG | 1548 |
| NM_005080_790-808 | CAGUGGGGACGUCAUCAGC | 1549 | GCUGAUGACGUCCCCACUG | 1550 |
| NM_005080_970-988 | UCUCAGUGAAGGAAGAACC | 1551 | GGUUCUUCCUUCACUGAGA | 1552 |
| NM_005080_1162-1180 | ACACUUUUGCCAAUGAACU | 1553 | AGUUCAUUGGCAAAAGUGU | 1554 |
| NM_005080_1368-1386 | CUUUUGACAUCCAGCAGUC | 1555 | GACUGCUGGAUGUCAAAAG | 1556 |
| NM_005080_1515-1533 | UAGACAAAUGUCUUGAAGU | 1557 | ACUUCAAGACAUUUGUCUA | 1558 |
| NM_005080_1541-1559 | GAAUUUAUGAAUGGUUCUU | 1559 | AAGAACCAUUCAUAAAUUC | 1560 |
| NM_005080_1542-1560 | AAUUUAUGAAUGGUUCUUU | 1561 | AAAGAACCAUUCAUAAAUU | 1562 |
| NM_005080_1571-1589 | UUCCCCCUUUUUGGCAUCC | 1563 | GGAUGCCAAAAAGGGGGAA | 1564 |
| NM_005080_151-169 | GCCCUGCCGCUCAUGGUGC | 1565 | GCACCAUGAGCGGCAGGGC | 1566 |
| NM_005080_160-178 | CUCAUGGUGCCAGCCCAGA | 1567 | UCUGGGCUGGCACCAUGAG | 1568 |
| NM_005080_326-344 | CUCGAAUGAGUGAGCUGGA | 1569 | UCCAGCUCACUCAUUCGAG | 1570 |
| NM_005080_327-345 | UCGAAUGAGUGAGCUGGAA | 1571 | UUCCAGCUCACUCAUUCGA | 1572 |
| NM_005080_331-349 | AUGAGUGAGCUGGAACAGC | 1573 | GCUGUUCCAGCUCACUCAU | 1574 |
| NM_005080_424-442 | CUUGUAGUUGAGAACCAGG | 1575 | CCUGGUUCUCAACUACAAG | 1576 |
| NM_005080_483-501 | AGAGGAGGCGGAAGCCAAG | 1577 | CTTGGCTTCCGCCTCCTCT | 1578 |
| NM_005080_579-597 | GGCCCAGUUGUCACCCCUC | 1579 | GAGGGGUGACAACUGGGCC | 1580 |
| NM_005080_745-763 | UCUACCCAGAAGGACCCAG | 1581 | CUGGGUCCUUCUGGGUAGA | 1582 |
| NM_005080_746-764 | CUACCCAGAAGGACCCAGU | 1583 | ACUGGGUCCUUCUGGGUAG | 1584 |
| NM_005080_812-830 | GCUGGAAGCCAUUAAUGAA | 1585 | UUCAUUAAUGGCUUCCAGC | 1586 |
| NM_005080_871-889 | UAGAGAUACCCUCUGAGAC | 1587 | GUCUCAGAGGGUAUCUCUA | 1588 |
| NM_005080_892-910 | AGAGCCAAGCUAAUGUGGU | 1589 | ACCACAUUAGCUUGGCUCU | 1590 |
| NM_005080_978-996 | AAGGAAGAACCUGUAGAAG | 1591 | CUUCUACAGGUUCUUCCUU | 1592 |
| NM_005080_982-1000 | AAGAACCUGUAGAAGAUGA | 1593 | UCAUCUUCUACAGGUUCUU | 1594 |
| NM_005080_257-275 | AGGAGAAGGCGCUGAGGAG | 1595 | CUCCUCAGCGCCUUCUCCU | 1596 |
| NM_005080_364-382 | GAAGAAGAGAACCAAAAAC | 1597 | GTTTTTGGTTCTCTTCTTC | 1598 |
| NM_005080_816-834 | GAAGCCAUUAAUGAACUAA | 1599 | UUAGUUCAUUAAUGGCUUC | 1600 |
| NM_005080_884-902 | UGAGACAGAGAGCCAAGCU | 1601 | AGCUUGGCUCUCUGUCUCA | 1602 |
| NM_005080_925-943 | AAGCACCUCUCAGCCCCUC | 1603 | GAGGGGCUGAGAGGUGCUU | 1604 |
| NM_005080_1440-1458 | UACAGCUUUUAAGAUUGUA | 1605 | UACAAUCUUAAAAGCUGUA | 1606 |
| NM_005080_784-802 | CUCUGUCAGUGGGGACGUC | 1607 | GACGUCCCCACUGACAGAG | 1608 |
| NM_005080_1593-1611 | CUUGCCUCCAGUUUUAGGU | 1609 | ACCUAAAACUGGAGGCAAG | 1610 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_301-319 | CAGACUGCCAGAGAUCGAA | 1611 | UUCGAUCUCUGGCAGUCUG | 1612 |
| NM_005080_674-692 | CAACUUGGACCCAGUCAUG | 1613 | CAUGACUGGGUCCAAGUUG | 1614 |
| NM_005080_783-801 | UCUCUGUCAGUGGGGACGU | 1615 | ACGUCCCCACUGACAGAGA | 1616 |
| NM_005080_921-939 | GAGGAAGCACCUCUCAGCC | 1617 | GGCUGAGAGGUGCUUCCUC | 1618 |
| NM_005080_1226-1244 | CCCUUUUCCUUGACUAUUA | 1619 | UAAUAGUCAAGGAAAAGGG | 1620 |
| NM_005080_1283-1301 | CAUUCAAAAAGCCAAAAUA | 1621 | UAUUUUGGCUUUUUGAAUG | 1622 |
| NM_005080_1416-1434 | AGAAAUAUUACUAUAAUUG | 1623 | CAAUUAUAGUAAUAUUUCU | 1624 |
| NM_005080_1420-1438 | AUAUUACUAUAAUUGAGAA | 1625 | UUCUCAAUUAUAGUAAUAU | 1626 |
| NM_005080_1488-1506 | CUAAAAUACUUAUUAUGUA | 1627 | UACAUAAUAAGUAUUUUAG | 1628 |
| NM_005080_1492-1510 | AAUACUUAUUAUGUAAGGG | 1629 | CCCUUACAUAAUAAGUAUU | 1630 |
| NM_005080_111-129 | GGGGCAGCCCGCCUCCGCC | 1631 | GGCGGAGGCGGGCUGCCCC | 1632 |
| NM_005080_1639-1657 | GAACACCUGCUGAGGGGGC | 1633 | GCCCCCUCAGCAGGUGUUC | 1634 |
| NM_005080_1685-1703 | GAUCAAGAAUCUUUUGUGA | 1635 | UCACAAAAGAUUCUUGAUC | 1636 |
| NM_005080_1733-1751 | GAUGGAAUUUUUUCCUGCU | 1637 | AGCAGGAAAAAAUUCCAUC | 1638 |
| NM_005080_1734-1752 | AUGGAAUUUUUUCCUGCUA | 1639 | UAGCAGGAAAAAAUUCCAU | 1640 |
| NM_005080_1737-1755 | GAAUUUUUUCCUGCUAGUG | 1641 | CACUAGCAGGAAAAAAUUC | 1642 |
| NM_005080_1756-1774 | UAGCUUCUGAAAGGUGCUU | 1643 | AAGCACCUUUCAGAAGCUA | 1644 |
| NM_005080_1757-1775 | AGCUUCUGAAAGGUGCUUU | 1645 | AAAGCACCUUUCAGAAGCU | 1646 |
| NM_005080_152-170 | CCCUGCCGCUCAUGGUGCC | 1647 | GGCACCAUGAGCGGCAGGG | 1648 |
| NM_005080_153-171 | CCUGCCGCUCAUGGUGCCA | 1649 | UGGCACCAUGAGCGGCAGG | 1650 |
| NM_005080_163-181 | AUGGUGCCAGCCCAGAGAG | 1651 | CUCUCUGGGCUGGCACCAU | 1652 |
| NM_005080_167-185 | UGCCAGCCCAGAGAGGGGC | 1653 | GCCCCUCUCUGGGCUGGCA | 1654 |
| NM_005080_200-218 | CGAGCGGGGGGCUGCCCCA | 1655 | UGGGGCAGCCCCCCGCUCG | 1656 |
| NM_005080_252-270 | CCCCGAGGAGAAGGCGCUG | 1657 | CAGCGCCUUCUCCUCGGGG | 1658 |
| NM_005080_255-273 | CGAGGAGAAGGCGCUGAGG | 1659 | CCUCAGCGCCUUCUCCUCG | 1660 |
| NM_005080_260-278 | AGAAGGCGCUGAGGAGGAA | 1661 | UUCCUCCUCAGCGCCUUCU | 1662 |
| NM_005080_271-289 | AGGAGGAAACUGAAAAACA | 1663 | UGUUUUUCAGUUUCCUCCU | 1664 |
| NM_005080_297-315 | AGCUCAGACUGCCAGAGAU | 1665 | AUCUCUGGCAGUCUGAGCU | 1666 |
| NM_005080_300-318 | UCAGACUGCCAGAGAUCGA | 1667 | UCGAUCUCUGGCAGUCUGA | 1668 |
| NM_005080_335-353 | GUGAGCUGGAACAGCAAGU | 1669 | ACUUGCUGUUCCAGCUCAC | 1670 |
| NM_005080_368-386 | AAGAGAACCAAAAACUUUU | 1671 | AAAAGUUUUUGGUUCUCUU | 1672 |
| NM_005080_378-396 | AAAACUUUUGCUAGAAAAU | 1673 | AUUUUCUAGCAAAAGUUUU | 1674 |
| NM_005080_379-397 | AAACUUUUGCUAGAAAAUC | 1675 | GAUUUUCUAGCAAAAGUUU | 1676 |
| NM_005080_380-398 | AACUUUUGCUAGAAAAUCA | 1677 | UGAUUUUCUAGCAAAAGUU | 1678 |
| NM_005080_389-407 | UAGAAAAUCAGCUUUUACG | 1679 | CGUAAAAGCUGAUUUUCUA | 1680 |
| NM_005080_426-444 | UGUAGUUGAGAACCAGGAG | 1681 | CUCCUGGUUCUCAACUACA | 1682 |

TABLE 8-continued

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_427-445 | GUAGUUGAGAACCAGGAGU | 1683 | ACUCCUGGUUCUCAACUAC | 1684 |
| NM_005080_485-503 | AGGAGGCGGAAGCCAAGGG | 1685 | CCCUUGGCUUCCGCCUCCU | 1686 |
| NM_005080_487-505 | GAGGCGGAAGCCAAGGGGA | 1687 | TCCCCUUGGCUUCCGCCUC | 1688 |
| NM_005080_488-506 | AGGCGGAAGCCAAGGGGAA | 1689 | TTCCCCUUGGCUUCCGCCU | 1690 |
| NM_005080_511-529 | GUGAGGCCAGUGGCCGGGU | 1691 | ACCCGGCCACUGGCCUCAC | 1692 |
| NM_005080_526-544 | GGGUCUGCUGAGUCCGCAG | 1693 | CUGCGGACUCAGCAGACCC | 1694 |
| NM_005080_575-593 | UGCAGGCCCAGUUGUCACC | 1695 | GGUGACAACUGGGCCUGCA | 1696 |
| NM_005080_593-611 | CCCUCCAGAACAUCUCCCC | 1697 | GGGGAGAUGUUCUGGAGGG | 1698 |
| NM_005080_595-613 | CUCCAGAACAUCUCCCCAU | 1699 | AUGGGGAGAUGUUCUGGAG | 1700 |
| NM_005080_654-672 | AUCCUGUUGGGCAUUCUGG | 1701 | CCAGAAUGCCCAACAGGAU | 1702 |
| NM_005080_675-693 | AACUUGGACCCAGUCAUGU | 1703 | ACAUGACUGGGUCCAAGUU | 1704 |
| NM_005080_683-701 | CCCAGUCAUGUUCUUCAAA | 1705 | UUUGAAGAACAUGACUGGG | 1706 |
| NM_005080_684-702 | CCAGUCAUGUUCUUCAAAU | 1707 | AUUUGAAGAACAUGACUGG | 1708 |
| NM_005080_693-711 | UUCUUCAAAUGCCCUUCCC | 1709 | GGGAAGGGCAUUUGAAGAA | 1710 |
| NM_005080_694-712 | UCUUCAAAUGCCCUUCCCC | 1711 | GGGGAAGGGCAUUUGAAGA | 1712 |
| NM_005080_726-744 | CUGGAGGAGCUCCCAGAGG | 1713 | CCUCUGGGAGCUCCUCCAG | 1714 |
| NM_005080_744-762 | GUCUACCCAGAAGGACCCA | 1715 | UGGGUCCUUCUGGGUAGAC | 1716 |
| NM_005080_765-783 | UCCUUACCAGCCUCCCUUU | 1717 | AAAGGGAGGCUGGUAAGGA | 1718 |
| NM_005080_768-786 | UUACCAGCCUCCCUUUCUC | 1719 | GAGAAAGGGAGGCUGGUAA | 1720 |
| NM_005080_777-795 | UCCCUUUCUCUGUCAGUGG | 1721 | CCACUGACAGAGAAAGGGA | 1722 |
| NM_005080_802-820 | CAUCAGCCAAGCUGGAAGC | 1723 | GCUUCCAGCUUGGCUGAUG | 1724 |
| NM_005080_877-895 | UACCCUCUGAGACAGAGAG | 1725 | CUCUCUGUCUCAGAGGGUA | 1726 |
| NM_005080_878-896 | ACCCUCUGAGACAGAGAGC | 1727 | GCUCUCUGUCUCAGAGGGU | 1728 |
| NM_005080_885-903 | GAGACAGAGAGCCAAGCUA | 1729 | UAGCUUGGCUCUCUGUCUC | 1730 |
| NM_005080_886-904 | AGACAGAGAGCCAAGCUAA | 1731 | UUAGCUUGGCUCUCUGUCU | 1732 |
| NM_005080_966-984 | AUUGUCUCAGUGAAGGAAG | 1733 | CUUCCUUCACUGAGACAAU | 1734 |
| NM_005080_969-987 | GUCUCAGUGAAGGAAGAAC | 1735 | GUUCUUCCUUCACUGAGAC | 1736 |
| NM_005080_1245-1263 | CACUGCCUGGAGGAUAGCA | 1737 | UGCUAUCCUCCAGGCAGUG | 1738 |
| NM_005080_1738-1756 | AAUUUUUUCCUGCUAGUGU | 1739 | ACACUAGCAGGAAAAAAUU | 1740 |
| NM_005080_194-212 | AGGCAGCGAGCGGGGGCU | 1741 | AGCCCCCGCUCGCUGCCU | 1742 |
| NM_005080_209-227 | GGCUGCCCCAGGCGCGCAA | 1743 | UUGCGCGCCUGGGGCAGCC | 1744 |
| NM_005080_269-287 | UGAGGAGGAAACUGAAAAA | 1745 | UUUUUCAGUUUCCUCCUCA | 1746 |
| NM_005080_902-920 | UAAUGUGGUAGUGAAAAUC | 1747 | GAUUUUCACUACCACAUUA | 1748 |
| NM_005080_50-68 | UGGUGGUGGUGGCAGCCGC | 1749 | GCGGCUGCCACCACCACCA | 1750 |
| NM_005080_1017-1035 | GGUAUCUCAAAUCUGCUUU | 1751 | AAAGCAGAUUUGAGAUACC | 1752 |
| NM_005080_1021-1039 | UCUCAAAUCUGCUUUCAUC | 1753 | GAUGAAAGCAGAUUUGAGA | 1754 |
| NM_005080_1022-1040 | CUCAAAUCUGCUUUCAUCC | 1755 | GGAUGAAAGCAGAUUUGAG | 1756 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_1062-1080 | UCCUGCCUACUGGAUGCUU | 1757 | AAGCAUCCAGUAGGCAGGA | 1758 |
| NM_005080_1074-1092 | GAUGCUUACAGUGACUGUG | 1759 | CACAGUCACUGUAAGCAUC | 1760 |
| NM_005080_1116-1134 | UUCAGUGACAUGUCCUCUC | 1761 | GAGAGGACAUGUCACUGAA | 1762 |
| NM_005080_1149-1167 | CAUUCUUGGGAGGACACUU | 1763 | AAGUGUCCUCCCAAGAAUG | 1764 |
| NM_005080_1150-1168 | AUUCUUGGGAGGACACUUU | 1765 | AAAGUGUCCUCCCAAGAAU | 1766 |
| NM_005080_1161-1179 | GACACUUUUGCCAAUGAAC | 1767 | GUUCAUUGGCAAAAGUGUC | 1768 |
| NM_005080_1223-1241 | UUGCCCUUUUCCUUGACUA | 1769 | UAGUCAAGGAAAAGGGCAA | 1770 |
| NM_005080_1280-1298 | CUUCAUUCAAAAAGCCAAA | 1771 | UUUGGCUUUUUGAAUGAAG | 1772 |
| NM_005080_1281-1299 | UUCAUUCAAAAAGCCAAAA | 1773 | UUUUGGCUUUUUGAAUGAA | 1774 |
| NM_005080_1284-1302 | AUUCAAAAAGCCAAAAUAG | 1775 | CUAUUUUGGCUUUUUGAAU | 1776 |
| NM_005080_1286-1304 | UCAAAAAGCCAAAAUAGAG | 1777 | CUCUAUUUUGGCUUUUUGA | 1778 |
| NM_005080_1288-1306 | AAAAAGCCAAAAUAGAGAG | 1779 | CUCUCUAUUUUGGCUUUUU | 1780 |
| NM_005080_1365-1383 | UGUCUUUUGACAUCCAGCA | 1781 | UGCUGGAUGUCAAAAGACA | 1782 |
| NM_005080_1417-1435 | GAAAUAUUACUAUAAUUGA | 1783 | UCAAUUAUAGUAAUAUUUC | 1784 |
| NM_005080_1421-1439 | UAUUACUAUAAUUGAGAAC | 1785 | GUUCUCAAUUAUAGUAAUA | 1786 |
| NM_005080_1434-1452 | GAGAACUACAGCUUUUAAG | 1787 | CUUAAAAGCUGUAGUUCUC | 1788 |
| NM_005080_1452-1470 | GAUUGUACUUUUAUCUUAA | 1789 | UUAAGAUAAAAGUACAAUC | 1790 |
| NM_005080_105-123 | UCUGUCGGGGCAGCCCGCC | 1791 | GGCGGGCUGCCCCGACAGA | 1792 |
| NM_005080_1455-1473 | UGUACUUUUAUCUUAAAAG | 1793 | CUUUUAAGAUAAAAGUACA | 1794 |
| NM_005080_112-130 | GGGCAGCCCGCCUCCGCCG | 1795 | CGGCGGAGGCGGGCUGCCC | 1796 |
| NM_005080_113-131 | GGCAGCCCGCCUCCGCCGC | 1797 | GCGGCGGAGGCGGGCUGCC | 1798 |
| NM_005080_1543-1561 | AUUUAUGAAUGGUUCUUUA | 1799 | UAAAGAACCAUUCAUAAAU | 1800 |
| NM_005080_1544-1562 | UUUAUGAAUGGUUCUUUAU | 1801 | AUAAAGAACCAUUCAUAAA | 1802 |
| NM_005080_1557-1575 | CUUUAUCAUUUCUCUUCCC | 1803 | GGGAAGAGAAAUGAUAAAG | 1804 |
| NM_005080_115-133 | CAGCCCGCCUCCGCCGCCG | 1805 | CGGCGGCGGAGGCGGGCUG | 1806 |
| NM_005080_1564-1582 | AUUUCUCUUCCCCCUUUUU | 1807 | AAAAAGGGGGAAGAGAAAU | 1808 |
| NM_005080_1572-1590 | UCCCCCUUUUUGGCAUCCU | 1809 | AGGAUGCCAAAAAGGGGGA | 1810 |
| NM_005080_1575-1593 | CCCUUUUUGGCAUCCUGGC | 1811 | GCCAGGAUGCCAAAAAGGG | 1812 |
| NM_005080_1576-1594 | CCUUUUUGGCAUCCUGGCU | 1813 | AGCCAGGAUGCCAAAAAGG | 1814 |
| NM_005080_117-135 | GCCCGCCUCCGCCGCCGGA | 1815 | UCCGGCGGCGGAGGCGGGC | 1816 |
| NM_005080_1582-1600 | UGGCAUCCUGGCUUGCCUC | 1817 | GAGGCAAGCCAGGAUGCCA | 1818 |
| NM_005080_1587-1605 | UCCUGGCUUGCCUCCAGUU | 1819 | AACUGGAGGCAAGCCAGGA | 1820 |
| NM_005080_118-136 | CCCGCCUCCGCCGCCGGAG | 1821 | CUCCGGCGGCGGAGGCGGG | 1822 |
| NM_005080_119-137 | CCGCCUCCGCCGCCGGAGC | 1823 | GCUCCGGCGGCGGAGGCGG | 1824 |
| NM_005080_120-138 | CGCCUCCGCCGCCGGAGCC | 1825 | GGCUCCGGCGGCGGAGGCG | 1826 |
| NM_005080_124-142 | UCCGCCGCCGGAGCCCCGG | 1827 | CCGGGGCUCCGGCGGCGGA | 1828 |

TABLE 8-continued

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_126-144 | CGCCGCCGGAGCCCCGGCC | 1829 | GGCCGGGGCTCCGGCGGCG | 1830 |
| NM_005080_1676-1694 | UUCAAGUAAGAUCAAGAAU | 1831 | AUUCUUGAUCUUACUUGAA | 1832 |
| NM_005080_127-145 | GCCGCCGGAGCCCCGGCCG | 1833 | CGGCCGGGGCTCCGGCGGC | 1834 |
| NM_005080_129-147 | CGCCGGAGCCCCGGCCGGC | 1835 | GCCGGCCGGGGCTCCGGCG | 1836 |
| NM_005080_130-148 | GCCGGAGCCCCGGCCGGCC | 1837 | GGCCGGCCGGGGCTCCGGC | 1838 |
| NM_005080_131-149 | CCGGAGCCCCGGCCGGCCA | 1839 | TGGCCGGCCGGGGCTCCGG | 1840 |
| NM_005080_1720-1738 | UAUGUAAAUGCUUGAUGGA | 1841 | UCCAUCAAGCAUUUACAUA | 1842 |
| NM_005080_1724-1742 | UAAAUGCUUGAUGGAAUUU | 1843 | AAAUUCCAUCAAGCAUUUA | 1844 |
| NM_005080_132-150 | CGGAGCCCCGGCCGGCCAG | 1845 | CTGGCCGGCCGGGGCTCCG | 1846 |
| NM_005080_133-151 | GGAGCCCCGGCCGGCCAGG | 1847 | CCTGGCCGGCCGGGGCTCC | 1848 |
| NM_005080_134-152 | GAGCCCCGGCCGGCCAGGC | 1849 | GCCTGGCCGGCCGGGGCTC | 1850 |
| NM_005080_136-154 | GCCCCGGCCGGCCAGGCCC | 1851 | GGGCCTGGCCGGCCGGGGC | 1852 |
| NM_005080_1777-1795 | UCCAUUUAUUUAAAACUAC | 1853 | GUAGUUUUAAAUAAAUGGA | 1854 |
| NM_005080_137-155 | CCCCGGCCGGCCAGGCCCU | 1855 | AGGGCCUGGCCGGCCGGGG | 1856 |
| NM_005080_139-157 | CCGGCCGGCCAGGCCCUGC | 1857 | GCAGGGCCUGGCCGGCCGG | 1858 |
| NM_005080_140-158 | CGGCCGGCCAGGCCCUGCC | 1859 | GGCAGGGCCUGGCCGGCCG | 1860 |
| NM_005080_141-159 | GGCCGGCCAGGCCCUGCCG | 1861 | CGGCAGGGCCUGGCCGGCC | 1862 |
| NM_005080_142-160 | GCCGGCCAGGCCCUGCCGC | 1863 | GCGGCAGGGCCUGGCCGGC | 1864 |
| NM_005080_143-161 | CCGGCCAGGCCCUGCCGCU | 1865 | AGCGGCAGGGCCUGGCCGG | 1866 |
| NM_005080_144-162 | CGGCCAGGCCCUGCCGCUC | 1867 | GAGCGGCAGGGCCUGGCCG | 1868 |
| NM_005080_161-179 | UCAUGGUGCCAGCCCAGAG | 1869 | CUCUGGGCUGGCACCAUGA | 1870 |
| NM_005080_162-180 | CAUGGUGCCAGCCCAGAGA | 1871 | UCUCUGGGCUGGCACCAUG | 1872 |
| NM_005080_164-182 | UGGUGCCAGCCCAGAGAGG | 1873 | CCUCUCUGGGCUGGCACCA | 1874 |
| NM_005080_165-183 | GGUGCCAGCCCAGAGAGGG | 1875 | CCCUCUCUGGGCUGGCACC | 1876 |
| NM_005080_166-184 | GUGCCAGCCCAGAGAGGGG | 1877 | CCCCUCUCUGGGCUGGCAC | 1878 |
| NM_005080_201-219 | GAGCGGGGGCUGCCCCAG | 1879 | CUGGGGCAGCCCCCGCUC | 1880 |
| NM_005080_202-220 | AGCGGGGGCUGCCCCAGG | 1881 | CCUGGGGCAGCCCCCGCU | 1882 |
| NM_005080_203-221 | GCGGGGGCUGCCCCAGGC | 1883 | GCCUGGGGCAGCCCCCGC | 1884 |
| NM_005080_204-222 | CGGGGGCUGCCCCAGGCG | 1885 | CGCCUGGGGCAGCCCCCG | 1886 |
| NM_005080_208-226 | GGGCUGCCCCAGGCGCGCA | 1887 | UGCGCGCCUGGGGCAGCCC | 1888 |
| NM_005080_212-230 | UGCCCCAGGCGCGCAAGCG | 1889 | CGCUUGCGCGCCUGGGGCA | 1890 |
| NM_005080_248-266 | UGAGCCCCGAGGAGAAGGC | 1891 | GCCUUCUCCUCGGGGCUCA | 1892 |
| NM_005080_251-269 | GCCCCGAGGAGAAGGCGCU | 1893 | AGCGCCUUCUCCUCGGGGC | 1894 |
| NM_005080_258-276 | GGAGAAGGCGCUGAGGAGG | 1895 | CCUCCUCAGCGCCUUCUCC | 1896 |
| NM_005080_262-280 | AAGGCGCUGAGGAGGAAAC | 1897 | GUUUCCUCCUCAGCGCCUU | 1898 |
| NM_005080_265-283 | GCGCUGAGGAGGAAACUGA | 1899 | UCAGUUUCCUCCUCAGCGC | 1900 |
| NM_005080_266-284 | CGCUGAGGAGGAAACUGAA | 1901 | UUCAGUUUCCUCCUCAGCG | 1902 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_267-285 | GCUGAGGAGGAAACUGAAA | 1903 | UUUCAGUUUCCUCCUCAGC | 1904 |
| NM_005080_268-286 | CUGAGGAGGAAACUGAAAA | 1905 | UUUUCAGUUUCCUCCUCAG | 1906 |
| NM_005080_270-288 | GAGGAGGAAACUGAAAAAC | 1907 | GUUUUUCAGUUUCCUCCUC | 1908 |
| NM_005080_272-290 | GGAGGAAACUGAAAAACAG | 1909 | CUGUUUUUCAGUUUCCUCC | 1910 |
| NM_005080_273-291 | GAGGAAACUGAAAAACAGA | 1911 | UCUGUUUUUCAGUUUCCUC | 1912 |
| NM_005080_277-295 | AAACUGAAAAACAGAGUAG | 1913 | CUACUCUGUUUUUCAGUUU | 1914 |
| NM_005080_328-346 | CGAAUGAGUGAGCUGGAAC | 1915 | GUUCCAGCUCACUCAUUCG | 1916 |
| NM_005080_329-347 | GAAUGAGUGAGCUGGAACA | 1917 | UGUUCCAGCUCACUCAUUC | 1918 |
| NM_005080_334-352 | AGUGAGCUGGAACAGCAAG | 1919 | CUUGCUGUUCCAGCUCACU | 1920 |
| NM_005080_336-354 | UGAGCUGGAACAGCAAGUG | 1921 | CACUUGCUGUUCCAGCUCA | 1922 |
| NM_005080_337-355 | GAGCUGGAACAGCAAGUGG | 1923 | CCACUUGCUGUUCCAGCUC | 1924 |
| NM_005080_338-356 | AGCUGGAACAGCAAGUGGU | 1925 | ACCACUUGCUGUUCCAGCU | 1926 |
| NM_005080_356-374 | UAGAUUUAGAAGAAGAGAA | 1927 | UUCUCUUCUUCUAAAUCUA | 1928 |
| NM_005080_357-375 | AGAUUUAGAAGAAGAGAAC | 1929 | GUUCUCUUCUUCUAAAUCU | 1930 |
| NM_005080_359-377 | AUUUAGAAGAAGAGAACCA | 1931 | UGGUUCUCUUCUUCUAAAU | 1932 |
| NM_005080_360-378 | UUUAGAAGAAGAGAACCAA | 1933 | UUGGUUCUCUUCUUCUAAA | 1934 |
| NM_005080_362-380 | UAGAAGAAGAGAACCAAAA | 1935 | UUUUGGUUCUCUUCUUCUA | 1936 |
| NM_005080_367-385 | GAAGAGAACCAAAAACUUU | 1937 | AAAGUUUUUGGUUCUCUUC | 1938 |
| NM_005080_382-400 | CUUUUGCUAGAAAAUCAGC | 1939 | GCUGAUUUUCUAGCAAAAG | 1940 |
| NM_005080_386-404 | UGCUAGAAAAUCAGCUUUU | 1941 | AAAAGCUGAUUUUCUAGCA | 1942 |
| NM_005080_401-419 | UUUUACGAGAGAAAACUCA | 1943 | UGAGUUUUCUCUCGUAAAA | 1944 |
| NM_005080_458-476 | UGGGGAUGGAUGCCCUGGU | 1945 | ACCAGGGCAUCCAUCCCCA | 1946 |
| NM_005080_484-502 | GAGGAGGCGGAAGCCAAGG | 1947 | CCTTGGCTTCCGCCTCCTC | 1948 |
| NM_005080_489-507 | GGCGGAAGCCAAGGGGAAU | 1949 | AUUCCCCUUGGCUUCCGCC | 1950 |
| NM_005080_574-592 | GUGCAGGCCCAGUUGUCAC | 1951 | GUGACAACUGGGCCUGCAC | 1952 |
| NM_005080_594-612 | CCUCCAGAACAUCUCCCCA | 1953 | UGGGGAGAUGUUCUGGAGG | 1954 |
| NM_005080_604-622 | AUCUCCCCAUGGAUUCUGG | 1955 | CCAGAAUCCAUGGGGAGAU | 1956 |
| NM_005080_627-645 | AUUGACUCUUCAGAUUCAG | 1957 | CUGAAUCUGAAGAGUCAAU | 1958 |
| NM_005080_635-653 | UUCAGAUUCAGAGUCUGAU | 1959 | AUCAGACUCUGAAUCUGAA | 1960 |
| NM_005080_636-654 | UCAGAUUCAGAGUCUGAUA | 1961 | UAUCAGACUCUGAAUCUGA | 1962 |
| NM_005080_666-684 | AUUCUGGACAACUUGGACC | 1963 | GGUCCAAGUUGUCCAGAAU | 1964 |
| NM_005080_667-685 | UUCUGGACAACUUGGACCC | 1965 | GGGUCCAAGUUGUCCAGAA | 1966 |
| NM_005080_669-687 | CUGGACAACUUGGACCCAG | 1967 | CUGGGUCCAAGUUGUCCAG | 1968 |
| NM_005080_681-699 | GACCCAGUCAUGUUCUUCA | 1969 | UGAAGAACAUGACUGGGUC | 1970 |
| NM_005080_690-708 | AUGUUCUUCAAAUGCCCUU | 1971 | AAGGGCAUUUGAAGAACAU | 1972 |

TABLE 8-continued

XBP-1 human/Rhesus siRNAs

| Oligo Name/ Positions on target sequence (5'to 3') | sense (5'-3') | SEQ ID NO: | antisense (5'-3') | SEQ ID NO: |
|---|---|---|---|---|
| NM_005080_718-736 | CUGCCAGCCUGGAGGAGCU | 1973 | AGCUCCUCCAGGCUGGCAG | 1974 |
| NM_005080_722-740 | CAGCCUGGAGGAGCUCCCA | 1975 | UGGGAGCUCCUCCAGGCUG | 1976 |
| NM_005080_723-741 | AGCCUGGAGGAGCUCCCAG | 1977 | CUGGGAGCUCCUCCAGGCU | 1978 |
| NM_005080_724-742 | GCCUGGAGGAGCUCCCAGA | 1979 | UCUGGGAGCUCCUCCAGGC | 1980 |
| NM_005080_725-743 | CCUGGAGGAGCUCCCAGAG | 1981 | CUCUGGGAGCUCCUCCAGG | 1982 |
| NM_005080_727-745 | UGGAGGAGCUCCCAGAGGU | 1983 | ACCUCUGGGAGCUCCUCCA | 1984 |
| NM_005080_728-746 | GGAGGAGCUCCCAGAGGUC | 1985 | GACCUCUGGGAGCUCCUCC | 1986 |
| NM_005080_739-757 | CAGAGGUCUACCCAGAAGG | 1987 | CCUUCUGGGUAGACCUCUG | 1988 |
| NM_005080_747-765 | UACCCAGAAGGACCCAGUU | 1989 | AACUGGGUCCUUCUGGGUA | 1990 |
| NM_005080_763-781 | GUUCCUUACCAGCCUCCCU | 1991 | AGGGAGGCUGGUAAGGAAC | 1992 |
| NM_005080_764-782 | UUCCUUACCAGCCUCCCUU | 1993 | AAGGGAGGCUGGUAAGGAA | 1994 |
| NM_005080_766-784 | CCUUACCAGCCUCCCUUUC | 1995 | GAAAGGGAGGCUGGUAAGG | 1996 |
| NM_005080_770-788 | ACCAGCCUCCCUUUCUCUG | 1997 | CAGAGAAAGGGAGGCUGGU | 1998 |
| NM_005080_774-792 | GCCUCCCUUUCUCUGUCAG | 1999 | CUGACAGAGAAAGGGAGGC | 2000 |
| NM_005080_780-798 | CUUUCUCUGUCAGUGGGGA | 2001 | UCCCCACUGACAGAGAAAG | 2002 |
| NM_005080_781-799 | UUUCUCUGUCAGUGGGGAC | 2003 | GUCCCCACUGACAGAGAAA | 2004 |
| NM_005080_805-823 | CAGCCAAGCUGGAAGCCAU | 2005 | AUGGCUUCCAGCUUGGCUG | 2006 |
| NM_005080_44-62 | GAGCUAUGGUGGUGGUGGC | 2007 | GCCACCACCACCAUAGCUC | 2008 |
| NM_005080_45-63 | AGCUAUGGUGGUGGUGGCA | 2009 | UGCCACCACCACCAUAGCU | 2010 |
| NM_005080_868-886 | UCUUAGAGAUACCCUCUGA | 2011 | UCAGAGGGUAUCUCUAAGA | 2012 |
| NM_005080_875-893 | GAUACCCUCUGAGACAGAG | 2013 | CUCUGUCUCAGAGGGUAUC | 2014 |
| NM_005080_47-65 | CUAUGGUGGUGGUGGCAGC | 2015 | GCUGCCACCACCACCAUAG | 2016 |
| NM_005080_879-897 | CCCUCUGAGACAGAGAGCC | 2017 | GGCUCUCUGUCUCAGAGGG | 2018 |
| NM_005080_880-898 | CCUCUGAGACAGAGAGCCA | 2019 | UGGCUCUCUGUCUCAGAGG | 2020 |
| NM_005080_881-899 | CUCUGAGACAGAGAGCCAA | 2021 | UUGGCUCUCUGUCUCAGAG | 2022 |
| NM_005080_882-900 | UCUGAGACAGAGAGCCAAG | 2023 | CUUGGCUCUCUGUCUCAGA | 2024 |
| NM_005080_883-901 | CUGAGACAGAGAGCCAAGC | 2025 | GCUUGGCUCUCUGUCUCAG | 2026 |
| NM_005080_49-67 | AUGGUGGUGGUGGCAGCCG | 2027 | CGGCUGCCACCACCACCAU | 2028 |
| NM_005080_914-932 | GAAAAUCGAGGAAGCACCU | 2029 | AGGUGCUUCCUCGAUUUUC | 2030 |
| NM_005080_915-933 | AAAAUCGAGGAAGCACCUC | 2031 | GAGGUGCUUCCUCGAUUUU | 2032 |
| NM_005080_926-944 | AGCACCUCUCAGCCCCUCA | 2033 | UGAGGGGCUGAGAGGUGCU | 2034 |
| NM_005080_945-963 | GAGAAUGAUCACCCUGAAU | 2035 | AUUCAGGGUGAUCAUUCUC | 2036 |
| NM_005080_958-976 | CUGAAUUCAUUGUCUCAGU | 2037 | ACUGAGACAAUGAAUUCAG | 2038 |
| NM_005080_959-977 | UGAAUUCAUUGUCUCAGUG | 2039 | CACUGAGACAAUGAAUUCA | 2040 |
| NM_005080_962-980 | AUUCAUUGUCUCAGUGAAG | 2041 | CUUCACUGAGACAAUGAAU | 2042 |

TABLE 8-continued

XBP-1 human/Rhesus siRNAs

| Oligo Name/ Positions on target sequence (5' to 3') | sense (5'-3') | SEQ ID NO: | antisense (5'-3') | SEQ ID NO: |
|---|---|---|---|---|
| NM_005080_975-993 | GUGAAGGAAGAACCUGUAG | 2043 | CUACAGGUUCUUCCUUCAC | 2044 |
| NM_005080_983-1001 | AGAACCUGUAGAAGAUGAC | 2045 | GUCAUCUUCUACAGGUUCU | 2046 |
| NM_005080_128-146 | CCGCCGGAGCCCCGGCCGG | 2047 | CCGGCCGGGGCUCCGGCGG | 2048 |
| NM_005080_249-267 | GAGCCCCGAGGAGAAGGCG | 2049 | CGCCUUCUCCUCGGGGCUC | 2050 |
| NM_005080_697-715 | UCAAAUGCCCUUCCCCAGA | 2051 | UCUGGGGAAGGGCAUUUGA | 2052 |
| NM_005080_729-747 | GAGGAGCUCCCAGAGGUCU | 2053 | AGACCUCUGGGAGCUCCUC | 2054 |
| NM_005080_776-794 | CUCCCUUUCUCUGUCAGUG | 2055 | CACUGACAGAGAAAGGGAG | 2056 |
| NM_005080_803-821 | AUCAGCCAAGCUGGAAGCC | 2057 | GGCUUCCAGCUUGGCUGAU | 2058 |
| NM_005080_254-272 | CCGAGGAGAAGGCGCUGAG | 2059 | CUCAGCGCCUUCUCCUCGG | 2060 |
| NM_005080_383-401 | UUUUGCUAGAAAAUCAGCU | 2061 | AGCUGAUUUUCUAGCAAAA | 2062 |
| NM_005080_116-134 | AGCCCGCCUCCGCCGCCGG | 2063 | CCGGCGGCGGAGGCGGGCU | 2064 |
| NM_005080_123-141 | CUCCGCCGCCGGAGCCCCG | 2065 | CGGGGCUCCGGCGGCGGAG | 2066 |
| NM_005080_125-143 | CCGCCGCCGGAGCCCCGGC | 2067 | GCCGGGGCUCCGGCGGCGG | 2068 |
| NM_005080_135-153 | AGCCCCGGCCGGCCAGGCC | 2069 | GGCCTGGCCGGCCGGGGCT | 2070 |
| NM_005080_253-271 | CCCGAGGAGAAGGCGCUGA | 2071 | UCAGCGCCUUCUCCUCGGG | 2072 |
| NM_005080_274-292 | AGGAAACUGAAAAACAGAG | 2073 | CUCUGUUUUUCAGUUUCCU | 2074 |
| NM_005080_655-673 | UCCUGUUGGGCAUUCUGGA | 2075 | UCCAGAAUGCCCAACAGGA | 2076 |
| NM_005080_775-793 | CCUCCCUUUCUCUGUCAGU | 2077 | ACUGACAGAGAAAGGGAGG | 2078 |
| NM_005080_46-64 | GCUAUGGUGGUGGUGGCAG | 2079 | CUGCCACCACCACCAUAGC | 2080 |
| NM_005080_1456-1474 | GUACUUUUAUCUUAAAAGG | 2081 | CCUUUUAAGAUAAAAGUAC | 2082 |
| NM_005080_1545-1563 | UUAUGAAUGGUUCUUUAUC | 2083 | GAUAAAGAACCAUUCAUAA | 2084 |
| NM_005080_1558-1576 | UUUAUCAUUUCUCUUCCCC | 2085 | GGGGAAGAGAAAUGAUAAA | 2086 |
| NM_005080_121-139 | GCCUCCGCCGCCGGAGCCC | 2087 | GGGCUCCGGCGGCGGAGGC | 2088 |
| NM_005080_122-140 | CCUCCGCCGCCGGAGCCCC | 2089 | GGGGCUCCGGCGGCGGAGG | 2090 |
| NM_005080_247-265 | CUGAGCCCCGAGGAGAAGG | 2091 | CCUUCUCCUCGGGGCUCAG | 2092 |
| NM_005080_275-293 | GGAAACUGAAAAACAGAGU | 2093 | ACUCUGUUUUUCAGUUUCC | 2094 |
| NM_005080_276-294 | GAAACUGAAAAACAGAGUA | 2095 | UACUCUGUUUUUCAGUUUC | 2096 |
| NM_005080_358-376 | GAUUUAGAAGAAGAGAACC | 2097 | GGUUCUCUUCUUCUAAAUC | 2098 |
| NM_005080_387-405 | GCUAGAAAAUCAGCUUUUA | 2099 | UAAAAGCUGAUUUUCUAGC | 2100 |
| NM_005080_628-646 | UUGACUCUUCAGAUUCAGA | 2101 | UCUGAAUCUGAAGAGUCAA | 2102 |
| NM_005080_656-674 | CCUGUUGGGCAUUCUGGAC | 2103 | GUCCAGAAUGCCCAACAGG | 2104 |
| NM_005080_719-737 | UGCCAGCCUGGAGGAGCUC | 2105 | GAGCUCCUCCAGGCUGGCA | 2106 |
| NM_005080_720-738 | GCCAGCCUGGAGGAGCUCC | 2107 | GGAGCUCCUCCAGGCUGGC | 2108 |
| NM_005080_721-739 | CCAGCCUGGAGGAGCUCCC | 2109 | GGGAGCUCCUCCAGGCUGG | 2110 |
| NM_005080_782-800 | UUCUCUGUCAGUGGGGACG | 2111 | CGUCCCCACUGACAGAGAA | 2112 |

TABLE 8-continued

XBP-1 human/Rhesus siRNAs

| Oligo Name/<br>Positions on target<br>sequence (5'to 3') | sense (5'-3') | SEQ<br>ID<br>NO: | antisense (5'-3') | SEQ<br>ID<br>NO: |
|---|---|---|---|---|
| NM_005080_867-885 | GUCUUAGAGAUACCCUCUG | 2113 | CAGAGGGUAUCUCUAAGAC | 2114 |
| NM_005080_48-66 | UAUGGUGGUGGUGGCAGCC | 2115 | GGCUGCCACCACCACCAUA | 2116 |
| NM_005080_963-981 | UUCAUUGUCUCAGUGAAGG | 2117 | CCUUCACUGAGACAAUGAA | 2118 |

Gene XBP1
reference transcript NM_005080 (human XBP1 mRNA, FIG. 2)
Notes
19mers found in both human and rhesus

TABLE 9

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_390-408 | AGAAAAUCAGCUUUUACGANN | 2203 | UCGUAAAAGCUGAUUUUCUNN | 2204 |
| NM_005080_1184-1202 | UCCCCAGCUGAUUAGUGUCNN | 2205 | GACACUAAUCAGCUGGGGANN | 2206 |
| NM_005080_1494-1512 | UACUUAUUAUGUAAGGGUCNN | 2207 | GACCCUUACAUAAUAAGUANN | 2208 |
| NM_005080_1463-1481 | UAUCUUAAAAGGGUGGUAGNN | 2209 | CUACCACCCUUUUAAGAUANN | 2210 |
| NM_005080_610-628 | CCAUGGAUUCUGGCGGUAUNN | 2211 | AUACCGCCAGAAUCCAUGGNN | 2212 |
| NM_005080_823-841 | UUAAUGAACUAAUUCGUUUNN | 2213 | AAACGAAUUAGUUCAUUAANN | 2214 |
| NM_005080_1507-1525 | AGGGUCAUUAGACAAAUGUNN | 2215 | ACAUUUGUCUAAUGACCCUNN | 2216 |
| NM_005080_827-845 | UGAACUAAUUCGUUUUGACNN | 2217 | GUCAAAACGAAUUAGUUCANN | 2218 |
| NM_005080_1503-1521 | UGUAAGGGUCAUUAGACAANN | 2219 | UUGUCUAAUGACCCUUACANN | 2220 |
| NM_005080_829-847 | AACUAAUUCGUUUUGACCANN | 2221 | UGGUCAAAACGAAUUAGUUNN | 2222 |
| NM_005080_1783-1801 | UAUUUAAAACUACCCAUGCNN | 2223 | GCAUGGGUAGUUUUAAAUANN | 2224 |
| NM_005080_1183-1201 | UUCCCCAGCUGAUUAGUGUNN | 2225 | ACACUAAUCAGCUGGGGAANN | 2226 |
| NM_005080_1501-1519 | UAUGUAAGGGUCAUUAGACNN | 2227 | GUCUAAUGACCCUUACAUANN | 2228 |
| NM_005080_1504-1522 | GUAAGGGUCAUUAGACAAANN | 2229 | UUUGUCUAAUGACCCUUACNN | 2230 |
| NM_005080_734-752 | GCUCCCAGAGGUCUACCCANN | 2231 | UGGGUAGACCUCUGGGAGCNN | 2232 |
| NM_005080_893-911 | GAGCCAAGCUAAUGUGGUANN | 2233 | UACCACAUUAGCUUGGCUCNN | 2234 |
| NM_005080_1064-1082 | CUGCCUACUGGAUGCUUACNN | 2235 | GUAAGCAUCCAGUAGGCAGNN | 2236 |
| NM_005080_1066-1084 | GCCUACUGGAUGCUUACAGNN | 2237 | CUGUAAGCAUCCAGUAGGCNN | 2238 |
| NM_005080_1136-1154 | GCUUGGUGUAAACCAUUCUNN | 2239 | AGAAUGGUUUACACCAAGCNN | 2240 |
| NM_005080_1137-1155 | CUUGGUGUAAACCAUUCUUNN | 2241 | AAGAAUGGUUUACACCAAGNN | 2242 |
| NM_005080_1182-1200 | UUUCCCCAGCUGAUUAGUGNN | 2243 | CACUAAUCAGCUGGGGAAANN | 2244 |
| NM_005080_1186-1204 | CCCAGCUGAUUAGUGUCUANN | 2245 | UAGACACUAAUCAGCUGGGNN | 2246 |
| NM_005080_1189-1207 | AGCUGAUUAGUGUCUAAGGNN | 2247 | CCUUAGACACUAAUCAGCUNN | 2248 |
| NM_005080_1224-1242 | UGCCCUUUUCCUUGACUAUNN | 2249 | AUAGUCAAGGAAAAGGGCANN | 2250 |
| NM_005080_1229-1247 | UUUUCCUUGACUAUUACACNN | 2251 | GUGUAAUAGUCAAGGAAAANN | 2252 |
| NM_005080_1235-1253 | UUGACUAUUACACUGCCUGNN | 2253 | CAGGCAGUGUAAUAGUCAANN | 2254 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
| --- | --- | --- | --- | --- |
| NM_005080_1236-1254 | UGACUAUUACACUGCCUGGNN | 2255 | CCAGGCAGUGUAAUAGUCANN | 2256 |
| NM_005080_1438-1456 | ACUACAGCUUUUAAGAUUGNN | 2257 | CAAUCUUAAAAGCUGUAGNN | 2258 |
| NM_005080_1441-1459 | ACAGCUUUUAAGAUUGUACNN | 2259 | GUACAAUCUUAAAAGCUGUNN | 2260 |
| NM_005080_1442-1460 | CAGCUUUUAAGAUUGUACUNN | 2261 | AGUACAAUCUUAAAAGCUGNN | 2262 |
| NM_005080_1493-1511 | AUACUUAUUAUGUAAGGGUNN | 2263 | ACCCUUACAUAAUAAGUAUNN | 2264 |
| NM_005080_1502-1520 | AUGUAAGGGUCAUUAGACANN | 2265 | UGUCUAAUGACCCUUACAUNN | 2266 |
| NM_005080_1506-1524 | AAGGGUCAUUAGACAAAUGNN | 2267 | CAUUUGUCUAAUGACCCUUNN | 2268 |
| NM_005080_1594-1612 | UUGCCUCCAGUUUUAGGUCNN | 2269 | GACCUAAAACUGGAGGCAANN | 2270 |
| NM_005080_1790-1808 | AACUACCCAUGCAAUUAAANN | 2271 | UUUAAUUGCAUGGGUAGUNN | 2272 |
| NM_005080_304-322 | ACUGCCAGAGAUCGAAAGANN | 2273 | UCUUUCGAUCUCUGGCAGUNN | 2274 |
| NM_005080_305-323 | CUGCCAGAGAUCGAAAGAANN | 2275 | UUCUUUCGAUCUCUGGCAGNN | 2276 |
| NM_005080_395-413 | AUCAGCUUUUACGAGAGAANN | 2277 | UUCUCUCGUAAAAGCUGAUNN | 2278 |
| NM_005080_609-627 | CCCAUGGAUUCUGGCGGUANN | 2279 | UACCGCCAGAAUCCAUGGGNN | 2280 |
| NM_005080_611-629 | CAUGGAUUCUGGCGGUAUUNN | 2281 | AAUACCGCCAGAAUCCAUGNN | 2282 |
| NM_005080_617-635 | UUCUGGCGGUAUUGACUCUNN | 2283 | AGAGUCAAUACCGCCAGAANN | 2284 |
| NM_005080_621-639 | GGCGGUAUUGACUCUUCAGNN | 2285 | CUGAAGAGUCAAUACCGCCNN | 2286 |
| NM_005080_641-659 | UUCAGAGUCUGAUAUCCUGNN | 2287 | CAGGAUAUCAGACUCUGAANN | 2288 |
| NM_005080_648-666 | UCUGAUAUCCUGUUGGGCANN | 2289 | UGCCCAACAGGAUAUCAGANN | 2290 |
| NM_005080_651-669 | GAUAUCCUGUUGGGCAUUCNN | 2291 | GAAUGCCCAACAGGAUAUCNN | 2292 |
| NM_005080_735-753 | CUCCCAGAGGUCUACCCAGNN | 2293 | CUGGGUAGACCUCUGGGAGNN | 2294 |
| NM_005080_753-771 | GAAGGACCCAGUUCCUUACNN | 2295 | GUAAGGAACUGGGUCCUUCNN | 2296 |
| NM_005080_794-812 | GGGGACGUCAUCAGCCAAGNN | 2297 | CUUGGCUGAUGACGUCCCNN | 2298 |
| NM_005080_826-844 | AUGAACUAAUUCGUUUUGANN | 2299 | UCAAAACGAAUUAGUUCAUNN | 2300 |
| NM_005080_836-854 | UCGUUUUGACCACAUAUAUNN | 2301 | AUAUAUGUGGUCAAAACGANN | 2302 |
| NM_005080_840-858 | UUUGACCACAUAUAUACCANN | 2303 | UGGUAUAUAUGUGGUCAAANN | 2304 |
| NM_005080_841-859 | UUGACCACAUAUAUACCAANN | 2305 | UUGGUAUAUAUGUGGUCANN | 2306 |
| NM_005080_847-865 | ACAUAUAUACCAAGCCCCUNN | 2307 | AGGGGCUUGGUAUAUAUGUNN | 2308 |
| NM_005080_894-912 | AGCCAAGCUAAUGUGGUAGNN | 2309 | CUACCACAUUAGCUUGGCUNN | 2310 |
| NM_005080_895-913 | GCCAAGCUAAUGUGGUAGUNN | 2311 | ACUACCACAUUAGCUUGGCNN | 2312 |
| NM_005080_896-914 | CCAAGCUAAUGUGGUAGUGNN | 2313 | CACUACCACAUUAGCUUGGNN | 2314 |
| NM_005080_899-917 | AGCUAAUGUGGUAGUGAANN | 2315 | UUUCACUACCACAUUAGCUNN | 2316 |
| NM_005080_908-926 | GGUAGUGAAAUCGAGGAANN | 2317 | UUCCUCGAUUUCACUACCNN | 2318 |
| NM_005080_917-935 | AAUCGAGGAAGCACCUCUCNN | 2319 | GAGAGGUGCUUCCUCGAUUNN | 2320 |
| NM_005080_937-955 | GCCCCUCAGAGAAUGAUCNN | 2321 | UGAUCAUUCUCUGAGGGGCNN | 2322 |
| NM_005080_950-968 | UGAUCACCCUGAAUUCAUUNN | 2323 | AAUGAAUUCAGGGUGAUCANN | 2324 |
| NM_005080_1185-1203 | CCCCAGCUGAUUAGUGUCUNN | 2325 | AGACACUAAUCAGCUGGGGNN | 2326 |
| NM_005080_1187-1205 | CCAGCUGAUUAGUGUCUAANN | 2327 | UUAGACACUAAUCAGCUGGNN | 2328 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_1153-1171 | CUUGGGAGGACACUUUUGCNN | 2329 | GCAAAAGUGUCCUCCCAAGNN | 2330 |
| NM_005080_1787-1805 | UAAAACUACCCAUGCAAUUNN | 2331 | AAUUGCAUGGGUAGUUUUANN | 2332 |
| NM_005080_606-624 | CUCCCCAUGGAUUCUGGCGNN | 2333 | CGCCAGAAUCCAUGGGGAGNN | 2334 |
| NM_005080_1019-1037 | UAUCUCAAAUCUGCUUUCANN | 2335 | UGAAAGCAGAUUUGAGAUANN | 2336 |
| NM_005080_1072-1090 | UGGAUGCUUACAGUGACUGNN | 2337 | CAGUCACUGUAAGCAUCCANN | 2338 |
| NM_005080_1228-1246 | CUUUUCCUUGACUAUUACANN | 2339 | UGUAAUAGUCAAGGAAAAGNN | 2340 |
| NM_005080_1461-1479 | UUUAUCUUAAAAGGGUGGUNN | 2341 | ACCACCCUUUUAAGAUAAANN | 2342 |
| NM_005080_1495-1513 | ACUUAUUAUGUAAGGGUCANN | 2343 | UGACCCUUACAUAAUAAGUNN | 2344 |
| NM_005080_1496-1514 | CUUAUUAUGUAAGGGUCAUNN | 2345 | AUGACCCUUACAUAAUAAGNN | 2346 |
| NM_005080_1500-1518 | UUAUGUAAGGGUCAUUAGANN | 2347 | UCUAAUGACCCUUACAUAANN | 2348 |
| NM_005080_1644-1662 | CCUGCUGAGGGGGCUCUUUNN | 2349 | AAAGAGCCCCCUCAGCAGGNN | 2350 |
| NM_005080_1708-1726 | AUAGAAAUUUACUAUGUAANN | 2351 | UUACAUAGUAAAUUUCUAUNN | 2352 |
| NM_005080_302-320 | AGACUGCCAGAGAUCGAAANN | 2353 | UUUCGAUCUCUGGCAGUCUNN | 2354 |
| NM_005080_607-625 | UCCCCAUGGAUUCUGGCGGNN | 2355 | CCGCCAGAAUCCAUGGGGANN | 2356 |
| NM_005080_824-842 | UAAUGAACUAAUUCGUUUUNN | 2357 | AAAACGAAUUAGUUCAUUANN | 2358 |
| NM_005080_953-971 | UCACCCUGAAUUCAUUGUCNN | 2359 | GACAAUGAAUUCAGGGUGANN | 2360 |
| NM_005080_1011-1029 | GAGCUGGGUAUCUCAAAUCNN | 2361 | GAUUUGAGAUACCCAGCUCNN | 2362 |
| NM_005080_1230-1248 | UUUCCUUGACUAUUACACUNN | 2363 | AGUGUAAUAGUCAAGGAAANN | 2364 |
| NM_005080_1231-1249 | UUCCUUGACUAUUACACUGNN | 2365 | CAGUGUAAUAGUCAAGGAANN | 2366 |
| NM_005080_1290-1308 | AAAGCCAAAAUAGAGAGUANN | 2367 | UACUCUCUAUUUUGGCUUUNN | 2368 |
| NM_005080_1331-1349 | AUUUGUUCAGAUCUCAUAGNN | 2369 | CUAUGAGAUCUGAACAAAUNN | 2370 |
| NM_005080_1460-1478 | UUUUAUCUUAAAAGGGUGGNN | 2371 | CCACCCUUUUAAGAUAAAANN | 2372 |
| NM_005080_1670-1688 | GUAUACUUCAAGUAAGAUCNN | 2373 | GAUCUUACUUGAAGUAUACNN | 2374 |
| NM_005080_1671-1689 | UAUACUUCAAGUAAGAUCANN | 2375 | UGAUCUUACUUGAAGUAUANN | 2376 |
| NM_005080_1735-1753 | UGGAAUUUUUCCUGCUAGNN | 2377 | CUAGCAGGAAAAAUUCCANN | 2378 |
| NM_005080_1744-1762 | UUCCUGCUAGUGUAGCUUCNN | 2379 | GAAGCUACACUAGCAGGAANN | 2380 |
| NM_005080_1796-1814 | CCAUGCAAUUAAAAGGUACNN | 2381 | GUACCUUUUAAUUGCAUGGNN | 2382 |
| NM_005080_343-361 | GAACAGCAAGUGGUAGAUUNN | 2383 | AAUCUACCACUUGCUGUUCNN | 2384 |
| NM_005080_374-392 | ACCAAAAACUUUUGCUAGANN | 2385 | UCUAGCAAAAGUUUUUGGUNN | 2386 |
| NM_005080_375-393 | CCAAAAACUUUUGCUAGAANN | 2387 | UUCUAGCAAAAGUUUUUGGNN | 2388 |
| NM_005080_608-626 | CCCCAUGGAUUCUGGCGGNN | 2389 | ACCGCCAGAAUCCAUGGGGNN | 2390 |
| NM_005080_652-670 | AUACCUGUUGGGCAUUCUNN | 2391 | AGAAUGCCCAACAGGAUAUNN | 2392 |
| NM_005080_686-704 | AGUCAUGUUCUUCAAAUGCNN | 2393 | GCAUUUGAAGAACAUGACUNN | 2394 |
| NM_005080_909-927 | GUAGUGAAAAUCGAGGAAGNN | 2395 | CUUCCUCGAUUUUCACUACNN | 2396 |
| NM_005080_951-969 | GAUCACCCUGAAUUCAUUGNN | 2397 | CAAUGAAUUCAGGGUGAUCNN | 2398 |
| NM_005080_952-970 | AUCACCCUGAAUUCAUUGUNN | 2399 | ACAAUGAAUUCAGGGUGAUNN | 2400 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
| --- | --- | --- | --- | --- |
| NM_005080_825-843 | AAUGAACUAAUUCGUUUUGNN | 2401 | CAAAACGAAUUAGUUCAUUNN | 2402 |
| NM_005080_1194-1212 | AUUAGUGUCUAAGGAAUGANN | 2403 | UCAUUCCUUAGACACUAAUNN | 2404 |
| NM_005080_831-849 | CUAAUUCGUUUUGACCACANN | 2405 | UGUGGUCAAAACGAAUUAGNN | 2406 |
| NM_005080_835-853 | UUCGUUUUGACCACAUAUANN | 2407 | UAUAUGUGGUCAAAACGAANN | 2408 |
| NM_005080_869-887 | CUUAGAGAUACCCUCUGAGNN | 2409 | CUCAGAGGGUAUCUCUAAGNN | 2410 |
| NM_005080_1246-1264 | ACUGCCUGGAGGAUAGCAGNN | 2411 | CUGCUAUCCUCCAGGCAGUNN | 2412 |
| NM_005080_1453-1471 | AUUGUACUUUUAUCUUAAANN | 2413 | UUUAAGAUAAAAGUACAAUNN | 2414 |
| NM_005080_1512-1530 | CAUUAGACAAAUGUCUUGANN | 2415 | UCAAGACAUUUGUCUAAUGNN | 2416 |
| NM_005080_1546-1564 | UAUGAAUGGUUCUUUAUCANN | 2417 | UGAUAAAGAACCAUUCAUANN | 2418 |
| NM_005080_1789-1807 | AAACUACCCAUGCAAUUAANN | 2419 | UUAAUUGCAUGGGUAGUUUNN | 2420 |
| NM_005080_325-343 | GCUCGAAUGAGUGAGCUGGNN | 2421 | CCAGCUCACUCAUUCGAGCNN | 2422 |
| NM_005080_393-411 | AAAUCAGCUUUUACGAGAGNN | 2423 | CUCUCGUAAAAGCUGAUUUNN | 2424 |
| NM_005080_788-806 | GUCAGUGGGGACGUCAUCNN | 2425 | UGAUGACGUCCCCACUGACNN | 2426 |
| NM_005080_821-839 | CAUUAAUGAACUAAUUCGUNN | 2427 | ACGAAUUAGUUCAUUAAUGNN | 2428 |
| NM_005080_1514-1532 | UUAGACAAAUGUCUUGAAGNN | 2429 | CUUCAAGACAUUUGUCUAANN | 2430 |
| NM_005080_1797-1815 | CAUGCAAUUAAAAGGUACANN | 2431 | UGUACCUUUUAAUUGCAUGNN | 2432 |
| NM_005080_833-851 | AAUUCGUUUUGACCACAUANN | 2433 | UAUGUGGUCAAAACGAAUUNN | 2434 |
| NM_005080_1509-1527 | GGUCAUUAGACAAAUGUCUNN | 2435 | AGACAUUUGUCUAAUGACCNN | 2436 |
| NM_005080_1802-1820 | AAUUAAAAGGUACAAUGCANN | 2437 | UGCAUUGUACCUUUUAAUUNN | 2438 |
| NM_005080_391-409 | GAAAAUCAGCUUUUACGAGNN | 2439 | CUCGUAAAAGCUGAUUUUCNN | 2440 |
| NM_005080_843-861 | GACCACAUAUAUACCAAGCNN | 2441 | GCUUGGUAUAUAUGUGGUCNN | 2442 |
| NM_005080_1508-1526 | GGGUCAUUAGACAAAUGUCNN | 2443 | GACAUUUGUCUAAUGACCCNN | 2444 |
| NM_005080_1754-1772 | UGUAGCUUCUGAAAGGUGCNN | 2445 | GCACCUUUCAGAAGCUACANN | 2446 |
| NM_005080_430-448 | GUUGAGAACCAGGAGUUAANN | 2447 | UUAACUCCUGGUUCUCAACNN | 2448 |
| NM_005080_437-455 | ACCAGGAGUUAAGACAGCGNN | 2449 | CGCUGUCUUAACUCCUGGUNN | 2450 |
| NM_005080_1465-1483 | UCUUAAAAGGGUGGUAGUUNN | 2451 | AACUACCACCCUUUUAAGANN | 2452 |
| NM_005080_1742-1760 | UUUUCCUGCUAGUGUAGCUNN | 2453 | AGCUACACUAGCAGGAAAANN | 2454 |
| NM_005080_438-456 | CCAGGAGUUAAGACAGCGCNN | 2455 | GCGCUGUCUUAACUCCUGGNN | 2456 |
| NM_005080_1060-1078 | CUUCCUGCCUACUGGAUGCNN | 2457 | GCAUCCAGUAGGCAGGAAGNN | 2458 |
| NM_005080_1067-1085 | CCUACUGGAUGCUUACAGUNN | 2459 | ACUGUAAGCAUCCAGUAGGNN | 2460 |
| NM_005080_1197-1215 | AGUGUCUAAGGAAUGAUCCNN | 2461 | GGAUCAUUCCUUAGACACUNN | 2462 |
| NM_005080_1198-1216 | GUGUCUAAGGAAUGAUCCANN | 2463 | UGGAUCAUUCCUUAGACACNN | 2464 |
| NM_005080_1424-1442 | UACUAUAAUUGAGAACUACNN | 2465 | GUAGUUCUCAAUUAUAGUANN | 2466 |
| NM_005080_1464-1482 | AUCUUAAAAGGGUGGUAGUNN | 2467 | ACUACCACCCUUUUAAGAUNN | 2468 |
| NM_005080_616-634 | AUUCUGGCGGUAUUGACUCNN | 2469 | GAGUCAAUACCGCCAGAAUNN | 2470 |
| NM_005080_757-775 | GACCCAGUUCCUUACCAGCNN | 2471 | GCUGGUAAGGAACUGGGUCNN | 2472 |
| NM_005080_785-803 | UCUGUCAGUGGGGACGUCANN | 2473 | UGACGUCCCCACUGACAGANN | 2474 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
| --- | --- | --- | --- | --- |
| NM_005080_819-837 | GCCAUUAAUGAACUAAUUCNN | 2475 | GAAUUAGUUCAUUAAUGGCNN | 2476 |
| NM_005080_842-860 | UGACCACAUAUAUACCAAGNN | 2477 | CUUGGUAUAUAUGUGGUCANN | 2478 |
| NM_005080_845-863 | CCACAUAUAUACCAAGCCCNN | 2479 | GGGCUUGGUAUAUAUGUGGNN | 2480 |
| NM_005080_1013-1031 | GCUGGGUAUCUCAAAUCUGNN | 2481 | CAGAUUUGAGAUACCCAGCNN | 2482 |
| NM_005080_1431-1449 | AUUGAGAACUACAGCUUUUNN | 2483 | AAAAGCUGUAGUUCUCAAUNN | 2484 |
| NM_005080_1673-1691 | UACUUCAAGUAAGAUCAAGNN | 2485 | CUUGAUCUUACUUGAAGUANN | 2486 |
| NM_005080_283-301 | AAAAACAGAGUAGCAGCUCNN | 2487 | GAGCUGCUACUCUGUUUUUNN | 2488 |
| NM_005080_838-856 | GUUUUGACCACAUAUAUACNN | 2489 | GUAUAUAUGUGGUCAAAACNN | 2490 |
| NM_005080_279-297 | ACUGAAAAACAGAGUAGCANN | 2491 | UGCUACUCUGUUUUUCAGUNN | 2492 |
| NM_005080_633-651 | UCUUCAGAUUCAGAGUCUGNN | 2493 | CAGACUCUGAAUCUGAAGANN | 2494 |
| NM_005080_1024-1042 | CAAAUCUGCUUUCAUCCAGNN | 2495 | CUGGAUGAAAGCAGAUUUGNN | 2496 |
| NM_005080_1147-1165 | ACCAUUCUUGGGAGGACACNN | 2497 | GUGUCCUCCCAAGAAUGGUNN | 2498 |
| NM_005080_1154-1172 | UUGGGAGGACACUUUUGCCNN | 2499 | GGCAAAAGUGUCCUCCCAANN | 2500 |
| NM_005080_1188-1206 | CAGCUGAUUAGUGUCUAAGNN | 2501 | CUUAGACACUAAUCAGCUGNN | 2502 |
| NM_005080_1192-1210 | UGAUUAGUGUCUAAGGAAUNN | 2503 | AUUCCUUAGACACUAAUCANN | 2504 |
| NM_005080_1195-1213 | UUAGUGUCUAAGGAAUGAUNN | 2505 | AUCAUUCCUUAGACACUAANN | 2506 |
| NM_005080_1238-1256 | ACUAUUACACUGCCUGGAGNN | 2507 | CUCCAGGCAGUGUAAUAGUNN | 2508 |
| NM_005080_1548-1566 | UGAAUGGUUCUUUAUCAUUNN | 2509 | AAUGAUAAAGAACCAUUCANN | 2510 |
| NM_005080_1549-1567 | GAAUGGUUCUUUAUCAUUUNN | 2511 | AAAUGAUAAAGAACCAUUCNN | 2512 |
| NM_005080_1677-1695 | UCAAGUAAGAUCAAGAAUCNN | 2513 | GAUUCUUGAUCUUACUUGANN | 2514 |
| NM_005080_1707-1725 | UAUAGAAAUUUACUAUGUANN | 2515 | UACAUAGUAAAUUUCUAUANN | 2516 |
| NM_005080_1713-1731 | AAUUUACUAUGUAAAUGCUNN | 2517 | AGCAUUUACAUAGUAAAUUNN | 2518 |
| NM_005080_1786-1804 | UUAAAACUACCCAUGCAAUNN | 2519 | AUUGCAUGGGUAGUUUUAANN | 2520 |
| NM_005080_210-228 | GCUGCCCCAGGCGCGCAAGNN | 2521 | CUUGCGCGCCUGGGGCAGCNN | 2522 |
| NM_005080_278-296 | AACUGAAAAACAGAGUAGCNN | 2523 | GCUACUCUGUUUUUCAGUUNN | 2524 |
| NM_005080_284-302 | AAAACAGAGUAGCAGCUCANN | 2525 | UGAGCUGCUACUCUGUUUUNN | 2526 |
| NM_005080_290-308 | GAGUAGCAGCUCAGACUGCNN | 2527 | GCAGUCUGAGCUGCUACUCNN | 2528 |
| NM_005080_342-360 | GGAACAGCAAGUGGUAGAUNN | 2529 | AUCUACCACUUGCUGUUCCNN | 2530 |
| NM_005080_431-449 | UUGAGAACCAGGAGUUAAGNN | 2531 | CUUAACUCCUGGUUCUCAANN | 2532 |
| NM_005080_576-594 | GCAGGCCCAGUUGUCACCCNN | 2533 | GGGUGACAACUGGGCCUGCNN | 2534 |
| NM_005080_602-620 | ACAUCUCCCCAUGGAUUCUNN | 2535 | AGAAUCCAUGGGGAGAUGUNN | 2536 |
| NM_005080_618-636 | UCUGGCGGUAUUGACUCUUNN | 2537 | AAGAGUCAAUACCGCCAGANN | 2538 |
| NM_005080_678-696 | UUGGACCCAGUCAUGUUCUNN | 2539 | AGAACAUGACUGGGUCCAANN | 2540 |
| NM_005080_796-814 | GGACGUCAUCAGCCAAGCUNN | 2541 | AGCUUGGCUGAUGACGUCCNN | 2542 |
| NM_005080_940-958 | CCUCAGAGAAUGAUCACCCNN | 2543 | GGGUGAUCAUUCUCUGAGGNN | 2544 |
| NM_005080_954-972 | CACCCUGAAUUCAUUGUCUNN | 2545 | AGACAAUGAAUUCAGGGUGNN | 2546 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_977-995 | GAAGGAAGAACCUGUAGAANN | 2547 | UUCUACAGGUUCUUCCUUCNN | 2548 |
| NM_005080_1018-1036 | GUAUCUCAAAUCUGCUUUCNN | 2549 | GAAAGCAGAUUUGAGAUACNN | 2550 |
| NM_005080_1026-1044 | AAUCUGCUUUCAUCCAGCCNN | 2551 | GGCUGGAUGAAAGCAGAUUNN | 2552 |
| NM_005080_1138-1156 | UUGGUGUAAACCAUUCUUGNN | 2553 | CAAGAAUGGUUUACACCAANN | 2554 |
| NM_005080_1141-1159 | GUGUAAACCAUUCUUGGGANN | 2555 | UCCCAAGAAUGGUUUACACNN | 2556 |
| NM_005080_1142-1160 | UGUAAACCAUUCUUGGGAGNN | 2557 | CUCCCAAGAAUGGUUUACANN | 2558 |
| NM_005080_1155-1173 | UGGGAGGACACUUUUGCCANN | 2559 | UGGCAAAAGUGUCCUCCCANN | 2560 |
| NM_005080_1158-1176 | GAGGACACUUUUGCCAAUGNN | 2561 | CAUUGGCAAAAGUGUCCUCNN | 2562 |
| NM_005080_1193-1211 | GAUUAGUGUCUAAGGAAUGNN | 2563 | CAUUCCUUAGACACUAAUCNN | 2564 |
| NM_005080_1196-1214 | UAGUGUCUAAGGAAUGAUCNN | 2565 | GAUCAUUCCUUAGACACUANN | 2566 |
| NM_005080_1219-1237 | ACUGUUGCCCUUUUCCUUGNN | 2567 | CAAGGAAAAGGGCAACAGUNN | 2568 |
| NM_005080_107-125 | UGUCGGGGCAGCCCGCCUCNN | 2569 | GAGGCGGGCUGCCCCGACANN | 2570 |
| NM_005080_108-126 | GUCGGGGCAGCCCGCCUCCNN | 2571 | GGAGGCGGGCUGCCCCGACNN | 2572 |
| NM_005080_1505-1523 | UAAGGGUCAUUAGACAAAUNN | 2573 | AUUUGUCUAAUGACCCUUANN | 2574 |
| NM_005080_1567-1585 | UCUCUUCCCCCUUUUUGGCNN | 2575 | GCCAAAAAGGGGGAAGAGANN | 2576 |
| NM_005080_1672-1690 | AUACUUCAAGUAAGAUCAANN | 2577 | UUGAUCUUACUUGAAGUAUNN | 2578 |
| NM_005080_1678-1696 | CAAGUAAGAUCAAGAAUCUNN | 2579 | AGAUUCUUGAUCUUACUUGNN | 2580 |
| NM_005080_1778-1796 | CCAUUUAUUUAAAACUACCNN | 2581 | GGUAGUUUUAAAUAAAUGGNN | 2582 |
| NM_005080_1779-1797 | CAUUUAUUUAAAACUACCCNN | 2583 | GGGUAGUUUUAAAUAAAUGNN | 2584 |
| NM_005080_280-298 | CUGAAAAACAGAGUAGCAGNN | 2585 | CUGCUACUCUGUUUUUCAGNN | 2586 |
| NM_005080_282-300 | GAAAAACAGAGUAGCAGCUNN | 2587 | AGCUGCUACUCUGUUUUUCNN | 2588 |
| NM_005080_288-306 | CAGAGUAGCAGCUCAGACUNN | 2589 | AGUCUGAGCUGCUACUCUGNN | 2590 |
| NM_005080_291-309 | AGUAGCAGCUCAGACUGCCNN | 2591 | GGCAGUCUGAGCUGCUACUNN | 2592 |
| NM_005080_347-365 | AGCAAGUGGUAGAUUUAGANN | 2593 | UCUAAAUCUACCACUUGCUNN | 2594 |
| NM_005080_397-415 | CAGCUUUUACGAGAGAAAANN | 2595 | UUUUCUCUCGUAAAAGCUGNN | 2596 |
| NM_005080_398-416 | AGCUUUUACGAGAGAAAACNN | 2597 | GUUUUCUCUCGUAAAAGCUNN | 2598 |
| NM_005080_399-417 | GCUUUUACGAGAGAAAACUNN | 2599 | AGUUUUCUCUCGUAAAAGCNN | 2600 |
| NM_005080_512-530 | UGAGGCCAGUGGCCGGGUCNN | 2601 | GACCCGGCCACUGGCCUCANN | 2602 |
| NM_005080_517-535 | CCAGUGGCCGGGUCUGCUGNN | 2603 | CAGCAGACCCGGCCACUGGNN | 2604 |
| NM_005080_596-614 | UCCAGAACAUCUCCCCAUGNN | 2605 | CAUGGGGAGAUGUUCUGGANN | 2606 |
| NM_005080_598-616 | CAGAACAUCUCCCCAUGGANN | 2607 | UCCAUGGGGAGAUGUUCUGNN | 2608 |
| NM_005080_601-619 | AACAUCUCCCCAUGGAUUCNN | 2609 | GAAUCCAUGGGGAGAUGUUNN | 2610 |
| NM_005080_605-623 | UCUCCCCAUGGAUUCUGGCNN | 2611 | GCCAGAAUCCAUGGGGAGANN | 2612 |
| NM_005080_661-679 | UGGGCAUUCUGGACAACUUNN | 2613 | AAGUUGUCCAGAAUGCCCANN | 2614 |
| NM_005080_688-706 | UCAUGUUCUUCAAAUGCCCNN | 2615 | GGGCAUUUGAAGAACAUGANN | 2616 |
| NM_005080_691-709 | UGUUCUUCAAAUGCCCUUCNN | 2617 | GAAGGGCAUUUGAAGAACANN | 2618 |
| NM_005080_828-846 | GAACUAAUUCGUUUUGACCNN | 2619 | GGUCAAAACGAAUUAGUUCNN | 2620 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_830-848 | ACUAAUUCGUUUUGACCACNN | 2621 | GUGGUCAAAACGAAUUAGUNN | 2622 |
| NM_005080_834-852 | AUUCGUUUUGACCACAUAUNN | 2623 | AUAUGUGGUCAAAACGAAUNN | 2624 |
| NM_005080_846-864 | CACAUAUAUACCAAGCCCCNN | 2625 | GGGGCUUGGUAUAUAUGUGNN | 2626 |
| NM_005080_870-888 | UUAGAGAUACCCUCUGAGANN | 2627 | UCUCAGAGGGUAUCUCUAANN | 2628 |
| NM_005080_891-909 | GAGAGCCAAGCUAAUGUGGNN | 2629 | CCACAUUAGCUUGGCUCUCNN | 2630 |
| NM_005080_900-918 | GCUAAUGUGGUAGUGAAAANN | 2631 | UUUUCACUACCACAUUAGCNN | 2632 |
| NM_005080_911-929 | AGUGAAAAUCGAGGAAGCANN | 2633 | UGCUUCCUCGAUUUUCACUNN | 2634 |
| NM_005080_912-930 | GUGAAAAUCGAGGAAGCACNN | 2635 | GUGCUUCCUCGAUUUUCACNN | 2636 |
| NM_005080_979-997 | AGGAAGAACCUGUAGAAGANN | 2637 | UCUUCUACAGGUUCUUCCUNN | 2638 |
| NM_005080_1366-1384 | GUCUUUUGACAUCCAGCAGNN | 2639 | CUGCUGGAUGUCAAAAGACNN | 2640 |
| NM_005080_150-168 | GGCCCUGCCGCUCAUGGUGNN | 2641 | CACCAUGAGCGGCAGGGCCNN | 2642 |
| NM_005080_1437-1455 | AACUACAGCUUUUAAGAUUNN | 2643 | AAUCUUAAAAGCUGUAGUUNN | 2644 |
| NM_005080_482-500 | AAGAGGAGGCGGAAGCCAANN | 2645 | TTGGCTTCCGCCTCCTCTTNN | 2646 |
| NM_005080_580-598 | GCCCAGUUGUCACCCCUCCNN | 2647 | GGAGGGGUGACAACUGGGCNN | 2648 |
| NM_005080_613-631 | UGGAUUCUGGCGGUAUUGANN | 2649 | UCAAUACCGCCAGAAUCCANN | 2650 |
| NM_005080_1065-1083 | UGCCUACUGGAUGCUUACANN | 2651 | UGUAAGCAUCCAGUAGGCANN | 2652 |
| NM_005080_614-632 | GGAUUCUGGCGGUAUUGACNN | 2653 | GUCAAUACCGCCAGAAUCCNN | 2654 |
| NM_005080_640-658 | AUUCAGAGUCUGAUAUCCUNN | 2655 | AGGAUAUCAGACUCUGAAUNN | 2656 |
| NM_005080_1014-1032 | CUGGGUAUCUCAAAUCUGCNN | 2657 | GCAGAUUUGAGAUACCCAGNN | 2658 |
| NM_005080_1015-1033 | UGGGUAUCUCAAAUCUGCUNN | 2659 | AGCAGAUUUGAGAUACCCANN | 2660 |
| NM_005080_1146-1164 | AACCAUUCUUGGGAGGACANN | 2661 | UGUCCUCCCAAGAAUGGUUNN | 2662 |
| NM_005080_1232-1250 | UCCUUGACUAUUACACUGCNN | 2663 | GCAGUGUAAUAGUCAAGGANN | 2664 |
| NM_005080_1234-1252 | CUUGACUAUUACACUGCCUNN | 2665 | AGGCAGUGUAAUAGUCAAGNN | 2666 |
| NM_005080_1237-1255 | GACUAUUACACUGCCUGGANN | 2667 | UCCAGGCAGUGUAAUAGUCNN | 2668 |
| NM_005080_1443-1461 | AGCUUUUAAGAUUGUACUUNN | 2669 | AAGUACAAUCUUAAAAGCUNN | 2670 |
| NM_005080_1462-1480 | UUAUCUUAAAAGGGUGGUANN | 2671 | UACCACCCUUUUAAGAUAANN | 2672 |
| NM_005080_1510-1528 | GUCAUUAGACAAAUGUCUUNN | 2673 | AAGACAUUUGUCUAAUGACNN | 2674 |
| NM_005080_1591-1609 | GGCUUGCCUCCAGUUUUAGNN | 2675 | CUAAAACUGGAGGCAAGCCNN | 2676 |
| NM_005080_1615-1633 | UUAGUUUGCUUCUGUAAGCNN | 2677 | GCUUACAGAAGCAAACUAANN | 2678 |
| NM_005080_1716-1734 | UUACUAUGUAAAUGCUUGANN | 2679 | UCAAGCAUUUACAUAGUAANN | 2680 |
| NM_005080_1718-1736 | ACUAUGUAAAUGCUUGAUGNN | 2681 | CAUCAAGCAUUUACAUAGUNN | 2682 |
| NM_005080_1725-1743 | AAAUGCUUGAUGGAAUUUUNN | 2683 | AAAAUUCCAUCAAGCAUUUNN | 2684 |
| NM_005080_1748-1766 | UGCUAGUGUAGCUUCUGAANN | 2685 | UUCAGAAGCUACACUAGCANN | 2686 |
| NM_005080_1780-1798 | AUUUAUUUAAAACUACCCANN | 2687 | UGGGUAGUUUUAAAUAAAUNN | 2688 |
| NM_005080_1794-1812 | ACCCAUGCAAUUAAAAGGUNN | 2689 | ACCUUUUAAUUGCAUGGGUNN | 2690 |
| NM_005080_156-174 | GCCGCUCAUGGUGCCAGCCNN | 2691 | GGCUGGCACCAUGAGCGGCNN | 2692 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
| --- | --- | --- | --- | --- |
| NM_005080_299-317 | CUCAGACUGCCAGAGAUCGNN | 2693 | CGAUCUCUGGCAGUCUGAGNN | 2694 |
| NM_005080_344-362 | AACAGCAAGUGGUAGAUUUNN | 2695 | AAAUCUACCACUUGCUGUUNN | 2696 |
| NM_005080_371-389 | AGAACCAAAACUUUUGCUNN | 2697 | AGCAAAAGUUUUGGUUCUNN | 2698 |
| NM_005080_373-391 | AACCAAAACUUUUGCUAGNN | 2699 | CUAGCAAAAGUUUUGGUUNN | 2700 |
| NM_005080_524-542 | CCGGGUCUGCUGAGUCCGCNN | 2701 | GCGGACUCAGCAGACCCGGNN | 2702 |
| NM_005080_525-543 | CGGGUCUGCUGAGUCCGCANN | 2703 | UGCGGACUCAGCAGACCCGNN | 2704 |
| NM_005080_612-630 | AUGGAUUCUGGCGGUAUUGNN | 2705 | CAAUACCGCCAGAAUCCAUNN | 2706 |
| NM_005080_615-633 | GAUUCUGGCGGUAUUGACUNN | 2707 | AGUCAAUACCGCCAGAAUCNN | 2708 |
| NM_005080_645-663 | GAGUCUGAUAUCCUGUUGGNN | 2709 | CCAACAGGAUAUCAGACUCNN | 2710 |
| NM_005080_792-810 | GUGGGGACGUCAUCAGCCANN | 2711 | UGGCUGAUGACGUCCCCACNN | 2712 |
| NM_005080_905-923 | UGGGUAGUGAAAAUCGAGNN | 2713 | CUCGAUUUUCACUACCACANN | 2714 |
| NM_005080_976-994 | UGAAGGAAGAACCUGUAGANN | 2715 | UCUACAGGUUCUUCCUUCANN | 2716 |
| NM_005080_1244-1262 | ACACUGCCUGGAGGAUAGCNN | 2717 | GCUAUCCUCCAGGCAGUGUNN | 2718 |
| NM_005080_1791-1809 | ACUACCCAUGCAAUUAAAANN | 2719 | UUUUAAUUGCAUGGGUAGUNN | 2720 |
| NM_005080_755-773 | AGGACCCAGUUCCUUACCANN | 2721 | UGGUAAGGAACUGGGUCCUNN | 2722 |
| NM_005080_799-817 | CGUCAUCAGCCAAGCUGGANN | 2723 | UCCAGCUUGGCUGAUGACGNN | 2724 |
| NM_005080_832-850 | UAAUUCGUUUUGACCACAUNN | 2725 | AUGUGGUCAAAACGAAUUANN | 2726 |
| NM_005080_839-857 | UUUUGACCACAUAUAUACCNN | 2727 | GGUAUAUAUGUGGUCAAAANN | 2728 |
| NM_005080_100-118 | CUGCUUCUGUCGGGCAGCNN | 2729 | GCUGCCCGACAGAAGCAGNN | 2730 |
| NM_005080_281-299 | UGAAAAACAGAGUAGCAGCNN | 2731 | GCUGCUACUCUGUUUUUCANN | 2732 |
| NM_005080_822-840 | AUUAAUGAACUAAUUCGUUNN | 2733 | AACGAAUUAGUUCAUUAAUNN | 2734 |
| NM_005080_1152-1170 | UCUUGGGAGGACACUUUUGNN | 2735 | CAAAAGUGUCCUCCCAAGANN | 2736 |
| NM_005080_1191-1209 | CUGAUUAGUGUCUAAGGAANN | 2737 | UUCCUUAGACACUAAUCAGNN | 2738 |
| NM_005080_1225-1243 | GCCCUUUUCCUUGACUAUUNN | 2739 | AAUAGUCAAGGAAAAGGGCNN | 2740 |
| NM_005080_1227-1245 | CCUUUUCCUUGACUAUUACNN | 2741 | GUAAUAGUCAAGGAAAAGGNN | 2742 |
| NM_005080_1239-1257 | CUAUUACACUGCCUGGAGGNN | 2743 | CCUCCAGGCAGUGUAAUAGNN | 2744 |
| NM_005080_1430-1448 | AAUUGAGAACUACAGCUUUNN | 2745 | AAAGCUGUAGUUCUCAAUUNN | 2746 |
| NM_005080_1499-1517 | AUUAUGUAAGGGUCAUUAGNN | 2747 | CUAAUGACCCUUACAUAAUNN | 2748 |
| NM_005080_1553-1571 | GGUUCUUUAUCAUUUCUCUNN | 2749 | AGAGAAAUGAUAAAGAACCNN | 2750 |
| NM_005080_1585-1603 | CAUCCUGGCUUGCCUCCAGNN | 2751 | CUGGAGGCAAGCCAGGAUGNN | 2752 |
| NM_005080_1592-1610 | GCUUGCCUCCAGUUUUAGGNN | 2753 | CCUAAAACUGGAGGCAAGCNN | 2754 |
| NM_005080_1743-1761 | UUUCCUGCUAGUGUAGCUUNN | 2755 | AAGCUACACUAGCAGGAAANN | 2756 |
| NM_005080_154-172 | CUGCCGCUCAUGGUGCCAGNN | 2757 | CUGGCACCAUGAGCGGCAGNN | 2758 |
| NM_005080_193-211 | GAGGCAGCGAGCGGGGGCNN | 2759 | GCCCCCGCUCGCUGCCUCNN | 2760 |
| NM_005080_199-217 | GCGAGCGGGGGCUGCCCCNN | 2761 | GGGGCAGCCCCCGCUCGCNN | 2762 |
| NM_005080_292-310 | GUAGCAGCUCAGACUGCCANN | 2763 | UGGCAGUCUGAGCUGCUACNN | 2764 |
| NM_005080_341-359 | UGGAACAGCAAGUGGUAGANN | 2765 | UCUACCACUUGCUGUUCCANN | 2766 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_377-395 | AAAAACUUUUGCUAGAAAANN | 2767 | UUUUCUAGCAAAAGUUUUUNN | 2768 |
| NM_005080_519-537 | AGUGGCCGGGUCUGCUGAGNN | 2769 | CUCAGCAGACCCGGCCACUNN | 2770 |
| NM_005080_522-540 | GGCCGGGUCUGCUGAGUCCNN | 2771 | GGACUCAGCAGACCCGGCCNN | 2772 |
| NM_005080_577-595 | CAGGCCCAGUUGUCACCCCNN | 2773 | GGGGUGACAACUGGGCCUGNN | 2774 |
| NM_005080_599-617 | AGAACAUCUCCCCAUGGAUNN | 2775 | AUCCAUGGGGAGAUGUUCUNN | 2776 |
| NM_005080_754-772 | AAGGACCCAGUUCCUUACCNN | 2777 | GGUAAGGAACUGGGUCCUUNN | 2778 |
| NM_005080_888-906 | ACAGAGAGCCAAGCUAAUGNN | 2779 | CAUUAGCUUGGCUCUCUGUNN | 2780 |
| NM_005080_939-957 | CCCUCAGAGAAUGAUCACCNN | 2781 | GGUGAUCAUUCUCUGAGGGNN | 2782 |
| NM_005080_964-982 | UCAUUGUCUCAGUGAAGGANN | 2783 | UCCUUCACUGAGACAAUGANN | 2784 |
| NM_005080_1012-1030 | AGCUGGGUAUCUCAAAUCUNN | 2785 | AGAUUUGAGAUACCCAGCUNN | 2786 |
| NM_005080_1016-1034 | GGGUAUCUCAAAUCUGCUUNN | 2787 | AAGCAGAUUUGAGAUACCCNN | 2788 |
| NM_005080_1020-1038 | AUCUCAAAUCUGCUUUCAUNN | 2789 | AUGAAAGCAGAUUUGAGAUNN | 2790 |
| NM_005080_1025-1043 | AAAUCUGCUUUCAUCCAGCNN | 2791 | GCUGGAUGAAAGCAGAUUUNN | 2792 |
| NM_005080_1027-1045 | AUCUGCUUUCAUCCAGCCANN | 2793 | UGGCUGGAUGAAAGCAGAUNN | 2794 |
| NM_005080_1028-1046 | UCUGCUUUCAUCCAGCCACNN | 2795 | GUGGCUGGAUGAAAGCAGANN | 2796 |
| NM_005080_1030-1048 | UGCUUUCAUCCAGCCACUGNN | 2797 | CAGUGGCUGGAUGAAAGCNN | 2798 |
| NM_005080_1031-1049 | GCUUUCAUCCAGCCACUGCNN | 2799 | GCAGUGGCUGGAUGAAAGCNN | 2800 |
| NM_005080_1032-1050 | CUUUCAUCCAGCCACUGCCNN | 2801 | GGCAGUGGCUGGAUGAAAGNN | 2802 |
| NM_005080_1033-1051 | UUUCAUCCAGCCACUGCCCNN | 2803 | GGGCAGUGGCUGGAUGAAANN | 2804 |
| NM_005080_1056-1074 | CCAUCUUCCUGCCUACUGGNN | 2805 | CCAGUAGGCAGGAAGAUGGNN | 2806 |
| NM_005080_1057-1075 | CAUCUUCCUGCCUACUGGANN | 2807 | UCCAGUAGGCAGGAAGAUGNN | 2808 |
| NM_005080_1058-1076 | AUCUUCCUGCCUACUGGAUNN | 2809 | AUCCAGUAGGCAGGAAGAUNN | 2810 |
| NM_005080_1059-1077 | UCUUCCUGCCUACUGGAUGNN | 2811 | CAUCCAGUAGGCAGGAAGANN | 2812 |
| NM_005080_1061-1079 | UUCCUGCCUACUGGAUGCUNN | 2813 | AGCAUCCAGUAGGCAGGAANN | 2814 |
| NM_005080_1063-1081 | CCUGCCUACUGGAUGCUUANN | 2815 | UAAGCAUCCAGUAGGCAGGNN | 2816 |
| NM_005080_1069-1087 | UACUGGAUGCUUACAGUGANN | 2817 | UCACUGUAAGCAUCCAGUANN | 2818 |
| NM_005080_1071-1089 | CUGGAUGCUUACAGUGACUNN | 2819 | AGUCACUGUAAGCAUCCAGNN | 2820 |
| NM_005080_1073-1091 | GGAUGCUUACAGUGACUGUNN | 2821 | ACAGUCACUGUAAGCAUCCNN | 2822 |
| NM_005080_1075-1093 | AUGCUUACAGUGACUGUGGNN | 2823 | CCACAGUCACUGUAAGCAUNN | 2824 |
| NM_005080_1076-1094 | UGCUUACAGUGACUGUGGANN | 2825 | UCCACAGUCACUGUAAGCANN | 2826 |
| NM_005080_1078-1096 | CUUACAGUGACUGUGGAUANN | 2827 | UAUCCACAGUCACUGUAAGNN | 2828 |
| NM_005080_1139-1157 | UGGUGUAAACCAUUCUUGGNN | 2829 | CCAAGAAUGGUUUACACCANN | 2830 |
| NM_005080_1140-1158 | GGUGUAAACCAUUCUUGGGNN | 2831 | CCCAAGAAUGGUUUACACCNN | 2832 |
| NM_005080_1143-1161 | GUAAACCAUUCUUGGGAGGNN | 2833 | CCUCCCAAGAAUGGUUUACNN | 2834 |
| NM_005080_1144-1162 | UAAACCAUUCUUGGGAGGANN | 2835 | UCCUCCCAAGAAUGGUUUANN | 2836 |
| NM_005080_1145-1163 | AAACCAUUCUUGGGAGGACNN | 2837 | GUCCUCCCAAGAAUGGUUUNN | 2838 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_1148-1166 | CCAUUCUUGGGAGGACACUNN | 2839 | AGUGUCCUCCCAAGAAUGGNN | 2840 |
| NM_005080_1156-1174 | GGGAGGACACUUUUGCCAANN | 2841 | UUGGCAAAAGUGUCCUCCCNN | 2842 |
| NM_005080_1157-1175 | GGAGGACACUUUUGCCAAUNN | 2843 | AUUGGCAAAAGUGUCCUCCNN | 2844 |
| NM_005080_1159-1177 | AGGACACUUUUGCCAAUGANN | 2845 | UCAUUGGCAAAAGUGUCCUNN | 2846 |
| NM_005080_1160-1178 | GGACACUUUUGCCAAUGAANN | 2847 | UUCAUUGGCAAAAGUGUCCNN | 2848 |
| NM_005080_1190-1208 | GCUGAUUAGUGUCUAAGGANN | 2849 | UCCUUAGACACUAAUCAGCNN | 2850 |
| NM_005080_1218-1236 | UACUGUUGCCCUUUUCCUUNN | 2851 | AAGGAAAAGGGCAACAGUANN | 2852 |
| NM_005080_1220-1238 | CUGUUGCCCUUUUCCUUGANN | 2853 | UCAAGGAAAAGGGCAACAGNN | 2854 |
| NM_005080_1221-1239 | UGUUGCCCUUUUCCUUGACNN | 2855 | GUCAAGGAAAAGGGCAACANN | 2856 |
| NM_005080_1233-1251 | CCUUGACUAUUACACUGCCNN | 2857 | GGCAGUGUAAUAGUCAAGGNN | 2858 |
| NM_005080_1240-1258 | UAUUACACUGCCUGGAGGANN | 2859 | UCCUCCAGGCAGUGUAAUANN | 2860 |
| NM_005080_1241-1259 | AUUACACUGCCUGGAGGAUNN | 2861 | AUCCUCCAGGCAGUGUAAUNN | 2862 |
| NM_005080_1242-1260 | UUACACUGCCUGGAGGAUANN | 2863 | UAUCCUCCAGGCAGUGUAANN | 2864 |
| NM_005080_1243-1261 | UACACUGCCUGGAGGAUAGNN | 2865 | CUAUCCUCCAGGCAGUGUANN | 2866 |
| NM_005080_1282-1300 | UCAUUCAAAAGCCAAAAUNN | 2867 | AUUUUGGCUUUUUGAAUGNN | 2868 |
| NM_005080_1287-1305 | CAAAAGCCAAAAUAGAGANN | 2869 | UCUCUAUUUUGGCUUUUUGNN | 2870 |
| NM_005080_1289-1307 | AAAAGCCAAAAUAGAGAGUNN | 2871 | ACUCUCUAUUUUGGCUUUUNN | 2872 |
| NM_005080_1310-1328 | ACAGUCCUAGAGAAUUCCUNN | 2873 | AGGAAUUCUCUAGGACUGUNN | 2874 |
| NM_005080_1330-1348 | UAUUUGUUCAGAUCUCAUANN | 2875 | UAUGAGAUCUGAACAAAUANN | 2876 |
| NM_005080_1332-1350 | UUUGUUCAGAUCUCAUAGANN | 2877 | UCUAUGAGAUCUGAACAAANN | 2878 |
| NM_005080_1333-1351 | UUGUUCAGAUCUCAUAGAUNN | 2879 | AUCUAUGAGAUCUGAACAANN | 2880 |
| NM_005080_1369-1387 | UUUUGACAUCCAGCAGUCCNN | 2881 | GGACUGCUGGAUGUCAAAANN | 2882 |
| NM_005080_1370-1388 | UUUGACAUCCAGCAGUCCANN | 2883 | UGGACUGCUGGAUGUCAAANN | 2884 |
| NM_005080_1371-1389 | UUGACAUCCAGCAGUCCAANN | 2885 | UUGGACUGCUGGAUGUCAANN | 2886 |
| NM_005080_101-119 | UGCUUCUGUCGGGGCAGCCNN | 2887 | GGCUGCCCCGACAGAAGCANN | 2888 |
| NM_005080_1418-1436 | AAAUAUUACUAUAAUUGAGNN | 2889 | CUCAAUUAUAGUAAUAUUUNN | 2890 |
| NM_005080_1419-1437 | AAUAUUACUAUAAUUGAGANN | 2891 | UCUCAAUUAUAGUAAUAUUNN | 2892 |
| NM_005080_1422-1440 | AUUACUAUAAUUGAGAACUNN | 2893 | AGUUCUCAAUUAUAGUAAUNN | 2894 |
| NM_005080_102-120 | GCUUCUGUCGGGGCAGCCCNN | 2895 | GGGCUGCCCCGACAGAAGCNN | 2896 |
| NM_005080_1423-1441 | UUACUAUAAUUGAGAACUANN | 2897 | UAGUUCUCAAUUAUAGUAANN | 2898 |
| NM_005080_1425-1443 | ACUAUAAUUGAGAACUACANN | 2899 | UGUAGUUCUCAAUUAUAGUNN | 2900 |
| NM_005080_1427-1445 | UAUAAUUGAGAACUACAGCNN | 2901 | GCUGUAGUUCUCAAUUAUANN | 2902 |
| NM_005080_1428-1446 | AUAAUUGAGAACUACAGCUNN | 2903 | AGCUGUAGUUCUCAAUUAUNN | 2904 |
| NM_005080_1429-1447 | UAAUUGAGAACUACAGCUUNN | 2905 | AAGCUGUAGUUCUCAAUUANN | 2906 |
| NM_005080_1432-1450 | UUGAGAACUACAGCUUUUANN | 2907 | UAAAAGCUGUAGUUCUCAANN | 2908 |
| NM_005080_1433-1451 | UGAGAACUACAGCUUUUAANN | 2909 | UUAAAAGCUGUAGUUCUCANN | 2910 |
| NM_005080_1435-1453 | AGAACUACAGCUUUUAAGANN | 2911 | UCUUAAAAGCUGUAGUUCUNN | 2912 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_1439-1457 | CUACAGCUUUUAAGAUUGUNN | 2913 | ACAAUCUUAAAAGCUGUAGNN | 2914 |
| NM_005080_104-122 | UUCUGUCGGGGCAGCCCGCNN | 2915 | GCGGGCUGCCCCGACAGAANN | 2916 |
| NM_005080_1444-1462 | GCUUUUAAGAUUGUACUUUNN | 2917 | AAAGUACAAUCUUAAAAGCNN | 2918 |
| NM_005080_1445-1463 | CUUUUAAGAUUGUACUUUUNN | 2919 | AAAAGUACAAUCUUAAAAGNN | 2920 |
| NM_005080_1446-1464 | UUUUAAGAUUGUACUUUUANN | 2921 | UAAAAGUACAAUCUUAAAANN | 2922 |
| NM_005080_1447-1465 | UUUAAGAUUGUACUUUUAUNN | 2923 | AUAAAAGUACAAUCUUAAANN | 2924 |
| NM_005080_1448-1466 | UUAAGAUUGUACUUUUAUCNN | 2925 | GAUAAAAGUACAAUCUUAANN | 2926 |
| NM_005080_1451-1469 | AGAUUGUACUUUUAUCUUANN | 2927 | UAAGAUAAAAGUACAAUCNN | 2928 |
| NM_005080_1454-1472 | UUGUACUUUUAUCUUAAAANN | 2929 | UUUUAAGAUAAAAGUACAANN | 2930 |
| NM_005080_1458-1476 | ACUUUUAUCUUAAAAGGGUNN | 2931 | ACCCUUUUAAGAUAAAAGUNN | 2932 |
| NM_005080_1459-1477 | CUUUUAUCUUAAAAGGGUGNN | 2933 | CACCCUUUUAAGAUAAAAGNN | 2934 |
| NM_005080_106-124 | CUGUCGGGCAGCCCGCCUNN | 2935 | AGGCGGGCUGCCCCGACAGNN | 2936 |
| NM_005080_1466-1484 | CUUAAAAGGGUGGUAGUUUNN | 2937 | AAACUACCACCCUUUUAAGNN | 2938 |
| NM_005080_1486-1504 | CCCUAAAAUACUUAUUAUGNN | 2939 | CAUAAUAAGUAUUUUAGGGNN | 2940 |
| NM_005080_1487-1505 | CCUAAAAUACUUAUUAUGUNN | 2941 | ACAUAAUAAGUAUUUUAGGNN | 2942 |
| NM_005080_1489-1507 | UAAAAUACUUAUUAUGUAANN | 2943 | UUACAUAAUAAGUAUUUUANN | 2944 |
| NM_005080_1490-1508 | AAAAUACUUAUUAUGUAAGNN | 2945 | CUUACAUAAUAAGUAUUUUNN | 2946 |
| NM_005080_1491-1509 | AAAUACUUAUUAUGUAAGGNN | 2947 | CCUUACAUAAUAAGUAUUUNN | 2948 |
| NM_005080_109-127 | UCGGGGCAGCCCGCCUCCGNN | 2949 | CGGAGGCGGGCUGCCCCGANN | 2950 |
| NM_005080_1497-1515 | UUAUUAUGUAAGGGUCAUUNN | 2951 | AAUGACCCUUACAUAAUAANN | 2952 |
| NM_005080_1498-1516 | UAUUAUGUAAGGGUCAUUANN | 2953 | UAAUGACCCUUACAUAAUANN | 2954 |
| NM_005080_110-128 | CGGGGCAGCCCGCCUCCGCNN | 2955 | GCGGAGGCGGGCUGCCCCGNN | 2956 |
| NM_005080_1511-1529 | UCAUUAGACAAAUGUCUUGNN | 2957 | CAAGACAUUUGUCUAAUGANN | 2958 |
| NM_005080_1513-1531 | AUUAGACAAAUGUCUUGAANN | 2959 | UUCAAGACAUUUGUCUAAUNN | 2960 |
| NM_005080_1516-1534 | AGACAAAUGUCUUGAAGUANN | 2961 | UACUUCAAGACAUUUGUCUNN | 2962 |
| NM_005080_1517-1535 | GACAAAUGUCUUGAAGUAGNN | 2963 | CUACUUCAAGACAUUUGUCNN | 2964 |
| NM_005080_1518-1536 | ACAAAUGUCUUGAAGUAGANN | 2965 | UCUACUUCAAGACAUUUGUNN | 2966 |
| NM_005080_1547-1565 | AUGAAUGGUUCUUUAUCAUNN | 2967 | AUGAUAAAGAACCAUUCAUNN | 2968 |
| NM_005080_1550-1568 | AAUGGUUCUUUAUCAUUUCNN | 2969 | GAAAUGAUAAAGAACCAUUNN | 2970 |
| NM_005080_1551-1569 | AUGGUUCUUUAUCAUUUCUNN | 2971 | AGAAAUGAUAAAGAACCAUNN | 2972 |
| NM_005080_1552-1570 | UGGUUCUUUAUCAUUUCUCNN | 2973 | GAGAAAUGAUAAAGAACCANN | 2974 |
| NM_005080_1554-1572 | GUUCUUUAUCAUUUCUCUUNN | 2975 | AAGAGAAAUGAUAAAGAACNN | 2976 |
| NM_005080_1559-1577 | UUAUCAUUUCUCUUCCCCCNN | 2977 | GGGGGAAGAGAAAUGAUAANN | 2978 |
| NM_005080_1560-1578 | UAUCAUUUCUCUUCCCCCUNN | 2979 | AGGGGGAAGAGAAAUGAUANN | 2980 |
| NM_005080_1563-1581 | CAUUUCUCUUCCCCCUUUUNN | 2981 | AAAAGGGGGAAGAGAAAUGNN | 2982 |
| NM_005080_1565-1583 | UUUCUCUUCCCCCUUUUUGNN | 2983 | CAAAAGGGGGAAGAGAAANN | 2984 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
| --- | --- | --- | --- | --- |
| NM_005080_1566-1584 | UUCUCUUCCCCCUUUUUGGNN | 2985 | CCAAAAAGGGGGAAGAGAANN | 2986 |
| NM_005080_1570-1588 | CUUCCCCCUUUUUGGCAUCNN | 2987 | GAUGCCAAAAAGGGGGAAGNN | 2988 |
| NM_005080_1573-1591 | CCCCCUUUUUGGCAUCCUGNN | 2989 | CAGGAUGCCAAAAAGGGGNN | 2990 |
| NM_005080_1578-1596 | UUUUUGGCAUCCUGGCUUGNN | 2991 | CAAGCCAGGAUGCCAAAAANN | 2992 |
| NM_005080_1579-1597 | UUUUGGCAUCCUGGCUUGCNN | 2993 | GCAAGCCAGGAUGCCAAAANN | 2994 |
| NM_005080_1580-1598 | UUUGGCAUCCUGGCUUGCCNN | 2995 | GGCAAGCCAGGAUGCCAAANN | 2996 |
| NM_005080_1581-1599 | UUGGCAUCCUGGCUUGCCUNN | 2997 | AGGCAAGCCAGGAUGCCAANN | 2998 |
| NM_005080_1583-1601 | GGCAUCCUGGCUUGCCUCCNN | 2999 | GGAGGCAAGCCAGGAUGCCNN | 3000 |
| NM_005080_1584-1602 | GCAUCCUGGCUUGCCUCCANN | 3001 | UGGAGGCAAGCCAGGAUGCNN | 3002 |
| NM_005080_1586-1604 | AUCCUGGCUUGCCUCCAGUNN | 3003 | ACUGGAGGCAAGCCAGGAUNN | 3004 |
| NM_005080_1589-1607 | CUGGCUUGCCUCCAGUUUUNN | 3005 | AAAACUGGAGGCAAGCCAGNN | 3006 |
| NM_005080_1590-1608 | UGGCUUGCCUCCAGUUUUANN | 3007 | UAAAACUGGAGGCAAGCCANN | 3008 |
| NM_005080_1595-1613 | UGCCUCCAGUUUUAGGUCCNN | 3009 | GGACCUAAAACUGGAGGCANN | 3010 |
| NM_005080_1616-1634 | UAGUUUGCUUCUGUAAGCANN | 3011 | UGCUUACAGAAGCAAACUANN | 3012 |
| NM_005080_1617-1635 | AGUUUGCUUCUGUAAGCAANN | 3013 | UUGCUUACAGAAGCAAACUNN | 3014 |
| NM_005080_1643-1661 | ACCUGCUGAGGGGCUCUUNN | 3015 | AAGAGCCCCCUCAGCAGGUNN | 3016 |
| NM_005080_1645-1663 | CUGCUGAGGGGCUCUUUCNN | 3017 | GAAAGAGCCCCCUCAGCAGNN | 3018 |
| NM_005080_1646-1664 | UGCUGAGGGGCUCUUUCCNN | 3019 | GGAAAGAGCCCCCUCAGCANN | 3020 |
| NM_005080_1647-1665 | GCUGAGGGGCUCUUUCCCNN | 3021 | GGGAAAGAGCCCCCUCAGCNN | 3022 |
| NM_005080_1648-1666 | CUGAGGGGCUCUUUCCCUNN | 3023 | AGGGAAAGAGCCCCCUCAGNN | 3024 |
| NM_005080_1649-1667 | UGAGGGGCUCUUUCCCUCNN | 3025 | GAGGGAAAGAGCCCCCUCANN | 3026 |
| NM_005080_1679-1697 | AAGUAAGAUCAAGAAUCUUNN | 3027 | AAGAUUCUUGAUCUUACUUNN | 3028 |
| NM_005080_1680-1698 | AGUAAGAUCAAGAAUCUUUNN | 3029 | AAAGAUUCUUGAUCUUACUNN | 3030 |
| NM_005080_1681-1699 | GUAAGAUCAAGAAUCUUUUNN | 3031 | AAAAGAUUCUUGAUCUUACNN | 3032 |
| NM_005080_1682-1700 | UAAGAUCAAGAAUCUUUUGNN | 3033 | CAAAAGAUUCUUGAUCUUANN | 3034 |
| NM_005080_1683-1701 | AAGAUCAAGAAUCUUUUGUNN | 3035 | ACAAAAGAUUCUUGAUCUUNN | 3036 |
| NM_005080_1684-1702 | AGAUCAAGAAUCUUUUGUGNN | 3037 | CACAAAAGAUUCUUGAUCUNN | 3038 |
| NM_005080_1687-1705 | UCAAGAAUCUUUUGUGAAANN | 3039 | UUUCACAAAAGAUUCUUGANN | 3040 |
| NM_005080_1709-1727 | UAGAAAUUUACUAUGUAAANN | 3041 | UUUACAUAGUAAAUUUCUANN | 3042 |
| NM_005080_1710-1728 | AGAAAUUUACUAUGUAAAUNN | 3043 | AUUUACAUAGUAAAUUUCUNN | 3044 |
| NM_005080_1711-1729 | GAAAUUUACUAUGUAAAUGNN | 3045 | CAUUUACAUAGUAAAUUUCNN | 3046 |
| NM_005080_1712-1730 | AAAUUUACUAUGUAAAUGCNN | 3047 | GCAUUUACAUAGUAAAUUUNN | 3048 |
| NM_005080_1714-1732 | AUUUACUAUGUAAAUGCUUNN | 3049 | AAGCAUUUACAUAGUAAAUNN | 3050 |
| NM_005080_1715-1733 | UUUACUAUGUAAAUGCUUGNN | 3051 | CAAGCAUUUACAUAGUAAANN | 3052 |
| NM_005080_1717-1735 | UACUAUGUAAAUGCUUGAUNN | 3053 | AUCAAGCAUUUACAUAGUANN | 3054 |
| NM_005080_1719-1737 | CUAUGUAAAUGCUUGAUGGNN | 3055 | CCAUCAAGCAUUUACAUAGNN | 3056 |
| NM_005080_1721-1739 | AUGUAAAUGCUUGAUGGAANN | 3057 | UUCCAUCAAGCAUUUACAUNN | 3058 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_1722-1740 | UGUAAAUGCUUGAUGGAAUNN | 3059 | AUUCCAUCAAGCAUUUACANN | 3060 |
| NM_005080_1723-1741 | GUAAAUGCUUGAUGGAAUUNN | 3061 | AAUUCCAUCAAGCAUUUACNN | 3062 |
| NM_005080_1726-1744 | AAUGCUUGAUGGAAUUUUUNN | 3063 | AAAAAUUCCAUCAAGCAUUNN | 3064 |
| NM_005080_1727-1745 | AUGCUUGAUGGAAUUUUUUNN | 3065 | AAAAAAUUCCAUCAAGCAUNN | 3066 |
| NM_005080_1728-1746 | UGCUUGAUGGAAUUUUUUCNN | 3067 | GAAAAAAUUCCAUCAAGCANN | 3068 |
| NM_005080_1729-1747 | GCUUGAUGGAAUUUUUUCCNN | 3069 | GGAAAAAAUUCCAUCAAGCNN | 3070 |
| NM_005080_1736-1754 | GGAAUUUUUUCCUGCUAGUNN | 3071 | ACUAGCAGGAAAAAAUUCCNN | 3072 |
| NM_005080_1739-1757 | AUUUUUUCCUGCUAGUGUANN | 3073 | UACACUAGCAGGAAAAAAUNN | 3074 |
| NM_005080_1746-1764 | CCUGCUAGUGUAGCUUCUGNN | 3075 | CAGAAGCUACACUAGCAGGNN | 3076 |
| NM_005080_1747-1765 | CUGCUAGUGUAGCUUCUGANN | 3077 | UCAGAAGCUACACUAGCAGNN | 3078 |
| NM_005080_1749-1767 | GCUAGUGUAGCUUCUGAAANN | 3079 | UUUCAGAAGCUACACUAGCNN | 3080 |
| NM_005080_1750-1768 | CUAGUGUAGCUUCUGAAAGNN | 3081 | CUUUCAGAAGCUACACUAGNN | 3082 |
| NM_005080_1751-1769 | UAGUGUAGCUUCUGAAAGGNN | 3083 | CCUUUCAGAAGCUACACUANN | 3084 |
| NM_005080_1752-1770 | AGUGUAGCUUCUGAAAGGUNN | 3085 | ACCUUUCAGAAGCUACACUNN | 3086 |
| NM_005080_1753-1771 | GUGUAGCUUCUGAAAGGUGNN | 3087 | CACCUUUCAGAAGCUACACNN | 3088 |
| NM_005080_1755-1773 | GUAGCUUCUGAAAGGUGCUNN | 3089 | AGCACCUUUCAGAAGCUACNN | 3090 |
| NM_005080_1758-1776 | GCUUCUGAAAGGUGCUUUCNN | 3091 | GAAAGCACCUUUCAGAAGCNN | 3092 |
| NM_005080_1781-1799 | UUUAUUUAAAACUACCCAUNN | 3093 | AUGGGUAGUUUUAAAUAAANN | 3094 |
| NM_005080_1782-1800 | UUAUUUAAAACUACCCAUGNN | 3095 | CAUGGGUAGUUUUAAAUAANN | 3096 |
| NM_005080_1784-1802 | AUUUAAAACUACCCAUGCANN | 3097 | UGCAUGGGUAGUUUUAAAUNN | 3098 |
| NM_005080_1785-1803 | UUUAAAACUACCCAUGCAANN | 3099 | UUGCAUGGGUAGUUUUAAANN | 3100 |
| NM_005080_1788-1806 | AAAACUACCCAUGCAAUUANN | 3101 | UAAUUGCAUGGGUAGUUUUNN | 3102 |
| NM_005080_1792-1810 | CUACCCAUGCAAUUAAAAGNN | 3103 | CUUUUAAUUGCAUGGGUAGNN | 3104 |
| NM_005080_1793-1811 | UACCCAUGCAAUUAAAAGGNN | 3105 | CCUUUUAAUUGCAUGGGUANN | 3106 |
| NM_005080_1795-1813 | CCCAUGCAAUUAAAAGGUANN | 3107 | UACCUUUUAAUUGCAUGGGNN | 3108 |
| NM_005080_1798-1816 | AUGCAAUUAAAAGGUACAANN | 3109 | UUGUACCUUUUAAUUGCAUNN | 3110 |
| NM_005080_1799-1817 | UGCAAUUAAAAGGUACAAUNN | 3111 | AUUGUACCUUUUAAUUGCANN | 3112 |
| NM_005080_1800-1818 | GCAAUUAAAAGGUACAAUGNN | 3113 | CAUUGUACCUUUUAAUUGCNN | 3114 |
| NM_005080_1801-1819 | CAAUUAAAAGGUACAAUGCNN | 3115 | GCAUUGUACCUUUUAAUUGNN | 3116 |
| NM_005080_146-164 | GCCAGGCCCUGCCGCUCAUNN | 3117 | AUGAGCGGCAGGGCCUGGCNN | 3118 |
| NM_005080_147-165 | CCAGGCCCUGCCGCUCAUGNN | 3119 | CAUGAGCGGCAGGGCCUGGNN | 3120 |
| NM_005080_148-166 | CAGGCCCUGCCGCUCAUGGNN | 3121 | CCAUGAGCGGCAGGGCCUGNN | 3122 |
| NM_005080_149-167 | AGGCCCUGCCGCUCAUGGUNN | 3123 | ACCAUGAGCGGCAGGGCCUNN | 3124 |
| NM_005080_155-173 | UGCCGCUCAUGGUGCCAGCNN | 3125 | GCUGGCACCAUGAGCGGCANN | 3126 |
| NM_005080_157-175 | CCGCUCAUGGUGCCAGCCCNN | 3127 | GGGCUGGCACCAUGAGCGGNN | 3128 |
| NM_005080_158-176 | CGCUCAUGGUGCCAGCCCANN | 3129 | UGGGCUGGCACCAUGAGCGNN | 3130 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
| --- | --- | --- | --- | --- |
| NM_005080_159-177 | GCUCAUGGUGCCAGCCCAGNN | 3131 | CUGGGCUGGCACCAUGAGCNN | 3132 |
| NM_005080_188-206 | GCCCGGAGGCAGCGAGCGGNN | 3133 | CCGCUCGCUGCCUCCGGGCNN | 3134 |
| NM_005080_189-207 | CCCGGAGGCAGCGAGCGGGNN | 3135 | CCCGCUCGCUGCCUCCGGGNN | 3136 |
| NM_005080_195-213 | GGCAGCGAGCGGGGGCUGNN | 3137 | CAGCCCCCCGCUCGCUGCCNN | 3138 |
| NM_005080_196-214 | GCAGCGAGCGGGGGCUGCNN | 3139 | GCAGCCCCCCGCUCGCUGCNN | 3140 |
| NM_005080_197-215 | CAGCGAGCGGGGGCUGCCNN | 3141 | GGCAGCCCCCCGCUCGCUGNN | 3142 |
| NM_005080_198-216 | AGCGAGCGGGGGCUGCCCNN | 3143 | GGGCAGCCCCCCGCUCGCUNN | 3144 |
| NM_005080_205-223 | GGGGGCUGCCCCAGGCGCNN | 3145 | GCGCCUGGGGCAGCCCCCNN | 3146 |
| NM_005080_206-224 | GGGGGCUGCCCCAGGCGCGNN | 3147 | CGCGCCUGGGGCAGCCCCCNN | 3148 |
| NM_005080_207-225 | GGGGCUGCCCCAGGCGCGCNN | 3149 | GCGCGCCUGGGGCAGCCCCNN | 3150 |
| NM_005080_211-229 | CUGCCCCAGGCGCGCAAGCNN | 3151 | GCUUGCGCGCCUGGGGCAGNN | 3152 |
| NM_005080_250-268 | AGCCCCGAGGAGAAGGCGCNN | 3153 | GCGCCUUCUCCUCGGGGCUNN | 3154 |
| NM_005080_256-274 | GAGGAGAAGGCGCUGAGGANN | 3155 | UCCUCAGCGCCUUCUCCUCNN | 3156 |
| NM_005080_263-281 | AGGCGCUGAGGAGGAAACUNN | 3157 | AGUUUCCUCCUCAGCGCCUNN | 3158 |
| NM_005080_264-282 | GGCGCUGAGGAGGAAACUGNN | 3159 | CAGUUUCCUCCUCAGCGCCNN | 3160 |
| NM_005080_285-303 | AAACAGAGUAGCAGCUCAGNN | 3161 | CUGAGCUGCUACUCUGUUUNN | 3162 |
| NM_005080_286-304 | AACAGAGUAGCAGCUCAGANN | 3163 | UCUGAGCUGCUACUCUGUUNN | 3164 |
| NM_005080_287-305 | ACAGAGUAGCAGCUCAGACNN | 3165 | GUCUGAGCUGCUACUCUGUNN | 3166 |
| NM_005080_294-312 | AGCAGCUCAGACUGCCAGNN | 3167 | UCUGGCAGUCUGAGCUGCUNN | 3168 |
| NM_005080_295-313 | GCAGCUCAGACUGCCAGANN | 3169 | CUCUGGCAGUCUGAGCUGCNN | 3170 |
| NM_005080_296-314 | CAGCUCAGACUGCCAGAGANN | 3171 | UCUCUGGCAGUCUGAGCUGNN | 3172 |
| NM_005080_298-316 | GCUCAGACUGCCAGAGAUCNN | 3173 | GAUCUCUGGCAGUCUGAGCNN | 3174 |
| NM_005080_303-321 | GACUGCCAGAGAUCGAAAGNN | 3175 | CUUUCGAUCUCUGGCAGUCNN | 3176 |
| NM_005080_332-350 | UGAGUGAGCUGGAACAGCANN | 3177 | UGCUGUUCCAGCUCACUCANN | 3178 |
| NM_005080_339-357 | GCUGGAACAGCAAGUGGUANN | 3179 | UACCACUUGCUGUUCCAGCNN | 3180 |
| NM_005080_340-358 | CUGGAACAGCAAGUGGUAGNN | 3181 | CUACCACUUGCUGUUCCAGNN | 3182 |
| NM_005080_345-363 | ACAGCAAGUGGUAGAUUUANN | 3183 | UAAAUCUACCACUUGCUGUNN | 3184 |
| NM_005080_346-364 | CAGCAAGUGGUAGAUUUAGNN | 3185 | CUAAAUCUACCACUUGCUGNN | 3186 |
| NM_005080_348-366 | GCAAGUGGUAGAUUUAGAANN | 3187 | UUCUAAAUCUACCACUUGCNN | 3188 |
| NM_005080_349-367 | CAAGUGGUAGAUUUAGAAGNN | 3189 | CUUCUAAAUCUACCACUUGNN | 3190 |
| NM_005080_352-370 | GUGGUAGAUUUAGAAGAAGNN | 3191 | CUUCUUCUAAAUCUACCACNN | 3192 |
| NM_005080_353-371 | UGGUAGAUUUAGAAGAAGANN | 3193 | UCUUCUUCUAAAUCUACCANN | 3194 |
| NM_005080_354-372 | GGUAGAUUUAGAAGAAGAGNN | 3195 | CUCUUCUUCUAAAUCUACCNN | 3196 |
| NM_005080_355-373 | GUAGAUUUAGAAGAAGAGANN | 3197 | UCUCUUCUUCUAAAUCUACNN | 3198 |
| NM_005080_361-379 | UUAGAAGAAGAGAACCAAANN | 3199 | UUUGGUUCUCUUCUUCUAANN | 3200 |
| NM_005080_366-384 | AGAAGAGAACCAAAAACUUNN | 3201 | AAGUUUUUGGUUCUCUUCUNN | 3202 |
| NM_005080_369-387 | AGAGAACCAAAAACUUUUGNN | 3203 | CAAAAGUUUUUGGUUCUCUNN | 3204 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
| --- | --- | --- | --- | --- |
| NM_005080_370-388 | GAGAACCAAAAACUUUUGCNN | 3205 | GCAAAAGUUUUUGGUUCUCNN | 3206 |
| NM_005080_372-390 | GAACCAAAAACUUUUGCUANN | 3207 | UAGCAAAAGUUUUUGGUUCNN | 3208 |
| NM_005080_376-394 | CAAAAACUUUUGCUAGAAANN | 3209 | UUUCUAGCAAAAGUUUUUGNN | 3210 |
| NM_005080_381-399 | ACUUUUGCUAGAAAAUCAGNN | 3211 | CUGAUUUUCUAGCAAAAGUNN | 3212 |
| NM_005080_384-402 | UUUGCUAGAAAAUCAGCUUNN | 3213 | AAGCUGAUUUUCUAGCAAANN | 3214 |
| NM_005080_388-406 | CUAGAAAAUCAGCUUUUACNN | 3215 | GUAAAAGCUGAUUUUCUAGNN | 3216 |
| NM_005080_392-410 | AAAAUCAGCUUUUACGAGANN | 3217 | UCUCGUAAAAGCUGAUUUUNN | 3218 |
| NM_005080_394-412 | AAUCAGCUUUUACGAGAGANN | 3219 | UCUCUCGUAAAAGCUGAUUNN | 3220 |
| NM_005080_396-414 | UCAGCUUUUACGAGAGAAANN | 3221 | UUUCUCUCGUAAAAGCUGANN | 3222 |
| NM_005080_400-418 | CUUUUACGAGAGAAAACUCNN | 3223 | GAGUUUUCUCUCGUAAAAGNN | 3224 |
| NM_005080_421-439 | GGCCUUGUAGUUGAGAACCNN | 3225 | GGUUCUCAACUACAAGGCCNN | 3226 |
| NM_005080_422-440 | GCCUUGUAGUUGAGAACCANN | 3227 | UGGUUCUCAACUACAAGGCNN | 3228 |
| NM_005080_423-441 | CCUUGUAGUUGAGAACCAGNN | 3229 | CUGGUUCUCAACUACAAGGNN | 3230 |
| NM_005080_425-443 | UUGUAGUUGAGAACCAGGANN | 3231 | UCCUGGUUCUCAACUACAANN | 3232 |
| NM_005080_428-446 | UAGUUGAGAACCAGGAGUUNN | 3233 | AACUCCUGGUUCUCAACUANN | 3234 |
| NM_005080_429-447 | AGUUGAGAACCAGGAGUUANN | 3235 | UAACUCCUGGUUCUCAACUNN | 3236 |
| NM_005080_432-450 | UGAGAACCAGGAGUUAAGANN | 3237 | UCUUAACUCCUGGUUCUCANN | 3238 |
| NM_005080_433-451 | GAGAACCAGGAGUUAAGACNN | 3239 | GUCUUAACUCCUGGUUCUCNN | 3240 |
| NM_005080_434-452 | AGAACCAGGAGUUAAGACANN | 3241 | UGUCUUAACUCCUGGUUCUNN | 3242 |
| NM_005080_435-453 | GAACCAGGAGUUAAGACAGNN | 3243 | CUGUCUUAACUCCUGGUUCNN | 3244 |
| NM_005080_436-454 | AACCAGGAGUUAAGACAGCNN | 3245 | GCUGUCUUAACUCCUGGUUNN | 3246 |
| NM_005080_459-477 | GGGGAUGGAUGCCCUGGUUNN | 3247 | AACCAGGGCAUCCAUCCCCNN | 3248 |
| NM_005080_460-478 | GGGAUGGAUGCCCUGGUUGNN | 3249 | CAACCAGGGCAUCCAUCCCNN | 3250 |
| NM_005080_462-480 | GAUGGAUGCCCUGGUUGCUNN | 3251 | AGCAACCAGGGCAUCCAUCNN | 3252 |
| NM_005080_486-504 | GGAGGCGGAAGCCAAGGGGNN | 3253 | CCCCUUGGCUUCCGCCUCCNN | 3254 |
| NM_005080_510-528 | AGUGAGGCCAGUGGCCGGGNN | 3255 | CCCGGCCACUGGCCUCACUNN | 3256 |
| NM_005080_513-531 | GAGGCCAGUGGCCGGGUCUNN | 3257 | AGACCCGGCCACUGGCCUCNN | 3258 |
| NM_005080_514-532 | AGGCCAGUGGCCGGGUCUGNN | 3259 | CAGACCCGGCCACUGGCCUNN | 3260 |
| NM_005080_515-533 | GGCCAGUGGCCGGGUCUGCNN | 3261 | GCAGACCCGGCCACUGGCCNN | 3262 |
| NM_005080_516-534 | GCCAGUGGCCGGGUCUGCUNN | 3263 | AGCAGACCCGGCCACUGGCNN | 3264 |
| NM_005080_520-538 | GUGGCCGGGUCUGCUGAGUNN | 3265 | ACUCAGCAGACCCGGCCACNN | 3266 |
| NM_005080_521-539 | UGGCCGGGUCUGCUGAGUCNN | 3267 | GACUCAGCAGACCCGGCCANN | 3268 |
| NM_005080_523-541 | GCCGGGUCUGCUGAGUCCGNN | 3269 | CGGACUCAGCAGACCCGGCNN | 3270 |
| NM_005080_578-596 | AGGCCCAGUUGUCACCCCUNN | 3271 | AGGGGUGACAACUGGGCCUNN | 3272 |
| NM_005080_581-599 | CCCAGUUGUCACCCCUCCANN | 3273 | UGGAGGGGUGACAACUGGGNN | 3274 |
| NM_005080_582-600 | CCAGUUGUCACCCCUCCAGNN | 3275 | CUGGAGGGGUGACAACUGGNN | 3276 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_583-601 | CAGUUGUCACCCCUCCAGANN | 3277 | UCUGGAGGGGUGACAACUGNN | 3278 |
| NM_005080_584-602 | AGUUGUCACCCCUCCAGAANN | 3279 | UUCUGGAGGGGUGACAACUNN | 3280 |
| NM_005080_585-603 | GUUGUCACCCCUCCAGAACNN | 3281 | GUUCUGGAGGGGUGACAACNN | 3282 |
| NM_005080_586-604 | UUGUCACCCCUCCAGAACANN | 3283 | UGUUCUGGAGGGGUGACAANN | 3284 |
| NM_005080_587-605 | UGUCACCCCUCCAGAACAUNN | 3285 | AUGUUCUGGAGGGGUGACANN | 3286 |
| NM_005080_588-606 | GUCACCCCUCCAGAACAUCNN | 3287 | GAUGUUCUGGAGGGGUGACNN | 3288 |
| NM_005080_589-607 | UCACCCCUCCAGAACAUCUNN | 3289 | AGAUGUUCUGGAGGGGUGANN | 3290 |
| NM_005080_590-608 | CACCCCUCCAGAACAUCUCNN | 3291 | GAGAUGUUCUGGAGGGGUGNN | 3292 |
| NM_005080_591-609 | ACCCCUCCAGAACAUCUCCNN | 3293 | GGAGAUGUUCUGGAGGGGUNN | 3294 |
| NM_005080_597-615 | CCAGAACAUCUCCCCAUGGNN | 3295 | CCAUGGGGAGAUGUUCUGGNN | 3296 |
| NM_005080_600-618 | GAACAUCUCCCCAUGGAUUNN | 3297 | AAUCCAUGGGGAGAUGUUCNN | 3298 |
| NM_005080_603-621 | CAUCUCCCCAUGGAUUCUGNN | 3299 | CAGAAUCCAUGGGGAGAUGNN | 3300 |
| NM_005080_619-637 | CUGGCGGUAUUGACUCUUCNN | 3301 | GAAGAGUCAAUACCGCCAGNN | 3302 |
| NM_005080_620-638 | UGGCGGUAUUGACUCUUCANN | 3303 | UGAAGAGUCAAUACCGCCANN | 3304 |
| NM_005080_622-640 | GCGGUAUUGACUCUUCAGNN | 3305 | UCUGAAGAGUCAAUACCGCNN | 3306 |
| NM_005080_623-641 | CGGUAUUGACUCUUCAGAUNN | 3307 | AUCUGAAGAGUCAAUACCGNN | 3308 |
| NM_005080_624-642 | GGUAUUGACUCUUCAGAUUNN | 3309 | AAUCUGAAGAGUCAAUACCNN | 3310 |
| NM_005080_625-643 | GUAUUGACUCUUCAGAUUCNN | 3311 | GAAUCUGAAGAGUCAAUACNN | 3312 |
| NM_005080_626-644 | UAUUGACUCUUCAGAUUCANN | 3313 | UGAAUCUGAAGAGUCAAUANN | 3314 |
| NM_005080_629-647 | UGACUCUUCAGAUUCAGAGNN | 3315 | CUCUGAAUCUGAAGAGUCANN | 3316 |
| NM_005080_632-650 | CUCUUCAGAUUCAGAGUCUNN | 3317 | AGACUCUGAAUCUGAAGAGNN | 3318 |
| NM_005080_634-652 | CUUCAGAUUCAGAGUCUGANN | 3319 | UCAGACUCUGAAUCUGAAGNN | 3320 |
| NM_005080_637-655 | CAGAUUCAGAGUCUGAUAUNN | 3321 | AUAUCAGACUCUGAAUCUGNN | 3322 |
| NM_005080_638-656 | AGAUUCAGAGUCUGAUAUCNN | 3323 | GAUAUCAGACUCUGAAUCUNN | 3324 |
| NM_005080_639-657 | GAUUCAGAGUCUGAUAUCCNN | 3325 | GGAUAUCAGACUCUGAAUCNN | 3326 |
| NM_005080_642-660 | UCAGAGUCUGAUAUCCUGUNN | 3327 | ACAGGAUAUCAGACUCUGANN | 3328 |
| NM_005080_643-661 | CAGAGUCUGAUAUCCUGUUNN | 3329 | AACAGGAUAUCAGACUCUGNN | 3330 |
| NM_005080_644-662 | AGAGUCUGAUAUCCUGUUGNN | 3331 | CAACAGGAUAUCAGACUCUNN | 3332 |
| NM_005080_646-664 | AGUCUGAUAUCCUGUUGGGNN | 3333 | CCCAACAGGAUAUCAGACUNN | 3334 |
| NM_005080_649-667 | CUGAUAUCCUGUUGGGCAUNN | 3335 | AUGCCCAACAGGAUAUCAGNN | 3336 |
| NM_005080_650-668 | UGAUAUCCUGUUGGGCAUUNN | 3337 | AAUGCCCAACAGGAUAUCANN | 3338 |
| NM_005080_653-671 | UAUCCUGUUGGGCAUUCUGNN | 3339 | CAGAAUGCCCAACAGGAUANN | 3340 |
| NM_005080_658-676 | UGUUGGGCAUUCUGGACAANN | 3341 | UUGUCCAGAAUGCCCAACANN | 3342 |
| NM_005080_659-677 | GUUGGGCAUUCUGGACAACNN | 3343 | GUUGUCCAGAAUGCCCAACNN | 3344 |
| NM_005080_660-678 | UUGGGCAUUCUGGACAACUNN | 3345 | AGUUGUCCAGAAUGCCCAANN | 3346 |
| NM_005080_663-681 | GGCAUUCUGGACAACUUGGNN | 3347 | CCAAGUUGUCCAGAAUGCCNN | 3348 |
| NM_005080_664-682 | GCAUUCUGGACAACUUGGANN | 3349 | UCCAAGUUGUCCAGAAUGCNN | 3350 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_668-686 | UCUGGACAACUUGGACCCANN | 3351 | UGGGUCCAAGUUGUCCAGANN | 3352 |
| NM_005080_671-689 | GGACAACUUGGACCCAGUCNN | 3353 | GACUGGGUCCAAGUUGUCCNN | 3354 |
| NM_005080_676-694 | ACUUGGACCCAGUCAUGUUNN | 3355 | AACAUGACUGGGUCCAAGUNN | 3356 |
| NM_005080_677-695 | CUUGGACCCAGUCAUGUUCNN | 3357 | GAACAUGACUGGGUCCAAGNN | 3358 |
| NM_005080_679-697 | UGGACCCAGUCAUGUUCUUNN | 3359 | AAGAACAUGACUGGGUCCANN | 3360 |
| NM_005080_680-698 | GGACCCAGUCAUGUUCUUCNN | 3361 | GAAGAACAUGACUGGGUCCNN | 3362 |
| NM_005080_682-700 | ACCCAGUCAUGUUCUUCAANN | 3363 | UUGAAGAACAUGACUGGGUNN | 3364 |
| NM_005080_687-705 | GUCAUGUUCUUCAAAUGCCNN | 3365 | GGCAUUUGAAGAACAUGACNN | 3366 |
| NM_005080_689-707 | CAUGUUCUUCAAAUGCCCUNN | 3367 | AGGGCAUUUGAAGAACAUGNN | 3368 |
| NM_005080_695-713 | CUUCAAAUGCCCUUCCCCANN | 3369 | UGGGGAAGGGCAUUUGAAGNN | 3370 |
| NM_005080_696-714 | UUCAAAUGCCCUUCCCCAGNN | 3371 | CUGGGGAAGGGCAUUUGAANN | 3372 |
| NM_005080_698-716 | CAAAUGCCCUUCCCCAGAGNN | 3373 | CUCUGGGGAAGGGCAUUUGNN | 3374 |
| NM_005080_731-749 | GGAGCUCCCAGAGGUCUACNN | 3375 | GUAGACCUCUGGGAGCUCCNN | 3376 |
| NM_005080_732-750 | GAGCUCCCAGAGGUCUACCNN | 3377 | GGUAGACCUCUGGGAGCUCNN | 3378 |
| NM_005080_733-751 | AGCUCCCAGAGGUCUACCCNN | 3379 | GGGUAGACCUCUGGGAGCUNN | 3380 |
| NM_005080_736-754 | UCCCAGAGGUCUACCCAGANN | 3381 | UCUGGGUAGACCUCUGGGANN | 3382 |
| NM_005080_737-755 | CCCAGAGGUCUACCCAGAANN | 3383 | UUCUGGGUAGACCUCUGGGNN | 3384 |
| NM_005080_738-756 | CCAGAGGUCUACCCAGAAGNN | 3385 | CUUCGGGUAGACCUCUGGNN | 3386 |
| NM_005080_740-758 | AGAGGUCUACCCAGAAGGANN | 3387 | UCCUUCUGGGUAGACCUCNN | 3388 |
| NM_005080_741-759 | GAGGUCUACCCAGAAGGACNN | 3389 | GUCCUUCUGGGUAGACCUCNN | 3390 |
| NM_005080_742-760 | AGGUCUACCCAGAAGGACCNN | 3391 | GGUCCUUCUGGGUAGACCUNN | 3392 |
| NM_005080_743-761 | GGUCUACCCAGAAGGACCCNN | 3393 | GGGUCCUUCUGGGUAGACCNN | 3394 |
| NM_005080_748-766 | ACCCAGAAGGACCCAGUUCNN | 3395 | GAACUGGGUCCUUCUGGGUNN | 3396 |
| NM_005080_749-767 | CCCAGAAGGACCCAGUUCCNN | 3397 | GGAACUGGGUCCUUCUGGGNN | 3398 |
| NM_005080_750-768 | CCAGAAGGACCCAGUUCCUNN | 3399 | AGGAACUGGGUCCUUCUGGNN | 3400 |
| NM_005080_751-769 | CAGAAGGACCCAGUUCCUUNN | 3401 | AAGGAACUGGGUCCUUCUGNN | 3402 |
| NM_005080_752-770 | AGAAGGACCCAGUUCCUUANN | 3403 | UAAGGAACUGGGUCCUUCUNN | 3404 |
| NM_005080_756-774 | GGACCCAGUUCCUUACCAGNN | 3405 | CUGGUAAGGAACUGGGUCCNN | 3406 |
| NM_005080_758-776 | ACCCAGUUCCUUACCAGCCNN | 3407 | GGCUGGUAAGGAACUGGGUNN | 3408 |
| NM_005080_759-777 | CCCAGUUCCUUACCAGCCUNN | 3409 | AGGCUGGUAAGGAACUGGGNN | 3410 |
| NM_005080_760-778 | CCAGUUCCUUACCAGCCUCNN | 3411 | GAGGCUGGUAAGGAACUGGNN | 3412 |
| NM_005080_761-779 | CAGUUCCUUACCAGCCUCCNN | 3413 | GGAGGCUGGUAAGGAACUGNN | 3414 |
| NM_005080_762-780 | AGUUCCUUACCAGCCUCCCNN | 3415 | GGGAGGCUGGUAAGGAACUNN | 3416 |
| NM_005080_767-785 | CUUACCAGCCUCCCUUUCUNN | 3417 | AGAAAGGGAGGCUGGUAAGNN | 3418 |
| NM_005080_769-787 | UACCAGCCUCCCUUUCUCUNN | 3419 | AGAGAAAGGGAGGCUGGUANN | 3420 |
| NM_005080_773-791 | AGCCUCCCUUUCUCUGUCANN | 3421 | UGACAGAGAAAGGGAGGCUNN | 3422 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_779-797 | CCUUUCUCUGUCAGUGGGGNN | 3423 | CCCCACUGACAGAGAAAGGNN | 3424 |
| NM_005080_786-804 | CUGUCAGUGGGGACGUCAUNN | 3425 | AUGACGUCCCCACUGACAGNN | 3426 |
| NM_005080_787-805 | UGUCAGUGGGGACGUCAUCNN | 3427 | GAUGACGUCCCCACUGACANN | 3428 |
| NM_005080_789-807 | UCAGUGGGGACGUCAUCAGNN | 3429 | CUGAUGACGUCCCCACUGANN | 3430 |
| NM_005080_793-811 | UGGGGACGUCAUCAGCCAANN | 3431 | UUGGCUGAUGACGUCCCCANN | 3432 |
| NM_005080_795-813 | GGGACGUCAUCAGCCAAGCNN | 3433 | GCUUGGCUGAUGACGUCCCNN | 3434 |
| NM_005080_797-815 | GACGUCAUCAGCCAAGCUGNN | 3435 | CAGCUUGGCUGAUGACGUCNN | 3436 |
| NM_005080_798-816 | ACGUCAUCAGCCAAGCUGGNN | 3437 | CCAGCUUGGCUGAUGACGUNN | 3438 |
| NM_005080_800-818 | GUCAUCAGCCAAGCUGGAANN | 3439 | UUCCAGCUUGGCUGAUGACNN | 3440 |
| NM_005080_804-822 | UCAGCCAAGCUGGAAGCCANN | 3441 | UGGCUUCCAGCUUGGCUGANN | 3442 |
| NM_005080_806-824 | AGCCAAGCUGGAAGCCAUUNN | 3443 | AAUGGCUUCCAGCUUGGCUNN | 3444 |
| NM_005080_807-825 | GCCAAGCUGGAAGCCAUUANN | 3445 | UAAUGGCUUCCAGCUUGGCNN | 3446 |
| NM_005080_808-826 | CCAAGCUGGAAGCCAUUAANN | 3447 | UUAAUGGCUUCCAGCUUGGNN | 3448 |
| NM_005080_809-827 | CAAGCUGGAAGCCAUUAAUNN | 3449 | AUUAAUGGCUUCCAGCUUGNN | 3450 |
| NM_005080_810-828 | AAGCUGGAAGCCAUUAAUGNN | 3451 | CAUUAAUGGCUUCCAGCUUNN | 3452 |
| NM_005080_811-829 | AGCUGGAAGCCAUUAAUGANN | 3453 | UCAUUAAUGGCUUCCAGCUNN | 3454 |
| NM_005080_813-831 | CUGGAAGCCAUUAAUGAACNN | 3455 | GUUCAUUAAUGGCUUCCAGNN | 3456 |
| NM_005080_814-832 | UGGAAGCCAUUAAUGAACUNN | 3457 | AGUUCAUUAAUGGCUUCCANN | 3458 |
| NM_005080_818-836 | AGCCAUUAAUGAACUAAUUNN | 3459 | AAUUAGUUCAUUAAUGGCUNN | 3460 |
| NM_005080_820-838 | CCAUUAAUGAACUAAUUCGNN | 3461 | CGAAUUAGUUCAUUAAUGGNN | 3462 |
| NM_005080_837-855 | CGUUUUGACCACAUAUAUANN | 3463 | UAUAUAUGUGGUCAAAACGNN | 3464 |
| NM_005080_844-862 | ACCACAUAUAUACCAAGCCNN | 3465 | GGCUUGGUAUAUAUGUGGUNN | 3466 |
| NM_005080_872-890 | AGAGAUACCCUCUGAGACANN | 3467 | UGUCUCAGAGGGUAUCUCUNN | 3468 |
| NM_005080_873-891 | GAGAUACCCUCUGAGACAGNN | 3469 | CUGUCUCAGAGGGUAUCUCNN | 3470 |
| NM_005080_874-892 | AGAUACCCUCUGAGACAGANN | 3471 | UCUGUCUCAGAGGGUAUCUNN | 3472 |
| NM_005080_876-894 | AUACCCUCUGAGACAGAGANN | 3473 | UCUCUGUCUCAGAGGGUAUNN | 3474 |
| NM_005080_889-907 | CAGAGAGCCAAGCUAAUGUNN | 3475 | ACAUUAGCUUGGCUCUCUGNN | 3476 |
| NM_005080_890-908 | AGAGAGCCAAGCUAAUGUGNN | 3477 | CACAUUAGCUUGGCUCUCUNN | 3478 |
| NM_005080_897-915 | CAAGCUAAUGUGGUAGUGANN | 3479 | UCACUACCACAUUAGCUUGNN | 3480 |
| NM_005080_898-916 | AAGCUAAUGUGGUAGUGAANN | 3481 | UUCACUACCACAUUAGCUUNN | 3482 |
| NM_005080_901-919 | CUAAUGUGGUAGUGAAAAUNN | 3483 | AUUUUCACUACCACAUUAGNN | 3484 |
| NM_005080_903-921 | AAUGUGGUAGUGAAAAUCGNN | 3485 | CGAUUUUCACUACCACAUUNN | 3486 |
| NM_005080_904-922 | AUGUGGUAGUGAAAAUCGANN | 3487 | UCGAUUUUCACUACCACAUNN | 3488 |
| NM_005080_906-924 | GUGGUAGUGAAAAUCGAGGNN | 3489 | CCUCGAUUUUCACUACCACNN | 3490 |
| NM_005080_907-925 | UGGUAGUGAAAAUCGAGGANN | 3491 | UCCUCGAUUUUCACUACCANN | 3492 |
| NM_005080_910-928 | UAGUGAAAAUCGAGGAAGCNN | 3493 | GCUUCCUCGAUUUUCACUANN | 3494 |
| NM_005080_913-931 | UGAAAAUCGAGGAAGCACCNN | 3495 | GGUGCUUCCUCGAUUUUCANN | 3496 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
| --- | --- | --- | --- | --- |
| NM_005080_916-934 | AAAUCGAGGAAGCACCUCUCNN | 3497 | AGAGGUGCUUCCUCGAUUUNN | 3498 |
| NM_005080_918-936 | AUCGAGGAAGCACCUCUCANN | 3499 | UGAGAGGUGCUUCCUCGAUNN | 3500 |
| NM_005080_919-937 | UCGAGGAAGCACCUCUCAGNN | 3501 | CUGAGAGGUGCUUCCUCGANN | 3502 |
| NM_005080_920-938 | CGAGGAAGCACCUCUCAGCNN | 3503 | GCUGAGAGGUGCUUCCUCGNN | 3504 |
| NM_005080_922-940 | AGGAAGCACCUCUCAGCCCNN | 3505 | GGGCUGAGAGGUGCUUCCUNN | 3506 |
| NM_005080_923-941 | GGAAGCACCUCUCAGCCCCNN | 3507 | GGGGCUGAGAGGUGCUUCCNN | 3508 |
| NM_005080_929-947 | ACCUCUCAGCCCCUCAGAGNN | 3509 | CUCUGAGGGGCUGAGAGGUNN | 3510 |
| NM_005080_930-948 | CCUCUCAGCCCCUCAGAGANN | 3511 | UCUCUGAGGGGCUGAGAGGNN | 3512 |
| NM_005080_931-949 | CUCUCAGCCCCUCAGAGAANN | 3513 | UUCUCUGAGGGGCUGAGAGNN | 3514 |
| NM_005080_932-950 | UCUCAGCCCCUCAGAGAAUNN | 3515 | AUUCUCUGAGGGGCUGAGANN | 3516 |
| NM_005080_933-951 | CUCAGCCCCUCAGAGAAUGNN | 3517 | CAUUCUCUGAGGGGCUGAGNN | 3518 |
| NM_005080_934-952 | UCAGCCCCUCAGAGAAUGANN | 3519 | UCAUUCUCUGAGGGGCUGANN | 3520 |
| NM_005080_935-953 | CAGCCCCUCAGAGAAUGAUNN | 3521 | AUCAUUCUCUGAGGGGCUGNN | 3522 |
| NM_005080_936-954 | AGCCCCUCAGAGAAUGAUCNN | 3523 | GAUCAUUCUCUGAGGGGCUNN | 3524 |
| NM_005080_938-956 | CCCCUCAGAGAAUGAUCACNN | 3525 | GUGAUCAUUCUCUGAGGGGNN | 3526 |
| NM_005080_941-959 | CUCAGAGAAUGAUCACCCUNN | 3527 | AGGGUGAUCAUUCUCUGAGNN | 3528 |
| NM_005080_942-960 | UCAGAGAAUGAUCACCCUGNN | 3529 | CAGGGUGAUCAUUCUCUGANN | 3530 |
| NM_005080_943-961 | CAGAGAAUGAUCACCCUGANN | 3531 | UCAGGGUGAUCAUUCUCUGNN | 3532 |
| NM_005080_944-962 | AGAGAAUGAUCACCCUGAANN | 3533 | UUCAGGGUGAUCAUUCUCUNN | 3534 |
| NM_005080_946-964 | AGAAUGAUCACCCUGAAUUNN | 3535 | AAUUCAGGGUGAUCAUUCUNN | 3536 |
| NM_005080_947-965 | GAAUGAUCACCCUGAAUUCNN | 3537 | GAAUUCAGGGUGAUCAUUCNN | 3538 |
| NM_005080_948-966 | AAUGAUCACCCUGAAUUCANN | 3539 | UGAAUUCAGGGUGAUCAUUNN | 3540 |
| NM_005080_949-967 | AUGAUCACCCUGAAUUCAUNN | 3541 | AUGAAUUCAGGGUGAUCAUNN | 3542 |
| NM_005080_955-973 | ACCCUGAAUUCAUUGUCUCNN | 3543 | GAGACAAUGAAUUCAGGGUNN | 3544 |
| NM_005080_956-974 | CCCUGAAUUCAUUGUCUCANN | 3545 | UGAGACAAUGAAUUCAGGGNN | 3546 |
| NM_005080_957-975 | CCUGAAUUCAUUGUCUCAGNN | 3547 | CUGAGACAAUGAAUUCAGGNN | 3548 |
| NM_005080_960-978 | GAAUUCAUUGUCUCAGUGANN | 3549 | UCACUGAGACAAUGAAUUCNN | 3550 |
| NM_005080_961-979 | AAUUCAUUGUCUCAGUGAANN | 3551 | UUCACUGAGACAAUGAAUUNN | 3552 |
| NM_005080_965-983 | CAUUGUCUCAGUGAAGGAANN | 3553 | UUCCUUCACUGAGACAAUGNN | 3554 |
| NM_005080_967-985 | UUGUCUCAGUGAAGGAAGANN | 3555 | UCUUCCUUCACUGAGACAANN | 3556 |
| NM_005080_968-986 | UGUCUCAGUGAAGGAAGAANN | 3557 | UUCUUCCUUCACUGAGACANN | 3558 |
| NM_005080_971-989 | CUCAGUGAAGGAAGAACCUNN | 3559 | AGGUUCUUCCUUCACUGAGNN | 3560 |
| NM_005080_972-990 | UCAGUGAAGGAAGAACCUGNN | 3561 | CAGGUUCUUCCUUCACUGANN | 3562 |
| NM_005080_973-991 | CAGUGAAGGAAGAACCUGUNN | 3563 | ACAGGUUCUUCCUUCACUGNN | 3564 |
| NM_005080_980-998 | GGAAGAACCUGUAGAAGAUNN | 3565 | AUCUUCUACAGGUUCUUCCNN | 3566 |
| NM_005080_984-1002 | GAACCUGUAGAAGAUGACCNN | 3567 | GGUCAUCUUCUACAGGUUCNN | 3568 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_986-1004 | ACCUGUAGAAGAUGACCUCNN | 3569 | GAGGUCAUCUUCUACAGGUNN | 3570 |
| NM_005080_1023-1041 | UCAAAUCUGCUUUCAUCCANN | 3571 | UGGAUGAAAGCAGAUUUGANN | 3572 |
| NM_005080_1151-1169 | UUCUUGGGAGGACACUUUUNN | 3573 | AAAAGUGUCCUCCCAAGAANN | 3574 |
| NM_005080_1367-1385 | UCUUUUGACAUCCAGCAGUNN | 3575 | ACUGCUGGAUGUCAAAAGANN | 3576 |
| NM_005080_1414-1432 | UAAGAAAUAUUACUAUAAUNN | 3577 | AUUAUAGUAAUAUUUCUUANN | 3578 |
| NM_005080_1415-1433 | AAGAAAUAUUACUAUAAUUNN | 3579 | AAUUAUAGUAAUAUUUCUUNN | 3580 |
| NM_005080_1674-1692 | ACUUCAAGUAAGAUCAAGANN | 3581 | UCUUGAUCUUACUUGAAGUNN | 3582 |
| NM_005080_1675-1693 | CUUCAAGUAAGAUCAAGAANN | 3583 | UUCUUGAUCUUACUUGAAGNN | 3584 |
| NM_005080_330-348 | AAUGAGUGAGCUGGAACAGNN | 3585 | CUGUUCCAGCUCACUCAUNN | 3586 |
| NM_005080_333-351 | GAGUGAGCUGGAACAGCAANN | 3587 | UUGCUGUUCCAGCUCACUCNN | 3588 |
| NM_005080_592-610 | CCCCUCCAGAACAUCUCCCNN | 3589 | GGGAGAUGUUCUGGAGGGGNN | 3590 |
| NM_005080_665-683 | CAUUCUGGACAACUUGGACNN | 3591 | GUCCAAGUUGUCCAGAAUGNN | 3592 |
| NM_005080_815-833 | GGAAGCCAUUAAUGAACUANN | 3593 | UAGUUCAUUAAUGGCUUCCNN | 3594 |
| NM_005080_1029-1047 | CUGCUUUCAUCCAGCCACUNN | 3595 | AGUGGCUGGAUGAAAGCAGNN | 3596 |
| NM_005080_1077-1095 | GCUUACAGUGACUGUGGAUNN | 3597 | AUCCACAGUCACUGUAAGCNN | 3598 |
| NM_005080_1222-1240 | GUUGCCCUUUUCCUUGACUNN | 3599 | AGUCAAGGAAAAGGGCAACNN | 3600 |
| NM_005080_1285-1303 | UUCAAAAAGCCAAAAUAGANN | 3601 | UCUAUUUUGGCUUUUUGAANN | 3602 |
| NM_005080_1334-1352 | UGUUCAGAUCUCAUAGAUGNN | 3603 | CAUCUAUGAGAUCUGAACANN | 3604 |
| NM_005080_1335-1353 | GUUCAGAUCUCAUAGAUGANN | 3605 | UCAUCUAUGAGAUCUGAACNN | 3606 |
| NM_005080_1436-1454 | GAACUACAGCUUUUAAGAUNN | 3607 | AUCUUAAAAGCUGUAGUUCNN | 3608 |
| NM_005080_1449-1467 | UAAGAUUGUACUUUUAUCUNN | 3609 | AGAUAAAAGUACAAUCUUANN | 3610 |
| NM_005080_1450-1468 | AAGAUUGUACUUUUAUCUUNN | 3611 | AAGAUAAAAGUACAAUCUUNN | 3612 |
| NM_005080_114-132 | GCAGCCCGCCUCCGCCGCCNN | 3613 | GGCGGCGGAGGCGGGCUGCNN | 3614 |
| NM_005080_1555-1573 | UUCUUUAUCAUUUCUCUUCNN | 3615 | GAAGAGAAAUGAUAAAGAANN | 3616 |
| NM_005080_1556-1574 | UCUUUAUCAUUUCUCUUCCNN | 3617 | GGAAGAGAAAUGAUAAAGANN | 3618 |
| NM_005080_1561-1579 | AUCAUUUCUCUUCCCCCUUNN | 3619 | AAGGGGGAAGAGAAAUGAUNN | 3620 |
| NM_005080_1562-1580 | UCAUUUCUCUUCCCCCUUUNN | 3621 | AAAGGGGGAAGAGAAAUGANN | 3622 |
| NM_005080_1569-1587 | UCUUCCCCCUUUUUGGCAUNN | 3623 | AUGCCAAAAGGGGGAAGANN | 3624 |
| NM_005080_1588-1606 | CCUGGCUUGCCUCCAGUUUNN | 3625 | AAACUGGAGGCAAGCCAGGNN | 3626 |
| NM_005080_1640-1658 | AACACCUGCUGAGGGGGCUNN | 3627 | AGCCCCCUCAGCAGGUGUUNN | 3628 |
| NM_005080_1641-1659 | ACACCUGCUGAGGGGGCUCNN | 3629 | GAGCCCCCUCAGCAGGUGUNN | 3630 |
| NM_005080_1642-1660 | CACCUGCUGAGGGGGCUCUNN | 3631 | AGAGCCCCCUCAGCAGGUGNN | 3632 |
| NM_005080_1650-1668 | GAGGGGGCUCUUUCCCUCANN | 3633 | UGAGGGAAAGAGCCCCCUCNN | 3634 |
| NM_005080_1686-1704 | AUCAAGAAUCUUUUGUGAANN | 3635 | UUCACAAAAGAUUCUUGAUNN | 3636 |
| NM_005080_1745-1763 | UCCUGCUAGUGUAGCUUCUNN | 3637 | AGAAGCUACACUAGCAGGANN | 3638 |
| NM_005080_138-156 | CCCGGCCGGCCAGGCCCUGNN | 3639 | CAGGGCCUGGCCGGCCGGGNN | 3640 |
| NM_005080_145-163 | GGCCAGGCCCUGCCGCUCANN | 3641 | UGAGCGGCAGGGCCUGGCCNN | 3642 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_190-208 | CCGGAGGCAGCGAGCGGGGNN | 3643 | CCCCGCTCGCTGCCTCCGGNN | 3644 |
| NM_005080_191-209 | CGGAGGCAGCGAGCGGGGGNN | 3645 | CCCCCGCTCGCTGCCTCCGNN | 3646 |
| NM_005080_192-210 | GGAGGCAGCGAGCGGGGGGNN | 3647 | CCCCCCGCTCGCTGCCTCCNN | 3648 |
| NM_005080_259-277 | GAGAAGGCGCUGAGGAGGANN | 3649 | UCCUCCUCAGCGCCUUCUCNN | 3650 |
| NM_005080_261-279 | GAAGGCGCUGAGGAGGAAANN | 3651 | UUUCCUCCUCAGCGCCUUCNN | 3652 |
| NM_005080_289-307 | AGAGUAGCAGCUCAGACUGNN | 3653 | CAGUCUGAGCUGCUACUCUNN | 3654 |
| NM_005080_363-381 | AGAAGAAGAGAACCAAAAANN | 3655 | TTTTTGGTTCTCTTCTTCTNN | 3656 |
| NM_005080_365-383 | AAGAAGAGAACCAAAAACUNN | 3657 | AGUUUUUGGUUCUCUUCUUNN | 3658 |
| NM_005080_385-403 | UUGCUAGAAAAUCAGCUUUNN | 3659 | AAAGCUGAUUUUCUAGCAANN | 3660 |
| NM_005080_461-479 | GGAUGGAUGCCCUGGUUGCNN | 3661 | GCAACCAGGGCAUCCAUCCNN | 3662 |
| NM_005080_490-508 | GCGGAAGCCAAGGGGAAUGNN | 3663 | CAUUCCCCUUGGCUUCCGCNN | 3664 |
| NM_005080_518-536 | CAGUGGCCGGGUCUGCUGANN | 3665 | UCAGCAGACCCGGCCACUGNN | 3666 |
| NM_005080_673-691 | ACAACUUGGACCCAGUCAUNN | 3667 | AUGACUGGGUCCAAGUUGUNN | 3668 |
| NM_005080_685-703 | CAGUCAUGUUCUUCAAAUGNN | 3669 | CAUUUGAAGAACAUGACUGNN | 3670 |
| NM_005080_730-748 | AGGAGCUCCCAGAGGUCUANN | 3671 | UAGACCUCUGGGAGCUCCUNN | 3672 |
| NM_005080_772-790 | CAGCCCUCCCUUUCUCUGUCNN | 3673 | GACAGAGAAAGGGAGGCUGNN | 3674 |
| NM_005080_801-819 | UCAUCAGCCAAGCUGGAAGNN | 3675 | CUUCCAGCUUGGCUGAUGANN | 3676 |
| NM_005080_817-835 | AAGCCAUUAAUGAACUAAUNN | 3677 | AUUAGUUCAUUAAUGGCUUNN | 3678 |
| NM_005080_887-905 | GACAGAGAGCCAAGCUAAUNN | 3679 | AUUAGCUUGGCUCUCUGUCNN | 3680 |
| NM_005080_924-942 | GAAGCACCUCUCAGCCCCUNN | 3681 | AGGGGCUGAGAGGUGCUUCNN | 3682 |
| NM_005080_927-945 | GCACCUCUCAGCCCCUCAGNN | 3683 | CUGAGGGGCUGAGAGGUGCNN | 3684 |
| NM_005080_928-946 | CACCUCUCAGCCCCUCAGANN | 3685 | UCUGAGGGGCUGAGAGGUGNN | 3686 |
| NM_005080_974-992 | AGUGAAGGAAGAACCUGUANN | 3687 | UACAGGUUCUUCCUUCACUNN | 3688 |
| NM_005080_985-1003 | AACCUGUAGAAGAUGACCUNN | 3689 | AGGUCAUCUUCUACAGGUUNN | 3690 |
| NM_005080_187-205 | AGCCCGGAGGCAGCGAGCGNN | 3691 | CGCTCGCTGCCTCCGGGCTNN | 3692 |
| NM_005080_672-690 | GACAACUUGGACCCAGUCANN | 3693 | UGACUGGGUCCAAGUUGUCNN | 3694 |
| NM_005080_771-789 | CCAGCCCUCCCUUUCUCUGUNN | 3695 | ACAGAGAAAGGGAGGCUGGNN | 3696 |
| NM_005080_1740-1758 | UUUUUUCCUGCUAGUGUAGNN | 3697 | CUACACUAGCAGGAAAAAANN | 3698 |
| NM_005080_1741-1759 | UUUUUCCUGCUAGUGUAGCNN | 3699 | GCUACACUAGCAGGAAAAANN | 3700 |
| NM_005080_662-680 | GGGCAUUCUGGACAACUUGNN | 3701 | CAAGUUGUCCAGAAUGCCCNN | 3702 |
| NM_005080_1070-1088 | ACUGGAUGCUUACAGUGACNN | 3703 | GUCACUGUAAGCAUCCAGUNN | 3704 |
| NM_005080_631-649 | ACUCUUCAGAUUCAGAGUCNN | 3705 | GACUCUGAAUCUGAAGAGUNN | 3706 |
| NM_005080_647-665 | GUCUGAUAUCCUGUUGGGCNN | 3707 | GCCCAACAGGAUAUCAGACNN | 3708 |
| NM_005080_791-809 | AGUGGGGACGUCAUCAGCCNN | 3709 | GGCUGAUGACGUCCCCACUNN | 3710 |
| NM_005080_981-999 | GAAGAACCUGUAGAAGAUGNN | 3711 | CAUCUUCUACAGGUUCUUCNN | 3712 |
| NM_005080_1068-1086 | CUACUGGAUGCUUACAGUGNN | 3713 | CACUGUAAGCAUCCAGUAGNN | 3714 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
| --- | --- | --- | --- | --- |
| NM_005080_1391-1409 | GUAUUGAGACAUAUUACUGNN | 3715 | CAGUAAUAUGUCUCAAUACNN | 3716 |
| NM_005080_1426-1444 | CUAUAAUUGAGAACUACAGNN | 3717 | CUGUAGUUCUCAAUUAUAGNN | 3718 |
| NM_005080_103-121 | CUUCUGUCGGGGCAGCCCGNN | 3719 | CGGGCUGCCCCGACAGAAGNN | 3720 |
| NM_005080_1457-1475 | UACUUUUAUCUUAAAAGGGNN | 3721 | CCCUUUUAAGAUAAAAGUANN | 3722 |
| NM_005080_1568-1586 | CUCUUCCCCCUUUUUGGCANN | 3723 | UGCCAAAAAGGGGGAAGAGNN | 3724 |
| NM_005080_1574-1592 | CCCCUUUUUGGCAUCCUGGNN | 3725 | CCAGGAUGCCAAAAAGGGGNN | 3726 |
| NM_005080_1577-1595 | CUUUUUGGCAUCCUGGCUUNN | 3727 | AAGCCAGGAUGCCAAAAAGNN | 3728 |
| NM_005080_1730-1748 | CUUGAUGGAAUUUUUUCCUNN | 3729 | AGGAAAAAAUUCCAUCAAGNN | 3730 |
| NM_005080_1731-1749 | UUGAUGGAAUUUUUUCCUGNN | 3731 | CAGGAAAAAAUUCCAUCAANN | 3732 |
| NM_005080_1732-1750 | UGAUGGAAUUUUUUCCUGCNN | 3733 | GCAGGAAAAAAUUCCAUCANN | 3734 |
| NM_005080_293-311 | UAGCAGCUCAGACUGCCAGNN | 3735 | CUGGCAGUCUGAGCUGCUANN | 3736 |
| NM_005080_350-368 | AAGUGGUAGAUUUAGAAGANN | 3737 | UCUUCUAAAUCUACCACUUNN | 3738 |
| NM_005080_351-369 | AGUGGUAGAUUUAGAAGAANN | 3739 | UUCUUCUAAAUCUACCACUNN | 3740 |
| NM_005080_630-648 | GACUCUUCAGAUUCAGAGUNN | 3741 | ACUCUGAAUCUGAAGAGUCNN | 3742 |
| NM_005080_657-675 | CUGUUGGGCAUUCUGGACANN | 3743 | UGUCCAGAAUGCCCAACAGNN | 3744 |
| NM_005080_670-688 | UGGACAACUUGGACCCAGUNN | 3745 | ACUGGGUCCAAGUUGUCCANN | 3746 |
| NM_005080_692-710 | GUUCUUCAAAUGCCCUUCCNN | 3747 | GGAAGGGCAUUUGAAGAACNN | 3748 |
| NM_005080_778-796 | CCCUUUCUCUGUCAGUGGGNN | 3749 | CCCACUGACAGAGAAAGGGNN | 3750 |
| NM_005080_790-808 | CAGUGGGGACGUCAUCAGCNN | 3751 | GCUGAUGACGUCCCCACUGNN | 3752 |
| NM_005080_970-988 | UCUCAGUGAAGGAAGAACCNN | 3753 | GGUUCUUCCUUCACUGAGANN | 3754 |
| NM_005080_1162-1180 | ACACUUUUGCCAAUGAACUNN | 3755 | AGUUCAUUGGCAAAAGUGUNN | 3756 |
| NM_005080_1368-1386 | CUUUUGACAUCCAGCAGUCNN | 3757 | GACUGCUGGAUGUCAAAAGNN | 3758 |
| NM_005080_1515-1533 | UAGACAAAUGUCUUGAAGUNN | 3759 | ACUUCAAGACAUUUGUCUANN | 3760 |
| NM_005080_1541-1559 | GAAUUUAUGAAUGGUUCUUNN | 3761 | AAGAACCAUUCAUAAAUUCNN | 3762 |
| NM_005080_1542-1560 | AAUUUAUGAAUGGUUCUUUNN | 3763 | AAAGAACCAUUCAUAAAUUNN | 3764 |
| NM_005080_1571-1589 | UUCCCCCUUUUUGGCAUCCNN | 3765 | GGAUGCCAAAAAGGGGGAANN | 3766 |
| NM_005080_151-169 | GCCCUGCCGCUCAUGGUGCNN | 3767 | GCACCAUGAGCGGCAGGGCNN | 3768 |
| NM_005080_160-178 | CUCAUGGUGCCAGCCCAGANN | 3769 | UCUGGGCUGGCACCAUGAGNN | 3770 |
| NM_005080_326-344 | CUCGAAUGAGUGAGCUGGANN | 3771 | UCCAGCUCACUCAUUCGAGNN | 3772 |
| NM_005080_327-345 | UCGAAUGAGUGAGCUGGAANN | 3773 | UUCCAGCUCACUCAUUCGANN | 3774 |
| NM_005080_331-349 | AUGAGUGAGCUGGAACAGCNN | 3775 | GCUGUUCCAGCUCACUCAUNN | 3776 |
| NM_005080_424-442 | CUUGUAGUUGAGAACCAGGNN | 3777 | CCUGGUUCUCAACUACAAGNN | 3778 |
| NM_005080_483-501 | AGAGGAGGCGGAAGCCAAGNN | 3779 | CTTGGCTTCCGCCTCCTCTNN | 3780 |
| NM_005080_579-597 | GGCCCAGUUGUCACCCCUCNN | 3781 | GAGGGGUGACAACUGGGCCNN | 3782 |
| NM_005080_745-763 | UCUACCCAGAAGGACCCAGNN | 3783 | CUGGGUCCUUCUGGGUAGANN | 3784 |
| NM_005080_746-764 | CUACCCAGAAGGACCCAGUNN | 3785 | ACUGGGUCCUUCUGGGUAGNN | 3786 |
| NM_005080_812-830 | GCUGGAAGCCAUUAAUGAANN | 3787 | UUCAUUAAUGGCUUCCAGCNN | 3788 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_871-889 | UAGAGAUACCCUCUGAGACNN | 3789 | GUCUCAGAGGGUAUCUCUANN | 3790 |
| NM_005080_892-910 | AGAGCCAAGCUAAUGUGGUNN | 3791 | ACCACAUUAGCUUGGCUCUNN | 3792 |
| NM_005080_978-996 | AAGGAAGAACCUGUAGAAGNN | 3793 | CUUCUACAGGUUCUUCCUUNN | 3794 |
| NM_005080_982-1000 | AAGAACCUGUAGAAGAUGANN | 3795 | UCAUCUUCUACAGGUUCUUNN | 3796 |
| NM_005080_257-275 | AGGAGAAGGCGCUGAGGAGNN | 3797 | CUCCUCAGCGCCUUCUCCUNN | 3798 |
| NM_005080_364-382 | GAAGAAGAGAACCAAAAACNN | 3799 | GUUUUUGGUUCUCUUCUUCNN | 3800 |
| NM_005080_816-834 | GAAGCCAUUAAUGAACUAANN | 3801 | UUAGUUCAUUAAUGGCUUCNN | 3802 |
| NM_005080_884-902 | UGAGACAGAGAGCCAAGCUNN | 3803 | AGCUUGGCUCUCUGUCUCANN | 3804 |
| NM_005080_925-943 | AAGCACCUCUCAGCCCCUCNN | 3805 | GAGGGGCUGAGAGGUGCUUNN | 3806 |
| NM_005080_1440-1458 | UACAGCUUUUAAGAUUGUANN | 3807 | UACAAUCUUAAAAGCUGUANN | 3808 |
| NM_005080_784-802 | CUCUGUCAGUGGGGACGUCNN | 3809 | GACGUCCCCACUGACAGAGNN | 3810 |
| NM_005080_1593-1611 | CUUGCCUCCAGUUUUAGGUNN | 3811 | ACCUAAAACUGGAGGCAAGNN | 3812 |
| NM_005080_301-319 | CAGACUGCCAGAGAUCGAANN | 3813 | UUCGAUCUCUGGCAGUCUGNN | 3814 |
| NM_005080_674-692 | CAACUUGGACCCAGUCAUGNN | 3815 | CAUGACUGGGUCCAAGUUGNN | 3816 |
| NM_005080_783-801 | UCUCUGUCAGUGGGGACGUNN | 3817 | ACGUCCCCACUGACAGAGANN | 3818 |
| NM_005080_921-939 | GAGGAAGCACCUCUCAGCCNN | 3819 | GGCUGAGAGGUGCUUCCUCNN | 3820 |
| NM_005080_1226-1244 | CCCUUUUCCUUGACUAUUANN | 3821 | UAAUAGUCAAGGAAAAGGGNN | 3822 |
| NM_005080_1283-1301 | CAUUCAAAAAGCCAAAAUANN | 3823 | UAUUUUGGCUUUUUGAAUGNN | 3824 |
| NM_005080_1416-1434 | AGAAAUAUUACUAUAAUUGNN | 3825 | CAAUUAUAGUAAUAUUUCUNN | 3826 |
| NM_005080_1420-1438 | AUAUUACUAUAAUUGAGAANN | 3827 | UUCUCAAUUAUAGUAAUAUNN | 3828 |
| NM_005080_1488-1506 | CUAAAAUACUUAUUAUGUANN | 3829 | UACAUAAUAAGUAUUUUAGNN | 3830 |
| NM_005080_1492-1510 | AAUACUUAUUAUGUAAGGGNN | 3831 | CCCUUACAUAAUAAGUAUUNN | 3832 |
| NM_005080_111-129 | GGGGCAGCCCGCCUCCGCCNN | 3833 | GGCGGAGGCGGGCUGCCCCNN | 3834 |
| NM_005080_1639-1657 | GAACACCUGCUGAGGGGGCNN | 3835 | GCCCCCUCAGCAGGUGUUCNN | 3836 |
| NM_005080_1685-1703 | GAUCAAGAAUCUUUUGUGANN | 3837 | UCACAAAAGAUUCUUGAUCNN | 3838 |
| NM_005080_1733-1751 | GAUGGAAUUUUUUCCUGCUNN | 3839 | AGCAGGAAAAAAUUCCAUCNN | 3840 |
| NM_005080_1734-1752 | AUGGAAUUUUUUCCUGCUANN | 3841 | UAGCAGGAAAAAAUUCCAUNN | 3842 |
| NM_005080_1737-1755 | GAAUUUUUUCCUGCUAGUGNN | 3843 | CACUAGCAGGAAAAAAUUCNN | 3844 |
| NM_005080_1756-1774 | UAGCUUCUGAAAGGUGCUUNN | 3845 | AAGCACCUUUCAGAAGCUANN | 3846 |
| NM_005080_1757-1775 | AGCUUCUGAAAGGUGCUUUNN | 3847 | AAAGCACCUUUCAGAAGCUNN | 3848 |
| NM_005080_152-170 | CCCUGCCGCUCAUGGUGCCNN | 3849 | GGCACCAUGAGCGGCAGGGNN | 3850 |
| NM_005080_153-171 | CCUGCCGCUCAUGGUGCCANN | 3851 | UGGCACCAUGAGCGGCAGGNN | 3852 |
| NM_005080_163-181 | AUGGUGCCAGCCCAGAGAGNN | 3853 | CUCUCUGGGCUGGCACCAUNN | 3854 |
| NM_005080_167-185 | UGCCAGCCCAGAGAGGGGCNN | 3855 | GCCCCUCUCUGGGCUGGCANN | 3856 |
| NM_005080_200-218 | CGAGCGGGGGCUGCCCCANN | 3857 | UGGGGCAGCCCCCCGCUCGNN | 3858 |
| NM_005080_252-270 | CCCCGAGGAGAAGGCGCUGNN | 3859 | CAGCGCCUUCUCCUCGGGGNN | 3860 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_255-273 | CGAGGAGAAGGCGCUGAGGNN | 3861 | CCUCAGCGCCUUCUCCUCGNN | 3862 |
| NM_005080_260-278 | AGAAGGCGCUGAGGAGGAANN | 3863 | UUCCUCCUCAGCGCCUUCUNN | 3864 |
| NM_005080_271-289 | AGGAGGAAACUGAAAAACANN | 3865 | UGUUUUUCAGUUUCCUCCUNN | 3866 |
| NM_005080_297-315 | AGCUCAGACUGCCAGAGAUNN | 3867 | AUCUCUGGCAGUCUGAGCUNN | 3868 |
| NM_005080_300-318 | UCAGACUGCCAGAGAUCGANN | 3869 | UCGAUCUCUGGCAGUCUGANN | 3870 |
| NM_005080_335-353 | GUGAGCUGGAACAGCAAGUNN | 3871 | ACUUGCUGUUCCAGCUCACNN | 3872 |
| NM_005080_368-386 | AAGAGAACCAAAAACUUUUNN | 3873 | AAAAGUUUUUGGUUCUCUUNN | 3874 |
| NM_005080_378-396 | AAAACUUUUGCUAGAAAAUNN | 3875 | AUUUUCUAGCAAAAGUUUUNN | 3876 |
| NM_005080_379-397 | AAACUUUUGCUAGAAAAUCNN | 3877 | GAUUUUCUAGCAAAAGUUUNN | 3878 |
| NM_005080_380-398 | AACUUUUGCUAGAAAAUCANN | 3879 | UGAUUUUCUAGCAAAAGUUNN | 3880 |
| NM_005080_389-407 | UAGAAAAUCAGCUUUUACGNN | 3881 | CGUAAAAGCUGAUUUUCUANN | 3882 |
| NM_005080_426-444 | UGUAGUUGAGAACCAGGAGNN | 3883 | CUCCUGGUUCUCAACUACANN | 3884 |
| NM_005080_427-445 | GUAGUUGAGAACCAGGAGUNN | 3885 | ACUCCUGGUUCUCAACUACNN | 3886 |
| NM_005080_485-503 | AGGAGGCGGAAGCCAAGGGNN | 3887 | CCCTTGGCTTCCGCCTCCTNN | 3888 |
| NM_005080_487-505 | GAGGCGGAAGCCAAGGGGANN | 3889 | TCCCCTTGGCTTCCGCCTCNN | 3890 |
| NM_005080_488-506 | AGGCGGAAGCCAAGGGGAANN | 3891 | TTCCCCTTGGCTTCCGCCTNN | 3892 |
| NM_005080_511-529 | GUGAGGCCAGUGGCCGGGUNN | 3893 | ACCCGGCCACUGGCCUCACNN | 3894 |
| NM_005080_526-544 | GGGUCUGCUGAGUCCGCAGNN | 3895 | CUGCGGACUCAGCAGACCCNN | 3896 |
| NM_005080_575-593 | UGCAGGCCCAGUUGUCACCNN | 3897 | GGUGACAACUGGGCCUGCANN | 3898 |
| NM_005080_593-611 | CCCUCCAGAACAUCUCCCCNN | 3899 | GGGGAGAUGUUCUGGAGGGNN | 3900 |
| NM_005080_595-613 | CUCCAGAACAUCUCCCCAUNN | 3901 | AUGGGGAGAUGUUCUGGAGNN | 3902 |
| NM_005080_654-672 | AUCCUGUUGGGCAUUCUGGNN | 3903 | CCAGAAUGCCCAACAGGAUNN | 3904 |
| NM_005080_675-693 | AACUUGGACCCAGUCAUGUNN | 3905 | ACAUGACUGGGUCCAAGUUNN | 3906 |
| NM_005080_683-701 | CCCAGUCAUGUUCUUCAAANN | 3907 | UUUGAAGAACAUGACUGGGNN | 3908 |
| NM_005080_684-702 | CCAGUCAUGUUCUUCAAAUNN | 3909 | AUUUGAAGAACAUGACUGGNN | 3910 |
| NM_005080_693-711 | UUCUUCAAAUGCCCUUCCCNN | 3911 | GGGAAGGGCAUUUGAAGAANN | 3912 |
| NM_005080_694-712 | UCUUCAAAUGCCCUUCCCCNN | 3913 | GGGGAAGGGCAUUUGAAGANN | 3914 |
| NM_005080_726-744 | CUGGAGGAGCUCCCAGAGGNN | 3915 | CCUCUGGGAGCUCCUCCAGNN | 3916 |
| NM_005080_744-762 | GUCUACCCAGAAGGACCCANN | 3917 | UGGGUCCUUCUGGGUAGACNN | 3918 |
| NM_005080_765-783 | UCCUUACCAGCCUCCCUUUNN | 3919 | AAAGGGAGGCUGGUAAGGANN | 3920 |
| NM_005080_768-786 | UUACCAGCCUCCCUUUCUCNN | 3921 | GAGAAAGGGAGGCUGGUAANN | 3922 |
| NM_005080_777-795 | UCCCUUUCUCUGUCAGUGGNN | 3923 | CCACUGACAGAGAAAGGGANN | 3924 |
| NM_005080_802-820 | CAUCAGCCAAGCUGGAAGCNN | 3925 | GCUUCCAGCUUGGCUGAUGNN | 3926 |
| NM_005080_877-895 | UACCCUCUGAGACAGAGAGNN | 3927 | CUCUCUGUCUCAGAGGGUANN | 3928 |
| NM_005080_878-896 | ACCCUCUGAGACAGAGAGCNN | 3929 | GCUCUCUGUCUCAGAGGGUNN | 3930 |
| NM_005080_885-903 | GAGACAGAGAGCCAAGCUANN | 3931 | UAGCUUGGCUCUCUGUCUCNN | 3932 |
| NM_005080_886-904 | AGACAGAGAGCCAAGCUAANN | 3933 | UUAGCUUGGCUCUCUGUCUNN | 3934 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_966-984 | AUUGUCUCAGUGAAGGAAGNN | 3935 | CUUCCUUCACUGAGACAAUNN | 3936 |
| NM_005080_969-987 | GUCUCAGUGAAGGAAGAACNN | 3937 | GUUCUUCCUUCACUGAGACNN | 3938 |
| NM_005080_1245-1263 | CACUGCCUGGAGGAUAGCANN | 3939 | UGCUAUCCUCCAGGCAGUGNN | 3940 |
| NM_005080_1738-1756 | AAUUUUUUCCUGCUAGUGUNN | 3941 | ACACUAGCAGGAAAAAAUUNN | 3942 |
| NM_005080_194-212 | AGGCAGCGAGCGGGGGGCUNN | 3943 | AGCCCCCCGCUCGCUGCCUNN | 3944 |
| NM_005080_209-227 | GGCUGCCCCAGGCGCGCAANN | 3945 | UUGCGCGCCUGGGGCAGCCNN | 3946 |
| NM_005080_269-287 | UGAGGAGGAAACUGAAAAANN | 3947 | UUUUUCAGUUUCCUCCUCANN | 3948 |
| NM_005080_902-920 | UAAUGUGGUAGUGAAAAUCNN | 3949 | GAUUUUCACUACCACAUUANN | 3950 |
| NM_005080_50-68 | UGGUGGUGGUGGCAGCCGCNN | 3951 | GCGGCUGCCACCACCACCANN | 3952 |
| NM_005080_1017-1035 | GGUAUCUCAAAUCUGCUUUNN | 3953 | AAAGCAGAUUUGAGAUACCNN | 3954 |
| NM_005080_1021-1039 | UCUCAAAUCUGCUUUCAUCNN | 3955 | GAUGAAAGCAGAUUUGAGANN | 3956 |
| NM_005080_1022-1040 | CUCAAAUCUGCUUUCAUCCNN | 3957 | GGAUGAAAGCAGAUUUGAGNN | 3958 |
| NM_005080_1062-1080 | UCCUGCCUACUGGAUGCUUNN | 3959 | AAGCAUCCAGUAGGCAGGANN | 3960 |
| NM_005080_1074-1092 | GAUGCUUACAGUGACUGUGNN | 3961 | CACAGUCACUGUAAGCAUCNN | 3962 |
| NM_005080_1116-1134 | UUCAGUGACAUGUCCUCUCNN | 3963 | GAGAGGACAUGUCACUGAANN | 3964 |
| NM_005080_1149-1167 | CAUUCUUGGGAGGACACUUNN | 3965 | AAGUGUCCUCCCAAGAAUGNN | 3966 |
| NM_005080_1150-1168 | AUUCUUGGGAGGACACUUUNN | 3967 | AAAGUGUCCUCCCAAGAAUNN | 3968 |
| NM_005080_1161-1179 | GACACUUUUGCCAAUGAACNN | 3969 | GUUCAUUGGCAAAAGUGUCNN | 3970 |
| NM_005080_1223-1241 | UUGCCCUUUUCCUUGACUANN | 3971 | UAGUCAAGGAAAAGGGCAANN | 3972 |
| NM_005080_1280-1298 | CUUCAUUCAAAAAGCCAAANN | 3973 | UUUGGCUUUUUGAAUGAAGNN | 3974 |
| NM_005080_1281-1299 | UUCAUUCAAAAAGCCAAAANN | 3975 | UUUUGGCUUUUUGAAUGAANN | 3976 |
| NM_005080_1284-1302 | AUUCAAAAAGCCAAAAUAGNN | 3977 | CUAUUUUGGCUUUUUGAAUNN | 3978 |
| NM_005080_1286-1304 | UCAAAAAGCCAAAAUAGAGNN | 3979 | CUCUAUUUUGGCUUUUUGANN | 3980 |
| NM_005080_1288-1306 | AAAAAGCCAAAAUAGAGAGNN | 3981 | CUCUCUAUUUUGGCUUUUUNN | 3982 |
| NM_005080_1365-1383 | UGUCUUUUGACAUCCAGCANN | 3983 | UGCUGGAUGUCAAAAGACANN | 3984 |
| NM_005080_1417-1435 | GAAAUAUUACUAUAAUUGANN | 3985 | UCAAUUAUAGUAAUAUUUCNN | 3986 |
| NM_005080_1421-1439 | UAUUACUAUAAUUGAGAACNN | 3987 | GUUCUCAAUUAUAGUAAUANN | 3988 |
| NM_005080_1434-1452 | GAGAACUACAGCUUUUAAGNN | 3989 | CUUAAAAGCUGUAGUUCUCNN | 3990 |
| NM_005080_1452-1470 | GAUUGUACUUUUAUCUUAANN | 3991 | UUAAGAUAAAAGUACAAUCNN | 3992 |
| NM_005080_105-123 | UCUGUCGGGGCAGCCCGCCNN | 3993 | GGCGGGCUGCCCCGACAGANN | 3994 |
| NM_005080_1455-1473 | UGUACUUUUAUCUUAAAAGNN | 3995 | CUUUUAAGAUAAAAGUACANN | 3996 |
| NM_005080_112-130 | GGGCAGCCCGCCUCCGCCGNN | 3997 | CGGCGGAGGCGGGCUGCCCNN | 3998 |
| NM_005080_113-131 | GGCAGCCCGCCUCCGCCGCNN | 3999 | GCGGCGGAGGCGGGCUGCCNN | 4000 |
| NM_005080_1543-1561 | AUUUAUGAAUGGUUCUUUANN | 4001 | UAAAGAACCAUUCAUAAAUNN | 4002 |
| NM_005080_1544-1562 | UUUAUGAAUGGUUCUUUAUNN | 4003 | AUAAAGAACCAUUCAUAAANN | 4004 |
| NM_005080_1557-1575 | CUUUAUCAUUUCUCUUCCCNN | 4005 | GGGAAGAGAAAUGAUAAAGNN | 4006 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_115-133 | CAGCCCGCCUCCGCCGCCGNN | 4007 | CGGCGGCGGAGGCGGGCUGNN | 4008 |
| NM_005080_1564-1582 | AUUUCUCUUCCCCCUUUUUNN | 4009 | AAAAAGGGGGAAGAGAAAUNN | 4010 |
| NM_005080_1572-1590 | UCCCCCUUUUUGGCAUCCUNN | 4011 | AGGAUGCCAAAAAGGGGGANN | 4012 |
| NM_005080_1575-1593 | CCCUUUUUGGCAUCCUGGCNN | 4013 | GCCAGGAUGCCAAAAAGGGNN | 4014 |
| NM_005080_1576-1594 | CCUUUUUGGCAUCCUGGCUNN | 4015 | AGCCAGGAUGCCAAAAAGGNN | 4016 |
| NM_005080_117-135 | GCCCGCCUCCGCCGCCGGANN | 4017 | UCCGGCGGCGGAGGCGGGCNN | 4018 |
| NM_005080_1582-1600 | UGGCAUCCUGGCUUGCCUCNN | 4019 | GAGGCAAGCCAGGAUGCCANN | 4020 |
| NM_005080_1587-1605 | UCCUGGCUUGCCUCCAGUUNN | 4021 | AACUGGAGGCAAGCCAGGANN | 4022 |
| NM_005080_118-136 | CCCGCCUCCGCCGCCGGAGNN | 4023 | CUCCGGCGGCGGAGGCGGGNN | 4024 |
| NM_005080_119-137 | CCGCCUCCGCCGCCGGAGCNN | 4025 | GCUCCGGCGGCGGAGGCGGNN | 4026 |
| NM_005080_120-138 | CGCCUCCGCCGCCGGAGCCNN | 4027 | GGCUCCGGCGGCGGAGGCGNN | 4028 |
| NM_005080_124-142 | UCCGCCGCCGGAGCCCCGGNN | 4029 | CCGGGGCUCCGGCGGCGGANN | 4030 |
| NM_005080_126-144 | CGCCGCCGGAGCCCCGGCCNN | 4031 | GGCCGGGGCUCCGGCGGCGNN | 4032 |
| NM_005080_1676-1694 | UUCAAGUAAGAUCAAGAAUNN | 4033 | AUUCUUGAUCUUACUUGAANN | 4034 |
| NM_005080_127-145 | GCCGCCGGAGCCCCGGCCGNN | 4035 | CGGCCGGGGCUCCGGCGGCNN | 4036 |
| NM_005080_129-147 | CGCCGGAGCCCCGGCCGGCNN | 4037 | GCCGGCCGGGGCUCCGGCGNN | 4038 |
| NM_005080_130-148 | GCCGGAGCCCCGGCCGGCCNN | 4039 | GGCCGGCCGGGGCUCCGGCNN | 4040 |
| NM_005080_131-149 | CCGGAGCCCCGGCCGGCCANN | 4041 | TGGCCGGCCGGGGCUCCGGNN | 4042 |
| NM_005080_1720-1738 | UAUGUAAAUGCUUGAUGGANN | 4043 | UCCAUCAAGCAUUUACAUANN | 4044 |
| NM_005080_1724-1742 | UAAAUGCUUGAUGGAAUUUNN | 4045 | AAAUUCCAUCAAGCAUUUANN | 4046 |
| NM_005080_132-150 | CGGAGCCCCGGCCGGCCAGNN | 4047 | CUGGCCGGCCGGGGCUCCGNN | 4048 |
| NM_005080_133-151 | GGAGCCCCGGCCGGCCAGGNN | 4049 | CCUGGCCGGCCGGGGCUCCNN | 4050 |
| NM_005080_134-152 | GAGCCCCGGCCGGCCAGGCNN | 4051 | GCCUGGCCGGCCGGGGCUCNN | 4052 |
| NM_005080_136-154 | GCCCCGGCCGGCCAGGCCCNN | 4053 | GGGCCUGGCCGGCCGGGGCNN | 4054 |
| NM_005080_1777-1795 | UCCAUUUAUUUAAAACUACNN | 4055 | GUAGUUUUAAAUAAAUGGANN | 4056 |
| NM_005080_137-155 | CCCCGGCCGGCCAGGCCCUNN | 4057 | AGGGCCUGGCCGGCCGGGGNN | 4058 |
| NM_005080_139-157 | CCGGCCGGCCAGGCCCUGCNN | 4059 | GCAGGGCCUGGCCGGCCGGNN | 4060 |
| NM_005080_140-158 | CGGCCGGCCAGGCCCUGCCNN | 4061 | GGCAGGGCCUGGCCGGCCGNN | 4062 |
| NM_005080_141-159 | GGCCGGCCAGGCCCUGCCGNN | 4063 | CGGCAGGGCCUGGCCGGCCNN | 4064 |
| NM_005080_142-160 | GCCGGCCAGGCCCUGCCGCNN | 4065 | GCGGCAGGGCCUGGCCGGCNN | 4066 |
| NM_005080_143-161 | CCGGCCAGGCCCUGCCGCUNN | 4067 | AGCGGCAGGGCCUGGCCGGNN | 4068 |
| NM_005080_144-162 | CGGCCAGGCCCUGCCGCUCNN | 4069 | GAGCGGCAGGGCCUGGCCGNN | 4070 |
| NM_005080_161-179 | UCAUGGUGCCAGCCCAGAGNN | 4071 | CUCUGGGCUGGCACCAUGANN | 4072 |
| NM_005080_162-180 | CAUGGUGCCAGCCCAGAGANN | 4073 | UCUCUGGGCUGGCACCAUGNN | 4074 |
| NM_005080_164-182 | UGGUGCCAGCCCAGAGAGGNN | 4075 | CCUCUCUGGGCUGGCACCANN | 4076 |
| NM_005080_165-183 | GGUGCCAGCCCAGAGAGGGNN | 4077 | CCCUCUCUGGGCUGGCACCNN | 4078 |
| NM_005080_166-184 | GUGCCAGCCCAGAGAGGGGNN | 4079 | CCCCUCUCUGGGCUGGCACNN | 4080 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_201-219 | GAGCGGGGGCUGCCCCAGNN | 4081 | CUGGGGCAGCCCCCCGCUCNN | 4082 |
| NM_005080_202-220 | AGCGGGGGCUGCCCCAGGNN | 4083 | CCUGGGGCAGCCCCCCGCUNN | 4084 |
| NM_005080_203-221 | GCGGGGGCUGCCCCAGGCNN | 4085 | GCCUGGGGCAGCCCCCCGCNN | 4086 |
| NM_005080_204-222 | CGGGGGGCUGCCCCAGGCGNN | 4087 | CGCCUGGGGCAGCCCCCCGNN | 4088 |
| NM_005080_208-226 | GGGCUGCCCCAGGCGCGCANN | 4089 | UGCGCGCCUGGGGCAGCCCNN | 4090 |
| NM_005080_212-230 | UGCCCCAGGCGCGCAAGCGNN | 4091 | CGCUUGCGCGCCUGGGGCANN | 4092 |
| NM_005080_248-266 | UGAGCCCCGAGGAGAAGGCNN | 4093 | GCCUUCUCCUCGGGGCUCANN | 4094 |
| NM_005080_251-269 | GCCCCGAGGAGAAGGCGCUNN | 4095 | AGCGCCUUCUCCUCGGGGCNN | 4096 |
| NM_005080_258-276 | GGAGAAGGCGCUGAGGAGGNN | 4097 | CCUCCUCAGCGCCUUCUCCNN | 4098 |
| NM_005080_262-280 | AAGGCGCUGAGGAGGAAACNN | 4099 | GUUUCCUCCUCAGCGCCUUNN | 4100 |
| NM_005080_265-283 | GCGCUGAGGAGGAAACUGANN | 4101 | UCAGUUUCCUCCUCAGCGCNN | 4102 |
| NM_005080_266-284 | CGCUGAGGAGGAAACUGAANN | 4103 | UUCAGUUUCCUCCUCAGCGNN | 4104 |
| NM_005080_267-285 | GCUGAGGAGGAAACUGAAANN | 4105 | UUUCAGUUUCCUCCUCAGCNN | 4106 |
| NM_005080_268-286 | CUGAGGAGGAAACUGAAAANN | 4107 | UUUUCAGUUUCCUCCUCAGNN | 4108 |
| NM_005080_270-288 | GAGGAGGAAACUGAAAAACNN | 4109 | GUUUUUCAGUUUCCUCCUCNN | 4110 |
| NM_005080_272-290 | GGAGGAAACUGAAAAACAGNN | 4111 | CUGUUUUUCAGUUUCCUCCNN | 4112 |
| NM_005080_273-291 | GAGGAAACUGAAAAACAGANN | 4113 | UCUGUUUUUCAGUUUCCUCNN | 4114 |
| NM_005080_277-295 | AAACUGAAAAACAGAGUAGNN | 4115 | CUACUCUGUUUUUCAGUUUNN | 4116 |
| NM_005080_328-346 | CGAAUGAGUGAGCUGGAACNN | 4117 | GUUCCAGCUCACUCAUUCGNN | 4118 |
| NM_005080_329-347 | GAAUGAGUGAGCUGGAACANN | 4119 | UGUUCCAGCUCACUCAUUCNN | 4120 |
| NM_005080_334-352 | AGUGAGCUGGAACAGCAAGNN | 4121 | CUUGCUGUUCCAGCUCACUNN | 4122 |
| NM_005080_336-354 | UGAGCUGGAACAGCAAGUGNN | 4123 | CACUUGCUGUUCCAGCUCANN | 4124 |
| NM_005080_337-355 | GAGCUGGAACAGCAAGUGGNN | 4125 | CCACUUGCUGUUCCAGCUCNN | 4126 |
| NM_005080_338-356 | AGCUGGAACAGCAAGUGGUNN | 4127 | ACCACUUGCUGUUCCAGCUNN | 4128 |
| NM_005080_356-374 | UAGAUUUAGAAGAAGAGAANN | 4129 | UUCUCUUCUUCUAAAUCUANN | 4130 |
| NM_005080_357-375 | AGAUUUAGAAGAAGAGAACNN | 4131 | GUUCUCUUCUUCUAAAUCUNN | 4132 |
| NM_005080_359-377 | AUUUAGAAGAAGAGAACCANN | 4133 | UGGUUCUCUUCUUCUAAAUNN | 4134 |
| NM_005080_360-378 | UUUAGAAGAAGAGAACCAANN | 4135 | UUGGUUCUCUUCUUCUAAANN | 4136 |
| NM_005080_362-380 | UAGAAGAAGAGAACCAAAANN | 4137 | UUUUGGUUCUCUUCUUCUANN | 4138 |
| NM_005080_367-385 | GAAGAGAACCAAAAACUUUNN | 4139 | AAAGUUUUUGGUUCUCUUCNN | 4140 |
| NM_005080_382-400 | CUUUUGCUAGAAAAUCAGCNN | 4141 | GCUGAUUUUCUAGCAAAAGNN | 4142 |
| NM_005080_386-404 | UGCUAGAAAAUCAGCUUUUNN | 4143 | AAAAGCUGAUUUUCUAGCANN | 4144 |
| NM_005080_401-419 | UUUUACGAGAGAAAACUCANN | 4145 | UGAGUUUUCUCUCGUAAAANN | 4146 |
| NM_005080_458-476 | UGGGGAUGGAUGCCCUGGUNN | 4147 | ACCAGGGCAUCCAUCCCCANN | 4148 |
| NM_005080_484-502 | GAGGAGGCGGAAGCCAAGGNN | 4149 | CCUUGGCUUCCGCCUCCUCNN | 4150 |
| NM_005080_489-507 | GGCGGAAGCCAAGGGGAAUNN | 4151 | AUUCCCCUUGGCUUCCGCCNN | 4152 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
| --- | --- | --- | --- | --- |
| NM_005080_574-592 | GUGCAGGCCCAGUUGUCACNN | 4153 | GUGACAACUGGGCCUGCACNN | 4154 |
| NM_005080_594-612 | CCUCCAGAACAUCUCCCCANN | 4155 | UGGGGAGAUGUUCUGGAGGNN | 4156 |
| NM_005080_604-622 | AUCUCCCCAUGGAUUCUGGNN | 4157 | CCAGAAUCCAUGGGGAGAUNN | 4158 |
| NM_005080_627-645 | AUUGACUCUUCAGAUUCAGNN | 4159 | CUGAAUCUGAAGAGUCAAUNN | 4160 |
| NM_005080_635-653 | UUCAGAUUCAGAGUCUGAUNN | 4161 | AUCAGACUCUGAAUCUGAANN | 4162 |
| NM_005080_636-654 | UCAGAUUCAGAGUCUGAUANN | 4163 | UAUCAGACUCUGAAUCUGANN | 4164 |
| NM_005080_666-684 | AUUCUGGACAACUUGGACCNN | 4165 | GGUCCAAGUUGUCCAGAAUNN | 4166 |
| NM_005080_667-685 | UUCUGGACAACUUGGACCCNN | 4167 | GGGUCCAAGUUGUCCAGAANN | 4168 |
| NM_005080_669-687 | CUGGACAACUUGGACCCAGNN | 4169 | CUGGGUCCAAGUUGUCCAGNN | 4170 |
| NM_005080_681-699 | GACCCAGUCAUGUUCUUCANN | 4171 | UGAAGAACAUGACUGGGUCNN | 4172 |
| NM_005080_690-708 | AUGUUCUUCAAAUGCCCUUNN | 4173 | AAGGGCAUUUGAAGAACAUNN | 4174 |
| NM_005080_718-736 | CUGCCAGCCUGGAGGAGCUNN | 4175 | AGCUCCUCCAGGCUGGCAGNN | 4176 |
| NM_005080_722-740 | CAGCCUGGAGGAGCUCCCANN | 4177 | UGGGAGCUCCUCCAGGCUGNN | 4178 |
| NM_005080_723-741 | AGCCUGGAGGAGCUCCCAGNN | 4179 | CUGGGAGCUCCUCCAGGCUNN | 4180 |
| NM_005080_724-742 | GCCUGGAGGAGCUCCCAGANN | 4181 | UCUGGGAGCUCCUCCAGGCNN | 4182 |
| NM_005080_725-743 | CCUGGAGGAGCUCCCAGAGNN | 4183 | CUCUGGGAGCUCCUCCAGGNN | 4184 |
| NM_005080_727-745 | UGGAGGAGCUCCCAGAGGUNN | 4185 | ACCUCUGGGAGCUCCUCCANN | 4186 |
| NM_005080_728-746 | GGAGGAGCUCCCAGAGGUCNN | 4187 | GACCUCUGGGAGCUCCUCCNN | 4188 |
| NM_005080_739-757 | CAGAGGUCUACCCAGAAGGNN | 4189 | CCUUCUGGGUAGACCUCUGNN | 4190 |
| NM_005080_747-765 | UACCCAGAAGGACCCAGUUNN | 4191 | AACUGGGUCCUUCUGGGUANN | 4192 |
| NM_005080_763-781 | GUUCCUUACCAGCCUCCCUNN | 4193 | AGGGAGGCUGGUAAGGAACNN | 4194 |
| NM_005080_764-782 | UUCCUUACCAGCCUCCCUUNN | 4195 | AAGGGAGGCUGGUAAGGAANN | 4196 |
| NM_005080_766-784 | CCUUACCAGCCUCCCUUUCNN | 4197 | GAAAGGGAGGCUGGUAAGGNN | 4198 |
| NM_005080_770-788 | ACCAGCCUCCCUUUCUCUGNN | 4199 | CAGAGAAAGGGAGGCUGGUNN | 4200 |
| NM_005080_774-792 | GCCUCCCUUUCUCUGUCAGNN | 4201 | CUGACAGAGAAAGGGAGGCNN | 4202 |
| NM_005080_780-798 | CUUUCUCUGUCAGUGGGANN | 4203 | UCCCCACUGACAGAGAAAGNN | 4204 |
| NM_005080_781-799 | UUUCUCUGUCAGUGGGACNN | 4205 | GUCCCACUGACAGAGAAANN | 4206 |
| NM_005080_805-823 | CAGCCAAGCUGGAAGCCAUNN | 4207 | AUGGCUUCCAGCUUGGCUGNN | 4208 |
| NM_005080_44-62 | GAGCUAUGGUGGUGGUGGCNN | 4209 | GCCACCACCACCAUAGCUCNN | 4210 |
| NM_005080_45-63 | AGCUAUGGUGGUGGUGGCANN | 4211 | UGCCACCACCACCAUAGCUNN | 4212 |
| NM_005080_868-886 | UCUUAGAGAUACCCUCUGANN | 4213 | UCAGAGGGUAUCUCUAAGANN | 4214 |
| NM_005080_875-893 | GAUACCCUCUGAGACAGAGNN | 4215 | CUCUGUCUCAGAGGGUAUCNN | 4216 |
| NM_005080_47-65 | CUAUGGUGGUGGUGGCAGCNN | 4217 | GCUGCCACCACCACCAUAGNN | 4218 |
| NM_005080_879-897 | CCCUCUGAGACAGAGAGCCNN | 4219 | GGCUCUCUGUCUCAGAGGGNN | 4220 |
| NM_005080_880-898 | CCUCUGAGACAGAGAGCCANN | 4221 | UGGCUCUCUGUCUCAGAGGNN | 4222 |
| NM_005080_881-899 | CUCUGAGACAGAGAGCCAANN | 4223 | UUGGCUCUCUGUCUCAGAGNN | 4224 |
| NM_005080_882-900 | UCUGAGACAGAGAGCCAAGNN | 4225 | CUUGGCUCUCUGUCUCAGANN | 4226 |

TABLE 9-continued

XBP-1 human/Rhesus siRNAs with 3' dinucleotide overhangs.

| Oligo Name/<br>location of<br>target sequence | sense (5'-3')<br>with 3' dinucleotide<br>overhang | SEQ<br>ID<br>NO: | antisense (5'-3')<br>with 3' dinucleotide<br>overhang | SEQ<br>ID<br>NO: |
|---|---|---|---|---|
| NM_005080_883-901 | CUGAGACAGAGAGCCAAGCNN | 4227 | GCUUGGCUCUCUGUCUCAGNN | 4228 |
| NM_005080_49-67 | AUGGUGGUGGUGGCAGCCGNN | 4229 | CGGCUGCCACCACCACCAUNN | 4230 |
| NM_005080_914-932 | GAAAAUCGAGGAAGCACCUNN | 4231 | AGGUGCUUCCUCGAUUUUCNN | 4232 |
| NM_005080_915-933 | AAAAUCGAGGAAGCACCUCNN | 4233 | GAGGUGCUUCCUCGAUUUUNN | 4234 |
| NM_005080_926-944 | AGCACCUCUCAGCCCCUCANN | 4235 | UGAGGGGCUGAGAGGUGCUNN | 4236 |
| NM_005080_945-963 | GAGAAUGAUCACCCUGAAUNN | 4237 | AUUCAGGGUGAUCAUUCUCNN | 4238 |
| NM_005080_958-976 | CUGAAUUCAUUGUCUCAGUNN | 4239 | ACUGAGACAAUGAAUUCAGNN | 4240 |
| NM_005080_959-977 | UGAAUUCAUUGUCUCAGUGNN | 4241 | CACUGAGACAAUGAAUUCANN | 4242 |
| NM_005080_962-980 | AUUCAUUGUCUCAGUGAAGNN | 4243 | CUUCACUGAGACAAUGAAUNN | 4244 |
| NM_005080_975-993 | GUGAAGGAAGAACCUGUAGNN | 4245 | CUACAGGUUCUUCCUUCACNN | 4246 |
| NM_005080_983-1001 | AGAACCUGUAGAAGAUGACNN | 4247 | GUCAUCUUCUACAGGUUCUNN | 4248 |
| NM_005080_128-146 | CCGCCGGAGCCCCGGCCGGNN | 4249 | CCGGCCGGGGCUCCGGCGGNN | 4250 |
| NM_005080_249-267 | GAGCCCCGAGGAGAAGGCGNN | 4251 | CGCCUUCUCCUCGGGGCUCNN | 4252 |
| NM_005080_697-715 | UCAAAUGCCCUUCCCCAGANN | 4253 | UCUGGGGAAGGGCAUUUGANN | 4254 |
| NM_005080_729-747 | GAGGAGCUCCCAGAGGUCUNN | 4255 | AGACCUCUGGGAGCUCCUCNN | 4256 |
| NM_005080_776-794 | CUCCCUUUCUCUGUCAGUGNN | 4257 | CACUGACAGAGAAAGGGAGNN | 4258 |
| NM_005080_803-821 | AUCAGCCAAGCUGGAAGCCNN | 4259 | GGCUUCCAGCUUGGCUGAUNN | 4260 |
| NM_005080_254-272 | CCGAGGAGAAGGCGCUGAGNN | 4261 | CUCAGCGCCUUCUCCUCGGNN | 4262 |
| NM_005080_383-401 | UUUUGCUAGAAAAUCAGCUNN | 4263 | AGCUGAUUUUCUAGCAAAANN | 4264 |
| NM_005080_116-134 | AGCCCGCCUCCGCCGCCGGNN | 4265 | CCGGCGGCGGAGGCGGGCUNN | 4266 |
| NM_005080_123-141 | CUCCGCCGCCGGAGCCCCGNN | 4267 | CGGGGCUCCGGCGGCGGAGNN | 4268 |
| NM_005080_125-143 | CCGCCGCCGGAGCCCCGGCNN | 4269 | GCCGGGGCUCCGGCGGCGGNN | 4270 |
| NM_005080_135-153 | AGCCCCGGCCGCCAGGCCNN | 4271 | GGCCUGGCCGGCCGGGGCUNN | 4272 |
| NM_005080_253-271 | CCCGAGGAGAAGGCGCUGANN | 4273 | UCAGCGCCUUCUCCUCGGGNN | 4274 |
| NM_005080_274-292 | AGGAAACUGAAAAACAGAGNN | 4275 | CUCUGUUUUUCAGUUUCCUNN | 4276 |
| NM_005080_655-673 | UCCUGUUGGGCAUUCUGGANN | 4277 | UCCAGAAUGCCCAACAGGANN | 4278 |
| NM_005080_775-793 | CCUCCCUUUCUCUGUCAGUNN | 4279 | ACUGACAGAGAAAGGGAGGNN | 4280 |
| NM_005080_46-64 | GCUAUGGUGGUGGUGGCAGNN | 4281 | CUGCCACCACCACCAUAGCNN | 4282 |
| NM_005080_1456-1474 | GUACUUUUAUCUUAAAAGGNN | 4283 | CCUUUUAAGAUAAAAGUACNN | 4284 |
| NM_005080_1545-1563 | UUAUGAAUGGUUCUUUAUCNN | 4285 | GAUAAAGAACCAUUCAUAANN | 4286 |
| NM_005080_1558-1576 | UUUAUCAUUUCUCUUCCCCNN | 4287 | GGGGAAGAGAAAUGAUAAANN | 4288 |
| NM_005080_121-139 | GCCUCCGCCGCCGGAGCCCNN | 4289 | GGGCUCCGGCGGCGGAGGCNN | 4290 |
| NM_005080_122-140 | CCUCCGCCGCCGGAGCCCCNN | 4291 | GGGGCUCCGGCGGCGGAGGNN | 4292 |
| NM_005080_247-265 | CUGAGCCCCGAGGAGAAGGNN | 4293 | CCUUCUCCUCGGGGCUCAGNN | 4294 |
| NM_005080_275-293 | GGAAACUGAAAAACAGAGUNN | 4295 | ACUCUGUUUUUCAGUUUCCNN | 4296 |
| NM_005080_276-294 | GAAACUGAAAAACAGAGUANN | 4297 | UACUCUGUUUUUCAGUUUCNN | 4298 |

TABLE 9-continued

XBP-1 human/Rhesus siRNAs with 3' dinucleotide overhangs.

| Oligo Name/ location of target sequence | sense (5'-3') with 3' dinucleotide overhang | SEQ ID NO: | antisense (5'-3') with 3' dinucleotide overhang | SEQ ID NO: |
|---|---|---|---|---|
| NM_005080_358-376 | GAUUUAGAAGAAGAGAACCNN | 4299 | GGUUCUCUUCUUCUAAAUCNN | 4300 |
| NM_005080_387-405 | GCUAGAAAAUCAGCUUUUANN | 4301 | UAAAAGCUGAUUUUCUAGCNN | 4302 |
| NM_005080_628-646 | UUGACUCUUCAGAUUCAGANN | 4303 | UCUGAAUCUGAAGAGUCAANN | 4304 |
| NM_005080_656-674 | CCUGUUGGGCAUUCUGGACNN | 4305 | GUCCAGAAUGCCCAACAGGNN | 4306 |
| NM_005080_719-737 | UGCCAGCCUGGAGGAGCUCNN | 4307 | GAGCUCCUCCAGGCUGGCANN | 4308 |
| NM_005080_720-738 | GCCAGCCUGGAGGAGCUCCNN | 4309 | GGAGCUCCUCCAGGCUGGCNN | 4310 |
| NM_005080_721-739 | CCAGCCUGGAGGAGCUCCCNN | 4311 | GGGAGCUCCUCCAGGCUGGNN | 4312 |
| NM_005080_782-800 | UUCUCUGUCAGUGGGGACGNN | 4313 | CGUCCCCACUGACAGAGAANN | 4314 |
| NM_005080_867-885 | GUCUUAGAGAUACCCUCUGNN | 4315 | CAGAGGGUAUCUCUAAGACNN | 4316 |
| NM_005080_48-66 | UAUGGUGGUGGUGGCAGCCNN | 4317 | GGCUGCCACCACCACCAUANN | 4318 |
| NM_005080_963-981 | UUCAUUGUCUCAGUGAAGGNN | 4319 | CCUUCACUGAGACAAUGAANN | 4320 |

Gene XBP1
reference transcript NM_005080 (human XBP 1 mRNA, FIG. 2)
Notes
19mers found in both human and rhesus

TABLE 10

XBP-1 Human/Rhesus siRNA analysis

| Oligo Name/ Location of Target sequence from 5' to 3' | human Antisense Count | human Antisense Score | human Sense Count | human Sense Score | rhesus Antisense Count | rhesus Antisense Score | rhesus Sense Count | rhesus Sense Score |
|---|---|---|---|---|---|---|---|---|
| NM_005080_390-408 | 1 | 4 | 6 | 3 | 2 | 3.4 | 2 | 2 |
| NM_005080_1184-1202 | 2 | 4 | 3 | 2 | 1 | 3.2 | 1 | 2 |
| NM_005080_1494-1512 | 1 | 4 | 3 | 3.2 | 12 | 3 | 2 | 3 |
| NM_005080_1463-1481 | 6 | 3.2 | 5 | 2 | 4 | 3.2 | 1 | 2 |
| NM_005080_610-628 | 3 | 3.2 | 6 | 3 | 6 | 3.2 | 2 | 2 |
| NM_005080_823-841 | 4 | 3.2 | 1 | 2 | 1 | 3.2 | 4 | 2 |
| NM_005080_1507-1525 | 3 | 3.2 | 2 | 2 | 3 | 3 | 2 | 2 |
| NM_005080_827-845 | 3 | 3.2 | 1 | 2.2 | 1 | 3 | 1 | 2 |
| NM_005080_1503-1521 | 5 | 3.2 | 2 | 2.8 | 1 | 2 | 1 | 1 |
| NM_005080_829-847 | 12 | 3.2 | 1 | 3 | 1 | 2 | 2 | 3 |
| NM_005080_1783-1801 | 12 | 3.2 | 3 | 2.2 | 2 | 1 | 1 | 2.2 |
| NM_005080_1183-1201 | 2 | 3 | 4 | 2 | 1 | 3.2 | 1 | 2 |
| NM_005080_1501-1519 | 4 | 3 | 2 | 2.8 | 2 | 3.2 | 1 | 2.2 |
| NM_005080_1504-1522 | 2 | 3 | 1 | 2 | 8 | 3.2 | 1 | 1 |
| NM_005080_734-752 | 6 | 3 | 1 | 2 | 1 | 3.2 | 3 | 2 |
| NM_005080_893-911 | 9 | 3 | 1 | 3 | 13 | 3.2 | 5 | 3 |
| NM_005080_1064-1082 | 6 | 3 | 5 | 3 | 1 | 3 | 3 | 2.2 |
| NM_005080_1066-1084 | 1 | 3 | 1 | 2 | 2 | 3 | 1 | 2.2 |
| NM_005080_1136-1154 | 7 | 3 | 1 | 0 | 5 | 3 | 1 | 2 |
| NM_005080_1137-1155 | 5 | 3 | 1 | 2 | 9 | 3 | 1 | 0 |
| NM_005080_1182-1200 | 1 | 3 | 1 | 2.8 | 1 | 3 | 2 | 2 |
| NM_005080_1186-1204 | 3 | 3 | 2 | 2 | 2 | 3 | 1 | 1.2 |
| NM_005080_1189-1207 | 1 | 3 | 3 | 2 | 5 | 3 | 3 | 2 |
| NM_005080_1224-1242 | 6 | 3 | 11 | 2 | 3 | 3 | 21 | 2 |
| NM_005080_1229-1247 | 4 | 3 | 6 | 2 | 1 | 3 | 3 | 2 |
| NM_005080_1235-1253 | 7 | 3 | 3 | 3 | 5 | 3 | 2 | 2.2 |
| NM_005080_1236-1254 | 8 | 3 | 2 | 3 | 7 | 3 | 1 | 3 |
| NM_005080_1438-1456 | 10 | 3 | 2 | 2.2 | 9 | 3 | 2 | 2.2 |
| NM_005080_1441-1459 | 3 | 3 | 3 | 2 | 11 | 3 | 4 | 2 |
| NM_005080_1442-1460 | 6 | 3 | 9 | 3.2 | 9 | 3 | 1 | 2 |
| NM_005080_1493-1511 | 1 | 3 | 2 | 3 | 1 | 3 | 1 | 2 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target sequence from 5' to 3' | Anti-sense Count | Anti-sense Score | Sense Count | Sense Score | Antisense Count | Antisense Score | Sense Count | Sense Score |
| NM_005080_1502-1520 | 3 | 3 | 2 | 2 | 1 | 3 | 1 | 2 |
| NM_005080_1506-1524 | 4 | 3 | 6 | 2 | 6 | 3 | 6 | 2 |
| NM_005080_1594-1612 | 2 | 3 | 6 | 2 | 2 | 3 | 3 | 2 |
| NM_005080_1790-1808 | 12 | 3 | 1 | 2 | 9 | 3 | 4 | 3 |
| NM_005080_304-322 | 3 | 3 | 9 | 3 | 1 | 3 | 16 | 3 |
| NM_005080_305-323 | 1 | 3 | 1 | 2 | 3 | 3 | 3 | 2.2 |
| NM_005080_395-413 | 3 | 3 | 9 | 2 | 3 | 3 | 2 | 2 |
| NM_005080_609-627 | 3 | 3 | 3 | 3 | 7 | 3 | 1 | 2 |
| NM_005080_611-629 | 2 | 3 | 2 | 2 | 1 | 3 | 2 | 2 |
| NM_005080_617-635 | 3 | 3 | 1 | 3 | 4 | 3 | 1 | 2.2 |
| NM_005080_621-639 | 1 | 3 | 1 | 2.2 | 1 | 3 | 1 | 2.2 |
| NM_005080_641-659 | 1 | 3 | 3 | 2 | 2 | 3 | 4 | 2 |
| NM_005080_648-666 | 5 | 3 | 2 | 2 | 4 | 3 | 1 | 2 |
| NM_005080_651-669 | 4 | 3 | 1 | 2 | 5 | 3 | 10 | 3 |
| NM_005080_735-753 | 1 | 3 | 1 | 2 | 4 | 3 | 2 | 2 |
| NM_005080_753-771 | 3 | 3 | 2 | 2 | 10 | 3 | 4 | 2 |
| NM_005080_794-812 | 3 | 3 | 2 | 2 | 6 | 3 | 1 | 2 |
| NM_005080_826-844 | 1 | 3 | 1 | 2.2 | 4 | 3 | 13 | 3 |
| NM_005080_836-854 | 2 | 3 | 1 | 3 | 8 | 3 | 2 | 3 |
| NM_005080_840-858 | 2 | 3 | 1 | 2.2 | 3 | 3 | 7 | 3 |
| NM_005080_841-859 | 8 | 3 | 1 | 1 | 6 | 3 | 1 | 2 |
| NM_005080_847-865 | 10 | 3 | 1 | 2 | 5 | 3 | 1 | 2 |
| NM_005080_894-912 | 2 | 3 | 4 | 3 | 1 | 3 | 1 | 3 |
| NM_005080_895-913 | 2 | 3 | 1 | 3 | 8 | 3 | 2 | 2.2 |
| NM_005080_896-914 | 3 | 3 | 2 | 2 | 7 | 3 | 2 | 2 |
| NM_005080_899-917 | 3 | 3 | 1 | 2 | 7 | 3 | 6 | 2 |
| NM_005080_908-926 | 2 | 3 | 2 | 2 | 1 | 3 | 2 | 3.2 |
| NM_005080_917-935 | 4 | 3 | 6 | 3.2 | 8 | 3 | 1 | 3.2 |
| NM_005080_937-955 | 2 | 3 | 2 | 2 | 9 | 3 | 1 | 2 |
| NM_005080_950-968 | 7 | 3 | 1 | 2 | 12 | 3 | 1 | 2.8 |
| NM_005080_1185-1203 | 1 | 3 | 1 | 2 | 1 | 2.8 | 1 | 2 |
| NM_005080_1187-1205 | 2 | 3 | 1 | 2.2 | 2 | 2.8 | 2 | 2.2 |
| NM_005080_1153-1171 | 6 | 3 | 2 | 2 | 1 | 2.4 | 3 | 2 |
| NM_005080_1787-1805 | 1 | 3 | 1 | 2 | 1 | 2.4 | 1 | 2 |
| NM_005080_606-624 | 4 | 3 | 2 | 2.2 | 1 | 2.4 | 1 | 1 |
| NM_005080_1019-1037 | 12 | 3 | 1 | 1 | 1 | 2.2 | 2 | 1 |
| NM_005080_1072-1090 | 14 | 3 | 8 | 2 | 2 | 2.2 | 9 | 2 |
| NM_005080_1228-1246 | 1 | 3 | 6 | 2 | 1 | 2.2 | 4 | 2 |
| NM_005080_1461-1479 | 12 | 3 | 2 | 1 | 1 | 2.2 | 1 | 2.2 |
| NM_005080_1495-1513 | 2 | 3 | 4 | 3 | 1 | 2.2 | 1 | 3 |
| NM_005080_1496-1514 | 2 | 3 | 2 | 2.8 | 1 | 2.2 | 1 | 2.8 |
| NM_005080_1500-1518 | 1 | 3 | 1 | 1.2 | 1 | 2.2 | 1 | 2.2 |
| NM_005080_1644-1662 | 9 | 3 | 7 | 2 | 1 | 2.2 | 3 | 2 |
| NM_005080_1708-1726 | 3 | 3 | 1 | 1 | 1 | 2.2 | 1 | 2 |
| NM_005080_302-320 | 1 | 3 | 5 | 3 | 1 | 2.2 | 1 | 2 |
| NM_005080_607-625 | 2 | 3 | 1 | 2 | 1 | 2.2 | 3 | 2.2 |
| NM_005080_824-842 | 4 | 3 | 1 | 2 | 1 | 2.2 | 4 | 2 |
| NM_005080_953-971 | 8 | 3 | 4 | 2 | 2 | 2.2 | 5 | 2 |
| NM_005080_1011-1029 | 2 | 3 | 4 | 2 | 1 | 2 | 1 | 2.4 |
| NM_005080_1230-1248 | 2 | 3 | 1 | 2 | 3 | 2 | 2 | 2.2 |
| NM_005080_1231-1249 | 4 | 3 | 1 | 2 | 1 | 2 | 4 | 3 |
| NM_005080_1290-1308 | 7 | 3 | 1 | 2 | 1 | 2 | 1 | 2 |
| NM_005080_1331-1349 | 4 | 3 | 5 | 2 | 2 | 2 | 11 | 2 |
| NM_005080_1460-1478 | 16 | 3 | 15 | 3 | 2 | 2 | 1 | 2.8 |
| NM_005080_1670-1688 | 1 | 3 | 24 | 3 | 2 | 2 | 1 | 2 |
| NM_005080_1671-1689 | 2 | 3 | 1 | 2.2 | 1 | 2 | 2 | 2.2 |
| NM_005080_1735-1753 | 21 | 3 | 3 | 2 | 2 | 2 | 4 | 2 |
| NM_005080_1744-1762 | 1 | 3 | 1 | 2 | 1 | 2 | 2 | 2 |
| NM_005080_1796-1814 | 12 | 3 | 2 | 0 | 1 | 2 | 1 | 0 |
| NM_005080_343-361 | 7 | 3 | 7 | 2 | 1 | 2 | 1 | 2 |
| NM_005080_374-392 | 1 | 3 | 3 | 2 | 1 | 2 | 2 | 2 |
| NM_005080_375-393 | 6 | 3 | 1 | 1 | 3 | 2 | 7 | 1 |
| NM_005080_608-626 | 1 | 3 | 1 | 2 | 2 | 2 | 1 | 2.4 |
| NM_005080_652-670 | 7 | 3 | 1 | 2 | 1 | 2 | 1 | 2 |
| NM_005080_686-704 | 9 | 3 | 1 | 2 | 9 | 2 | 1 | 2 |
| NM_005080_909-927 | 3 | 3 | 2 | 2 | 2 | 2 | 1 | 2 |
| NM_005080_951-969 | 3 | 3 | 1 | 2.8 | 6 | 2 | 4 | 2 |
| NM_005080_952-970 | 8 | 3 | 3 | 2 | 1 | 2 | 5 | 2 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target sequence from 5' to 3' | Antisense Count | Antisense Score | Sense Count | Sense Score | Antisense Count | Antisense Score | Sense Count | Sense Score |
| NM_005080_825-843 | 3 | 3 | 2 | 2.2 | 1 | 1.2 | 6 | 2.2 |
| NM_005080_1194-1212 | 4 | 3 | 1 | 2.2 | 2 | 1 | 2 | 3 |
| NM_005080_831-849 | 3 | 3 | 1 | 2 | 1 | 1 | 3 | 3.2 |
| NM_005080_835-853 | 1 | 3 | 1 | 3 | 1 | 1 | 2 | 3 |
| NM_005080_869-887 | 2 | 3 | 1 | 2.2 | 1 | 1 | 3 | 3.2 |
| NM_005080_1246-1264 | 3 | 2.8 | 1 | 2.2 | 1 | 2.8 | 2 | 2.2 |
| NM_005080_1453-1471 | 2 | 2.8 | 8 | 2 | 3 | 2.8 | 4 | 2 |
| NM_005080_1512-1530 | 5 | 2.8 | 10 | 2.2 | 2 | 2.8 | 11 | 3 |
| NM_005080_1546-1564 | 1 | 2.8 | 1 | 2 | 1 | 2.8 | 3 | 2 |
| NM_005080_1789-1807 | 1 | 2.8 | 1 | 3 | 1 | 2.8 | 1 | 3 |
| NM_005080_325-343 | 1 | 2.8 | 3 | 3 | 1 | 2.8 | 1 | 3 |
| NM_005080_393-411 | 2 | 2.8 | 4 | 3 | 1 | 2.8 | 8 | 3 |
| NM_005080_788-806 | 1 | 2.8 | 2 | 2 | 1 | 2.8 | 4 | 2 |
| NM_005080_821-839 | 1 | 2.8 | 11 | 3 | 1 | 2.8 | 1 | 2 |
| NM_005080_1514-1532 | 6 | 2.8 | 1 | 1 | 1 | 2.2 | 9 | 3 |
| NM_005080_1797-1815 | 1 | 2.8 | 2 | 1 | 11 | 2.2 | 1 | 1 |
| NM_005080_833-851 | 1 | 2.8 | 3 | 4 | 2 | 2.2 | 4 | 4 |
| NM_005080_1509-1527 | 1 | 2.8 | 1 | 2 | 2 | 2 | 1 | 2 |
| NM_005080_1802-1820 | 1 | 2.8 | 1 | 1.2 | 1 | 1.2 | 1 | 1.2 |
| NM_005080_391-409 | 1 | 2.4 | 1 | 2 | 1 | 3 | 1 | 2 |
| NM_005080_843-861 | 1 | 2.4 | 1 | 1 | 4 | 2.4 | 6 | 3 |
| NM_005080_1508-1526 | 1 | 2.4 | 7 | 3 | 1 | 2 | 1 | 2 |
| NM_005080_1754-1772 | 1 | 2.4 | 4 | 2 | 1 | 2 | 1 | 2 |
| NM_005080_430-448 | 4 | 2.4 | 1 | 2 | 1 | 2 | 3 | 2 |
| NM_005080_437-455 | 1 | 2.4 | 5 | 2.2 | 1 | 2 | 4 | 2.2 |
| NM_005080_1465-1483 | 1 | 2.2 | 2 | 2.2 | 2 | 3.2 | 7 | 3 |
| NM_005080_1742-1760 | 1 | 2.2 | 2 | 2 | 13 | 3.2 | 5 | 3 |
| NM_005080_438-456 | 1 | 2.2 | 1 | 1 | 12 | 3.2 | 1 | 2.2 |
| NM_005080_1060-1078 | 1 | 2.2 | 2 | 2 | 12 | 3 | 5 | 2 |
| NM_005080_1067-1085 | 1 | 2.2 | 2 | 2 | 6 | 3 | 1 | 3 |
| NM_005080_1197-1215 | 2 | 2.2 | 1 | 3 | 2 | 3 | 1 | 3 |
| NM_005080_1198-1216 | 1 | 2.2 | 3 | 3 | 9 | 3 | 2 | 3 |
| NM_005080_1424-1442 | 1 | 2.2 | 1 | 2.4 | 7 | 3 | 1 | 2.4 |
| NM_005080_1464-1482 | 2 | 2.2 | 4 | 2 | 1 | 3 | 6 | 2 |
| NM_005080_616-634 | 1 | 2.2 | 1 | 3 | 4 | 3 | 2 | 3 |
| NM_005080_757-775 | 1 | 2.2 | 1 | 2 | 12 | 3 | 1 | 2.2 |
| NM_005080_785-803 | 2 | 2.2 | 1 | 1.2 | 3 | 3 | 1 | 1 |
| NM_005080_819-837 | 1 | 2.2 | 2 | 1 | 4 | 3 | 12 | 2 |
| NM_005080_842-860 | 1 | 2.2 | 1 | 1 | 2 | 3 | 6 | 3 |
| NM_005080_845-863 | 1 | 2.2 | 4 | 3 | 1 | 3 | 11 | 3 |
| NM_005080_1013-1031 | 1 | 2.2 | 1 | 1 | 1 | 2.8 | 2 | 1 |
| NM_005080_1431-1449 | 6 | 2.2 | 1 | 1.2 | 1 | 2.8 | 1 | 1.2 |
| NM_005080_1673-1691 | 3 | 2.2 | 3 | 2.2 | 1 | 2.8 | 5 | 2.2 |
| NM_005080_283-301 | 2 | 2.2 | 2 | 2 | 5 | 2.8 | 1 | 2.2 |
| NM_005080_838-856 | 1 | 2.2 | 1 | 2 | 1 | 2.8 | 1 | 2 |
| NM_005080_279-297 | 2 | 2.2 | 7 | 2 | 1 | 2.4 | 2 | 1 |
| NM_005080_633-651 | 1 | 2.2 | 2 | 0 | 1 | 2.4 | 9 | 2 |
| NM_005080_1024-1042 | 2 | 2.2 | 9 | 2 | 1 | 2.2 | 4 | 2 |
| NM_005080_1147-1165 | 2 | 2.2 | 4 | 1 | 1 | 2.2 | 1 | 1 |
| NM_005080_1154-1172 | 1 | 2.2 | 4 | 2 | 4 | 2.2 | 5 | 2 |
| NM_005080_1188-1206 | 2 | 2.2 | 1 | 1 | 4 | 2.2 | 3 | 1 |
| NM_005080_1192-1210 | 2 | 2.2 | 4 | 2 | 1 | 2.2 | 2 | 2 |
| NM_005080_1195-1213 | 2 | 2.2 | 1 | 2.2 | 3 | 2.2 | 2 | 3 |
| NM_005080_1238-1256 | 2 | 2.2 | 2 | 3 | 2 | 2.2 | 1 | 3 |
| NM_005080_1548-1566 | 1 | 2.2 | 1 | 2.2 | 1 | 2.2 | 2 | 2.2 |
| NM_005080_1549-1567 | 3 | 2.2 | 1 | 2 | 9 | 2.2 | 3 | 2 |
| NM_005080_1677-1695 | 1 | 2.2 | 1 | 2.8 | 2 | 2.2 | 2 | 2 |
| NM_005080_1707-1725 | 1 | 2.2 | 4 | 2 | 1 | 2.2 | 2 | 2 |
| NM_005080_1713-1731 | 1 | 2.2 | 1 | 1 | 3 | 2.2 | 2 | 2 |
| NM_005080_1786-1804 | 6 | 2.2 | 1 | 2 | 6 | 2.2 | 3 | 2 |
| NM_005080_210-228 | 1 | 2.2 | 10 | 2 | 5 | 2.2 | 12 | 2 |
| NM_005080_278-296 | 1 | 2.2 | 6 | 1 | 2 | 2.2 | 14 | 1 |
| NM_005080_284-302 | 4 | 2.2 | 1 | 2 | 8 | 2.2 | 9 | 2 |
| NM_005080_290-308 | 2 | 2.2 | 1 | 2 | 3 | 2.2 | 1 | 2 |
| NM_005080_342-360 | 3 | 2.2 | 1 | 2 | 4 | 2.2 | 5 | 3 |
| NM_005080_431-449 | 8 | 2.2 | 1 | 1 | 4 | 2.2 | 1 | 1 |
| NM_005080_576-594 | 1 | 2.2 | 3 | 2 | 7 | 2.2 | 1 | 2 |
| NM_005080_602-620 | 3 | 2.2 | 2 | 2 | 2 | 2.2 | 4 | 2 |

TABLE 10-continued

XBP-1 Human/Rhesus siRNA analysis

| Oligo Name/ Location of Target sequence from 5' to 3' | off target | | | | | | | |
|---|---|---|---|---|---|---|---|---|
| | human | | | | rhesus | | | |
| | Antisense Count | Antisense Score | Sense Count | Sense Score | Antisense Count | Antisense Score | Sense Count | Sense Score |
| NM_005080_618-636 | 2 | 2.2 | 1 | 3 | 1 | 2.2 | 1 | 3 |
| NM_005080_678-696 | 1 | 2.2 | 1 | 1 | 6 | 2.2 | 1 | 2 |
| NM_005080_796-814 | 4 | 2.2 | 1 | 3 | 1 | 2.2 | 2 | 2.2 |
| NM_005080_940-958 | 1 | 2.2 | 9 | 3 | 3 | 2.2 | 1 | 2 |
| NM_005080_954-972 | 5 | 2.2 | 9 | 2 | 3 | 2.2 | 1 | 1 |
| NM_005080_977-995 | 2 | 2.2 | 1 | 2 | 1 | 2.2 | 1 | 1.2 |
| NM_005080_1018-1036 | 1 | 2.2 | 1 | 1 | 2 | 2 | 1 | 1 |
| NM_005080_1026-1044 | 2 | 2.2 | 8 | 2 | 1 | 2 | 2 | 2 |
| NM_005080_1138-1156 | 1 | 2.2 | 1 | 2 | 1 | 2 | 1 | 0 |
| NM_005080_1141-1159 | 1 | 2.2 | 3 | 2 | 1 | 2 | 8 | 2 |
| NM_005080_1142-1160 | 2 | 2.2 | 2 | 2.2 | 2 | 2 | 1 | 2.8 |
| NM_005080_1155-1173 | 1 | 2.2 | 3 | 2 | 2 | 2 | 3 | 2 |
| NM_005080_1158-1176 | 1 | 2.2 | 1 | 2.2 | 1 | 2 | 1 | 2 |
| NM_005080_1193-1211 | 2 | 2.2 | 1 | 2 | 2 | 2 | 1 | 2 |
| NM_005080_1196-1214 | 2 | 2.2 | 2 | 3 | 5 | 2 | 2 | 2.8 |
| NM_005080_1219-1237 | 2 | 2.2 | 3 | 2 | 3 | 2 | 7 | 2.2 |
| NM_005080_107-125 | 3 | 2.2 | 1 | 0 | 1 | 2 | 2 | 0 |
| NM_005080_108-126 | 4 | 2.2 | 1 | 0 | 1 | 2 | 2 | 0 |
| NM_005080_1505-1523 | 1 | 2.2 | 1 | 2 | 5 | 2 | 1 | 2 |
| NM_005080_1567-1585 | 4 | 2.2 | 1 | 1.2 | 1 | 2 | 1 | 2 |
| NM_005080_1672-1690 | 2 | 2.2 | 2 | 2.2 | 1 | 2 | 6 | 3 |
| NM_005080_1678-1696 | 4 | 2.2 | 1 | 2.8 | 1 | 2 | 2 | 2.8 |
| NM_005080_1778-1796 | 4 | 2.2 | 7 | 2 | 2 | 2 | 9 | 2 |
| NM_005080_1779-1797 | 1 | 2.2 | 9 | 2 | 4 | 2 | 1 | 1 |
| NM_005080_280-298 | 5 | 2.2 | 7 | 2 | 1 | 2 | 2 | 1 |
| NM_005080_282-300 | 2 | 2.2 | 2 | 2 | 1 | 2 | 2 | 2 |
| NM_005080_288-306 | 1 | 2.2 | 1 | 1 | 2 | 2 | 1 | 1 |
| NM_005080_291-309 | 3 | 2.2 | 2 | 2 | 5 | 2 | 1 | 2 |
| NM_005080_347-365 | 3 | 2.2 | 2 | 2.4 | 1 | 2 | 4 | 3 |
| NM_005080_397-415 | 4 | 2.2 | 20 | 3 | 1 | 2 | 1 | 2.2 |
| NM_005080_398-416 | 1 | 2.2 | 1 | 2.2 | 2 | 2 | 1 | 2.2 |
| NM_005080_399-417 | 2 | 2.2 | 1 | 2 | 2 | 2 | 3 | 2.2 |
| NM_005080_512-530 | 2 | 2.2 | 1 | 2 | 1 | 2 | 9 | 2 |
| NM_005080_517-535 | 2 | 2.2 | 1 | 0 | 1 | 2 | 1 | 0 |
| NM_005080_596-614 | 1 | 2.2 | 5 | 2 | 3 | 2 | 4 | 2 |
| NM_005080_598-616 | 1 | 2.2 | 4 | 2 | 3 | 2 | 7 | 2 |
| NM_005080_601-619 | 2 | 2.2 | 8 | 3 | 1 | 2 | 1 | 2.2 |
| NM_005080_605-623 | 2 | 2.2 | 5 | 2 | 5 | 2 | 9 | 2 |
| NM_005080_661-679 | 2 | 2.2 | 8 | 2 | 1 | 2 | 1 | 1 |
| NM_005080_688-706 | 1 | 2.2 | 2 | 0 | 2 | 2 | 2 | 1 |
| NM_005080_691-709 | 2 | 2.2 | 8 | 2 | 2 | 2 | 15 | 2 |
| NM_005080_828-846 | 1 | 2.2 | 3 | 3.2 | 1 | 2 | 1 | 2 |
| NM_005080_830-848 | 8 | 2.2 | 1 | 2.8 | 2 | 2 | 2 | 3 |
| NM_005080_834-852 | 2 | 2.2 | 6 | 3 | 3 | 2 | 3 | 3 |
| NM_005080_846-864 | 2 | 2.2 | 1 | 2 | 1 | 2 | 1 | 2 |
| NM_005080_870-888 | 4 | 2.2 | 1 | 2.2 | 1 | 2 | 7 | 3.2 |
| NM_005080_891-909 | 2 | 2.2 | 6 | 2 | 2 | 2 | 5 | 2 |
| NM_005080_900-918 | 2 | 2.2 | 1 | 2 | 2 | 2 | 1 | 2.2 |
| NM_005080_911-929 | 3 | 2.2 | 2 | 3 | 1 | 2 | 1 | 2.2 |
| NM_005080_912-930 | 3 | 2.2 | 7 | 3.2 | 1 | 2 | 1 | 2.2 |
| NM_005080_979-997 | 5 | 2.2 | 2 | 2 | 1 | 2 | 5 | 2.2 |
| NM_005080_1366-1384 | 5 | 2.2 | 2 | 1.2 | 1 | 1.2 | 1 | 1.2 |
| NM_005080_150-168 | 4 | 2.2 | 8 | 1 | 1 | 1.2 | 1 | 2 |
| NM_005080_1437-1455 | 1 | 2.2 | 2 | 2.2 | 1 | 1 | 1 | 2 |
| NM_005080_482-500 | 5 | 2.2 | 4 | 2 | 6 | 1 | 4 | 2 |
| NM_005080_580-598 | 1 | 2.2 | 1 | 2 | 1 | 1 | 3 | 2 |
| NM_005080_613-631 | 1 | 2 | 6 | 3 | 2 | 4.2 | 2 | 3 |
| NM_005080_1065-1083 | 4 | 2 | 1 | 3.4 | 3 | 4 | 3 | 2.2 |
| NM_005080_614-632 | 1 | 2 | 1 | 2 | 8 | 3.2 | 1 | 2 |
| NM_005080_640-658 | 1 | 2 | 3 | 2 | 3 | 3.2 | 1 | 2 |
| NM_005080_1014-1032 | 2 | 2 | 1 | 2 | 16 | 3 | 2 | 2 |
| NM_005080_1015-1033 | 3 | 2 | 2 | 1.2 | 1 | 3 | 1 | 2.2 |
| NM_005080_1146-1164 | 1 | 2 | 3 | 2 | 28 | 3 | 2 | 2 |
| NM_005080_1232-1250 | 1 | 2 | 1 | 2 | 5 | 3 | 1 | 3 |
| NM_005080_1234-1252 | 1 | 2 | 1 | 2 | 1 | 3 | 1 | 2.2 |
| NM_005080_1237-1255 | 1 | 2 | 4 | 3 | 10 | 3 | 5 | 3 |
| NM_005080_1443-1461 | 1 | 2 | 2 | 2 | 9 | 3 | 6 | 2.2 |
| NM_005080_1462-1480 | 2 | 2 | 2 | 2 | 4 | 3 | 3 | 3 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target sequence from 5' to 3' | Anti-sense Count | Anti-sense Score | Sense Count | Sense Score | Antisense Count | Antisense Score | Sense Count | Sense Score |
| NM_005080_1510-1528 | 1 | 2 | 1 | 2 | 4 | 3 | 1 | 2 |
| NM_005080_1591-1609 | 3 | 2 | 1 | 1 | 4 | 3 | 2 | 1.2 |
| NM_005080_1615-1633 | 1 | 2 | 1 | 2 | 2 | 3 | 8 | 2 |
| NM_005080_1716-1734 | 4 | 2 | 6 | 3 | 9 | 3 | 1 | 1 |
| NM_005080_1718-1736 | 1 | 2 | 7 | 3 | 20 | 3 | 1 | 2.2 |
| NM_005080_1725-1743 | 1 | 2 | 1 | 2.2 | 16 | 3 | 2 | 2 |
| NM_005080_1748-1766 | 1 | 2 | 1 | 4 | 7 | 3 | 2 | 3.2 |
| NM_005080_1780-1798 | 2 | 2 | 4 | 2 | 5 | 3 | 9 | 2 |
| NM_005080_1794-1812 | 2 | 2 | 1 | 2 | 6 | 3 | 2 | 2 |
| NM_005080_156-174 | 2 | 2 | 4 | 2 | 21 | 3 | 2 | 1 |
| NM_005080_299-317 | 1 | 2 | 2 | 2 | 10 | 3 | 2 | 2 |
| NM_005080_344-362 | 1 | 2 | 5 | 2.2 | 7 | 3 | 1 | 2.2 |
| NM_005080_371-389 | 3 | 2 | 6 | 3 | 20 | 3 | 1 | 2.2 |
| NM_005080_373-391 | 1 | 2 | 3 | 2 | 5 | 3 | 1 | 2 |
| NM_005080_524-542 | 4 | 2 | 2 | 2 | 3 | 3 | 4 | 3 |
| NM_005080_525-543 | 3 | 2 | 6 | 2 | 6 | 3 | 3 | 2 |
| NM_005080_612-630 | 1 | 2 | 3 | 2 | 1 | 3 | 8 | 3 |
| NM_005080_615-633 | 1 | 2 | 1 | 2 | 1 | 3 | 1 | 2 |
| NM_005080_645-663 | 1 | 2 | 1 | 1 | 6 | 3 | 3 | 1 |
| NM_005080_792-810 | 1 | 2 | 2 | 2.2 | 10 | 3 | 2 | 2 |
| NM_005080_905-923 | 2 | 2 | 1 | 2.2 | 1 | 3 | 4 | 3 |
| NM_005080_976-994 | 1 | 2 | 4 | 2 | 4 | 3 | 4 | 2 |
| NM_005080_1244-1262 | 3 | 2 | 7 | 2 | 1 | 2.8 | 5 | 2 |
| NM_005080_1791-1809 | 5 | 2 | 4 | 2 | 1 | 2.8 | 2 | 2.8 |
| NM_005080_755-773 | 5 | 2 | 4 | 2 | 1 | 2.8 | 4 | 2 |
| NM_005080_799-817 | 3 | 2 | 2 | 2 | 1 | 2.8 | 16 | 2 |
| NM_005080_832-850 | 3 | 2 | 3 | 3 | 1 | 2.8 | 4 | 3 |
| NM_005080_839-857 | 1 | 2 | 2 | 2.2 | 1 | 2.8 | 3 | 2 |
| NM_005080_100-118 | 3 | 2 | 6 | 2 | 1 | 2.4 | 2 | 1 |
| NM_005080_281-299 | 7 | 2 | 3 | 2 | 1 | 2.4 | 10 | 2 |
| NM_005080_822-840 | 1 | 2 | 5 | 2.2 | 1 | 2.4 | 1 | 2.2 |
| NM_005080_1152-1170 | 1 | 2 | 3 | 2 | 3 | 2.2 | 2 | 2.2 |
| NM_005080_1191-1209 | 3 | 2 | 4 | 1 | 1 | 2.2 | 3 | 2 |
| NM_005080_1225-1243 | 2 | 2 | 5 | 2 | 2 | 2.2 | 1 | 1 |
| NM_005080_1227-1245 | 3 | 2 | 1 | 1 | 1 | 2.2 | 1 | 1 |
| NM_005080_1239-1257 | 2 | 2 | 1 | 2 | 5 | 2.2 | 1 | 2 |
| NM_005080_1430-1448 | 2 | 2 | 2 | 2 | 4 | 2.2 | 2 | 2.2 |
| NM_005080_1499-1517 | 1 | 2 | 4 | 2.2 | 4 | 2.2 | 10 | 2.2 |
| NM_005080_1553-1571 | 1 | 2 | 2 | 2.2 | 2 | 2.2 | 8 | 2 |
| NM_005080_1585-1603 | 1 | 2 | 1 | 2 | 5 | 2.2 | 1 | 1 |
| NM_005080_1592-1610 | 3 | 2 | 2 | 2 | 2 | 2.2 | 3 | 2 |
| NM_005080_1743-1761 | 1 | 2 | 2 | 2 | 1 | 2.2 | 4 | 2 |
| NM_005080_154-172 | 1 | 2 | 1 | 2.2 | 2 | 2.2 | 5 | 3 |
| NM_005080_193-211 | 1 | 2 | 1 | 1 | 10 | 2.2 | 1 | 1 |
| NM_005080_199-217 | 10 | 2 | 3 | 2 | 5 | 2.2 | 4 | 3 |
| NM_005080_292-310 | 5 | 2 | 3 | 2 | 1 | 2.2 | 2 | 2 |
| NM_005080_341-359 | 1 | 2 | 1 | 2 | 2 | 2.2 | 1 | 2.2 |
| NM_005080_377-395 | 4 | 2 | 1 | 1 | 5 | 2.2 | 7 | 2 |
| NM_005080_519-537 | 1 | 2 | 3 | 1 | 12 | 2.2 | 4 | 2 |
| NM_005080_522-540 | 2 | 2 | 8 | 2 | 1 | 2.2 | 5 | 2 |
| NM_005080_577-595 | 2 | 2 | 6 | 2 | 8 | 2.2 | 3 | 2 |
| NM_005080_599-617 | 4 | 2 | 5 | 2 | 7 | 2.2 | 5 | 2 |
| NM_005080_754-772 | 2 | 2 | 5 | 3 | 1 | 2.2 | 1 | 2 |
| NM_005080_888-906 | 1 | 2 | 1 | 2.2 | 4 | 2.2 | 1 | 2 |
| NM_005080_939-957 | 1 | 2 | 1 | 2.8 | 2 | 2.2 | 1 | 2 |
| NM_005080_964-982 | 1 | 2 | 1 | 1 | 1 | 2.2 | 4 | 2 |
| NM_005080_1012-1030 | 6 | 2 | 4 | 3 | 4 | 2 | 3 | 3.2 |
| NM_005080_1016-1034 | 4 | 2 | 2 | 1.2 | 1 | 2 | 10 | 3 |
| NM_005080_1020-1038 | 7 | 2 | 2 | 2 | 2 | 2 | 4 | 2 |
| NM_005080_1025-1043 | 2 | 2 | 9 | 2 | 3 | 2 | 2 | 2.2 |
| NM_005080_1027-1045 | 1 | 2 | 1 | 2 | 1 | 2 | 1 | 2 |
| NM_005080_1028-1046 | 1 | 2 | 5 | 2 | 3 | 2 | 8 | 2 |
| NM_005080_1030-1048 | 1 | 2 | 2 | 2 | 1 | 2 | 1 | 2 |
| NM_005080_1031-1049 | 16 | 2 | 2 | 2 | 4 | 2 | 1 | 2 |
| NM_005080_1032-1050 | 3 | 2 | 21 | 3 | 2 | 2 | 4 | 2.8 |
| NM_005080_1033-1051 | 11 | 2 | 1 | 2 | 7 | 2 | 2 | 2.2 |
| NM_005080_1056-1074 | 1 | 2 | 6 | 2 | 2 | 2 | 13 | 2 |
| NM_005080_1057-1075 | 3 | 2 | 2 | 2.2 | 2 | 2 | 1 | 2 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target sequence from 5' to 3' | Antisense Count | Antisense Score | Sense Count | Sense Score | Antisense Count | Antisense Score | Sense Count | Sense Score |
| NM_005080_1058-1076 | 4 | 2 | 2 | 1 | 5 | 2 | 2 | 1 |
| NM_005080_1059-1077 | 5 | 2 | 2 | 2 | 13 | 2 | 3 | 2 |
| NM_005080_1061-1079 | 4 | 2 | 3 | 2 | 16 | 2 | 1 | 1.2 |
| NM_005080_1063-1081 | 11 | 2 | 3 | 2 | 1 | 2 | 4 | 2 |
| NM_005080_1069-1087 | 2 | 2 | 10 | 3 | 1 | 2 | 1 | 2 |
| NM_005080_1071-1089 | 2 | 2 | 2 | 3 | 1 | 2 | 2 | 3 |
| NM_005080_1073-1091 | 4 | 2 | 12 | 3 | 4 | 2 | 3 | 2 |
| NM_005080_1075-1093 | 6 | 2 | 2 | 2.2 | 6 | 2 | 3 | 2.2 |
| NM_005080_1076-1094 | 7 | 2 | 4 | 3 | 7 | 2 | 1 | 3 |
| NM_005080_1078-1096 | 4 | 2 | 3 | 2 | 3 | 2 | 12 | 2 |
| NM_005080_1139-1157 | 1 | 2 | 2 | 2 | 2 | 2 | 1 | 0 |
| NM_005080_1140-1158 | 4 | 2 | 3 | 2 | 2 | 2 | 1 | 2 |
| NM_005080_1143-1161 | 2 | 2 | 2 | 2.2 | 3 | 2 | 1 | 3 |
| NM_005080_1144-1162 | 1 | 2 | 2 | 2 | 1 | 2 | 3 | 2 |
| NM_005080_1145-1163 | 1 | 2 | 1 | 2.2 | 1 | 2 | 2 | 2 |
| NM_005080_1148-1166 | 2 | 2 | 4 | 2 | 1 | 2 | 2 | 2 |
| NM_005080_1156-1174 | 12 | 2 | 1 | 2.2 | 6 | 2 | 1 | 2 |
| NM_005080_1157-1175 | 1 | 2 | 2 | 2 | 1 | 2 | 1 | 1 |
| NM_005080_1159-1177 | 1 | 2 | 1 | 2 | 4 | 2 | 3 | 2 |
| NM_005080_1160-1178 | 1 | 2 | 1 | 1.2 | 3 | 2 | 2 | 2 |
| NM_005080_1190-1208 | 1 | 2 | 2 | 2.2 | 5 | 2 | 2 | 2 |
| NM_005080_1218-1236 | 2 | 2 | 1 | 2 | 16 | 2 | 4 | 2.2 |
| NM_005080_1220-1238 | 5 | 2 | 1 | 1 | 4 | 2 | 1 | 1 |
| NM_005080_1221-1239 | 5 | 2 | 1 | 1 | 10 | 2 | 1 | 1 |
| NM_005080_1233-1251 | 1 | 2 | 3 | 3 | 1 | 2 | 1 | 3 |
| NM_005080_1240-1258 | 6 | 2 | 1 | 2 | 4 | 2 | 1 | 2 |
| NM_005080_1241-1259 | 13 | 2 | 2 | 2 | 13 | 2 | 1 | 2 |
| NM_005080_1242-1260 | 3 | 2 | 3 | 2 | 4 | 2 | 3 | 2 |
| NM_005080_1243-1261 | 1 | 2 | 2 | 2 | 2 | 2 | 1 | 2.8 |
| NM_005080_1282-1300 | 12 | 2 | 5 | 2 | 8 | 2 | 2 | 1 |
| NM_005080_1287-1305 | 6 | 2 | 3 | 2 | 10 | 2 | 1 | 2 |
| NM_005080_1289-1307 | 2 | 2 | 21 | 3 | 1 | 2 | 4 | 2.2 |
| NM_005080_1310-1328 | 1 | 2 | 3 | 2 | 3 | 2 | 1 | 2.2 |
| NM_005080_1330-1348 | 6 | 2 | 2 | 2 | 4 | 2 | 7 | 2 |
| NM_005080_1332-1350 | 2 | 2 | 8 | 3 | 1 | 2 | 12 | 3 |
| NM_005080_1333-1351 | 2 | 2 | 1 | 2 | 1 | 2 | 1 | 2 |
| NM_005080_1369-1387 | 4 | 2 | 3 | 2 | 4 | 2 | 4 | 2 |
| NM_005080_1370-1388 | 1 | 2 | 7 | 2 | 1 | 2 | 5 | 2 |
| NM_005080_1371-1389 | 4 | 2 | 2 | 2 | 8 | 2 | 1 | 1 |
| NM_005080_101-119 | 1 | 2 | 2 | 2 | 2 | 2 | 2 | 1 |
| NM_005080_1418-1436 | 2 | 2 | 1 | 1 | 3 | 2 | 11 | 2 |
| NM_005080_1419-1437 | 3 | 2 | 3 | 2 | 9 | 2 | 8 | 2.2 |
| NM_005080_1422-1440 | 6 | 2 | 11 | 3 | 1 | 2 | 6 | 3 |
| NM_005080_102-120 | 3 | 2 | 1 | 2 | 5 | 2 | 8 | 2 |
| NM_005080_1423-1441 | 6 | 2 | 4 | 3 | 4 | 2 | 6 | 3 |
| NM_005080_1425-1443 | 1 | 2 | 2 | 2 | 1 | 2 | 1 | 2 |
| NM_005080_1427-1445 | 5 | 2 | 1 | 2 | 11 | 2 | 1 | 2 |
| NM_005080_1428-1446 | 6 | 2 | 1 | 2.2 | 7 | 2 | 1 | 2 |
| NM_005080_1429-1447 | 1 | 2 | 5 | 3 | 1 | 2 | 3 | 3 |
| NM_005080_1432-1450 | 3 | 2 | 3 | 2 | 2 | 2 | 1 | 2.8 |
| NM_005080_1433-1451 | 3 | 2 | 4 | 2 | 4 | 2 | 6 | 2 |
| NM_005080_1435-1453 | 1 | 2 | 1 | 2 | 2 | 2 | 4 | 2 |
| NM_005080_1439-1457 | 1 | 2 | 1 | 2 | 2 | 2 | 4 | 2 |
| NM_005080_104-122 | 1 | 2 | 5 | 3 | 4 | 2 | 7 | 2 |
| NM_005080_1444-1462 | 3 | 2 | 4 | 2 | 1 | 2 | 2 | 2 |
| NM_005080_1445-1463 | 10 | 2 | 3 | 2 | 17 | 2 | 3 | 2 |
| NM_005080_1446-1464 | 8 | 2 | 2 | 2 | 18 | 2 | 1 | 1 |
| NM_005080_1447-1465 | 1 | 2 | 2 | 2.2 | 3 | 2 | 3 | 2 |
| NM_005080_1448-1466 | 2 | 2 | 1 | 2 | 2 | 2 | 5 | 2 |
| NM_005080_1451-1469 | 2 | 2 | 1 | 1 | 1 | 2 | 1 | 1 |
| NM_005080_1454-1472 | 2 | 2 | 4 | 2 | 4 | 2 | 4 | 2 |
| NM_005080_1458-1476 | 6 | 2 | 3 | 2 | 4 | 2 | 10 | 2 |
| NM_005080_1459-1477 | 1 | 2 | 3 | 2 | 3 | 2 | 1 | 1.2 |
| NM_005080_106-124 | 2 | 2 | 1 | 1.2 | 1 | 2 | 9 | 2.2 |
| NM_005080_1466-1484 | 1 | 2 | 2 | 2 | 2 | 2 | 2 | 2 |
| NM_005080_1486-1504 | 2 | 2 | 3 | 2 | 2 | 2 | 1 | 0 |
| NM_005080_1487-1505 | 2 | 2 | 3 | 2 | 2 | 2 | 1 | 1 |
| NM_005080_1489-1507 | 4 | 2 | 5 | 2 | 1 | 2 | 1 | 1 |

TABLE 10-continued

XBP-1 Human/Rhesus siRNA analysis

| | | | off target | | | | | |
|---|---|---|---|---|---|---|---|---|
| Oligo Name/ | | human | | | | rhesus | | |
| Location of Target | Anti- | Anti- | | | | | | |
| sequence from | sense | sense | Sense | Sense | Antisense | Antisense | Sense | Sense |
| 5' to 3' | Count | Score | Count | Score | Count | Score | Count | Score |
| NM_005080_1490-1508 | 3 | 2 | 2 | 2 | 6 | 2 | 4 | 2 |
| NM_005080_1491-1509 | 3 | 2 | 2 | 2 | 2 | 2 | 2 | 2.2 |
| NM_005080_109-127 | 5 | 2 | 1 | 1 | 4 | 2 | 2 | 1 |
| NM_005080_1497-1515 | 1 | 2 | 2 | 3.2 | 1 | 2 | 2 | 3 |
| NM_005080_1498-1516 | 2 | 2 | 2 | 2.2 | 4 | 2 | 1 | 2 |
| NM_005080_110-128 | 3 | 2 | 2 | 1 | 4 | 2 | 1 | 1 |
| NM_005080_1511-1529 | 2 | 2 | 10 | 2 | 3 | 2 | 8 | 2 |
| NM_005080_1513-1531 | 5 | 2 | 1 | 1 | 3 | 2 | 1 | 2.8 |
| NM_005080_1516-1534 | 1 | 2 | 1 | 2 | 1 | 2 | 2 | 2.2 |
| NM_005080_1517-1535 | 2 | 2 | 1 | 1 | 2 | 2 | 2 | 1 |
| NM_005080_1518-1536 | 4 | 2 | 2 | 2 | 2 | 2 | 3 | 2 |
| NM_005080_1547-1565 | 2 | 2 | 1 | 2 | 4 | 2 | 2 | 2 |
| NM_005080_1550-1568 | 5 | 2 | 2 | 2 | 4 | 2 | 5 | 2 |
| NM_005080_1551-1569 | 1 | 2 | 2 | 1.2 | 1 | 2 | 1 | 1.2 |
| NM_005080_1552-1570 | 4 | 2 | 1 | 1.2 | 4 | 2 | 1 | 1.2 |
| NM_005080_1554-1572 | 3 | 2 | 1 | 1 | 7 | 2 | 1 | 1.2 |
| NM_005080_1559-1577 | 5 | 2 | 1 | 2 | 7 | 2 | 1 | 2 |
| NM_005080_1560-1578 | 5 | 2 | 1 | 1 | 5 | 2 | 1 | 1 |
| NM_005080_1563-1581 | 5 | 2 | 1 | 1.2 | 18 | 2 | 1 | 1 |
| NM_005080_1565-1583 | 7 | 2 | 2 | 1.2 | 11 | 2 | 3 | 1.2 |
| NM_005080_1566-1584 | 6 | 2 | 1 | 1.2 | 9 | 2 | 9 | 1.2 |
| NM_005080_1570-1588 | 2 | 2 | 1 | 2 | 5 | 2 | 1 | 2.2 |
| NM_005080_1573-1591 | 2 | 2 | 9 | 2 | 1 | 2 | 5 | 2 |
| NM_005080_1578-1596 | 2 | 2 | 1 | 2 | 5 | 2 | 3 | 2 |
| NM_005080_1579-1597 | 3 | 2 | 4 | 2 | 4 | 2 | 3 | 2 |
| NM_005080_1580-1598 | 3 | 2 | 2 | 2 | 4 | 2 | 5 | 2 |
| NM_005080_1581-1599 | 3 | 2 | 5 | 2 | 2 | 2 | 5 | 2 |
| NM_005080_1583-1601 | 4 | 2 | 4 | 2 | 4 | 2 | 1 | 1 |
| NM_005080_1584-1602 | 7 | 2 | 7 | 2 | 9 | 2 | 1 | 0 |
| NM_005080_1586-1604 | 4 | 2 | 1 | 1 | 3 | 2 | 2 | 1 |
| NM_005080_1589-1607 | 1 | 2 | 3 | 2 | 1 | 2 | 1 | 2 |
| NM_005080_1590-1608 | 4 | 2 | 9 | 3 | 4 | 2 | 1 | 2 |
| NM_005080_1595-1613 | 1 | 2 | 10 | 2 | 1 | 2 | 6 | 2 |
| NM_005080_1616-1634 | 3 | 2 | 1 | 2 | 1 | 2 | 2 | 2 |
| NM_005080_1617-1635 | 2 | 2 | 1 | 1 | 1 | 2 | 3 | 1 |
| NM_005080_1643-1661 | 2 | 2 | 5 | 2 | 3 | 2 | 1 | 1.2 |
| NM_005080_1645-1663 | 1 | 2 | 2 | 1 | 1 | 2 | 1 | 1 |
| NM_005080_1646-1664 | 3 | 2 | 5 | 1 | 3 | 2 | 1 | 1 |
| NM_005080_1647-1665 | 4 | 2 | 7 | 2 | 1 | 2 | 4 | 2 |
| NM_005080_1648-1666 | 7 | 2 | 4 | 2 | 5 | 2 | 10 | 2 |
| NM_005080_1649-1667 | 2 | 2 | 9 | 2 | 5 | 2 | 14 | 2 |
| NM_005080_1679-1697 | 5 | 2 | 2 | 2.2 | 5 | 2 | 2 | 2.2 |
| NM_005080_1680-1698 | 2 | 2 | 1 | 2.2 | 3 | 2 | 1 | 2.2 |
| NM_005080_1681-1699 | 7 | 2 | 1 | 2 | 7 | 2 | 1 | 3 |
| NM_005080_1682-1700 | 12 | 2 | 1 | 2 | 19 | 2 | 1 | 2.2 |
| NM_005080_1683-1701 | 6 | 2 | 15 | 3 | 7 | 2 | 3 | 3 |
| NM_005080_1684-1702 | 5 | 2 | 3 | 3 | 6 | 2 | 1 | 3 |
| NM_005080_1687-1705 | 4 | 2 | 4 | 1 | 2 | 2 | 1 | 1 |
| NM_005080_1709-1727 | 1 | 2 | 6 | 2 | 1 | 2 | 5 | 2 |
| NM_005080_1710-1728 | 3 | 2 | 6 | 2 | 2 | 2 | 5 | 2 |
| NM_005080_1711-1729 | 1 | 2 | 1 | 1 | 2 | 2 | 1 | 1.2 |
| NM_005080_1712-1730 | 10 | 2 | 1 | 2 | 10 | 2 | 1 | 2.2 |
| NM_005080_1714-1732 | 1 | 2 | 1 | 2 | 1 | 2 | 2 | 1 |
| NM_005080_1715-1733 | 2 | 2 | 1 | 2 | 3 | 2 | 1 | 1 |
| NM_005080_1717-1735 | 4 | 2 | 4 | 3 | 2 | 2 | 1 | 2.2 |
| NM_005080_1719-1737 | 7 | 2 | 1 | 2 | 13 | 2 | 2 | 2 |
| NM_005080_1721-1739 | 1 | 2 | 8 | 3 | 1 | 2 | 5 | 3 |
| NM_005080_1722-1740 | 4 | 2 | 10 | 3 | 2 | 2 | 6 | 3 |
| NM_005080_1723-1741 | 1 | 2 | 1 | 2 | 3 | 2 | 4 | 2.2 |
| NM_005080_1726-1744 | 2 | 2 | 1 | 2.8 | 11 | 2 | 1 | 2.2 |
| NM_005080_1727-1745 | 3 | 2 | 1 | 2 | 10 | 2 | 17 | 3 |
| NM_005080_1728-1746 | 10 | 2 | 2 | 2 | 3 | 2 | 1 | 2 |
| NM_005080_1729-1747 | 7 | 2 | 1 | 1 | 4 | 2 | 3 | 1 |
| NM_005080_1736-1754 | 10 | 2 | 1 | 2 | 2 | 2 | 4 | 2 |
| NM_005080_1739-1757 | 1 | 2 | 8 | 2 | 1 | 2 | 8 | 2 |
| NM_005080_1746-1764 | 2 | 2 | 4 | 2.2 | 1 | 2 | 1 | 2 |
| NM_005080_1747-1765 | 3 | 2 | 3 | 3 | 1 | 2 | 1 | 2.2 |
| NM_005080_1749-1767 | 3 | 2 | 1 | 2.2 | 3 | 2 | 2 | 3 |

TABLE 10-continued

XBP-1 Human/Rhesus siRNA analysis

| | off target | | | | | | | |
|---|---|---|---|---|---|---|---|---|
| | human | | | | rhesus | | | |
| Oligo Name/ Location of Target sequence from 5' to 3' | Anti-sense Count | Anti-sense Score | Sense Count | Sense Score | Antisense Count | Antisense Score | Sense Count | Sense Score |
| NM_005080_1750-1768 | 6 | 2 | 1 | 2 | 13 | 2 | 2 | 2 |
| NM_005080_1751-1769 | 5 | 2 | 3 | 2 | 14 | 2 | 2 | 2 |
| NM_005080_1752-1770 | 3 | 2 | 6 | 2 | 1 | 2 | 1 | 2 |
| NM_005080_1753-1771 | 1 | 2 | 7 | 2 | 3 | 2 | 1 | 2 |
| NM_005080_1755-1773 | 7 | 2 | 2 | 2 | 1 | 2 | 1 | 2 |
| NM_005080_1758-1776 | 7 | 2 | 7 | 2 | 12 | 2 | 3 | 2 |
| NM_005080_1781-1799 | 1 | 2 | 1 | 1.2 | 1 | 2 | 7 | 2 |
| NM_005080_1782-1800 | 1 | 2 | 1 | 2 | 3 | 2 | 2 | 2 |
| NM_005080_1784-1802 | 2 | 2 | 3 | 3 | 1 | 2 | 1 | 2 |
| NM_005080_1785-1803 | 4 | 2 | 1 | 2.2 | 2 | 2 | 1 | 2.2 |
| NM_005080_1788-1806 | 1 | 2 | 3 | 3 | 7 | 2 | 3 | 2.2 |
| NM_005080_1792-1810 | 2 | 2 | 1 | 2.8 | 1 | 2 | 2 | 2.8 |
| NM_005080_1793-1811 | 3 | 2 | 2 | 2 | 1 | 2 | 1 | 2.8 |
| NM_005080_1795-1813 | 5 | 2 | 1 | 2.4 | 1 | 2 | 2 | 2 |
| NM_005080_1798-1816 | 1 | 2 | 7 | 2 | 1 | 2 | 5 | 2 |
| NM_005080_1799-1817 | 1 | 2 | 4 | 2 | 1 | 2 | 5 | 2 |
| NM_005080_1800-1818 | 5 | 2 | 3 | 2 | 4 | 2 | 1 | 2 |
| NM_005080_1801-1819 | 2 | 2 | 3 | 2.2 | 4 | 2 | 2 | 1 |
| NM_005080_146-164 | 4 | 2 | 2 | 1 | 1 | 2 | 1 | 1 |
| NM_005080_147-165 | 2 | 2 | 2 | 1 | 1 | 2 | 23 | 2 |
| NM_005080_148-166 | 1 | 2 | 3 | 2 | 1 | 2 | 4 | 2 |
| NM_005080_149-167 | 1 | 2 | 1 | 1.2 | 2 | 2 | 1 | 1.2 |
| NM_005080_155-173 | 5 | 2 | 3 | 2 | 2 | 2 | 3 | 1 |
| NM_005080_157-175 | 7 | 2 | 7 | 2 | 5 | 2 | 11 | 2 |
| NM_005080_158-176 | 4 | 2 | 7 | 2 | 6 | 2 | 1 | 1 |
| NM_005080_159-177 | 4 | 2 | 5 | 2.2 | 3 | 2 | 1 | 1.2 |
| NM_005080_188-206 | 4 | 2 | 1 | 1 | 8 | 2 | 2 | 1 |
| NM_005080_189-207 | 1 | 2 | 1 | 1 | 2 | 2 | 3 | 1 |
| NM_005080_195-213 | 4 | 2 | 2 | 1 | 5 | 2 | 6 | 2 |
| NM_005080_196-214 | 4 | 2 | 2 | 1 | 2 | 2 | 2 | 2.2 |
| NM_005080_197-215 | 2 | 2 | 3 | 2 | 1 | 2 | 1 | 2.2 |
| NM_005080_198-216 | 4 | 2 | 1 | 2 | 4 | 2 | 2 | 2 |
| NM_005080_205-223 | 5 | 2 | 6 | 1 | 6 | 2 | 1 | 0 |
| NM_005080_206-224 | 7 | 2 | 8 | 1 | 1 | 2 | 10 | 1 |
| NM_005080_207-225 | 5 | 2 | 3 | 1 | 4 | 2 | 3 | 1 |
| NM_005080_211-229 | 2 | 2 | 15 | 2 | 2 | 2 | 3 | 2 |
| NM_005080_250-268 | 16 | 2 | 8 | 2 | 6 | 2 | 1 | 0 |
| NM_005080_256-274 | 11 | 2 | 1 | 0 | 7 | 2 | 2 | 0 |
| NM_005080_263-281 | 6 | 2 | 4 | 2.2 | 4 | 2 | 2 | 1 |
| NM_005080_264-282 | 5 | 2 | 1 | 2.2 | 4 | 2 | 2 | 2 |
| NM_005080_285-303 | 2 | 2 | 3 | 3 | 3 | 2 | 14 | 3 |
| NM_005080_286-304 | 8 | 2 | 1 | 2 | 9 | 2 | 2 | 2 |
| NM_005080_287-305 | 8 | 2 | 1 | 0 | 5 | 2 | 1 | 0 |
| NM_005080_294-312 | 5 | 2 | 2 | 2 | 1 | 2 | 1 | 1 |
| NM_005080_295-313 | 1 | 2 | 1 | 0 | 1 | 2 | 3 | 2 |
| NM_005080_296-314 | 1 | 2 | 2 | 1.2 | 1 | 2 | 2 | 2.2 |
| NM_005080_298-316 | 1 | 2 | 1 | 2.2 | 4 | 2 | 3 | 2 |
| NM_005080_303-321 | 1 | 2 | 1 | 2 | 1 | 2 | 1 | 2 |
| NM_005080_332-350 | 8 | 2 | 1 | 2 | 11 | 2 | 1 | 2 |
| NM_005080_339-357 | 3 | 2 | 1 | 1 | 1 | 2 | 1 | 1 |
| NM_005080_340-358 | 3 | 2 | 2 | 2 | 2 | 2 | 1 | 2 |
| NM_005080_345-363 | 1 | 2 | 5 | 2.2 | 6 | 2 | 1 | 2.2 |
| NM_005080_346-364 | 2 | 2 | 5 | 3 | 1 | 2 | 1 | 3 |
| NM_005080_348-366 | 1 | 2 | 3 | 2 | 1 | 2 | 2 | 2 |
| NM_005080_349-367 | 4 | 2 | 5 | 2 | 1 | 2 | 8 | 2 |
| NM_005080_352-370 | 3 | 2 | 3 | 2.2 | 6 | 2 | 3 | 2.2 |
| NM_005080_353-371 | 3 | 2 | 1 | 2.2 | 2 | 2 | 1 | 2.2 |
| NM_005080_354-372 | 8 | 2 | 7 | 2 | 12 | 2 | 4 | 2 |
| NM_005080_355-373 | 6 | 2 | 1 | 2 | 3 | 2 | 1 | 3 |
| NM_005080_361-379 | 2 | 2 | 2 | 1 | 5 | 2 | 1 | 1 |
| NM_005080_366-384 | 2 | 2 | 2 | 2 | 4 | 2 | 12 | 2.2 |
| NM_005080_369-387 | 9 | 2 | 3 | 2.2 | 4 | 2 | 6 | 2 |
| NM_005080_370-388 | 9 | 2 | 2 | 2 | 13 | 2 | 6 | 2 |
| NM_005080_372-390 | 3 | 2 | 1 | 2 | 1 | 2 | 1 | 2.2 |
| NM_005080_376-394 | 2 | 2 | 1 | 1 | 2 | 2 | 1 | 1 |
| NM_005080_381-399 | 8 | 2 | 2 | 2.2 | 5 | 2 | 1 | 1 |
| NM_005080_384-402 | 2 | 2 | 4 | 2.2 | 3 | 2 | 8 | 2 |
| NM_005080_388-406 | 1 | 2 | 1 | 1 | 1 | 2 | 1 | 1 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target sequence from 5' to 3' | Anti-sense Count | Anti-sense Score | Sense Count | Sense Score | Antisense Count | Antisense Score | Sense Count | Sense Score |
| NM_005080_392-410 | 1 | 2 | 1 | 2.2 | 1 | 2 | 1 | 2.2 |
| NM_005080_394-412 | 1 | 2 | 2 | 3 | 1 | 2 | 9 | 3 |
| NM_005080_396-414 | 1 | 2 | 2 | 2 | 2 | 2 | 2 | 3 |
| NM_005080_400-418 | 6 | 2 | 3 | 0 | 18 | 2 | 1 | 0 |
| NM_005080_421-439 | 2 | 2 | 9 | 2.2 | 1 | 2 | 9 | 1.2 |
| NM_005080_422-440 | 1 | 2 | 1 | 2 | 1 | 2 | 1 | 1 |
| NM_005080_423-441 | 1 | 2 | 1 | 2 | 1 | 2 | 1 | 1 |
| NM_005080_425-443 | 3 | 2 | 6 | 3 | 7 | 2 | 2 | 2 |
| NM_005080_428-446 | 4 | 2 | 1 | 2.2 | 4 | 2 | 2 | 2.2 |
| NM_005080_429-447 | 3 | 2 | 4 | 2.8 | 3 | 2 | 1 | 2 |
| NM_005080_432-450 | 4 | 2 | 5 | 2 | 1 | 2 | 1 | 2 |
| NM_005080_433-451 | 10 | 2 | 5 | 2 | 5 | 2 | 1 | 2 |
| NM_005080_434-452 | 5 | 2 | 3 | 2.2 | 3 | 2 | 4 | 1 |
| NM_005080_435-453 | 6 | 2 | 2 | 3 | 4 | 2 | 4 | 1 |
| NM_005080_436-454 | 4 | 2 | 1 | 2 | 7 | 2 | 4 | 2.2 |
| NM_005080_459-477 | 2 | 2 | 2 | 2.2 | 3 | 2 | 4 | 2.2 |
| NM_005080_460-478 | 1 | 2 | 5 | 3 | 2 | 2 | 4 | 2 |
| NM_005080_462-480 | 1 | 2 | 1 | 2 | 2 | 2 | 2 | 2 |
| NM_005080_486-504 | 5 | 2 | 1 | 1 | 3 | 2 | 1 | 1 |
| NM_005080_510-528 | 3 | 2 | 1 | 1 | 4 | 2 | 9 | 2 |
| NM_005080_513-531 | 2 | 2 | 2 | 2 | 1 | 2 | 1 | 2 |
| NM_005080_514-532 | 3 | 2 | 10 | 2 | 8 | 2 | 1 | 0 |
| NM_005080_515-533 | 1 | 2 | 7 | 2 | 3 | 2 | 1 | 0 |
| NM_005080_516-534 | 4 | 2 | 1 | 0 | 7 | 2 | 1 | 0 |
| NM_005080_520-538 | 1 | 2 | 3 | 1 | 13 | 2 | 3 | 2 |
| NM_005080_521-539 | 2 | 2 | 1 | 1 | 11 | 2 | 2 | 2 |
| NM_005080_523-541 | 6 | 2 | 2 | 2 | 2 | 2 | 2 | 2 |
| NM_005080_578-596 | 2 | 2 | 2 | 2 | 6 | 2 | 1 | 2 |
| NM_005080_581-599 | 4 | 2 | 1 | 1 | 2 | 2 | 1 | 1 |
| NM_005080_582-600 | 3 | 2 | 1 | 2 | 4 | 2 | 1 | 2 |
| NM_005080_583-601 | 4 | 2 | 2 | 2 | 17 | 2 | 1 | 2 |
| NM_005080_584-602 | 5 | 2 | 2 | 2 | 17 | 2 | 1 | 2 |
| NM_005080_585-603 | 3 | 2 | 2 | 2 | 4 | 2 | 2 | 2 |
| NM_005080_586-604 | 1 | 2 | 2 | 2 | 1 | 2 | 1 | 2.2 |
| NM_005080_587-605 | 3 | 2 | 6 | 3 | 4 | 2 | 1 | 2.2 |
| NM_005080_588-606 | 3 | 2 | 1 | 2 | 3 | 2 | 24 | 3 |
| NM_005080_589-607 | 2 | 2 | 1 | 1 | 3 | 2 | 1 | 1 |
| NM_005080_590-608 | 1 | 2 | 1 | 2 | 3 | 2 | 1 | 2 |
| NM_005080_591-609 | 3 | 2 | 1 | 2.2 | 5 | 2 | 7 | 2.2 |
| NM_005080_597-615 | 2 | 2 | 1 | 2.2 | 1 | 2 | 5 | 2.2 |
| NM_005080_600-618 | 1 | 2 | 1 | 2.2 | 3 | 2 | 9 | 2 |
| NM_005080_603-621 | 4 | 2 | 3 | 2 | 4 | 2 | 3 | 2 |
| NM_005080_619-637 | 3 | 2 | 4 | 3.2 | 1 | 2 | 7 | 3.2 |
| NM_005080_620-638 | 5 | 2 | 2 | 4.2 | 1 | 2 | 1 | 3 |
| NM_005080_622-640 | 1 | 2 | 1 | 2.2 | 2 | 2 | 1 | 2.2 |
| NM_005080_623-641 | 3 | 2 | 1 | 3 | 1 | 2 | 2 | 3 |
| NM_005080_624-642 | 2 | 2 | 1 | 3 | 1 | 2 | 1 | 2 |
| NM_005080_625-643 | 8 | 2 | 4 | 2.8 | 19 | 2 | 2 | 2 |
| NM_005080_626-644 | 9 | 2 | 1 | 2.8 | 5 | 2 | 1 | 2 |
| NM_005080_629-647 | 2 | 2 | 4 | 1 | 1 | 2 | 4 | 1 |
| NM_005080_632-650 | 1 | 2 | 2 | 0 | 3 | 2 | 7 | 1 |
| NM_005080_634-652 | 6 | 2 | 2 | 1 | 4 | 2 | 7 | 2 |
| NM_005080_637-655 | 2 | 2 | 2 | 2 | 2 | 2 | 1 | 2 |
| NM_005080_638-656 | 2 | 2 | 5 | 3 | 8 | 2 | 3 | 3 |
| NM_005080_639-657 | 1 | 2 | 1 | 2 | 1 | 2 | 1 | 2 |
| NM_005080_642-660 | 2 | 2 | 1 | 1 | 2 | 2 | 2 | 2 |
| NM_005080_643-661 | 1 | 2 | 3 | 2 | 3 | 2 | 4 | 3 |
| NM_005080_644-662 | 2 | 2 | 4 | 3 | 3 | 2 | 6 | 2.2 |
| NM_005080_646-664 | 2 | 2 | 2 | 1 | 5 | 2 | 1 | 1 |
| NM_005080_649-667 | 1 | 2 | 2 | 2 | 1 | 2 | 1 | 2 |
| NM_005080_650-668 | 1 | 2 | 1 | 2 | 1 | 2 | 1 | 3 |
| NM_005080_653-671 | 2 | 2 | 2 | 2 | 2 | 2 | 2 | 2 |
| NM_005080_658-676 | 2 | 2 | 2 | 1 | 1 | 2 | 1 | 1 |
| NM_005080_659-677 | 2 | 2 | 2 | 2 | 2 | 2 | 1 | 2 |
| NM_005080_660-678 | 1 | 2 | 6 | 2 | 2 | 2 | 1 | 1 |
| NM_005080_663-681 | 6 | 2 | 5 | 2 | 2 | 2 | 2 | 2 |
| NM_005080_664-682 | 4 | 2 | 4 | 2 | 1 | 2 | 9 | 2.2 |
| NM_005080_668-686 | 6 | 2 | 2 | 2.2 | 3 | 2 | 4 | 2.2 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target sequence from 5' to 3' | Anti-sense Count | Anti-sense Score | Sense Count | Sense Score | Antisense Count | Antisense Score | Sense Count | Sense Score |
| NM_005080_671-689 | 1 | 2 | 2 | 1 | 10 | 2 | 11 | 2 |
| NM_005080_676-694 | 3 | 2 | 1 | 2 | 4 | 2 | 9 | 3 |
| NM_005080_677-695 | 2 | 2 | 1 | 2 | 1 | 2 | 2 | 2 |
| NM_005080_679-697 | 1 | 2 | 1 | 2 | 1 | 2 | 1 | 2 |
| NM_005080_680-698 | 2 | 2 | 5 | 3 | 1 | 2 | 19 | 3.2 |
| NM_005080_682-700 | 7 | 2 | 2 | 2 | 4 | 2 | 1 | 2 |
| NM_005080_687-705 | 1 | 2 | 3 | 1 | 2 | 2 | 6 | 1 |
| NM_005080_689-707 | 2 | 2 | 1 | 2 | 3 | 2 | 2 | 2 |
| NM_005080_695-713 | 2 | 2 | 1 | 2 | 1 | 2 | 1 | 2 |
| NM_005080_696-714 | 3 | 2 | 1 | 1 | 1 | 2 | 1 | 2 |
| NM_005080_698-716 | 11 | 2 | 1 | 2 | 11 | 2 | 1 | 2 |
| NM_005080_731-749 | 1 | 2 | 1 | 1 | 1 | 2 | 1 | 2.2 |
| NM_005080_732-750 | 1 | 2 | 2 | 2 | 1 | 2 | 1 | 2 |
| NM_005080_733-751 | 1 | 2 | 1 | 2.8 | 1 | 2 | 1 | 2 |
| NM_005080_736-754 | 1 | 2 | 2 | 2 | 4 | 2 | 4 | 2 |
| NM_005080_737-755 | 1 | 2 | 6 | 3 | 4 | 2 | 1 | 2 |
| NM_005080_738-756 | 2 | 2 | 2 | 2.2 | 7 | 2 | 3 | 2.2 |
| NM_005080_740-758 | 4 | 2 | 7 | 3 | 5 | 2 | 1 | 3 |
| NM_005080_741-759 | 3 | 2 | 5 | 3 | 1 | 2 | 1 | 3 |
| NM_005080_742-760 | 1 | 2 | 4 | 3 | 3 | 2 | 1 | 3 |
| NM_005080_743-761 | 4 | 2 | 2 | 2 | 6 | 2 | 5 | 3 |
| NM_005080_748-766 | 6 | 2 | 1 | 1.2 | 4 | 2 | 2 | 2 |
| NM_005080_749-767 | 5 | 2 | 2 | 2 | 2 | 2 | 2 | 2 |
| NM_005080_750-768 | 4 | 2 | 3 | 2 | 2 | 2 | 2 | 2 |
| NM_005080_751-769 | 4 | 2 | 1 | 2 | 1 | 2 | 1 | 2.2 |
| NM_005080_752-770 | 7 | 2 | 2 | 2 | 3 | 2 | 1 | 2 |
| NM_005080_756-774 | 3 | 2 | 2 | 2 | 3 | 2 | 8 | 3 |
| NM_005080_758-776 | 1 | 2 | 1 | 2 | 1 | 2 | 1 | 1 |
| NM_005080_759-777 | 4 | 2 | 2 | 2 | 4 | 2 | 2 | 2 |
| NM_005080_760-778 | 1 | 2 | 1 | 2 | 3 | 2 | 1 | 2 |
| NM_005080_761-779 | 5 | 2 | 1 | 2.2 | 3 | 2 | 1 | 2 |
| NM_005080_762-780 | 7 | 2 | 2 | 2.2 | 1 | 2 | 1 | 2.2 |
| NM_005080_767-785 | 5 | 2 | 4 | 2 | 5 | 2 | 1 | 1 |
| NM_005080_769-787 | 4 | 2 | 1 | 1.2 | 7 | 2 | 5 | 2 |
| NM_005080_773-791 | 14 | 2 | 2 | 1 | 7 | 2 | 3 | 1 |
| NM_005080_779-797 | 6 | 2 | 6 | 2 | 21 | 2 | 9 | 2 |
| NM_005080_786-804 | 1 | 2 | 1 | 1.2 | 1 | 2 | 1 | 1 |
| NM_005080_787-805 | 2 | 2 | 2 | 2 | 1 | 2 | 2 | 2 |
| NM_005080_789-807 | 1 | 2 | 4 | 2.2 | 1 | 2 | 6 | 2.2 |
| NM_005080_793-811 | 4 | 2 | 1 | 2 | 11 | 2 | 1 | 2 |
| NM_005080_795-813 | 1 | 2 | 4 | 3 | 1 | 2 | 1 | 3 |
| NM_005080_797-815 | 3 | 2 | 5 | 3.2 | 3 | 2 | 1 | 2 |
| NM_005080_798-816 | 4 | 2 | 2 | 2.8 | 1 | 2 | 1 | 1 |
| NM_005080_800-818 | 5 | 2 | 2 | 1 | 3 | 2 | 1 | 1 |
| NM_005080_804-822 | 9 | 2 | 2 | 1 | 8 | 2 | 2 | 0 |
| NM_005080_806-824 | 11 | 2 | 3 | 2 | 11 | 2 | 5 | 2 |
| NM_005080_807-825 | 2 | 2 | 4 | 2.2 | 1 | 2 | 2 | 2 |
| NM_005080_808-826 | 2 | 2 | 1 | 2.2 | 1 | 2 | 1 | 2.2 |
| NM_005080_809-827 | 3 | 2 | 7 | 2 | 4 | 2 | 10 | 2 |
| NM_005080_810-828 | 1 | 2 | 5 | 2 | 3 | 2 | 2 | 2 |
| NM_005080_811-829 | 1 | 2 | 1 | 1 | 1 | 2 | 1 | 1 |
| NM_005080_813-831 | 6 | 2 | 2 | 2 | 7 | 2 | 2 | 2 |
| NM_005080_814-832 | 1 | 2 | 1 | 2 | 1 | 2 | 1 | 2 |
| NM_005080_818-836 | 4 | 2 | 1 | 2.2 | 2 | 2 | 1 | 2.2 |
| NM_005080_820-838 | 1 | 2 | 5 | 2 | 1 | 2 | 1 | 2 |
| NM_005080_837-855 | 1 | 2 | 3 | 2.8 | 6 | 2 | 1 | 2.2 |
| NM_005080_844-862 | 4 | 2 | 3 | 2 | 13 | 2 | 1 | 2.2 |
| NM_005080_872-890 | 2 | 2 | 1 | 3 | 4 | 2 | 1 | 3 |
| NM_005080_873-891 | 1 | 2 | 4 | 2 | 3 | 2 | 1 | 2 |
| NM_005080_874-892 | 4 | 2 | 7 | 3.2 | 2 | 2 | 1 | 2.4 |
| NM_005080_876-894 | 6 | 2 | 1 | 2.2 | 4 | 2 | 4 | 2.2 |
| NM_005080_889-907 | 1 | 2 | 2 | 2.2 | 1 | 2 | 2 | 2 |
| NM_005080_890-908 | 2 | 2 | 1 | 3 | 3 | 2 | 1 | 2 |
| NM_005080_897-915 | 1 | 2 | 2 | 3 | 5 | 2 | 4 | 3 |
| NM_005080_898-916 | 1 | 2 | 2 | 3 | 1 | 2 | 7 | 3 |
| NM_005080_901-919 | 4 | 2 | 3 | 2.2 | 3 | 2 | 2 | 2.2 |
| NM_005080_903-921 | 1 | 2 | 2 | 2 | 4 | 2 | 1 | 1 |
| NM_005080_904-922 | 1 | 2 | 3 | 2.2 | 4 | 2 | 1 | 2 |

TABLE 10-continued

XBP-1 Human/Rhesus siRNA analysis

| | off target | | | | | | | |
|---|---|---|---|---|---|---|---|---|
| Oligo Name/ | human | | | | | | | |
| Location of Target | Anti- | Anti- | | | rhesus | | | |
| sequence from 5' to 3' | sense Count | sense Score | Sense Count | Sense Score | Antisense Count | Antisense Score | Sense Count | Sense Score |
| NM_005080_906-924 | 2 | 2 | 4 | 3 | 2 | 2 | 5 | 3 |
| NM_005080_907-925 | 1 | 2 | 4 | 3 | 2 | 2 | 3 | 3 |
| NM_005080_910-928 | 5 | 2 | 2 | 2 | 4 | 2 | 1 | 1 |
| NM_005080_913-931 | 4 | 2 | 1 | 3.2 | 3 | 2 | 3 | 3.2 |
| NM_005080_916-934 | 3 | 2 | 7 | 3 | 3 | 2 | 4 | 3 |
| NM_005080_918-936 | 1 | 2 | 2 | 3 | 1 | 2 | 3 | 3 |
| NM_005080_919-937 | 3 | 2 | 3 | 3 | 1 | 2 | 4 | 3 |
| NM_005080_920-938 | 2 | 2 | 2 | 2 | 2 | 2 | 2 | 2 |
| NM_005080_922-940 | 5 | 2 | 4 | 2 | 9 | 2 | 3 | 2.2 |
| NM_005080_923-941 | 3 | 2 | 3 | 2 | 14 | 2 | 1 | 2 |
| NM_005080_929-947 | 8 | 2 | 8 | 2 | 5 | 2 | 5 | 2 |
| NM_005080_930-948 | 6 | 2 | 4 | 2 | 5 | 2 | 1 | 2 |
| NM_005080_931-949 | 3 | 2 | 1 | 2.2 | 2 | 2 | 10 | 3 |
| NM_005080_932-950 | 1 | 2 | 3 | 2 | 4 | 2 | 2 | 2 |
| NM_005080_933-951 | 5 | 2 | 10 | 3 | 2 | 2 | 4 | 2 |
| NM_005080_934-952 | 1 | 2 | 2 | 2.2 | 6 | 2 | 5 | 2 |
| NM_005080_935-953 | 2 | 2 | 3 | 2 | 7 | 2 | 1 | 2 |
| NM_005080_936-954 | 4 | 2 | 8 | 3 | 2 | 2 | 7 | 3 |
| NM_005080_938-956 | 1 | 2 | 1 | 2 | 1 | 2 | 1 | 2 |
| NM_005080_941-959 | 3 | 2 | 2 | 2 | 5 | 2 | 2 | 2 |
| NM_005080_942-960 | 1 | 2 | 1 | 2 | 1 | 2 | 1 | 1.2 |
| NM_005080_943-961 | 2 | 2 | 1 | 2 | 2 | 2 | 1 | 2 |
| NM_005080_944-962 | 3 | 2 | 3 | 3 | 6 | 2 | 1 | 2.2 |
| NM_005080_946-964 | 1 | 2 | 2 | 3 | 2 | 2 | 9 | 3 |
| NM_005080_947-965 | 1 | 2 | 2 | 2 | 2 | 2 | 4 | 2 |
| NM_005080_948-966 | 3 | 2 | 1 | 2.2 | 4 | 2 | 4 | 2.2 |
| NM_005080_949-967 | 1 | 2 | 1 | 2 | 3 | 2 | 4 | 2 |
| NM_005080_955-973 | 5 | 2 | 2 | 2 | 4 | 2 | 3 | 2 |
| NM_005080_956-974 | 2 | 2 | 9 | 2 | 2 | 2 | 4 | 2 |
| NM_005080_957-975 | 2 | 2 | 3 | 2 | 1 | 2 | 2 | 2.2 |
| NM_005080_960-978 | 7 | 2 | 2 | 1 | 2 | 2 | 1 | 1 |
| NM_005080_961-979 | 2 | 2 | 2 | 2 | 1 | 2 | 3 | 2 |
| NM_005080_965-983 | 2 | 2 | 1 | 1 | 2 | 2 | 3 | 2 |
| NM_005080_967-985 | 8 | 2 | 1 | 2 | 3 | 2 | 1 | 2 |
| NM_005080_968-986 | 12 | 2 | 1 | 2.2 | 13 | 2 | 2 | 2.2 |
| NM_005080_971-989 | 3 | 2 | 12 | 3 | 7 | 2 | 1 | 2 |
| NM_005080_972-990 | 8 | 2 | 3 | 2 | 23 | 2 | 2 | 2 |
| NM_005080_973-991 | 6 | 2 | 1 | 1 | 8 | 2 | 1 | 2 |
| NM_005080_980-998 | 8 | 2 | 3 | 2.2 | 7 | 2 | 1 | 2 |
| NM_005080_984-1002 | 14 | 2 | 3 | 2 | 18 | 2 | 1 | 2 |
| NM_005080_986-1004 | 1 | 2 | 2 | 2 | 5 | 2 | 2 | 2 |
| NM_005080_1023-1041 | 1 | 2 | 1 | 1.2 | 1 | 1.2 | 1 | 1.2 |
| NM_005080_1151-1169 | 2 | 2 | 3 | 2 | 6 | 1.2 | 5 | 2 |
| NM_005080_1367-1385 | 9 | 2 | 1 | 2.2 | 1 | 1.2 | 4 | 2.8 |
| NM_005080_1414-1432 | 2 | 2 | 1 | 1 | 1 | 1.2 | 7 | 2 |
| NM_005080_1415-1433 | 7 | 2 | 1 | 1 | 1 | 1.2 | 4 | 1 |
| NM_005080_1674-1692 | 3 | 2 | 8 | 3 | 1 | 1.2 | 3 | 2 |
| NM_005080_1675-1693 | 1 | 2 | 2 | 2 | 1 | 1.2 | 6 | 2 |
| NM_005080_330-348 | 4 | 2 | 6 | 2 | 1 | 1.2 | 2 | 2 |
| NM_005080_333-351 | 8 | 2 | 2 | 1 | 2 | 1.2 | 4 | 2 |
| NM_005080_592-610 | 3 | 2 | 3 | 2 | 1 | 1.2 | 1 | 2.2 |
| NM_005080_665-683 | 3 | 2 | 2 | 2 | 3 | 1.2 | 1 | 2.8 |
| NM_005080_815-833 | 3 | 2 | 2 | 2 | 2 | 1.2 | 1 | 2 |
| NM_005080_1029-1047 | 1 | 2 | 3 | 2.2 | 2 | 1 | 9 | 3 |
| NM_005080_1077-1095 | 9 | 2 | 1 | 3 | 1 | 1 | 1 | 3.2 |
| NM_005080_1222-1240 | 3 | 2 | 2 | 1 | 1 | 1 | 4 | 1 |
| NM_005080_1285-1303 | 13 | 2 | 1 | 2 | 1 | 1 | 1 | 2 |
| NM_005080_1334-1352 | 2 | 2 | 1 | 3 | 1 | 1 | 1 | 2 |
| NM_005080_1335-1353 | 4 | 2 | 1 | 2.2 | 1 | 1 | 6 | 3 |
| NM_005080_1436-1454 | 3 | 2 | 4 | 2 | 1 | 1 | 2 | 2 |
| NM_005080_1449-1467 | 3 | 2 | 3 | 3 | 1 | 1 | 9 | 3 |
| NM_005080_1450-1468 | 1 | 2 | 1 | 2.2 | 1 | 1 | 4 | 2.2 |
| NM_005080_114-132 | 13 | 2 | 1 | 0 | 1 | 1 | 7 | 2 |
| NM_005080_1555-1573 | 2 | 2 | 2 | 1 | 1 | 1 | 1 | 1 |
| NM_005080_1556-1574 | 5 | 2 | 1 | 1 | 1 | 1 | 2 | 2 |
| NM_005080_1561-1579 | 5 | 2 | 2 | 1 | 1 | 1 | 7 | 1 |
| NM_005080_1562-1580 | 7 | 2 | 1 | 1 | 1 | 1 | 1 | 1 |
| NM_005080_1569-1587 | 1 | 2 | 2 | 2 | 5 | 1 | 4 | 2.2 |

TABLE 10-continued

XBP-1 Human/Rhesus siRNA analysis

| Oligo Name/ Location of Target sequence from 5' to 3' | off target | | | | | | | |
|---|---|---|---|---|---|---|---|---|
| | human | | | | rhesus | | | |
| | Antisense Count | Antisense Score | Sense Count | Sense Score | Antisense Count | Antisense Score | Sense Count | Sense Score |
| NM_005080_1588-1606 | 2 | 2 | 2 | 1 | 1 | 1 | 1 | 1 |
| NM_005080_1640-1658 | 1 | 2 | 2 | 2 | 1 | 1 | 3 | 2 |
| NM_005080_1641-1659 | 2 | 2 | 1 | 2 | 1 | 1 | 1 | 2 |
| NM_005080_1642-1660 | 5 | 2 | 2 | 2 | 2 | 1 | 1 | 2 |
| NM_005080_1650-1668 | 1 | 2 | 4 | 2 | 1 | 1 | 4 | 2 |
| NM_005080_1686-1704 | 6 | 2 | 1 | 2.2 | 1 | 1 | 2 | 2.2 |
| NM_005080_1745-1763 | 1 | 2 | 1 | 2 | 1 | 1 | 1 | 2 |
| NM_005080_138-156 | 21 | 2 | 2 | 1 | 1 | 1 | 1 | 1 |
| NM_005080_145-163 | 10 | 2 | 5 | 1 | 1 | 1 | 3 | 1 |
| NM_005080_190-208 | 4 | 2 | 3 | 2 | 1 | 1 | 2 | 1 |
| NM_005080_191-209 | 13 | 2 | 3 | 1 | 2 | 1 | 5 | 1 |
| NM_005080_192-210 | 5 | 2 | 1 | 1 | 1 | 1 | 1 | 1 |
| NM_005080_259-277 | 6 | 2 | 1 | 1 | 3 | 1 | 3 | 1 |
| NM_005080_261-279 | 19 | 2 | 1 | 1 | 2 | 1 | 1 | 0 |
| NM_005080_289-307 | 1 | 2 | 1 | 1 | 2 | 1 | 1 | 1 |
| NM_005080_363-381 | 15 | 2 | 5 | 2 | 2 | 1 | 6 | 2 |
| NM_005080_365-383 | 5 | 2 | 2 | 2 | 2 | 1 | 3 | 1.2 |
| NM_005080_385-403 | 4 | 2 | 3 | 2 | 1 | 1 | 9 | 2 |
| NM_005080_461-479 | 1 | 2 | 1 | 1.2 | 2 | 1 | 5 | 2.2 |
| NM_005080_490-508 | 3 | 2 | 1 | 3 | 1 | 1 | 3 | 3 |
| NM_005080_518-536 | 3 | 2 | 1 | 1 | 2 | 1 | 1 | 1 |
| NM_005080_673-691 | 6 | 2 | 3 | 2.2 | 2 | 1 | 2 | 2.2 |
| NM_005080_685-703 | 1 | 2 | 3 | 2 | 1 | 1 | 3 | 2 |
| NM_005080_730-748 | 3 | 2 | 4 | 2 | 1 | 1 | 1 | 2 |
| NM_005080_772-790 | 3 | 2 | 1 | 2 | 1 | 1 | 7 | 2 |
| NM_005080_801-819 | 5 | 2 | 1 | 1 | 1 | 1 | 2 | 1 |
| NM_005080_817-835 | 2 | 2 | 1 | 2 | 1 | 1 | 3 | 2 |
| NM_005080_887-905 | 3 | 2 | 1 | 2.2 | 1 | 1 | 2 | 2 |
| NM_005080_924-942 | 7 | 2 | 2 | 1 | 4 | 1 | 1 | 1 |
| NM_005080_927-945 | 13 | 2 | 3 | 2 | 4 | 1 | 6 | 2 |
| NM_005080_928-946 | 1 | 2 | 3 | 2 | 1 | 1 | 2 | 2.8 |
| NM_005080_974-992 | 4 | 2 | 1 | 1 | 2 | 1 | 1 | 2 |
| NM_005080_985-1003 | 13 | 2 | 2 | 2 | 1 | 1 | 3 | 3 |
| NM_005080_187-205 | 4 | 2 | 8 | 2 | 1 | 0 | 1 | 0 |
| NM_005080_672-690 | 8 | 2 | 2 | 2 | 1 | 0 | 1 | 2 |
| NM_005080_771-789 | 3 | 2 | 10 | 2 | 1 | 0 | 6 | 1 |
| NM_005080_1740-1758 | 1 | 1.2 | 5 | 2 | 1 | 3.2 | 1 | 2.2 |
| NM_005080_1741-1759 | 1 | 1.2 | 2 | 1 | 3 | 3.2 | 1 | 2.2 |
| NM_005080_662-680 | 1 | 1.2 | 2 | 1 | 1 | 2.4 | 2 | 1 |
| NM_005080_1070-1088 | 1 | 1.2 | 6 | 2 | 4 | 2.2 | 14 | 2 |
| NM_005080_631-649 | 1 | 1.2 | 2 | 0 | 2 | 2.2 | 1 | 1 |
| NM_005080_647-665 | 2 | 1.2 | 2 | 2 | 2 | 2.2 | 1 | 2 |
| NM_005080_791-809 | 1 | 1.2 | 2 | 2.2 | 1 | 2.2 | 1 | 2.2 |
| NM_005080_981-999 | 2 | 1.2 | 1 | 2 | 14 | 2.2 | 1 | 2 |
| NM_005080_1068-1086 | 1 | 1.2 | 1 | 2 | 1 | 2 | 1 | 2 |
| NM_005080_1391-1409 | 1 | 1.2 | 1 | 1 | 1 | 2 | 1 | 1 |
| NM_005080_1426-1444 | 2 | 1.2 | 2 | 2.4 | 1 | 2 | 9 | 3 |
| NM_005080_103-121 | 1 | 1.2 | 6 | 3 | 8 | 2 | 9 | 3 |
| NM_005080_1457-1475 | 1 | 1.2 | 2 | 2.2 | 2 | 2 | 1 | 2 |
| NM_005080_1568-1586 | 2 | 1.2 | 1 | 2 | 5 | 2 | 10 | 2 |
| NM_005080_1574-1592 | 1 | 1.2 | 13 | 3 | 7 | 2 | 2 | 2 |
| NM_005080_1577-1595 | 1 | 1.2 | 1 | 1 | 5 | 2 | 3 | 1 |
| NM_005080_1730-1748 | 2 | 1.2 | 1 | 1 | 4 | 2 | 3 | 1 |
| NM_005080_1731-1749 | 4 | 1.2 | 1 | 1.2 | 4 | 2 | 3 | 1.2 |
| NM_005080_1732-1750 | 2 | 1.2 | 3 | 2 | 3 | 2 | 5 | 2 |
| NM_005080_293-311 | 2 | 1.2 | 4 | 2 | 3 | 2 | 5 | 2 |
| NM_005080_350-368 | 1 | 1.2 | 3 | 2.2 | 1 | 2 | 1 | 1.2 |
| NM_005080_351-369 | 1 | 1.2 | 1 | 2.2 | 5 | 2 | 1 | 2.2 |
| NM_005080_630-648 | 1 | 1.2 | 2 | 2 | 1 | 2 | 2 | 2 |
| NM_005080_657-675 | 2 | 1.2 | 1 | 1 | 2 | 2 | 1 | 1 |
| NM_005080_670-688 | 1 | 1.2 | 4 | 2 | 2 | 2 | 2 | 3 |
| NM_005080_692-710 | 2 | 1.2 | 1 | 1 | 1 | 2 | 6 | 1 |
| NM_005080_778-796 | 1 | 1.2 | 8 | 3 | 4 | 2 | 2 | 2 |
| NM_005080_790-808 | 1 | 1.2 | 8 | 2.2 | 1 | 2 | 3 | 3 |
| NM_005080_970-988 | 1 | 1.2 | 2 | 2 | 6 | 2 | 2 | 2 |
| NM_005080_1162-1180 | 1 | 1.2 | 7 | 3 | 3 | 1.2 | 1 | 2.2 |
| NM_005080_1368-1386 | 1 | 1.2 | 3 | 2.8 | 1 | 1.2 | 5 | 3 |
| NM_005080_1515-1533 | 1 | 1.2 | 1 | 2 | 2 | 1.2 | 2 | 2.2 |

TABLE 10-continued

XBP-1 Human/Rhesus siRNA analysis

| | off target | | | | | | | |
|---|---|---|---|---|---|---|---|---|
| | human | | | | rhesus | | | |
| Oligo Name/ Location of Target sequence from 5' to 3' | Anti- sense Count | Anti- sense Score | Sense Count | Sense Score | Antisense Count | Antisense Score | Sense Count | Sense Score |
|---|---|---|---|---|---|---|---|---|
| NM_005080_1541-1559 | 1 | 1.2 | 4 | 2 | 1 | 1.2 | 1 | 2 |
| NM_005080_1542-1560 | 1 | 1.2 | 1 | 2 | 1 | 1.2 | 2 | 2 |
| NM_005080_1571-1589 | 1 | 1.2 | 2 | 2 | 1 | 1.2 | 4 | 2 |
| NM_005080_151-169 | 1 | 1.2 | 11 | 2 | 1 | 1.2 | 8 | 3 |
| NM_005080_160-178 | 2 | 1.2 | 3 | 2 | 1 | 1.2 | 5 | 2 |
| NM_005080_326-344 | 1 | 1.2 | 1 | 3.2 | 1 | 1.2 | 1 | 3 |
| NM_005080_327-345 | 1 | 1.2 | 2 | 3.2 | 1 | 1.2 | 1 | 3 |
| NM_005080_331-349 | 2 | 1.2 | 4 | 2 | 2 | 1.2 | 1 | 1 |
| NM_005080_424-442 | 1 | 1.2 | 1 | 2.2 | 1 | 1.2 | 2 | 2 |
| NM_005080_483-501 | 3 | 1.2 | 1 | 1.2 | 3 | 1.2 | 1 | 1.2 |
| NM_005080_579-597 | 2 | 1.2 | 1 | 2.2 | 2 | 1.2 | 1 | 2 |
| NM_005080_745-763 | 1 | 1.2 | 1 | 2 | 1 | 1.2 | 1 | 2.2 |
| NM_005080_746-764 | 1 | 1.2 | 2 | 2 | 1 | 1.2 | 1 | 2 |
| NM_005080_812-830 | 2 | 1.2 | 5 | 2 | 1 | 1.2 | 4 | 2 |
| NM_005080_871-889 | 1 | 1.2 | 2 | 3 | 7 | 1.2 | 3 | 3 |
| NM_005080_892-910 | 2 | 1.2 | 3 | 3 | 8 | 1.2 | 1 | 2 |
| NM_005080_978-996 | 1 | 1.2 | 2 | 2 | 1 | 1.2 | 1 | 1.2 |
| NM_005080_982-1000 | 1 | 1.2 | 4 | 2.8 | 8 | 1.2 | 4 | 2.8 |
| NM_005080_257-275 | 1 | 1.2 | 2 | 1 | 1 | 1 | 3 | 1 |
| NM_005080_364-382 | 2 | 1.2 | 7 | 2 | 2 | 1 | 3 | 1 |
| NM_005080_816-834 | 1 | 1.2 | 2 | 2 | 2 | 1 | 2 | 2 |
| NM_005080_884-902 | 1 | 1.2 | 6 | 2 | 1 | 1 | 1 | 2 |
| NM_005080_925-943 | 1 | 1.2 | 6 | 2.2 | 4 | 1 | 1 | 2 |
| NM_005080_1440-1458 | 1 | 1 | 2 | 2 | 1 | 2.8 | 5 | 2 |
| NM_005080_784-802 | 1 | 1 | 2 | 2 | 20 | 2.8 | 1 | 1 |
| NM_005080_1593-1611 | 2 | 1 | 1 | 2 | 2 | 2.2 | 1 | 2 |
| NM_005080_301-319 | 1 | 1 | 10 | 3 | 2 | 2.2 | 9 | 3 |
| NM_005080_674-692 | 2 | 1 | 2 | 2.4 | 1 | 2.2 | 1 | 1.2 |
| NM_005080_783-801 | 1 | 1 | 2 | 2 | 2 | 2.2 | 3 | 1 |
| NM_005080_921-939 | 1 | 1 | 4 | 2 | 10 | 2.2 | 2 | 2 |
| NM_005080_1226-1244 | 2 | 1 | 3 | 1 | 4 | 2 | 1 | 1 |
| NM_005080_1283-1301 | 2 | 1 | 1 | 2 | 5 | 2 | 2 | 1.2 |
| NM_005080_1416-1434 | 1 | 1 | 1 | 1 | 9 | 2 | 10 | 2 |
| NM_005080_1420-1438 | 1 | 1 | 1 | 1 | 5 | 2 | 1 | 1 |
| NM_005080_1488-1506 | 1 | 1 | 3 | 2 | 1 | 2 | 2 | 1 |
| NM_005080_1492-1510 | 1 | 1 | 1 | 2.2 | 1 | 2 | 3 | 3 |
| NM_005080_111-129 | 1 | 1 | 3 | 1 | 10 | 2 | 1 | 1 |
| NM_005080_1639-1657 | 1 | 1 | 4 | 2 | 1 | 2 | 2 | 2 |
| NM_005080_1685-1703 | 1 | 1 | 2 | 2 | 8 | 2 | 1 | 2 |
| NM_005080_1733-1751 | 2 | 1 | 1 | 1 | 7 | 2 | 1 | 1 |
| NM_005080_1734-1752 | 1 | 1 | 5 | 2 | 7 | 2 | 1 | 1 |
| NM_005080_1737-1755 | 1 | 1 | 2 | 1 | 2 | 2 | 2 | 1 |
| NM_005080_1756-1774 | 2 | 1 | 3 | 2 | 7 | 2 | 2 | 2 |
| NM_005080_1757-1775 | 1 | 1 | 4 | 2 | 7 | 2 | 3 | 2 |
| NM_005080_152-170 | 1 | 1 | 6 | 2 | 5 | 2 | 4 | 2 |
| NM_005080_153-171 | 1 | 1 | 3 | 2 | 1 | 2 | 4 | 2 |
| NM_005080_163-181 | 2 | 1 | 3 | 2 | 1 | 2 | 4 | 2 |
| NM_005080_167-185 | 1 | 1 | 2 | 0 | 2 | 2 | 1 | 1 |
| NM_005080_200-218 | 1 | 1 | 1 | 2 | 9 | 2 | 1 | 2 |
| NM_005080_252-270 | 9 | 1 | 5 | 2 | 6 | 2 | 7 | 2 |
| NM_005080_255-273 | 2 | 1 | 1 | 1.2 | 3 | 2 | 1 | 1.2 |
| NM_005080_260-278 | 1 | 1 | 1 | 1 | 34 | 2 | 1 | 0 |
| NM_005080_271-289 | 2 | 1 | 3 | 2 | 8 | 2 | 4 | 2 |
| NM_005080_297-315 | 1 | 1 | 1 | 1.2 | 9 | 2 | 1 | 1.2 |
| NM_005080_300-318 | 1 | 1 | 2 | 2 | 1 | 2 | 1 | 2 |
| NM_005080_335-353 | 2 | 1 | 2 | 1 | 4 | 2 | 1 | 1 |
| NM_005080_368-386 | 1 | 1 | 1 | 2 | 1 | 2 | 6 | 2 |
| NM_005080_378-396 | 5 | 1 | 2 | 1 | 6 | 2 | 1 | 1 |
| NM_005080_379-397 | 5 | 1 | 4 | 2 | 7 | 2 | 3 | 2 |
| NM_005080_380-398 | 4 | 1 | 4 | 2 | 5 | 2 | 1 | 1 |
| NM_005080_389-407 | 1 | 1 | 3 | 2 | 1 | 2 | 1 | 1 |
| NM_005080_426-444 | 1 | 1 | 1 | 2 | 4 | 2 | 1 | 1 |
| NM_005080_427-445 | 1 | 1 | 4 | 1.2 | 3 | 2 | 1 | 1 |
| NM_005080_485-503 | 2 | 1 | 1 | 1.2 | 12 | 2 | 1 | 1 |
| NM_005080_487-505 | 1 | 1 | 2 | 1 | 6 | 2 | 1 | 1 |
| NM_005080_488-506 | 2 | 1 | 2 | 2 | 1 | 2 | 3 | 2 |
| NM_005080_511-529 | 1 | 1 | 1 | 1.2 | 4 | 2 | 21 | 2 |
| NM_005080_526-544 | 3 | 1 | 1 | 2 | 1 | 2 | 5 | 2.2 |

TABLE 10-continued

XBP-1 Human/Rhesus siRNA analysis

| | off target | | | | | | | |
|---|---|---|---|---|---|---|---|---|
| | human | | | | rhesus | | | |
| Oligo Name/ Location of Target sequence from 5' to 3' | Antisense Count | Antisense Score | Sense Count | Sense Score | Antisense Count | Antisense Score | Sense Count | Sense Score |
| NM_005080_575-593 | 1 | 1 | 2 | 2 | 2 | 2 | 1 | 2 |
| NM_005080_593-611 | 2 | 1 | 3 | 2.2 | 16 | 2 | 1 | 2 |
| NM_005080_595-613 | 1 | 1 | 8 | 2 | 4 | 2 | 4 | 2 |
| NM_005080_654-672 | 2 | 1 | 3 | 2 | 3 | 2 | 2 | 2 |
| NM_005080_675-693 | 3 | 1 | 1 | 2 | 1 | 2 | 4 | 2.2 |
| NM_005080_683-701 | 1 | 1 | 1 | 2 | 3 | 2 | 1 | 1 |
| NM_005080_684-702 | 1 | 1 | 2 | 2 | 3 | 2 | 4 | 2 |
| NM_005080_693-711 | 2 | 1 | 8 | 1 | 3 | 2 | 1 | 1 |
| NM_005080_694-712 | 3 | 1 | 12 | 2 | 2 | 2 | 8 | 2 |
| NM_005080_726-744 | 2 | 1 | 1 | 1.2 | 14 | 2 | 1 | 1.2 |
| NM_005080_744-762 | 2 | 1 | 2 | 2 | 2 | 2 | 3 | 2 |
| NM_005080_765-783 | 1 | 1 | 2 | 3 | 2 | 2 | 1 | 2.8 |
| NM_005080_768-786 | 3 | 1 | 2 | 2 | 2 | 2 | 3 | 2 |
| NM_005080_777-795 | 1 | 1 | 4 | 2 | 2 | 2 | 5 | 2 |
| NM_005080_802-820 | 1 | 1 | 2 | 1 | 7 | 2 | 3 | 2 |
| NM_005080_877-895 | 1 | 1 | 2 | 2.2 | 5 | 2 | 2 | 1 |
| NM_005080_878-896 | 1 | 1 | 2 | 2.2 | 2 | 2 | 1 | 2 |
| NM_005080_885-903 | 1 | 1 | 3 | 2 | 2 | 2 | 2 | 2 |
| NM_005080_886-904 | 1 | 1 | 3 | 2 | 2 | 2 | 2 | 2 |
| NM_005080_966-984 | 1 | 1 | 2 | 2.2 | 2 | 2 | 1 | 2.4 |
| NM_005080_969-987 | 1 | 1 | 5 | 2 | 12 | 2 | 2 | 2 |
| NM_005080_1245-1263 | 1 | 1 | 1 | 2 | 1 | 1.2 | 2 | 2 |
| NM_005080_1738-1756 | 1 | 1 | 9 | 2 | 2 | 1.2 | 1 | 1 |
| NM_005080_194-212 | 1 | 1 | 1 | 1 | 1 | 1.2 | 2 | 1 |
| NM_005080_209-227 | 1 | 1 | 1 | 1 | 1 | 1.2 | 1 | 1 |
| NM_005080_269-287 | 2 | 1 | 21 | 2 | 3 | 1.2 | 17 | 2 |
| NM_005080_902-920 | 1 | 1 | 1 | 1.2 | 5 | 1.2 | 1 | 2.2 |
| NM_005080_50-68 | 2 | 1 | 8 | 1 | 1 | 1.2 | 8 | 1 |
| NM_005080_1017-1035 | 1 | 1 | 1 | 2.2 | 1 | 1 | 4 | 3 |
| NM_005080_1021-1039 | 2 | 1 | 1 | 2 | 1 | 1 | 1 | 2 |
| NM_005080_1022-1040 | 1 | 1 | 1 | 1 | 1 | 1 | 2 | 2 |
| NM_005080_1062-1080 | 2 | 1 | 3 | 2 | 3 | 1 | 1 | 2 |
| NM_005080_1074-1092 | 1 | 1 | 1 | 2 | 2 | 1 | 2 | 2.2 |
| NM_005080_1116-1134 | 5 | 1 | 2 | 2.2 | 2 | 1 | 12 | 3 |
| NM_005080_1149-1167 | 1 | 1 | 1 | 2 | 1 | 1 | 10 | 3 |
| NM_005080_1150-1168 | 2 | 1 | 1 | 2 | 8 | 1 | 1 | 1.2 |
| NM_005080_1161-1179 | 1 | 1 | 1 | 2 | 1 | 1 | 1 | 2 |
| NM_005080_1223-1241 | 2 | 1 | 2 | 1 | 5 | 1 | 25 | 2 |
| NM_005080_1280-1298 | 1 | 1 | 1 | 1 | 1 | 1 | 1 | 1 |
| NM_005080_1281-1299 | 1 | 1 | 1 | 1 | 1 | 1 | 3 | 1 |
| NM_005080_1284-1302 | 4 | 1 | 1 | 1 | 1 | 1 | 1 | 1 |
| NM_005080_1286-1304 | 1 | 1 | 3 | 2 | 2 | 1 | 2 | 2 |
| NM_005080_1288-1306 | 2 | 1 | 5 | 2 | 3 | 1 | 1 | 2 |
| NM_005080_1365-1383 | 1 | 1 | 1 | 2.2 | 1 | 1 | 10 | 3 |
| NM_005080_1417-1435 | 2 | 1 | 4 | 2 | 1 | 1 | 5 | 2 |
| NM_005080_1421-1439 | 1 | 1 | 2 | 2 | 1 | 1 | 1 | 2 |
| NM_005080_1434-1452 | 3 | 1 | 1 | 2 | 1 | 1 | 1 | 2.2 |
| NM_005080_1452-1470 | 1 | 1 | 4 | 2 | 1 | 1 | 4 | 2 |
| NM_005080_105-123 | 1 | 1 | 1 | 1 | 2 | 1 | 3 | 2 |
| NM_005080_1455-1473 | 1 | 1 | 5 | 2 | 2 | 1 | 3 | 2 |
| NM_005080_112-130 | 1 | 1 | 2 | 1 | 1 | 1 | 1 | 1.2 |
| NM_005080_113-131 | 2 | 1 | 3 | 1 | 2 | 1 | 1 | 1 |
| NM_005080_1543-1561 | 3 | 1 | 3 | 2.2 | 2 | 1 | 1 | 2.2 |
| NM_005080_1544-1562 | 2 | 1 | 6 | 3 | 2 | 1 | 1 | 2 |
| NM_005080_1557-1575 | 1 | 1 | 6 | 2 | 4 | 1 | 6 | 1 |
| NM_005080_115-133 | 2 | 1 | 1 | 0 | 1 | 1 | 1 | 1.2 |
| NM_005080_1564-1582 | 1 | 1 | 3 | 1 | 4 | 1 | 4 | 1 |
| NM_005080_1572-1590 | 1 | 1 | 3 | 2 | 1 | 1 | 4 | 2 |
| NM_005080_1575-1593 | 1 | 1 | 5 | 2 | 1 | 1 | 4 | 2 |
| NM_005080_1576-1594 | 1 | 1 | 1 | 2 | 1 | 1 | 1 | 2 |
| NM_005080_117-135 | 4 | 1 | 3 | 1 | 14 | 1 | 10 | 1 |
| NM_005080_1582-1600 | 1 | 1 | 9 | 2 | 1 | 1 | 1 | 1 |
| NM_005080_1587-1605 | 1 | 1 | 5 | 2 | 3 | 1 | 12 | 2 |
| NM_005080_118-136 | 8 | 1 | 5 | 1 | 10 | 1 | 3 | 1 |
| NM_005080_119-137 | 7 | 1 | 2 | 1 | 4 | 1 | 1 | 1 |
| NM_005080_120-138 | 6 | 1 | 47 | 2 | 7 | 1 | 35 | 2 |
| NM_005080_124-142 | 6 | 1 | 1 | 0 | 1 | 1 | 1 | 0 |
| NM_005080_126-144 | 1 | 1 | 3 | 1 | 2 | 1 | 1 | 1 |

TABLE 10-continued

XBP-1 Human/Rhesus siRNA analysis

| | off target | | | | | | | |
|---|---|---|---|---|---|---|---|---|
| | human | | | | rhesus | | | |
| Oligo Name/ Location of Target sequence from 5' to 3' | Anti-sense Count | Anti-sense Score | Sense Count | Sense Score | Antisense Count | Antisense Score | Sense Count | Sense Score |
| NM_005080_1676-1694 | 1 | 1 | 2 | 2 | 1 | 1 | 5 | 2 |
| NM_005080_127-145 | 7 | 1 | 2 | 1 | 3 | 1 | 1 | 1 |
| NM_005080_129-147 | 3 | 1 | 18 | 2 | 2 | 1 | 2 | 1 |
| NM_005080_130-148 | 4 | 1 | 7 | 1 | 1 | 1 | 5 | 1 |
| NM_005080_131-149 | 1 | 1 | 1 | 0 | 1 | 1 | 6 | 1 |
| NM_005080_1720-1738 | 1 | 1 | 1 | 3 | 4 | 1 | 1 | 3 |
| NM_005080_1724-1742 | 1 | 1 | 2 | 2 | 2 | 1 | 2 | 2 |
| NM_005080_132-150 | 3 | 1 | 3 | 1 | 1 | 1 | 3 | 1 |
| NM_005080_133-151 | 5 | 1 | 1 | 1 | 3 | 1 | 3 | 1 |
| NM_005080_134-152 | 2 | 1 | 1 | 1.2 | 1 | 1 | 1 | 1 |
| NM_005080_136-154 | 3 | 1 | 1 | 1 | 2 | 1 | 7 | 1 |
| NM_005080_1777-1795 | 1 | 1 | 1 | 1 | 1 | 1 | 4 | 2 |
| NM_005080_137-155 | 4 | 1 | 4 | 1 | 4 | 1 | 7 | 1 |
| NM_005080_139-157 | 10 | 1 | 1 | 1.2 | 2 | 1 | 7 | 2 |
| NM_005080_140-158 | 1 | 1 | 1 | 1.2 | 2 | 1 | 1 | 1.2 |
| NM_005080_141-159 | 7 | 1 | 1 | 0 | 7 | 1 | 1 | 0 |
| NM_005080_142-160 | 4 | 1 | 1 | 0 | 1 | 1 | 1 | 0 |
| NM_005080_143-161 | 6 | 1 | 1 | 0 | 2 | 1 | 3 | 1 |
| NM_005080_144-162 | 1 | 1 | 5 | 1 | 4 | 1 | 9 | 1 |
| NM_005080_161-179 | 2 | 1 | 4 | 2 | 1 | 1 | 1 | 2 |
| NM_005080_162-180 | 4 | 1 | 6 | 2 | 2 | 1 | 6 | 3 |
| NM_005080_164-182 | 2 | 1 | 2 | 2 | 1 | 1 | 4 | 2 |
| NM_005080_165-183 | 1 | 1 | 7 | 2 | 4 | 1 | 1 | 1 |
| NM_005080_166-184 | 3 | 1 | 2 | 1 | 2 | 1 | 7 | 1 |
| NM_005080_201-219 | 4 | 1 | 4 | 2 | 1 | 1 | 1 | 2 |
| NM_005080_202-220 | 5 | 1 | 3 | 1 | 4 | 1 | 1 | 1 |
| NM_005080_203-221 | 3 | 1 | 6 | 1 | 3 | 1 | 1 | 1 |
| NM_005080_204-222 | 3 | 1 | 9 | 1 | 2 | 1 | 1 | 1 |
| NM_005080_208-226 | 3 | 1 | 2 | 1 | 2 | 1 | 4 | 1 |
| NM_005080_212-230 | 2 | 1 | 2 | 1 | 1 | 1 | 5 | 2 |
| NM_005080_248-266 | 4 | 1 | 1 | 1 | 5 | 1 | 11 | 1 |
| NM_005080_251-269 | 1 | 1 | 9 | 2 | 2 | 1 | 1 | 1 |
| NM_005080_258-276 | 2 | 1 | 2 | 2 | 1 | 1 | 12 | 2 |
| NM_005080_262-280 | 2 | 1 | 4 | 2 | 1 | 1 | 1 | 0 |
| NM_005080_265-283 | 2 | 1 | 2 | 2 | 3 | 1 | 4 | 2.2 |
| NM_005080_266-284 | 2 | 1 | 7 | 2 | 2 | 1 | 1 | 1 |
| NM_005080_267-285 | 4 | 1 | 2 | 1 | 1 | 1 | 1 | 1 |
| NM_005080_268-286 | 3 | 1 | 6 | 2 | 1 | 1 | 1 | 1 |
| NM_005080_270-288 | 3 | 1 | 4 | 2 | 1 | 1 | 6 | 2 |
| NM_005080_272-290 | 2 | 1 | 1 | 2 | 1 | 1 | 2 | 2 |
| NM_005080_273-291 | 2 | 1 | 4 | 1 | 3 | 1 | 1 | 2 |
| NM_005080_277-295 | 4 | 1 | 3 | 1 | 2 | 1 | 1 | 1 |
| NM_005080_328-346 | 1 | 1 | 2 | 2 | 1 | 1 | 8 | 3 |
| NM_005080_329-347 | 1 | 1 | 1 | 2 | 1 | 1 | 11 | 3 |
| NM_005080_334-352 | 1 | 1 | 4 | 1 | 1 | 1 | 2 | 1 |
| NM_005080_336-354 | 1 | 1 | 1 | 1 | 1 | 1 | 1 | 1 |
| NM_005080_337-355 | 4 | 1 | 1 | 1 | 2 | 1 | 1 | 1 |
| NM_005080_338-356 | 5 | 1 | 1 | 1 | 3 | 1 | 1 | 1.2 |
| NM_005080_356-374 | 1 | 1 | 1 | 1 | 1 | 1 | 1 | 2 |
| NM_005080_357-375 | 2 | 1 | 2 | 2 | 2 | 1 | 2 | 2 |
| NM_005080_359-377 | 1 | 1 | 1 | 2 | 1 | 1 | 2 | 2.8 |
| NM_005080_360-378 | 1 | 1 | 1 | 2 | 1 | 1 | 1 | 2 |
| NM_005080_362-380 | 4 | 1 | 1 | 1 | 4 | 1 | 1 | 1 |
| NM_005080_367-385 | 1 | 1 | 3 | 2 | 1 | 1 | 2 | 2 |
| NM_005080_382-400 | 6 | 1 | 8 | 2.2 | 2 | 1 | 5 | 1.2 |
| NM_005080_386-404 | 1 | 1 | 2 | 2 | 1 | 1 | 2 | 2 |
| NM_005080_401-419 | 2 | 1 | 3 | 1 | 1 | 1 | 1 | 1 |
| NM_005080_458-476 | 3 | 1 | 1 | 2 | 1 | 1 | 3 | 2 |
| NM_005080_484-502 | 3 | 1 | 6 | 2 | 2 | 1 | 1 | 1 |
| NM_005080_489-507 | 2 | 1 | 1 | 2 | 1 | 1 | 1 | 1.2 |
| NM_005080_574-592 | 1 | 1 | 3 | 2 | 5 | 1 | 4 | 2.2 |
| NM_005080_594-612 | 6 | 1 | 7 | 2 | 13 | 1 | 12 | 2 |
| NM_005080_604-622 | 4 | 1 | 2 | 2 | 3 | 1 | 3 | 2 |
| NM_005080_627-645 | 2 | 1 | 2 | 1 | 3 | 1 | 3 | 1 |
| NM_005080_635-653 | 1 | 1 | 4 | 2 | 3 | 1 | 2 | 2 |
| NM_005080_636-654 | 1 | 1 | 8 | 1.2 | 2 | 1 | 1 | 1.2 |
| NM_005080_666-684 | 2 | 1 | 4 | 2.2 | 7 | 1 | 9 | 3 |
| NM_005080_667-685 | 1 | 1 | 1 | 2 | 1 | 1 | 1 | 2 |

TABLE 10-continued

XBP-1 Human/Rhesus siRNA analysis

| | off target | | | | | | | |
|---|---|---|---|---|---|---|---|---|
| Oligo Name/ | human | | | | rhesus | | | |
| Location of Target | Anti- | Anti- | | | | | | |
| sequence from 5' to 3' | sense Count | sense Score | Sense Count | Sense Score | Antisense Count | Antisense Score | Sense Count | Sense Score |
| NM_005080_669-687 | 1 | 1 | 8 | 3 | 1 | 1 | 4 | 3 |
| NM_005080_681-699 | 2 | 1 | 4 | 2 | 1 | 1 | 2 | 2 |
| NM_005080_690-708 | 5 | 1 | 5 | 2 | 1 | 1 | 6 | 2 |
| NM_005080_718-736 | 4 | 1 | 1 | 1.2 | 5 | 1 | 1 | 1 |
| NM_005080_722-740 | 3 | 1 | 1 | 1 | 3 | 1 | 2 | 1 |
| NM_005080_723-741 | 3 | 1 | 1 | 1 | 3 | 1 | 1 | 1 |
| NM_005080_724-742 | 6 | 1 | 2 | 1 | 4 | 1 | 3 | 0 |
| NM_005080_725-743 | 5 | 1 | 2 | 1 | 2 | 1 | 7 | 1 |
| NM_005080_727-745 | 1 | 1 | 1 | 1 | 1 | 1 | 2 | 1.2 |
| NM_005080_728-746 | 1 | 1 | 2 | 1 | 3 | 1 | 4 | 1 |
| NM_005080_739-757 | 1 | 1 | 5 | 2.2 | 4 | 1 | 1 | 2.2 |
| NM_005080_747-765 | 1 | 1 | 1 | 2 | 7 | 1 | 8 | 3 |
| NM_005080_763-781 | 1 | 1 | 2 | 2 | 6 | 1 | 1 | 2 |
| NM_005080_764-782 | 3 | 1 | 1 | 2.8 | 3 | 1 | 1 | 2.2 |
| NM_005080_766-784 | 1 | 1 | 13 | 2 | 1 | 1 | 1 | 1 |
| NM_005080_770-788 | 1 | 1 | 2 | 1 | 1 | 1 | 4 | 2 |
| NM_005080_774-792 | 2 | 1 | 2 | 1 | 4 | 1 | 1 | 1 |
| NM_005080_780-798 | 5 | 1 | 1 | 1 | 20 | 1 | 1 | 1 |
| NM_005080_781-799 | 5 | 1 | 4 | 2 | 20 | 1 | 8 | 2 |
| NM_005080_805-823 | 1 | 1 | 1 | 1 | 1 | 1 | 3 | 1 |
| NM_005080_44-62 | 30 | 1 | 4 | 2 | 42 | 1 | 5 | 2.8 |
| NM_005080_45-63 | 2 | 1 | 3 | 0 | 5 | 1 | 5 | 0 |
| NM_005080_868-886 | 1 | 1 | 1 | 2.2 | 1 | 1 | 16 | 3 |
| NM_005080_875-893 | 1 | 1 | 1 | 3.2 | 1 | 1 | 3 | 3.2 |
| NM_005080_47-65 | 5 | 1 | 6 | 2 | 10 | 1 | 1 | 1 |
| NM_005080_879-897 | 1 | 1 | 3 | 2 | 2 | 1 | 1 | 1 |
| NM_005080_880-898 | 1 | 1 | 3 | 2 | 1 | 1 | 3 | 2 |
| NM_005080_881-899 | 1 | 1 | 15 | 2 | 1 | 1 | 18 | 2 |
| NM_005080_882-900 | 1 | 1 | 2 | 2 | 1 | 1 | 1 | 2 |
| NM_005080_883-901 | 1 | 1 | 1 | 2 | 4 | 1 | 1 | 2 |
| NM_005080_49-67 | 3 | 1 | 1 | 0 | 1 | 1 | 13 | 1 |
| NM_005080_914-932 | 1 | 1 | 1 | 3 | 1 | 1 | 2 | 4 |
| NM_005080_915-933 | 1 | 1 | 1 | 2 | 1 | 1 | 4 | 3 |
| NM_005080_926-944 | 10 | 1 | 1 | 2 | 7 | 1 | 1 | 2 |
| NM_005080_945-963 | 2 | 1 | 3 | 2 | 3 | 1 | 7 | 2 |
| NM_005080_958-976 | 2 | 1 | 1 | 0 | 1 | 1 | 1 | 1 |
| NM_005080_959-977 | 2 | 1 | 1 | 0 | 1 | 1 | 1 | 2 |
| NM_005080_962-980 | 1 | 1 | 1 | 1 | 1 | 1 | 1 | 1 |
| NM_005080_975-993 | 1 | 1 | 4 | 2 | 1 | 1 | 2 | 2 |
| NM_005080_983-1001 | 1 | 1 | 3 | 1 | 1 | 1 | 1 | 1 |
| NM_005080_128-146 | 2 | 1 | 2 | 1 | 1 | 0 | 8 | 2 |
| NM_005080_249-267 | 1 | 1 | 1 | 1 | 1 | 0 | 11 | 1 |
| NM_005080_697-715 | 1 | 1 | 2 | 2 | 1 | 0 | 1 | 2.2 |
| NM_005080_729-747 | 3 | 1 | 2 | 1 | 1 | 0 | 9 | 1.2 |
| NM_005080_776-794 | 1 | 0 | 4 | 1.2 | 1 | 2.2 | 2 | 1.2 |
| NM_005080_803-821 | 1 | 0 | 11 | 2 | 2 | 2.2 | 4 | 2 |
| NM_005080_254-272 | 9 | 0 | 6 | 2 | 1 | 2 | 2 | 2 |
| NM_005080_383-401 | 2 | 0 | 2 | 2 | 2 | 2 | 7 | 2 |
| NM_005080_116-134 | 2 | 0 | 7 | 1 | 14 | 1 | 6 | 1 |
| NM_005080_123-141 | 1 | 0 | 1 | 1 | 2 | 1 | 13 | 2 |
| NM_005080_125-143 | 1 | 0 | 1 | 0 | 2 | 1 | 1 | 0 |
| NM_005080_135-153 | 2 | 0 | 10 | 2 | 1 | 1 | 1 | 0 |
| NM_005080_253-271 | 9 | 0 | 13 | 2 | 2 | 1 | 11 | 2 |
| NM_005080_274-292 | 1 | 0 | 3 | 1 | 2 | 1 | 2 | 2 |
| NM_005080_655-673 | 2 | 0 | 3 | 2.8 | 1 | 1 | 1 | 2 |
| NM_005080_775-793 | 1 | 0 | 2 | 1.2 | 1 | 1 | 1 | 1 |
| NM_005080_46-64 | 1 | 0 | 3 | 1 | 15 | 1 | 9 | 1 |
| NM_005080_1456-1474 | 1 | 0 | 4 | 2 | 2 | 0 | 1 | 1.2 |
| NM_005080_1545-1563 | 1 | 0 | 9 | 3 | 1 | 0 | 1 | 1 |
| NM_005080_1558-1576 | 1 | 0 | 2 | 2 | 3 | 0 | 8 | 2 |
| NM_005080_121-139 | 1 | 0 | 1 | 0 | 1 | 0 | 48 | 2 |
| NM_005080_122-140 | 1 | 0 | 1 | 1 | 1 | 0 | 13 | 2 |
| NM_005080_247-265 | 1 | 0 | 1 | 1 | 1 | 0 | 1 | 1 |
| NM_005080_275-293 | 1 | 0 | 4 | 1 | 1 | 0 | 2 | 1 |
| NM_005080_276-294 | 1 | 0 | 1 | 1 | 1 | 0 | 1 | 1 |
| NM_005080_358-376 | 1 | 0 | 8 | 2.2 | 1 | 0 | 6 | 2.2 |
| NM_005080_387-405 | 1 | 0 | 2 | 2 | 1 | 0 | 3 | 2 |
| NM_005080_628-646 | 2 | 0 | 1 | 0 | 2 | 0 | 3 | 1 |

TABLE 10-continued

XBP-1 Human/Rhesus siRNA analysis

| Oligo Name/ Location of Target sequence from 5' to 3' | human | | | | off target | | | |
|---|---|---|---|---|---|---|---|---|
| | | | | | rhesus | | | |
| | Anti-sense Count | Anti-sense Score | Sense Count | Sense Score | Antisense Count | Antisense Score | Sense Count | Sense Score |
| NM_005080_656-674 | 2 | 0 | 1 | 1 | 1 | 0 | 1 | 1 |
| NM_005080_719-737 | 1 | 0 | 6 | 2 | 1 | 0 | 6 | 2 |
| NM_005080_720-738 | 2 | 0 | 4 | 1 | 3 | 0 | 1 | 1 |
| NM_005080_721-739 | 1 | 0 | 1 | 1.2 | 1 | 0 | 9 | 2 |
| NM_005080_782-800 | 5 | 0 | 3 | 2 | 20 | 0 | 12 | 2 |
| NM_005080_867-885 | 2 | 0 | 5 | 2 | 2 | 0 | 1 | 2.2 |
| NM_005080_48-66 | 2 | 0 | 3 | 1 | 1 | 0 | 1 | 0 |
| NM_005080_963-981 | 1 | 0 | 1 | 1 | 1 | 0 | 5 | 2 |

Gene XBP-1
reference transcript NM_005080 (human XBP-1 mRNA, FIG. 2)
Notes
19mers found in both human and rhesus

TABLE 11

XBP-1 mouse/Rhesus siRNAs

| Target sequence on rhesus mRNA transcript 5' to 3' | sense (5'-3') | SEQ ID NO: | antinsense (5'-3') | SEQ ID NO: |
|---|---|---|---|---|
| NM_013842_369-387 | AGAAAACUCACGGCCUUGU | 2119 | ACAAGGCCGUGAGUUUUCU | 2120 |
| NM_013842_237-255 | AACUGAAAAACAGAGUAGC | 321 | GCUACUCUGUUUUUCAGUU | 322 |
| NM_013842_491-509 | GGGUCUGCUGAGUCCGCAG | 1693 | CUGCGGACUCAGCAGACCC | 1694 |
| NM_013842_917-935 | AUCACCCUGAAUUCAUUGU | 197 | ACAAUGAAUUCAGGGUGAU | 198 |
| NM_013842_923-941 | CUGAAUUCAUUGUCUCAGU | 2037 | ACUGAGACAAUGAAUUCAG | 2038 |
| NM_013842_702-720 | CCCAGAGGUCUACCCAGAA | 1181 | UUCUGGGUAGACCUCUGGG | 1182 |
| NM_013842_926-944 | AAUUCAUUGUCUCAGUGAA | 1349 | UUCACUGAGACAAUGAAUU | 1350 |
| NM_013842_391-409 | UGAGAACCAGGAGUUAAGA | 1035 | UCUUAACUCCUGGUUCUCA | 1036 |
| NM_013842_775-793 | AAGCUGGAAGCCAUUAAUG | 1249 | CAUUAAUGGCUUCCAGCUU | 1250 |
| NM_013842_1150-1168 | CCCCAGCUGAUUAGUGUCU | 123 | AGACACUAAUCAGCUGGGG | 124 |
| NM_013842_776-794 | AGCUGGAAGCCAUUAAUGA | 1251 | UCAUUAAUGGCUUCCAGCU | 1252 |
| NM_013842_921-939 | CCCUGAAUUCAUUGUCUCA | 1343 | UGAGACAAUGAAUUCAGGG | 1344 |
| NM_013842_777-795 | GCUGGAAGCCAUUAAUGAA | 1585 | UUCAUUAAUGGCUUCCAGC | 1586 |
| NM_013842_539-557 | GUGCAGGCCCAGUUGUCAC | 1951 | GUGACAACUGGGCCUGCAC | 1952 |
| NM_013842_731-749 | CCUUACCAGCCUCCCUUUC | 1995 | GAAAGGGAGGCUGGUAAGG | 1996 |
| NM_013842_924-942 | UGAAUUCAUUGUCUCAGUG | 2039 | CACUGAGACAAUGAAUUCA | 2040 |
| NM_013842_1151-1169 | CCCAGCUGAUUAGUGUCUA | 43 | UAGACACUAAUCAGCUGGG | 44 |
| NM_013842_1152-1170 | CCAGCUGAUUAGUGUCUAA | 125 | UUAGACACUAAUCAGCUGG | 126 |
| NM_013842_1718-1736 | ACUAUGUAAAUGCUUGAUG | 479 | CAUCAAGCAUUUACAUAGU | 480 |
| NM_013842_368-386 | GAGAAAACUCACGGCCUUG | 2121 | CAAGGCCGUGAGUUUUCUC | 2122 |
| NM_013842_489-507 | CCGGGUCUGCUGAGUCCGC | 499 | GCGGACUCAGCAGACCCGG | 500 |
| NM_013842_238-256 | ACUGAAAAACAGAGUAGCA | 289 | UGCUACUCUGUUUUUCAGU | 290 |

TABLE 11-continued

XBP-1 mouse/Rhesus siRNAs

| Target sequence on rhesus mRNA transcript 5' to 3' | sense (5'-3') | SEQ ID NO: | antisense (5'-3') | SEQ ID NO: |
|---|---|---|---|---|
| NM_013842_240-258 | UGAAAAACAGAGUAGCAGC | 529 | GCUGCUACUCUGUUUUUCA | 530 |
| NM_013842_390-408 | UUGAGAACCAGGAGUUAAG | 329 | CUUAACUCCUGGUUCUCAA | 330 |
| NM_013842_487-505 | GGCCGGGUCUGCUGAGUCC | 569 | GGACUCAGCAGACCCGGCC | 570 |
| NM_013842_741-759 | CUCCCUUUCUCUGUCAGUG | 2055 | CACUGACAGAGAAAGGGAG | 2056 |
| NM_013842_918-936 | UCACCCUGAAUUCAUUGUC | 157 | GACAAUGAAUUCAGGGUGA | 158 |
| NM_013842_919-937 | CACCCUGAAUUCAUUGUCU | 343 | AGACAAUGAAUUCAGGGUG | 344 |
| NM_013842_1130-1148 | CUUUUGCCAAUGAACUUUU | 2123 | AAAAGUUCAUUGGCAAAAG | 2124 |
| NM_013842_1712-1730 | AAAUUUACUAUGUAAAUGC | 845 | GCAUUUACAUAGUAAAUUU | 846 |
| NM_013842_1714-1732 | AUUUACUAUGUAAAUGCUU | 847 | AAGCAUUUACAUAGUAAAU | 848 |
| NM_013842_1717-1735 | UACUAUGUAAAUGCUUGAU | 851 | AUCAAGCAUUUACAUAGUA | 852 |
| NM_013842_1719-1737 | CUAUGUAAAUGCUUGAUGG | 853 | CCAUCAAGCAUUUACAUAG | 854 |
| NM_013842_1775-1793 | CCAUUUAUUUAAAACUACC | 379 | GGUAGUUUUAAAUAAAUGG | 380 |
| NM_013842_1776-1794 | CAUUUAUUUAAAACUACCC | 381 | GGGUAGUUUUAAAUAAAUG | 382 |
| NM_013842_239-257 | CUGAAAAACAGAGUAGCAG | 383 | CUGCUACUCUGUUUUUCAG | 384 |
| NM_013842_347-365 | CUAGAAAAUCAGCUUUUAC | 1013 | GUAAAAGCUGAUUUUCUAG | 1014 |
| NM_013842_348-366 | UAGAAAAUCAGCUUUUACG | 1679 | CGUAAAAGCUGAUUUUCUA | 1680 |
| NM_013842_485-503 | GUGGCCGGGUCUGCUGAGU | 1063 | ACUCAGCAGACCCGGCCAC | 1064 |
| NM_013842_486-504 | UGGCCGGGUCUGCUGAGUC | 1065 | GACUCAGCAGACCCGGCCA | 1066 |
| NM_013842_488-506 | GCCGGGUCUGCUGAGUCCG | 1067 | CGGACUCAGCAGACCCGGC | 1068 |
| NM_013842_540-558 | UGCAGGCCCAGUUGUCACC | 1695 | GGUGACAACUGGGCCUGCA | 1696 |
| NM_013842_703-721 | CCAGAGGUCUACCCAGAAG | 1183 | CUUCUGGGUAGACCUCUGG | 1184 |
| NM_013842_705-723 | AGAGGUCUACCCAGAAGGA | 1185 | UCCUUCUGGGUAGACCUCU | 1186 |
| NM_013842_730-748 | UCCUUACCAGCCUCCCUUU | 1717 | AAAGGGAGGCUGGUAAGGA | 1718 |
| NM_013842_742-760 | UCCCUUUCUCUGUCAGUGG | 1721 | CCACUGACAGAGAAAGGGA | 1722 |
| NM_013842_744-762 | CCUUUCUCUGUCAGUGGGG | 1221 | CCCCACUGACAGAGAAAGG | 1222 |
| NM_013842_767-785 | CAUCAGCCAAGCUGGAAGC | 1723 | GCUUCCAGCUUGGCUGAUG | 1724 |
| NM_013842_771-789 | AGCCAAGCUGGAAGCCAUU | 1241 | AAUGGCUUCCAGCUUGGCU | 1242 |
| NM_013842_916-934 | GAUCACCCUGAAUUCAUUG | 195 | CAAUGAAUUCAGGGUGAUC | 196 |
| NM_013842_920-938 | ACCCUGAAUUCAUUGUCUC | 1341 | GAGACAAUGAAUUCAGGGU | 1342 |
| NM_013842_922-940 | CCUGAAUUCAUUGUCUCAG | 1345 | CUGAGACAAUGAAUUCAGG | 1346 |
| NM_013842_925-943 | GAAUUCAUUGUCUCAGUGA | 1347 | UCACUGAGACAAUGAAUUC | 1348 |
| NM_013842_1720-1738 | UAUGUAAAUGCUUGAUGGA | 1841 | UCCAUCAAGCAUUUACAUA | 1842 |
| NM_013842_232-250 | GAGGAAACUGAAAAACAGA | 1911 | UCUGUUUUUCAGUUUCCUC | 1912 |
| NM_013842_236-254 | AAACUGAAAAACAGAGUAG | 1913 | CUACUCUGUUUUUCAGUUU | 1914 |
| NM_013842_728-746 | GUUCCUUACCAGCCUCCCU | 1991 | AGGGAGGCUGGUAAGGAAC | 1992 |
| NM_013842_729-747 | UUCCUUACCAGCCUCCCUU | 1993 | AAGGGAGGCUGGUAAGGAA | 1994 |

TABLE 11-continued

XBP-1 mouse/Rhesus siRNAs

| Target sequence on rhesus mRNA transcript 5' to 3' | sense (5'-3') | SEQ ID NO: | antinsense (5'-3') | SEQ ID NO: |
|---|---|---|---|---|
| NM_013842_745-763 | CUUUCUCUGUCAGUGGGGA | 2001 | UCCCCACUGACAGAGAAAG | 2002 |
| NM_013842_766-784 | UCAUCAGCCAAGCUGGAAG | 1473 | CUUCCAGCUUGGCUGAUGA | 1474 |
| NM_013842_927-945 | AUUCAUUGUCUCAGUGAAG | 2041 | CUUCACUGAGACAAUGAAU | 2042 |
| NM_013842_234-252 | GGAAACUGAAAAACAGAGU | 2093 | ACUCUGUUUUUCAGUUUCC | 2094 |
| NM_013842_235-253 | GAAACUGAAAAACAGAGUA | 2095 | UACUCUGUUUUUCAGUUUC | 2096 |
| NM_013842_346-364 | GCUAGAAAAUCAGCUUUUA | 2099 | UAAAAGCUGAUUUUCUAGC | 2100 |
| NM_013842_490-508 | CGGGUCUGCUGAGUCCGCA | 501 | UGCGGACUCAGCAGACCCG | 502 |
| NM_013842_700-718 | CUCCCAGAGGUCUACCCAG | 91 | CUGGGUAGACCUCUGGGAG | 92 |
| NM_013842_1715-1733 | UUUACUAUGUAAAUGCUUG | 849 | CAAGCAUUUACAUAGUAAA | 850 |
| NM_013842_734-752 | UACCAGCCUCCCUUUCUCU | 1217 | AGAGAAAGGGAGGCUGGUA | 1218 |
| NM_013842_773-791 | CCAAGCUGGAAGCCAUUAA | 1245 | UUAAUGGCUUCCAGCUUGG | 1246 |
| NM_013842_778-796 | CUGGAAGCCAUUAAUGAAC | 1253 | GUUCAUUAAUGGCUUCCAG | 1254 |
| NM_013842_779-797 | UGGAAGCCAUUAAUGAACU | 1255 | AGUUCAUUAAUGGCUUCCA | 1256 |
| NM_013842_1774-1792 | UCCAUUUAUUUAAAACUAC | 1853 | GUAGUUUUAAAUAAAUGGA | 1854 |
| NM_013842_704-722 | CAGAGGUCUACCCAGAAGG | 1987 | CCUUCUGGGUAGACCUCUG | 1988 |
| NM_013842_1716-1734 | UUACUAUGUAAAUGCUUGA | 477 | UCAAGCAUUUACAUAGUAA | 478 |
| NM_013842_1713-1731 | AAUUUACUAUGUAAAUGCU | 315 | AGCAUUUACAUAGUAAAUU | 316 |
| NM_013842_768-786 | AUCAGCCAAGCUGGAAGCC | 2057 | GGCUUCCAGCUUGGCUGAU | 2058 |
| NM_013842_1129-1147 | ACUUUUGCCAAUGAACUUU | 2125 | AAAGUUCAUUGGCAAAAGU | 2126 |
| NM_013842_389-407 | GUUGAGAACCAGGAGUUAA | 245 | UUAACUCCUGGUUCUCAAC | 246 |
| NM_013842_701-719 | UCCCAGAGGUCUACCCAGA | 1179 | UCUGGGUAGACCUCUGGGA | 1180 |
| NM_013842_706-724 | GAGGUCUACCCAGAAGGAC | 1187 | GUCCUUCUGGGUAGACCUC | 1188 |
| NM_013842_707-725 | AGGUCUACCCAGAAGGACC | 1189 | GGUCCUUCUGGGUAGACCU | 1190 |
| NM_013842_727-745 | AGUUCCUUACCAGCCUCCC | 1213 | GGGAGGCUGGUAAGGAACU | 1214 |
| NM_013842_733-751 | UUACCAGCCUCCCUUUCUC | 1719 | GAGAAAGGGAGGCUGGUAA | 1720 |
| NM_013842_736-754 | CCAGCCUCCCUUUCUCUGU | 1493 | ACAGAGAAAGGGAGGCUGG | 1494 |
| NM_013842_738-756 | AGCCUCCCUUUCUCUGUCA | 1219 | UGACAGAGAAAGGGAGGCU | 1220 |
| NM_013842_743-761 | CCCUUUCUCUGUCAGUGGG | 1547 | CCCACUGACAGAGAAAGGG | 1548 |
| NM_013842_769-787 | UCAGCCAAGCUGGAAGCCA | 1239 | UGGCUUCCAGCUUGGCUGA | 1240 |
| NM_013842_772-790 | GCCAAGCUGGAAGCCAUUA | 1243 | UAAUGGCUUCCAGCUUGGC | 1244 |
| NM_013842_774-792 | CAAGCUGGAAGCCAUUAAU | 1247 | AUUAAUGGCUUCCAGCUUG | 1248 |
| NM_013842_231-249 | GGAGGAAACUGAAAAACAG | 1909 | CUGUUUUUCAGUUUCCUCC | 1910 |
| NM_013842_233-251 | AGGAAACUGAAAAACAGAG | 2073 | CUCUGUUUUUCAGUUUCCU | 2074 |
| NM_013842_735-753 | ACCAGCCUCCCUUUCUCUG | 1997 | CAGAGAAAGGGAGGCUGGU | 1998 |
| NM_013842_737-755 | CAGCCUCCCUUUCUCUGUC | 1471 | GACAGAGAAAGGGAGGCUG | 1472 |
| NM_013842_739-757 | GCCUCCCUUUCUCUGUCAG | 1999 | CUGACAGAGAAAGGGAGGC | 2000 |

TABLE 11-continued

XBP-1 mouse/Rhesus siRNAs

| Target sequence on rhesus mRNA transcript 5'to 3' | sense (5'-3') | SEQ ID NO: | antisense (5'-3') | SEQ ID NO: |
|---|---|---|---|---|
| NM_013842_740-758 | CCUCCCUUUCUCUGUCAGU | 2077 | ACUGACAGAGAAAGGGAGG | 2078 |
| NM_013842_746-764 | UUUCUCUGUCAGUGGGGAC | 2003 | GUCCCCACUGACAGAGAAA | 2004 |
| NM_013842_770-788 | CAGCCAAGCUGGAAGCCAU | 2005 | AUGGCUUCCAGCUUGGCUG | 2006 |
| NM_013842_26-44 | GCUAUGGUGGUGGUGGCAG | 2079 | CUGCCACCACCACCAUAGC | 2080 |
| NM_013842_27-45 | CUAUGGUGGUGGUGGCAGC | 2015 | GCUGCCACCACCACCAUAG | 2016 |
| NM_013842_732-750 | CUUACCAGCCUCCCUUUCU | 1215 | AGAAAGGGAGGCUGGUAAG | 1216 |

Gene XBP-1
reference transcript NM_013842 (*Mus musculus* XPB 1 mRNA, FIG. 3)
Notes
100 siRNA sequences common to both mouse and rhesus

TABLE 12

XBP-1 mouse/Rhesus siRNAs with 3'dinucleotide overhangs

| Target sequence on rhesus mRNA transcript 5' to 3' | sense (5'-3') with 3' dinucleotide overhand | SEQ ID NO: | antisense (5'-3') with 3' dinucleotide overhang | SEQ ID NO: |
|---|---|---|---|---|
| NM_013842_369-387 | AGAAAACUCACGGCCUUGNN | 4321 | ACAAGGCCGUGAGUUUUCUNN | 4322 |
| NM_013842_237-255 | AACUGAAAACAGAGUAGCNN | 2523 | GCUACUCUGUUUUUCAGUUNN | 2524 |
| NM_013842_491-509 | GGGUCUGCUGAGUCCGCAGNN | 3895 | CUGCGGACUCAGCAGACCCNN | 3896 |
| NM_013842_917-935 | AUCACCCUGAAUUCAUUGUNN | 2399 | ACAAUGAAUUCAGGGUGAUNN | 2400 |
| NM_013842_923-941 | CUGAAUUCAUUGUCUCAGUNN | 4239 | ACUGAGACAAUGAAUUCAGNN | 4240 |
| NM_013842_702-720 | CCCAGAGGUCUACCCAGAANN | 3383 | UUCUGGGUAGACCUCUGGGNN | 3384 |
| NM_013842_926-944 | AAUUCAUUGUCUCAGUGAANN | 3551 | UUCACUGAGACAAUGAAUUNN | 3552 |
| NM_013842_391-409 | UGAGAACCAGGAGUUAAGANN | 3237 | UCUUAACUCCUGGUUCUCANN | 3238 |
| NM_013842_775-793 | AAGCUGGAAGCCAUUAAUGNN | 3451 | CAUUAAUGGCUUCCAGCUUNN | 3452 |
| NM_013842_1150-1168 | CCCCAGCUGAUUAGUGUCUNN | 2325 | AGACACUAAUCAGCUGGGGNN | 2326 |
| NM_013842_776-794 | AGCUGGAAGCCAUUAAUGNN | 3453 | UCAUUAAUGGCUUCCAGCUNN | 3454 |
| NM_013842_921-939 | CCCUGAAUUCAUUGUCUCANN | 3545 | UGAGACAAUGAAUUCAGGGNN | 3546 |
| NM_013842_777-795 | GCUGGAAGCCAUUAAUGAANN | 3787 | UUCAUUAAUGGCUUCCAGCNN | 3788 |
| NM_013842_539-557 | GUGCAGGCCCAGUUGUCACNN | 4153 | GUGACAACUGGGCCUGCACNN | 4154 |
| NM_013842_731-749 | CCUUACCAGCCUCCCUUUCNN | 4197 | GAAAGGGAGGCUGGUAAGGNN | 4198 |
| NM_013842_924-942 | UGAAUUCAUUGUCUCAGUGNN | 4241 | CACUGAGACAAUGAAUUCANN | 4242 |
| NM_013842_1151-1169 | CCCAGCUGAUUAGUGUCUANN | 2245 | UAGACACUAAUCAGCUGGGNN | 2246 |
| NM_013842_1152-1170 | CCAGCUGAUUAGUGUCUAANN | 2327 | UUAGACACUAAUCAGCUGGNN | 2328 |
| NM_013842_1718-1736 | ACUAUGUAAAUGCUUGAUGNN | 2681 | CAUCAAGCAUUUACAUAGUNN | 2682 |
| NM_013842_368-386 | GAGAAAACUCACGGCCUUGNN | 4323 | CAAGGCCGUGAGUUUUCUCNN | 4324 |
| NM_013842_489-507 | CCGGGUCUGCUGAGUCCGCNN | 2701 | GCGGACUCAGCAGACCCGGNN | 2702 |
| NM_013842_238-256 | ACUGAAAACAGAGUAGCANN | 2491 | UGCUACUCUGUUUUUCAGUNN | 2492 |

TABLE 12-continued

XBP-1 mouse/Rhesus siRNAs with 3'dinucleotide overhangs

| Target sequence on rhesus mRNA transcript 5' to 3' | sense (5'-3') with 3' dinucleotide overhand | SEQ ID NO: | antisense (5'-3') with 3' dinucleotide overhang | SEQ ID NO: |
|---|---|---|---|---|
| NM_013842_240-258 | UGAAAAACAGAGUAGCAGCNN | 2731 | GCUGCUACUCUGUUUUUCANN | 2732 |
| NM_013842_390-408 | UUGAGAACCAGGAGUUAAGNN | 2531 | CUUAACUCCUGGUUCUCAANN | 2532 |
| NM_013842_487-505 | GGCCGGGUCUGCUGAGUCCNN | 2771 | GGACUCAGCAGACCCGGCCNN | 2772 |
| NM_013842_741-759 | CUCCCUUUCUCUGUCAGUGNN | 4257 | CACUGACAGAGAAAGGGAGNN | 4258 |
| NM_013842_918-936 | UCACCCUGAAUUCAUUGUCNN | 2359 | GACAAUGAAUUCAGGGUGANN | 2360 |
| NM_013842_919-937 | CACCCUGAAUUCAUUGUCUNN | 2545 | AGACAAUGAAUUCAGGGUGNN | 2546 |
| NM_013842_1130-1148 | CUUUUGCCAAUGAACUUUUNN | 4325 | AAAAGUUCAUUGGCAAAAGNN | 4326 |
| NM_013842_1712-1730 | AAAUUUACUAUGUAAAUGCNN | 3047 | GCAUUUACAUAGUAAAUUUNN | 3048 |
| NM_013842_1714-1732 | AUUUACUAUGUAAAUGCUUNN | 3049 | AAGCAUUUACAUAGUAAAUNN | 3050 |
| NM_013842_1717-1735 | UACUAUGUAAAUGCUUGAUNN | 3053 | AUCAAGCAUUUACAUAGUANN | 3054 |
| NM_013842_1719-1737 | CUAUGUAAAUGCUUGAUGGNN | 3055 | CCAUCAAGCAUUUACAUAGNN | 3056 |
| NM_013842_1775-1793 | CCAUUUAUUUAAAACUACCNN | 2581 | GGUAGUUUUAAAUAAAUGGNN | 2582 |
| NM_013842_1776-1794 | CAUUUAUUUAAAACUACCCNN | 2583 | GGGUAGUUUUAAAUAAAUGNN | 2584 |
| NM_013842_239-257 | CUGAAAAACAGAGUAGCAGNN | 2585 | CUGCUACUCUGUUUUUCAGNN | 2586 |
| NM_013842_347-365 | CUAGAAAAUCAGCUUUUACNN | 3215 | GUAAAAGCUGAUUUUCUAGNN | 3216 |
| NM_013842_348-366 | UAGAAAAUCAGCUUUUACGNN | 3881 | CGUAAAAGCUGAUUUUCUANN | 3882 |
| NM_013842_485-503 | GUGGCCGGGUCUGCUGAGUNN | 3265 | ACUCAGCAGACCCGGCCACNN | 3266 |
| NM_013842_486-504 | UGGCCGGGUCUGCUGAGUCNN | 3267 | GACUCAGCAGACCCGGCCANN | 3268 |
| NM_013842_488-506 | GCCGGGUCUGCUGAGUCCGNN | 3269 | CGGACUCAGCAGACCCGGCNN | 3270 |
| NM_013842_540-558 | UGCAGGCCCAGUUGUCACCNN | 3897 | GGUGACAACUGGGCCUGCANN | 3898 |
| NM_013842_703-721 | CCAGAGGUCUACCCAGAAGNN | 3385 | CUUCGGGUAGACCUCUGGNN | 3386 |
| NM_013842_705-723 | AGAGGUCUACCCAGAAGGANN | 3387 | UCCUUCUGGGUAGACCUCUNN | 3388 |
| NM_013842_730-748 | UCCUUACCAGCCUCCCUUUNN | 3919 | AAAGGGAGGCUGGUAAGGANN | 3920 |
| NM_013842_742-760 | UCCCUUUCUCUGUCAGUGGNN | 3923 | CCACUGACAGAGAAAGGGANN | 3924 |
| NM_013842_744-762 | CCUUUCUCUGUCAGUGGGGNN | 3423 | CCCCACUGACAGAGAAAGGNN | 3424 |
| NM_013842_767-785 | CAUCAGCCAAGCUGGAAGCNN | 3925 | GCUUCCAGCUUGGCUGAUGNN | 3926 |
| NM_013842_771-789 | AGCCAAGCUGGAAGCCAUUNN | 3443 | AAUGGCUUCCAGCUUGGCUNN | 3444 |
| NM_013842_916-934 | GAUCACCCUGAAUUCAUUGNN | 2397 | CAAUGAAUUCAGGGUGAUCNN | 2398 |
| NM_013842_920-938 | ACCCUGAAUUCAUUGUCUCNN | 3543 | GAGACAAUGAAUUCAGGGUNN | 3544 |
| NM_013842_922-940 | CCUGAAUUCAUUGUCUCAGNN | 3547 | CUGAGACAAUGAAUUCAGGNN | 3548 |
| NM_013842_925-943 | GAAUUCAUUGUCUCAGUGANN | 3549 | UCACUGAGACAAUGAAUUCNN | 3550 |
| NM_013842_1720-1738 | UAUGUAAAUGCUUGAUGGANN | 4043 | UCCAUCAAGCAUUUACAUANN | 4044 |
| NM_013842_232-250 | GAGGAAACUGAAAAACAGANN | 4113 | UCUGUUUUUCAGUUUCCUCNN | 4114 |
| NM_013842_236-254 | AAACUGAAAAACAGAGUAGNN | 4115 | CUACUCUGUUUUUCAGUUUNN | 4116 |
| NM_013842_728-746 | GUUCCUUACCAGCCUCCCUNN | 4193 | AGGGAGGCUGGUAAGGAACNN | 4194 |
| NM_013842_729-747 | UUCCUUACCAGCCUCCCUUNN | 4195 | AAGGGAGGCUGGUAAGGAANN | 4196 |
| NM_013842_745-763 | CUUUCUCUGUCAGUGGGGANN | 4203 | UCCCCACUGACAGAGAAAGNN | 4204 |

TABLE 12-continued

XBP-1 mouse/Rhesus siRNAs with 3'dinucleotide overhangs

| Target sequence on rhesus mRNA transcript 5' to 3' | sense (5'-3') with 3' dinucleotide overhand | SEQ ID NO: | antisense (5'-3') with 3' dinucleotide overhang | SEQ ID NO: |
|---|---|---|---|---|
| NM_013842_766-784 | UCAUCAGCCAAGCUGGAAGNN | 3675 | CUUCCAGCUUGGCUGAUGANN | 3676 |
| NM_013842_927-945 | AUUCAUUGUCUCAGUGAAGNN | 4243 | CUUCACUGAGACAAUGAAUNN | 4244 |
| NM_013842_234-252 | GGAAACUGAAAAACAGAGUNN | 4295 | ACUCUGUUUUUCAGUUUCCNN | 4296 |
| NM_013842_235-253 | GAAACUGAAAAACAGAGUANN | 4297 | UACUCUGUUUUUCAGUUUCNN | 4298 |
| NM_013842_346-364 | GCUAGAAAAUCAGCUUUUANN | 4301 | UAAAAGCUGAUUUUCUAGCNN | 4302 |
| NM_013842_490-508 | CGGGUCUGCUGAGUCCGCANN | 2703 | UGCGGACUCAGCAGACCCGNN | 2704 |
| NM_013842_700-718 | CUCCCAGAGGUCUACCCAGNN | 2293 | CUGGGUAGACCUCUGGGAGNN | 2294 |
| NM_013842_1715-1733 | UUUACUAUGUAAAUGCUUGNN | 3051 | CAAGCAUUUACAUAGUAAANN | 3052 |
| NM_013842_734-752 | UACCAGCCUCCCUUUCUCUNN | 3419 | AGAGAAAGGGAGGCUGGUANN | 3420 |
| NM_013842_773-791 | CCAAGCUGGAAGCCAUUAANN | 3447 | UUAAUGGCUUCCAGCUUGGNN | 3448 |
| NM_013842_778-796 | CUGGAAGCCAUUAAUGAACNN | 3455 | GUUCAUUAAUGGCUUCCAGNN | 3456 |
| NM_013842_779-797 | UGGAAGCCAUUAAUGAACUNN | 3457 | AGUUCAUUAAUGGCUUCCANN | 3458 |
| NM_013842_1774-1792 | UCCAUUUAUUUAAAACUACNN | 4055 | GUAGUUUUAAAUAAAUGGANN | 4056 |
| NM_013842_704-722 | CAGAGGUCUACCCAGAAGGNN | 4189 | CCUUCUGGGUAGACCUCUGNN | 4190 |
| NM_013842_1716-1734 | UUACUAUGUAAAUGCUUGANN | 2679 | UCAAGCAUUUACAUAGUAANN | 2680 |
| NM_013842_1713-1731 | AAUUUACUAUGUAAAUGCUNN | 2517 | AGCAUUUACAUAGUAAAUUNN | 2518 |
| NM_013842_768-786 | AUCAGCCAAGCUGGAAGCCNN | 4259 | GGCUUCCAGCUUGGCUGAUNN | 4260 |
| NM_013842_1129-1147 | ACUUUUGCCAAUGAACUUUNN | 4327 | AAAGUUCAUUGGCAAAAGUNN | 4328 |
| NM_013842_389-407 | GUUGAGAACCAGGAGUUAANN | 2447 | UUAACUCCUGGUUCUCAACNN | 2448 |
| NM_013842_701-719 | UCCCAGAGGUCUACCCAGANN | 3381 | UCUGGGUAGACCUCUGGGANN | 3382 |
| NM_013842_706-724 | GAGGUCUACCCAGAAGGACNN | 3389 | GUCCUUCGGGUAGACCUCNN | 3390 |
| NM_013842_707-725 | AGGUCUACCCAGAAGGACCNN | 3391 | GGUCCUUCUGGGUAGACCUNN | 3392 |
| NM_013842_727-745 | AGUUCCUUACCAGCCUCCCNN | 3415 | GGGAGGCUGGUAAGGAACUNN | 3416 |
| NM_013842_733-751 | UUACCAGCCUCCCUUUCUCNN | 3921 | GAGAAAGGGAGGCUGGUAANN | 3922 |
| NM_013842_736-754 | CCAGCCUCCCUUUCUCUGUNN | 3695 | ACAGAGAAAGGGAGGCUGGNN | 3696 |
| NM_013842_738-756 | AGCCUCCCUUUCUCUGUCANN | 3421 | UGACAGAGAAAGGGAGGCUNN | 3422 |
| NM_013842_743-761 | CCCUUUCUCUGUCAGUGGNN | 3749 | CCCACUGACAGAGAAAGGGNN | 3750 |
| NM_013842_769-787 | UCAGCCAAGCUGGAAGCCANN | 3441 | UGGCUUCCAGCUUGGCUGANN | 3442 |
| NM_013842_772-790 | GCCAAGCUGGAAGCCAUUANN | 3445 | UAAUGGCUUCCAGCUUGGCNN | 3446 |
| NM_013842_774-792 | CAAGCUGGAAGCCAUUAAUNN | 3449 | AUUAAUGGCUUCCAGCUUGNN | 3450 |
| NM_013842_231-249 | GGAGGAAACUGAAAAACAGNN | 4111 | CUGUUUUUCAGUUUCCUCCNN | 4112 |
| NM_013842_233-251 | AGGAAACUGAAAAACAGAGNN | 4275 | CUCUGUUUUUCAGUUUCCUNN | 4276 |
| NM_013842_735-753 | ACCAGCCUCCCUUUCUCUGNN | 4199 | CAGAGAAAGGGAGGCUGGUNN | 4200 |
| NM_013842_737-755 | CAGCCUCCCUUUCUCUGUCNN | 3673 | GACAGAGAAAGGGAGGCUGNN | 3674 |
| NM_013842_739-757 | GCCUCCCUUUCUCUGUCAGNN | 4201 | CUGACAGAGAAAGGGAGGCNN | 4202 |
| NM_013842_740-758 | CCUCCCUUUCUCUGUCAGUNN | 4279 | ACUGACAGAGAAAGGGAGGNN | 4280 |

TABLE 12-continued

XBP-1 mouse/Rhesus siRNAs with 3'dinucleotide overhangs

| Target sequence on rhesus mRNA transcript 5' to 3' | sense (5'-3') with 3' dinucleotide overhand | SEQ ID NO: | antisense (5'-3') with 3' dinucleotide overhang | SEQ ID NO: |
|---|---|---|---|---|
| NM_013842_746-764 | UUUCUCUGUCAGUGGGGACNN | 4205 | GUCCCCACUGACAGAGAAANN | 4206 |
| NM_013842_770-788 | CAGCCAAGCUGGAAGCCAUNN | 4207 | AUGGCUUCCAGCUUGGCUGNN | 4208 |
| NM_013842_26-44 | GCUAUGGUGGUGGUGGCAGNN | 4281 | CUGCCACCACCACCAUAGCNN | 4282 |
| NM_013842_27-45 | CUAUGGUGGUGGUGGCAGCNN | 4217 | GCUGCCACCACCACCAUAGNN | 4218 |
| NM_013842_732-750 | CUUACCAGCCUCCCUUUCUNN | 3417 | AGAAAGGGAGGCUGGUAAGNN | 3418 |

Gene XBP-1
reference transcript NM_013842 (*Mus musculus* XPB 1 mRNA, FIG. 3)
Notes
100 siRNA sequences common to both mouse and rhesus

TABLE 13

XBP-1 mouse/Rhesus analysis of siRNAs

| | off target | | | | | | | |
|---|---|---|---|---|---|---|---|---|
| | mouse | | | | rhesus | | | |
| Oligo Name | Antisense Count | Antisense Score | Sense Count | Sense Score | Antisense Count | Antisense Score | Sense Count | Sense Score |
|---|---|---|---|---|---|---|---|---|
| NM_013842_369-387 | 4 | 3.2 | 2 | 2 | 1 | 2.8 | 1 | 2.4 |
| NM_013842_237-255 | 3 | 3 | 1 | 2 | 2 | 2.2 | 14 | 1 |
| NM_013842_491-509 | 1 | 3 | 1 | 2 | 1 | 2 | 5 | 2.2 |
| NM_013842_917-935 | 9 | 3 | 1 | 2 | 1 | 2 | 5 | 2 |
| NM_013842_923-941 | 7 | 3 | 2 | 1 | 1 | 1 | 1 | 1 |
| NM_013842_702-720 | 2 | 2.8 | 8 | 2 | 4 | 2 | 1 | 2 |
| NM_013842_926-944 | 2 | 2.8 | 1 | 1 | 1 | 2 | 3 | 2 |
| NM_013842_391-409 | 2 | 2.4 | 7 | 3 | 1 | 2 | 1 | 2 |
| NM_013842_775-793 | 2 | 2.4 | 5 | 2 | 3 | 2 | 2 | 2 |
| NM_013842_1150-1168 | 3 | 2.2 | 1 | 2 | 1 | 2.8 | 1 | 2 |
| NM_013842_776-794 | 3 | 2.2 | 6 | 2 | 1 | 2 | 1 | 1 |
| NM_013842_921-939 | 1 | 2.2 | 1 | 2 | 2 | 2 | 4 | 2 |
| NM_013842_777-795 | 6 | 2.2 | 3 | 2 | 1 | 1.2 | 4 | 2 |
| NM_013842_539-557 | 2 | 2.2 | 4 | 2 | 5 | 1 | 4 | 2.2 |
| NM_013842_731-749 | 3 | 2.2 | 4 | 2.8 | 1 | 1 | 1 | 1 |
| NM_013842_924-942 | 2 | 2.2 | 3 | 2 | 1 | 1 | 1 | 2 |
| NM_013842_1151-1169 | 1 | 2 | 1 | 2.2 | 2 | 3 | 1 | 1.2 |
| NM_013842_1152-1170 | 1 | 2 | 1 | 2 | 2 | 3 | 2 | 2.2 |
| NM_013842_1718-1736 | 1 | 2 | 5 | 3 | 20 | 3 | 1 | 2.2 |
| NM_013842_368-386 | 1 | 2 | 2 | 2 | 1 | 3 | 1 | 2.2 |
| NM_013842_489-507 | 1 | 2 | 1 | 2 | 3 | 3 | 4 | 3 |
| NM_013842_238-256 | 1 | 2 | 10 | 3 | 1 | 2.4 | 2 | 1 |
| NM_013842_240-258 | 1 | 2 | 4 | 2 | 1 | 2.4 | 10 | 2 |
| NM_013842_390-408 | 2 | 2 | 18 | 3 | 4 | 2.2 | 1 | 1 |
| NM_013842_487-505 | 1 | 2 | 3 | 2 | 1 | 2.2 | 5 | 2 |
| NM_013842_741-759 | 3 | 2 | 2 | 1 | 1 | 2.2 | 2 | 1.2 |
| NM_013842_918-936 | 1 | 2 | 1 | 2 | 2 | 2.2 | 5 | 2 |
| NM_013842_919-937 | 2 | 2 | 2 | 2 | 3 | 2.2 | 1 | 1 |
| NM_013842_1130-1148 | 1 | 2 | 2 | 2 | 12 | 2 | 1 | 1 |
| NM_013842_1712-1730 | 4 | 2 | 1 | 2 | 10 | 2 | 1 | 2.2 |
| NM_013842_1714-1732 | 2 | 2 | 1 | 2 | 1 | 2 | 2 | 1 |
| NM_013842_1717-1735 | 4 | 2 | 6 | 3 | 2 | 2 | 1 | 2.2 |
| NM_013842_1719-1737 | 1 | 2 | 1 | 2 | 13 | 2 | 2 | 2 |
| NM_013842_1775-1793 | 2 | 2 | 4 | 2 | 2 | 2 | 9 | 2 |
| NM_013842_1776-1794 | 1 | 2 | 4 | 2 | 4 | 2 | 1 | 1 |
| NM_013842_239-257 | 9 | 2 | 3 | 2 | 1 | 2 | 2 | 1 |
| NM_013842_347-365 | 2 | 2 | 3 | 2 | 1 | 2 | 1 | 1 |
| NM_013842_348-366 | 3 | 2 | 5 | 2.2 | 1 | 2 | 1 | 1 |
| NM_013842_485-503 | 2 | 2 | 1 | 2.2 | 13 | 2 | 3 | 2 |
| NM_013842_486-504 | 2 | 2 | 1 | 2 | 11 | 2 | 2 | 2 |
| NM_013842_488-506 | 5 | 2 | 5 | 3 | 2 | 2 | 2 | 2 |
| NM_013842_540-558 | 6 | 2 | 4 | 2 | 2 | 2 | 1 | 2 |
| NM_013842_703-721 | 2 | 2 | 8 | 2 | 7 | 2 | 3 | 2.2 |

TABLE 13-continued

XBP-1 mouse/Rhesus analysis of siRNAs

| | off target | | | | | | | |
|---|---|---|---|---|---|---|---|---|
| | mouse | | | | rhesus | | | |
| Oligo Name | Antisense Count | Antisense Score | Sense Count | Sense Score | Antisense Count | Antisense Score | Sense Count | Sense Score |
| NM_013842_705-723 | 6 | 2 | 5 | 2.8 | 5 | 2 | 1 | 3 |
| NM_013842_730-748 | 2 | 2 | 1 | 2.8 | 2 | 2 | 1 | 2.8 |
| NM_013842_742-760 | 3 | 2 | 1 | 1 | 2 | 2 | 5 | 2 |
| NM_013842_744-762 | 3 | 2 | 1 | 1 | 21 | 2 | 9 | 2 |
| NM_013842_767-785 | 6 | 2 | 6 | 2.2 | 7 | 2 | 3 | 2 |
| NM_013842_771-789 | 7 | 2 | 3 | 1 | 11 | 2 | 5 | 2 |
| NM_013842_916-934 | 1 | 2 | 4 | 2.2 | 6 | 2 | 4 | 2 |
| NM_013842_920-938 | 1 | 2 | 3 | 2 | 4 | 2 | 3 | 2 |
| NM_013842_922-940 | 3 | 2 | 2 | 1 | 1 | 2 | 2 | 2.2 |
| NM_013842_925-943 | 1 | 2 | 1 | 2 | 2 | 2 | 1 | 1 |
| NM_013842_1720-1738 | 1 | 2 | 1 | 2.2 | 4 | 1 | 1 | 3 |
| NM_013842_232-250 | 7 | 2 | 1 | 1 | 3 | 1 | 1 | 2 |
| NM_013842_236-254 | 1 | 2 | 2 | 2 | 2 | 1 | 1 | 1 |
| NM_013842_728-746 | 22 | 2 | 2 | 2 | 6 | 1 | 1 | 2 |
| NM_013842_729-747 | 13 | 2 | 1 | 2.2 | 3 | 1 | 1 | 2.2 |
| NM_013842_745-763 | 4 | 2 | 2 | 1 | 20 | 1 | 1 | 1 |
| NM_013842_766-784 | 2 | 2 | 8 | 2 | 1 | 1 | 2 | 1 |
| NM_013842_927-945 | 2 | 2 | 5 | 2 | 1 | 1 | 1 | 1 |
| NM_013842_234-252 | 6 | 2 | 1 | 1 | 1 | 0 | 2 | 1 |
| NM_013842_235-253 | 2 | 2 | 1 | 1 | 1 | 0 | 1 | 1 |
| NM_013842_346-364 | 2 | 2 | 1 | 1 | 1 | 0 | 3 | 2 |
| NM_013842_490-508 | 1 | 1.2 | 12 | 3 | 6 | 3 | 3 | 2 |
| NM_013842_700-718 | 1 | 1.2 | 3 | 2.2 | 4 | 3 | 2 | 2 |
| NM_013842_1715-1733 | 1 | 1.2 | 6 | 3 | 3 | 2 | 1 | 1 |
| NM_013842_734-752 | 1 | 1.2 | 1 | 1 | 7 | 2 | 5 | 2 |
| NM_013842_773-791 | 2 | 1.2 | 1 | 2 | 1 | 2 | 1 | 2.2 |
| NM_013842_778-796 | 1 | 1.2 | 3 | 2 | 7 | 2 | 2 | 2 |
| NM_013842_779-797 | 1 | 1.2 | 5 | 3 | 1 | 2 | 1 | 2 |
| NM_013842_1774-1792 | 1 | 1.2 | 1 | 1 | 1 | 1 | 4 | 2 |
| NM_013842_704-722 | 2 | 1.2 | 1 | 2 | 4 | 1 | 1 | 2.2 |
| NM_013842_1716-1734 | 1 | 1 | 5 | 3 | 9 | 3 | 1 | 1 |
| NM_013842_1713-1731 | 1 | 1 | 1 | 2.2 | 3 | 2.2 | 2 | 2 |
| NM_013842_768-786 | 1 | 1 | 2 | 2.2 | 2 | 2.2 | 4 | 2 |
| NM_013842_1129-1147 | 1 | 1 | 2 | 2 | 1 | 2 | 1 | 1 |
| NM_013842_389-407 | 1 | 1 | 2 | 2 | 1 | 2 | 3 | 2 |
| NM_013842_701-719 | 2 | 1 | 1 | 1 | 4 | 2 | 4 | 2 |
| NM_013842_706-724 | 3 | 1 | 6 | 2 | 1 | 2 | 1 | 3 |
| NM_013842_707-725 | 2 | 1 | 1 | 1 | 3 | 2 | 1 | 3 |
| NM_013842_727-745 | 1 | 1 | 1 | 2 | 1 | 2 | 1 | 2.2 |
| NM_013842_733-751 | 2 | 1 | 1 | 2.2 | 2 | 2 | 3 | 2 |
| NM_013842_736-754 | 1 | 1 | 3 | 2 | 3 | 2 | 6 | 1 |
| NM_013842_738-756 | 2 | 1 | 7 | 2 | 7 | 2 | 3 | 1 |
| NM_013842_743-761 | 1 | 1 | 2 | 2 | 4 | 2 | 2 | 2 |
| NM_013842_769-787 | 1 | 1 | 2 | 2 | 8 | 2 | 2 | 0 |
| NM_013842_772-790 | 3 | 1 | 4 | 2 | 1 | 2 | 2 | 2 |
| NM_013842_774-792 | 2 | 1 | 2 | 2 | 4 | 2 | 10 | 2 |
| NM_013842_231-249 | 2 | 1 | 1 | 1.2 | 1 | 1 | 2 | 2 |
| NM_013842_233-251 | 4 | 1 | 4 | 2 | 2 | 1 | 2 | 2 |
| NM_013842_735-753 | 3 | 1 | 2 | 1 | 1 | 1 | 4 | 2 |
| NM_013842_737-755 | 4 | 1 | 3 | 2 | 1 | 1 | 7 | 2 |
| NM_013842_739-757 | 2 | 1 | 6 | 2 | 4 | 1 | 1 | 1 |
| NM_013842_740-758 | 1 | 1 | 9 | 2 | 1 | 1 | 1 | 1 |
| NM_013842_746-764 | 2 | 1 | 1 | 1 | 20 | 1 | 8 | 2 |
| NM_013842_770-788 | 2 | 1 | 4 | 1 | 1 | 1 | 3 | 1 |
| NM_013842_26-44 | 4 | 1 | 1 | 1 | 15 | 1 | 9 | 1 |
| NM_013842_27-45 | 2 | 1 | 2 | 2 | 10 | 1 | 1 | 1 |
| NM_013842_732-750 | 1 | 0 | 2 | 2.8 | 5 | 2 | 1 | 1 |

Gene XBP-1
reference transcript NM_013842 (*Mus musculis* XPB1 mRNA, FIG. 3)
Notes
100 siRNA sequences common to both mouse and rhesus Other embodiments are in the claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07875711B2). An electronic copy of the "Sequence Listing" will also be available from the USPTO upon request and payment of the fee set forth in 37 CFR 1.19(b)(3).

---

We claim:

1. A double-stranded ribonucleic acid (dsRNA) for inhibiting the expression of an XBP-1 gene, wherein said dsRNA comprises a sense strand and an antisense strand that together form a region of complementarity less than 30 base pairs in length and wherein the antisense strand is complementary to at least 15 contiguous nucleotides of 5' CACCCUGAAUU-CAUUGUCU 3' (SEQ ID NO:2149).

2. The dsRNA of claim 1, wherein said dsRNA comprises at least one modified nucleotide.

3. The dsRNA of claim 2, wherein at least one of said modified nucleotides is chosen from the group of: a 2'-O-methyl modified nucleotide, a nucleotide comprising a 5'-phosphorothioate group, and a terminal nucleotide linked to a cholesteryl derivative, vitamin E, or dodecanoic acid bisdecylamide group.

4. The dsRNA of claim 2, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

5. The dsRNA of claim 1, wherein the region of complementarity is at least 15 nucleotides in length.

6. The dsRNA of claim 1, wherein the region of complementarity is between 19 and 21 nucleotides in length.

7. A cell comprising the dsRNA of claim 1.

8. A pharmaceutical composition for inhibiting expression of an XBP-1 gene comprising the dsRNA of claim 1 and a pharmaceutically acceptable carrier.

9. A method of inhibiting XBP-1 expression in a cell, the method comprising:
 (a) introducing into the cell the dsRNA of claim 1; and
 (b) maintaining the cell produced in step (a) for a time sufficient to obtain degradation of the mRNA transcript of the XBP-1 gene, thereby inhibiting expression of the XBP-1 gene in the cell.

10. A vector comprising a regulatory sequence operably linked to a nucleotide sequence encoding at least one strand of the dsRNA of claim 1.

11. The vector of claim 10, wherein the region of complementarity is at least 15 nucleotides in length.

12. The vector of claim 10, wherein the region of complementarity is 19 to 21 nucleotides in length.

13. A cell comprising the vector of claim 10.

14. The dsRNA of claim 1, wherein the antisense strand comprises SEQ ID NO:2150.

15. The dsRNA of claim 1, wherein the antisense strand consists of SEQ ID NO:2150.

16. The dsRNA of claim 1, wherein the sense strand comprises SEQ ID NO:2149.

17. The dsRNA of claim 1, wherein the sense strand consists of SEQ ID NO:2149.

18. The dsRNA of claim 1, wherein the antisense strand consists of SEQ ID NO:2150 and the sense strand consists of SEQ ID NO:2149.

19. The dsRNA of claim 2 comprising a 5'-phosphorothioate group or a 2'-O-methyl modified nucleotide.

20. The dsRNA of claim 2, wherein the antisense strand comprises SEQ ID NO:2178.

21. The dsRNA of claim 2, wherein the antisense strand consists of SEQ ID NO:2178.

22. The dsRNA of claim 2, wherein the sense strand comprises SEQ ID NO:2177.

23. The dsRNA of claim 2, wherein the sense strand consists of SEQ ID NO:2177.

24. The dsRNA of claim 2, wherein the antisense strand consists of SEQ ID NO:2178 and the sense strand consists of SEQ ID NO:2177.

25. The dsRNA of claim 1 comprising one or more single-stranded nucleotide overhangs.

26. The dsRNA of claim 1 comprising a 3' dinucleotide overhang on the sense strand and a 3' dinucleotide overhang on the antisense strand.

27. The dsRNA of claim 1, wherein the region of complementarity is 19 nucleotides in length.

28. The dsRNA of claim 1, wherein each strand of the dsRNA is 21 nucleotides in length.

* * * * *